United States Patent
Hung et al.

(10) Patent No.: US 9,051,314 B2
(45) Date of Patent: Jun. 9, 2015

(54) BRIDGED HETEROCYCLIC COMPOUNDS AND METHODS OF USE

(71) Applicant: Medivation Technologies, Inc., San Francisco, CA (US)

(72) Inventors: David T. Hung, Redwood City, CA (US); Andrew Asher Protter, Palo Alto, CA (US); Sarvajit Chakravarty, Mountain View, CA (US); Rajendra Parasmal Jain, Pune (IN)

(73) Assignee: Medivation Technologies, Inc., San Francisco, CA (US)

( * ) Notice: Subject to any disclaimer, the term of this patent is extended or adjusted under 35 U.S.C. 154(b) by 0 days.

(21) Appl. No.: 14/033,234

(22) Filed: Sep. 20, 2013

(65) Prior Publication Data

US 2014/0024643 A1 Jan. 23, 2014

Related U.S. Application Data

(62) Division of application No. 12/410,425, filed on Mar. 24, 2009, now Pat. No. 8,546,381.

(60) Provisional application No. 61/039,058, filed on Mar. 24, 2008, provisional application No. 61/145,058, filed on Jan. 15, 2009.

(51) Int. Cl.
*A61K 31/54* (2006.01)
*C07D 451/00* (2006.01)
*C07D 471/18* (2006.01)
*C07D 471/08* (2006.01)

(52) U.S. Cl.
CPC .......... *C07D 451/00* (2013.01); *C07D 471/18* (2013.01); *C07D 471/08* (2013.01)

(58) Field of Classification Search
CPC ... C07D 451/00; C07D 471/08; C07D 471/18
See application file for complete search history.

(56) References Cited

U.S. PATENT DOCUMENTS

| | | | |
|---|---|---|---|
| 4,360,673 | A | 11/1982 | Berger et al. |
| 5,250,537 | A | 10/1993 | Mewshaw et al. |
| 5,620,988 | A | 4/1997 | Glase et al. |
| 6,187,785 | B1 | 2/2001 | Zefirov et al. |
| 6,251,893 | B1 | 6/2001 | Maddaford et al. |
| 7,071,206 | B2 | 7/2006 | Zefirov et al. |
| 8,338,408 | B2 | 12/2012 | Hung et al. |
| 8,338,447 | B2 | 12/2012 | Hung et al. |
| 8,541,437 | B2 | 9/2013 | Ivashchenko et al. |
| 8,546,381 | B2 | 10/2013 | Hung et al. |
| 8,569,287 | B2 | 10/2013 | Hung et al. |
| 8,741,919 | B2 | 6/2014 | Jain et al. |
| 8,791,132 | B2 | 7/2014 | Protter et al. |
| 8,815,843 | B2 | 8/2014 | Protter et al. |
| 8,859,561 | B2 | 10/2014 | Jain et al. |
| 2001/0020028 | A1 | 9/2001 | Zefirov et al. |
| 2002/0115682 | A1 | 8/2002 | Zefirov et al. |
| 2004/0044022 | A1 | 3/2004 | Zefirov, Jr. et al. |
| 2006/0140866 | A1 | 6/2006 | Zefirov et al. |
| 2007/0117834 | A1 | 5/2007 | Hung |
| 2007/0117835 | A1 | 5/2007 | Hung |
| 2007/0179174 | A1 | 8/2007 | Bachurin et al. |
| 2007/0225316 | A1 | 9/2007 | Bachurin et al. |
| 2008/0234310 | A1 | 9/2008 | Bachurin et al. |
| 2009/0247561 | A1 | 10/2009 | Zemoka et al. |
| 2009/0270412 | A1 | 10/2009 | Hung et al. |
| 2010/0022580 | A1 | 1/2010 | Hung et al. |
| 2010/0029706 | A1 | 2/2010 | Miller et al. |
| 2010/0087471 | A1 | 4/2010 | Schrimpf et al. |
| 2010/0099700 | A1 | 4/2010 | Hung |
| 2010/0152108 | A1 | 6/2010 | Hung et al. |
| 2010/0152163 | A1 | 6/2010 | Hung et al. |
| 2010/0152225 | A1 | 6/2010 | Hung |
| 2010/0178277 | A1 | 7/2010 | Hung et al. |
| 2010/0216814 | A1 | 8/2010 | Hung et al. |
| 2010/0249105 | A1 | 9/2010 | Schrimpf et al. |
| 2010/0286188 | A1 | 11/2010 | Bachurin et al. |
| 2011/0046368 | A1 | 2/2011 | Ivashchenko et al. |
| 2011/0112132 | A1 | 5/2011 | Bachurin et al. |
| 2011/0237582 | A1 | 9/2011 | Jain et al. |
| 2011/0245272 | A1 | 10/2011 | Jain et al. |
| 2011/0269777 | A1 | 11/2011 | Bachurin et al. |

(Continued)

FOREIGN PATENT DOCUMENTS

| | | |
|---|---|---|
| EP | 0 876 818 A2 | 11/1998 |
| EP | 2 236 511 A2 | 10/2010 |

(Continued)

OTHER PUBLICATIONS

Lohr et al, Psychiatry Research 57 (1995) 279-282.*
Bartolini, L. et al. (1996). "Aniracetam Restores Object Recognition Impaired by Age, Scopolamine, and Nucleus Basalis Lesions," *Pharmacology Biochemistry Behavior* 53(2):277-283.
Berge, S.M. et al. (Jan. 1977). "Pharmaceutical Salts," *J. Pharm. Sci.* 66(1):1-19.
Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.
Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.
Brown, C.M. et al. (1990). "$\alpha_2$-Adrenoceptor Subtypes and Imidazoline-Like Binding Sites in the Rat Brain," *Br. J. Pharmacol.* 99:803-809.

(Continued)

*Primary Examiner* — Wu-Cheng Winston Shen
*Assistant Examiner* — Jean Cornet
(74) *Attorney, Agent, or Firm* — Morrison & Foerster LLP

(57) ABSTRACT

This disclosure relates to new compounds that may be used to modulate a histamine receptor in an individual. Novel compounds are described, including new bridged heterocyclic [4,3-b]indole compounds. Pharmaceutical compositions are also provided. Pharmaceutical compositions comprising the compounds are also provided, as are methods of using the compounds in a variety of therapeutic applications, including the treatment of a cognitive disorder, psychotic disorder, neurotransmitter-mediated disorder and/or a neuronal disorder.

19 Claims, No Drawings

(56) References Cited

U.S. PATENT DOCUMENTS

| | | | |
|---|---|---|---|
| 2012/0101121 A1 | 4/2012 | Bachurin et al. |
| 2012/0136008 A1 | 5/2012 | Jain et al. |
| 2012/0172377 A1 | 7/2012 | Jain et al. |
| 2013/0053366 A1 | 2/2013 | Protter et al. |
| 2013/0053367 A1 | 2/2013 | Protter et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0172366 A1 | 7/2013 | Jain et al. |
| 2013/0184269 A1 | 7/2013 | Hung et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190322 A1 | 7/2013 | Hung et al. |
| 2013/0190323 A1 | 7/2013 | Hung et al. |
| 2013/0190328 A1 | 7/2013 | Jain et al. |
| 2013/0190331 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1 | 8/2013 | Chakravarty et al. |
| 2013/0217675 A1 | 8/2013 | Chakravarty et al. |
| 2013/0225558 A1 | 8/2013 | Chakravarty et al. |
| 2014/0088086 A1 | 3/2014 | Protter et al. |
| 2014/0088087 A1 | 3/2014 | Hung et al. |
| 2014/0155384 A1 | 6/2014 | Protter et al. |
| 2014/0194414 A1 | 7/2014 | Hung et al. |
| 2014/0206711 A1 | 7/2014 | Chakravarty et al. |
| 2014/0213577 A1 | 7/2014 | Hung et al. |
| 2014/0228353 A1 | 8/2014 | Protter et al. |
| 2014/0296209 A1 | 10/2014 | Protter et al. |
| 2014/0303144 A1 | 10/2014 | Protter et al. |

FOREIGN PATENT DOCUMENTS

| | | |
|---|---|---|
| WO | WO-2005/005951 A2 | 6/2005 |
| WO | WO-2005/005951 A3 | 6/2005 |
| WO | WO-2007/022502 A2 | 2/2007 |
| WO | WO-2007/022502 A3 | 2/2007 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/060190 A2 | 5/2008 |
| WO | WO-2008/060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/036998 A2 | 4/2010 |
| WO | WO-2010/036998 A3 | 4/2010 |
| WO | WO-2010/051501 A1 | 5/2010 |
| WO | WO-2010/051503 A1 | 5/2010 |
| WO | WO-2010/127177 A1 | 11/2010 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112964 A3 | 8/2012 |
| WO | WO-2012/112965 A1 | 8/2012 |
| WO | WO-2012/112966 A1 | 8/2012 |
| WO | WO-2012/154261 A1 | 11/2012 |
| WO | WO-2014/031165 A1 | 2/2014 |
| WO | WO-2014/031167 A1 | 2/2014 |
| WO | WO-2014/031170 A1 | 2/2014 |

OTHER PUBLICATIONS

Bubber, P. et al. (May 2005). "Mitochondrial Abnormalities in Alzheimer Brain: Mechanistic Implications," *Ann Neurol.* 57(5):695-703.

Cava, M.P. et al. (Nov. 1965). "A New Isoquinuclidine Synthesis. A New Route to *dl*-Dioscorone," *J. Org. Chem.* 30:3772-3775.

Cordero, F.M. et al. (1995). "Intramolecular Cycloadditions and Thermal Rearrangement of Cyclopropylidene Nitrones. Straightforward Access to Bicyclic Tetrahydrophridones," *Tetrahedron Lett.* 36(8):1343-1346.

Cordonnier, G. et al. (1994). "Synthesis of Uncommon Heterocyclic Systems: Pyrano- and [1]Benzopyrano[3,2-f]indolizines,"*Tetrahedron Lett.* 35(46):8617-8618.

De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.

Ennaceur, A. et al. (1988). "A New One-Trial Test for Neurobiological Studies of Memory in Rats. 1: Behavioral Data," *Behav. Brain. Res.* 31:47-59.

Extended European Search Report mailed on Feb. 5, 2013 for EP Application No. 10819490.3 filed on Sep. 23, 2010, 24 pages.

Extended European Search Report mailed Feb. 6, 2013 for EP Application No. 10819493.7, filed on Sep. 23, 2010, 7 pages.

Final Office Action mailed on Dec. 2, 2011, for U.S. Appl. No. 12/360,061, filed Jan. 26, 2009, 13 pages.

Final Office Action mailed on Jul. 19, 2012, for U.S. Appl. No. 12/410,425, filed Mar. 24, 2009, 10 pages.

Final Office Action mailed on Jul. 25, 2013, for U.S. Appl. No. 12/610,217, filed on Oct. 30, 2009, 11 pages.

García-Sáinz, J.A. et al. (Jul. 31, 1992). "Species Heterogeneity of Hepatic $\alpha_1$-Adrenoceptors: $\alpha_{1A}$-, $\alpha_{1B}$- and $\alpha_{1C}$-Subtypes," *Biochemical and Biophysical Research Communications* 186(2):760-767.

Gilliland, S.L. et al. (2000, e-pub. Feb. 29, 2000). "Characterization of Dopaminergic Compounds at $hD_{2short}$, $hD_{4.2}$ and $hD_{4.7}$ Receptors

(56) References Cited

OTHER PUBLICATIONS in Agonist-Stimulated [$^{35}$S]GTPγS Binding Assays," *Naunyn-Schmiedeberg's Archives of Pharmacology* 361:498-504.
Grandy, D.K. et al. (Dec. 1989). "Cloning of the cDNA and Gene for a Human D$_2$ Dopamine Receptor," *Proc. Natl. Acad. Sci. USA* 86:9762-9766.
Grossman, C.J. et al. (1993). "Development of a Radioligand Binding Assay for 5-HT$_4$ Receptors in Guinea-Pig and Rat Brain," *Br. J. Pharmacol.* 109:618-624.
Hardy, J. (1996). "New Insights Into the Genetics of Alzheimer's Disease," *Annals of Medicine* 28:255-258.
Hardy, J. (1997). "Amyloid, the Presenilins and Alzheimer's Disease," *Trends Neurosci.* 20(4):154-159.
Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.
Howard, A.S. et al. (1980). "Vinylogous Urethanes in Alkaloid Synthesis: Formal Syntheses of *Elaeocarpus* Alkaloids," *Tetrahedron Lett.* 21(14):1373-1374.
Hoyer, D. et al. (1985). "Characterization of the 5-HT$_{1B}$ Recognition Site in Rat Brain: Binding Studies with (-)[$^{125}$I]Iodocyanopindolol," *European Journal of Pharmacology* 118:1-12.
International Search Report mailed on Jun. 15, 2009 for PCT Patent Application No. PCT/US2009/038142, filed on Mar. 24, 2009, 2 pages.
International Search Report mailed on Nov. 10, 2010, for PCT Application No. PCT/US2010/050078, filed on Sep. 23, 2010, 2 pages.
International Search Report mailed on Nov. 10, 2010, for PCT Application No. PCT/US2010/50081, filed on Sep. 23, 2010, 3 pages.
Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.
Jerman, J.C. et al. (2001). "Pharmacological Characterisation of Human 5-HT$_2$ Receptor Subtypes," *European Journal of Pharmacology* 414:23-30.
Kenny, B.A. et al. (1995). "Characterization of an α$_{1D}$-Adrenoceptor Mediating the Contractile Response of Rat Aorta to Noradrenaline," *British Journal of Pharmacology* 115:981-986.
King, F.D. et al. (1993). "Substituted Benzamides With Conformationally Restricted Side Chains. 5. Azabicyclo[x.y.z] Derivatives as 5-HT4 Receptor Agonists and Gastric Motility Stimulants," *J. Med. Chem.* 36(6):683-689.
King, F.D. (1983). "A Facile Synthesis of Quinolizidines and Indolizidines," *Tetrahedron Lett.* 24(31):3281-3282.
Kohen, R. et al. (1996). "Cloning, Characterization and Chromosomal Localization of a Human 5-HT$_6$ Serotonin Receptor," *J. Neurochem.* 66(1):47-56.
Lee, J. et al. (2006). "The Role of Stimulus Salience in CPT-AX Performance of Schizophrenia Patients," *Schizophr. Res.* 81(2-3):191-197.
Levinoff, E.J. et al. (Jan. 2006). "Cognitive Estimation Impairment in Alzheimer Disease and Mild Cognitive Impairment," *Neuropsychology* 20(1)123-132.
Martin, G.R. (1994). "Receptors for 5-Hydroxytryptamine: Current Perspectives on Classification and Nomenclature," *Neuropharmacology* 33(3/4):261-273.
May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *The Journal of Pharmacology and Experimental Therapeutics* 306(1):301-309.
Mewshaw, R.E. et al. (1993). "Bridged γ-carbolines and Derivatives Possessing Selective and Combined Affinity for 5-HT$_2$ and D$_2$ Receptors," *J. Med. Chem.* 36(10):1488-1495.
Mewshaw, R.E. et al. (1993). "Synthesis and in Vitro Evaluation of 5,6,7,8,9,10-Hexahydro-7,10-iminocyclohept[*b*]indoles: High-Affinity Ligands for the *N,N'*-Di-*o*-tolylguanidine-Labeled σ Binding Site," *J. Med. Chem.* 36(3):343-352.
Michel, A.D. et al. (1989). "Identification of a Single α$_1$-Adrenoceptor Corresponding to the α$_{1A}$-Subtype in Rat Submaxillary Gland," *Br. J. Pharmacol.* 98:883-889.
Miller, K et al. (1992). "Membrane-Bound and Solubilized Brain 5HT$_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.
Miller, T.R. et al. (1999). "Analysis of Apparent Noncompetitive Responses to Competitive H$_1$-Histamine Receptor Antagonists in Fluorescent Imaging Plate Reader-Based Calcium Assays," *Journal of Biomolecular Screening* 4(5):249-258.
Monsma, F.J. Jr. et al. (1993). "Cloning and Expression of a Novel Serotonin Receptor with High Affinity for Tricyclic Psychotropic Drugs," *Molecular Pharmacology* 43:320-327.
Navarra, R. et al. (2008). "Effects of Atomoxetine and Methylphenidate on Attention and Impulsivity in the 5-Choice Serial Reaction Time Test," *Prog. Neuropsychopharmacol. Biol. Psychiatry* 32(1):34-41.
Non-Final Office Action mailed on Jun. 14, 2011, for U.S. Appl. No. 12/360,061, filed Jan. 26, 2009, 22 pages.
Non-Final Office Action mailed on Apr. 16, 2013, for U.S. Appl. No. 12/610,217, filed Oct. 30, 2009, 10 pages.
Non-Final Office Action mailed on Dec. 19, 2013, for U.S. Appl. No. 13/789,606, filed Mar. 7, 2013, 13 pages.
Non-Final Office Action mailed on Feb. 14, 2014, for U.S. Appl. No. 13/498,099, filed Jan. 14, 2013, 20 pages.
Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.
Piercey, M.F. et al. (1988). "Dramatic Limbic and Cortical Effects Mediated by High Affinity PCP Receptors," *Life Sciences* 43(4):379-385.
Prichep, L.S. et al. (1994). "Quantitative EEG Correlates of Cognitive Deterioration in the Elderly," *Neurobiology of Aging* 15(1):85-90.
Reddy, P.H. et al. (2005, e-pub. Apr. 19, 2005). "Are Mitochondria Critical in the Pathogenesis of Alzheimer's Disease?" *Brain Res Rev.* 49(3):618-632.
Rees, S. et al. (Oct. 11, 1994). "Cloning and Characterisation of the Human 5-HT$_{5A}$ Serotonin Receptor," *FEBS Letters* 355:242-246.
Reisberg, B. et al. (Sep. 1982). "The Global Deterioration Scale for Assessment of Primary Degenerative Dementia," *Am. J. Psychiatry* 139(9):1136-1139.
Riccio, C.A. et al. (2001). "Effects of Stimulants on the Continuous Performance Test (CPT): Implications for CPT use and Interpretation," *J. Neuropsychiatry Clin. Neurolsci.* 13(3):326-335.
Robbins, T. et al. (Oct. 2002, e-pub. Aug. 9, 2002). "The 5-Choice Serial Reaction Time Task: Behavioural Pharmacology and Functional Neurochemistry," *Psychopharmacology* 163(3-4):362-380.
Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.
Ruat, M. et al. (Mar. 1990). "Reversible and Irreversible Labeling and Autoradiographic Localization of the Cerebral Histamine H$_2$ Receptor Using [$^{125}$I]Iodinated Probes," *Proc. Natl. Acad. Sci. USA* 87(5):1658-1662.
Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.
Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.
Senogles, S.E. et al. (Mar. 15, 1990). "Specificity of Receptor-G Protein Interactions. Discrimination of G$_i$ Subtypes by the D$_2$ Dopamine Receptor in a Reconstituted System," *Journal of Biological Chemistry* 265(8):4507-4514.

(56) References Cited

OTHER PUBLICATIONS

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Vippagunta et al. (2001). "Crystalline Solids," *Advanced Drug Delivery Reviews* 48:3-26.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Williams, et al. (2002). *Foye's Principles of Medicinal Chemistry*, 5$^{th}$ Edition, pp. 59-63.

Wolf, W.A. et al. (1997). "The Serotonin 5-HT$_{2C}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion of the International Searching Authority mailed on Jun. 15, 2009 for PCT Patent Application No. PCT/US2009/038142, filed on Mar. 24, 2009, 8 pages.

Written Opinion mailed on Nov. 10, 2010, for PCT Application No. PCT/US2010/050078, filed on Sep. 23, 2010, 4 pages.

Written Opinion mailed on Nov. 10, 2010, for PCT Application No. PCT/US2010/50081, filed on Sep. 23, 2010, 5 pages.

Yanai, K. et al. (1994). "Binding Characteristics of a Histamine H$_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.

Zhu, Y. et al. (2001). "Cloning, Expression, and Pharmacological Characterization of a Novel Human Histamine Receptor," *Molecular Pharmacology* 59(3):434-441.

U.S. Appl. No. 13/789,361, filed Mar. 7, 2013, by Protter et al.
U.S. Appl. No. 13/791,750, filed Mar. 8, 2013, by Hung et al.
U.S. Appl. No. 13/791,648, filed Mar. 8, 2013, by Hung et al.
U.S. Appl. No. 14/000,171, filed Aug. 16, 2013, by Protter et al.
U.S. Appl. No. 14/000,176, filed Aug. 16, 2013, by Protter et al.
U.S. Appl. No. 14/000,179, filed Aug. 16, 2013, by Chakravarty et al.
U.S. Appl. No. 14/000,184, filed Aug. 16, 2013, by Protter et al.
U.S. Appl. No. 14/000,197, filed Aug. 16, 2013, by Protter et al.
U.S. Appl. No. 14/048,656, filed Oct. 8, 2013, by Hung et al.
Final Office Action mailed on Jul. 1, 2014, for U.S. Appl. No. 13/789,606, filed Mar. 7, 2013, 17 pages.
Non-Final Office Action mailed on Jul. 31, 2014, for U.S. Appl. No. 13/734,873, filed Jan. 4, 2013, 16 pages.
Non-Final Office Action mailed on Aug. 6, 2014, for U.S. Appl. No. 13/791,832, filed Mar. 8, 2013, 9 pages.
U.S. Appl. No. 14/485,238, filed Sep. 12, 2014, by Jain et al.

* cited by examiner

BRIDGED HETEROCYCLIC COMPOUNDS AND METHODS OF USE

CROSS-REFERENCE TO RELATED APPLICATIONS

This application is a division of U.S. Non-provisional patent application Ser. No. 12/410,425, filed Mar. 24, 2009, which claims priority to U.S. Provisional Patent Application No. 61/039,058 filed Mar. 24, 2008 and U.S. Provisional Patent Application No. 61/145,058 filed Jan. 15, 2009, the disclosures of each of which are incorporated herein by reference in their entireties.

STATEMENT OF RIGHTS TO INVENTIONS MADE UNDER FEDERALLY SPONSORED RESEARCH

Not applicable.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. Compounds that modulate these neurotransmitters may be useful therapeutics.

Histamine receptors belong to the superfamily of G protein-coupled seven transmembrane proteins, G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623 and PCT/US2008/008121. All references disclosed herein and throughout, such as publications, patents, patent applications and published patent applications, are incorporated herein by reference in their entireties.

Although dimebon holds great promise as a drug for the treatment of neurodegenerative disease and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Compounds detailed herein are described as histamine receptor modulator. Compositions comprising the compounds are provided, as are kits comprising the compound as well as methods of using and making the compounds. The compounds may find use in treating neurodegenerative diseases. Compounds of the invention may also find use in treating diseases and/or conditions in which modulation of aminergic G protein-coupled receptors and/or neurite outgrowth may be implicated in therapy. Compounds disclosed herein may find use in the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans. For example, compounds of the general formula (I) are described as new histamine receptor modulators and may also find use in treating neurodegenerative diseases.

Compounds of the formula (E) are detailed herein:

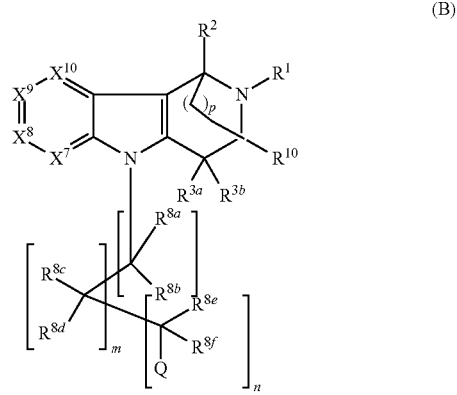

(B)

where:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, hydroxyl, alkoxyl or substituted or unsubstituted $C_1$-$C_8$ alkyl;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together to form a cycloalkyl moiety or a carbonyl moiety;

each $X^7$, $X^8$, $X^9$ and $X^{10}$ is independently N or $CR^4$;

m and q are independently 0 or 1;

p is 1 or 2;

n is 1 or 0, provided that n is 0 only when Q is a substituted heterocycle wherein the substituted heterocycle is a lactam;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal, $R^{8(a-f)}$ to form cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted-unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^{8(a-f)}$ to form a bond, the geminal $F^{8(a-f)}$ is other than hydroxyl;

$R^{10}$ is H, hydroxyl, alkoxyl or a substituted or unsubstituted $C_1$-$C_8$ alkyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, amino, substituted amino, alkoxy, aminoacyl, acyloxy, carbonylalkoxy, aminocarbonylalkoxy, acylamino, carboxy, alkynyl or cyano;

or a salt or solvate thereof.

Also detailed herein are compounds of formula (A-1):

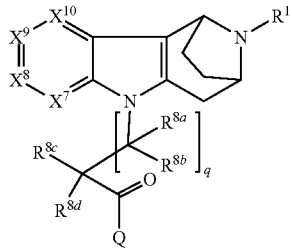

(A-1)

where:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

q is 0 or 1;

each $R^{8a}$, $R^{8b}$, $R^{8c}$ and $R^{8d}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-d)}$ to form a cycloalkyl moiety or a carbonyl moiety, is taken together with a geminal $R^{8(a-d)}$ to form a methylene or a substituted methylene, is taken together with a vicinal $R^{8(a-d)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-d)}$ to form a bond, provided that when an $R^{8(a-d)}$ is taken together with a vicinal $R^{8(a-d)}$ to form a bond, the geminal $R^{8(a-d)}$ is other than hydroxyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted heterocyclyl, unsubstituted amino, substituted amino or alkoxy;

or a salt thereof.

A compound of the formula (A-2) is also described:

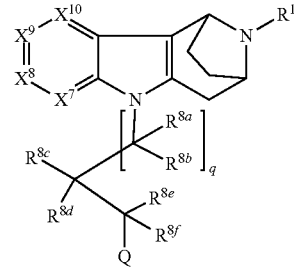

(A-2)

where:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

q is 0 or 1;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonyalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^{8(a-f)}$ to form a bond, the geminal $R^{8(a-f)}$ is other than hydroxyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or a unsubstituted heterocyclyl, unsubstituted amino, substituted amino, alkoxy, aminoacyl, acyloxy, carbonylalkoxy, aminocarbonylalkoxy or acylamino;

or a salt thereof.

Compounds of formula (F-1) are also provided:

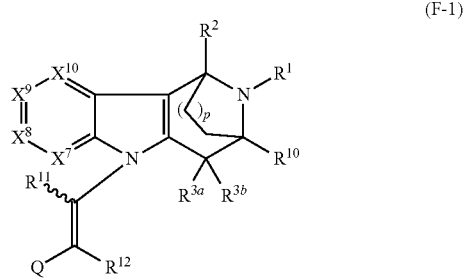

(F-1)

where:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^2$ and $R^{10}$ is independently H, hydroxyl, alkoxyl or substituted or unsubstituted $C_1$-$C_8$ alkyl;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or and $R^{3a}$ and $R^{3b}$ are taken together to form a cycloalkyl or a carbonyl moiety;

p is 1 or 2;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

$R^{11}$ and $R^{12}$ are independently H, $C_1$-$C_8$ alkyl, $C_1$-$C_8$ perhaloalkyl, carboxy, carbonylalkoxy, or taken together with the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or are taken together to form a bond, thereby providing an acetylenyl moiety; ∿ indicates the presence of either an E or Z double bond configuration when $R^{11}$ and $R^{12}$ are independently H or $C_1$-$C_8$ alkyl; and Q is a substituted or unsubstituted aryl, substituted or unsubstituted heteroaryl, substituted or unsubstituted cycloalkyl, substituted of unsubstituted cycloalkenyl, substituted or an unsubstituted heterocyclyl, unsubstituted amino, substituted amino, alkoxy, aminoacyl, acyloxy, carbonylalkoxy, aminocarbonylalkoxy, acylamino, carboxy, alkynyl or cyano;

or a salt thereof.

Also described is a compound of the formula (F-2):

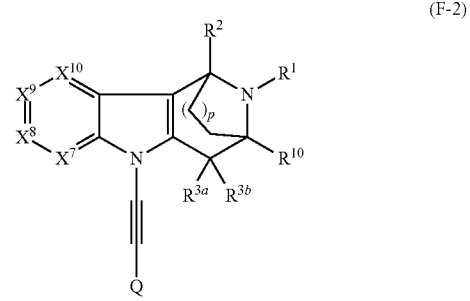

(F-2)

where:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^2$ and $R^{10}$ is independently H, hydroxyl, alkoxyl or substituted or unsubstituted $C_1$-$C_8$ alkyl;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together to form a cycloalkyl or a carbonyl moiety;

p is 1 or 2;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl; and Q is a substituted or unsubstituted aryl, substituted or unsubstituted heteroaryl, substituted or unsubstituted cycloalkyl, substituted or unsubstituted cycloalkenyl, substituted or an unsubstituted heterocyclyl, unsubstituted amino, substituted amino, alkoxy, aminoacyl, acyloxy, carbonylalkoxy, aminocarbonylalkoxy, acylamino, carboxy, alkynyl or cyano;

or a salt thereof.

Other compounds are detailed herein, including those of formula (B):

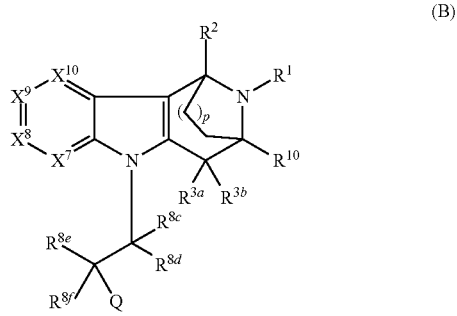

(B)

where:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, substituted or unsubstituted $C_1$-$C_8$ alkyl, halo, hydroxyl, alkoxy, cyano, nitro;

each $R^{3a}$ and $R^{3b}$ is independently H, substituted or unsubstituted $C_1$-$C_8$alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

each $X^7$, $X^8$, $X^9$ and $X^{10}$ is independently N or $CR^4$;
p is 1 or 2;
each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ alkyl or is taken together with the carbon to which it is attached and a geminal $R^8$ to form a cycloalkyl moiety or a carbonyl moiety;

$R^{10}$ is H, halo, a substituted or unsubstituted $C_1$-$C_8$ alkyl, hydroxyl or alkoxyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted heterocyclyl, unsubstituted amino, substituted amino, alkoxy, aminoacyl, acyloxy, carbonylalkoxy, aminocarbonylalkoxy or acylamino, or a salt or solvate thereof.

The invention also includes all salts of compounds referred to herein, such as pharmaceutically acceptable salts. The invention also includes any or all of the stereochemical forms, including any enantiomeric or diastereomeric forms, of the compounds described. Unless stereochemistry is explicitly indicated in a chemical structure or name, the structure or name is intended to embrace all possible stereoisomers of a compound depicted. All forms of the compounds are also embraced by the invention, such as crystalline or non-crystalline forms of the compounds. Compositions comprising a compound of the invention are also intended, such as a composition of substantially pure compound, including a specific stereochemical form thereof. Composition comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

The invention is also directed to pharmaceutical compositions comprising a compound of the invention and a pharmaceutically acceptable carrier or excipient. Kits comprising a compound of the invention and instructions for use are also embraced by this invention. Compounds as detailed herein or a pharmaceutically acceptable salt thereof are also provided for the manufacture of a medicament for the treatment of a cognitive disorder, psychotic disorder, neurotransmitter-mediated disorder or a neuronal disorder.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, Huntington's disease, Parkinson's disease, amyotrophic lateral sclerosis, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., $\alpha 1D$, $\alpha 2A$ and/or $\alpha 2B$), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least two of the following receptors are modulated: adrenergic receptor (e.g., $\alpha 1D$, $\alpha 2A$ and/or $\alpha 2B$), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least three of the following receptors are modulated: adrenergic receptor (e.g., $\alpha 1D$, $\alpha 2A$ and/or $\alpha 2B$), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, each of the following receptors is modulated: adrenergic receptor (e.g., $\alpha 1D$, $\alpha 2A$ and/or $\alpha 2B$), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least one of the following receptors is modulated: $\alpha 1D$, $\alpha 2D$, $\alpha 2B$, 5-HT2A, 5-HT2C, 5-HT6, 5HT7, D2L, H1, H2 and H3. In another variation, at least two or three or four or five or six or seven or eight or nine or ten or eleven of the following receptors are modulated: $\alpha 1D$, $\alpha 2D$, $\alpha 2B$, 5-HT2A, 5-HT2C, 5-HT6, 5HT7, D2L, H1, H2 and H3. In a particular variation, at least dopamine receptor D2L is modulated. In another particular variation, at least dopamine receptor D2L and serotonin receptor 5-HT2A are modulated. In a further particular variation, at least adrenergic receptors $\alpha 1D$, $\alpha 2A$, $\alpha 2B$ and serotonin receptor 5-HT6 are modulated. In another particular variation, at least adrenergic receptors $\alpha 1D$, $\alpha 2A$, $\alpha 2B$, serotonin receptor 5-HT6 and one or more of serotonin receptor 5-HT7, 5-HT2A, 5-HT2C and histamine receptor H1 and H2 are modulated. In a further particular variation, histamine receptor H1 is modulated. In another variation, compounds of the invention exhibit any receptor modulation activity detailed herein and further stimulate neurite The invention is also directed to pharmaceutical compositions comprising a compound of the invention and a pharmaceutically acceptable carrier or excipient. Kits comprising a compound of the invention and instructions for use are also embraced by this invention.

DETAILED DESCRIPTION OF THE INVENTION

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an $\alpha 1$-adrenergic receptor (e.g., $\alpha 1A$, $\alpha 1B$ and/or $\alpha 1D$) and/or a $\alpha 2$-adrenergic receptor (e.g., $\alpha 2A$, $\alpha 2B$ and/or $\alpha 2C$) and/or reduces or eliminates or increases or enhances or mimics an activity of a $\alpha 1$-adrenergic receptor (e.g., $\alpha 1A$, $\alpha 1B$ and/or $\alpha 1D$) and/or a $\alpha 2$-adrenergic receptor (e.g., $\alpha 2A$, $\alpha 2B$ and/or $\alpha 2C$) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of a provided adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 (D1) and/or a dopamine-2 (D2) receptor or reduces or eliminates or increases or enhances or mimics an activity of a dopamine-1 (D1) and/or a dopamine-2 (D2) receptor in a reversible or irreversible manner. Dopamine D2 receptors are divided into two categories, D2L and D2S, which are formed from a single gene by differential splicing, D2L receptors have a longer intracellular domain than D2S. In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that bind to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a 5-HT1A and/or a 5-HT1B and/or a 5-HT2A and/or a 5-HT2A and/or a 5-HT2B and/or a 5-HT2C and/or a 5-HT3 and/or a 5-HT4 and/or a 5-HT6 and/or a 5-HT7 receptor or reduces or eliminates or increases or enhances or mimics an activity of a 5-HT1A and/or a 5-HT1B and/or a 5-HT2A and/or a 5-HT2B and/or a 5-HT2C and/or a 5-HT3 and/or a 5-HT4 and/or a 5HT6 and/or a 5-HT7 receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that reduces or eliminates or increases or enhances an activity of a histamine receptor. As such, a "histamine receptor modulator" encompasses both a histamine receptor antagonist and a histamine receptor agonist. In some embodiments, the histamine receptor modulator reduces or eliminates or increases or enhances an activity of a histamine receptor in a reversible or irreversible manner. In some embodiments, the histamine receptor modulator reduces an activity of a histamine receptor by at least or about any of 10%, 20%, 30%, 40%, 50%, 60%, 70%, 80%, 90%, 95% or 100% as compared to the corresponding activity in the same individual prior to treatment with the histamine receptor modulator or compared to the corresponding activity in like individuals not receiving the histamine receptor modulator. In some embodiments, the histamine receptor modulator enhances an activity of a histamine receptor by at least or about any of 10%, 20%, 30%, 40%, 50%, 60%, 70%, 80%, 90%, 95% or 100 or 200% or 300% or 400% or 500% or more as compared to the corresponding activity in the same individual prior to treatment with the histamine receptor modulator or compared to the corresponding activity in like individuals not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to a human. An individual includes but is not limited to human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining a beneficial or desired result, such as a clinical result. For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom, and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease an/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extend of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions. Development may also refer to disease progression that may be initially undetectable and includes occurrence, recurrence and onset.

As used herein, an "at risk" individual is an individual who is at risk of developing a cognitive disorder, a psychotic divider, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.*, 20:154-9, 1997). Other markers of risk are mutations in the presenilin genes (e.g., PS1 or PS2), ApoE4 alleles, family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception, and/or thinking, which may be assessed by methods known in the art.

As used herein, the term, "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/of function of neurons, including death of neurons, and where a central feature of the disorder may be the impairment of cognition (e.g., memory, attention, perception and/or thinking). These disorders include pathogen-induced cognitive dysfunction, e.g., HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins NeuN (Neuronal Nuclei marker), MAP2, and class III tubulin. Included as neurons are, for example, hippocampal, cortical, midbrain dopaminergic, spinal motor, sensory, sympathetic, septal cholinergic and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g., large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type 1 transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. Aβ appears to have a central role in the neuropathology of Alzheimer's disease. Familial forms of the disease have been linked to mutations in APP and the presenilin genes (Tanzi et al., 1996, *Neurobiol. Dis.*, 3:159-168; Hardy, 199, *Ann. Med.*, 28:255-258). Diseased-linked mutations in these genes result in increased production of the 42-amino acid form of Aβ, the predominant form found in amyloid plaques. Mitochondrial dysfunction has also been reported to be an important component of Alzheimer's disease (Bubber et al., Mitochondrial abnormalities in Alzheimer brain: mechanistic Implications, *Ann Neurol.*, 2005, 57(5), 695-703; Wang et al., Insights into amyloid-β-induced mitochondrial dysfunction in Alzheimer disease, *Free Radical Biology & Medicine,* 2007, 43, 1569-1573; Swerdlow et al., Mitochondria in Alzheimer's disease *Int. Rev. Neurobiol.*, 2005, 53, 341-385; Reddy et al., Are mitochondria critical in the pathogenesis of Alzheimer's disease?, *Brain Res Rev.* 2005, 49(3), 618-32). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntingtin protein; the mutated huntingtin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" is used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflux impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. Ina specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg, et al. (1982) *Am. J. Psychiatry* 139: 1136-1139) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have place things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing in a computer analyzed EEG than GDS stage 1 elderly persons (Prichep, John, Ferris, Reisberg, et al. (1994) *Neurobiol. Aging* 15: 85-90).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (i.e., battlefield injuries, including post-concussion syndrome, and the like), neurotoxic treatment (i.e., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (i.e., where a nerve or nerves have been torn or ripped) or spinal cord injury (i.e., damage to white matter or myelinated fiber tracts that carry sensation and motor signals to and from the brain). Spinal cord injury can occur from many causes, including physical trauma (i.e., car accidents, sports injuries, and the like), tumors impinging on the spinal column, development disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at tunes, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age associated decrease in weight due to the death of muscular and/or fatty cells.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved, using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum, hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids includes, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc., disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets includes e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclkohexyl, or multiple rings, such as adamantyl. A cycloalkyl comprising more than one ring may be fused, spiro or bridged, or combinations thereof. In fused ring systems, one or more of the rings can be aryl or heteroaryl. A cycloalkyl having more than one ring where at least one ring is aromatic may be connected to the parent structure at either a non-aromatic ring position or at an aromatic ring position. In one variation, a cycloalkyl having more than one ring where at least one ring is aromatic is connected to the parent structure at a non-aromatic ring position. A preferred cycloalkyl is a saturated cyclic hydrocarbon having from 3 to 13 annular carbon atoms. A more preferred cycloalkyl is a saturated cyclic hydrocarbon having from 3 to 7 annular carbon atoms (a "$C_3$-$C_7$ cycloalkyl"). Examples of cycloalkyl groups include adamantyl, decahydronaphthalenyl, cyclopropyl, cyclobutyl, cyclopentyl and the like.

"Alkylene" refers to the same residues as alkyl, but having bivalency. Examples of alkylene include ethylene (—$CH_2CH_2$—) and propylene (—$CH_2CH_2CH_2$—).

"Alkenyl" refers to an unsaturated hydrocarbon group having at leas one site of olefinic unsaturation (i.e., having at least one moiety of the formula C=C) and preferably having from 2 to 10 carbon atoms and more preferably 2 to 8 carbon atoms. Examples of alkenyl include but are not limited to —CH$_2$—CH=CH—CH$_3$ and —CH$_2$—CH$_2$-cyclohexenyl, where the ethyl group of the later example can be attached to the cyclohexenyl moiety at any available position on the ring.

"Alkynyl" refers to an unsaturated hydrocarbon group having at least one site of acetylenic unsaturation (i.e., having at least one moiety of the formula C≡C) and preferably having from 2 to 10 carbon atoms and more preferably 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents s including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O))—, alkyl-C(O))—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic" or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridge, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 2 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. A "substituted aralkyl" refers to a residue in which an aryl moiety is attached to a substituted alkyl residue and wherein the aralkyl group may be attached to the parent structure at either the aryl or the alkyl residue.

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —NH$_2$.

"Substituted amino" refers to the group —NR$_a$R$_b$, where either (a) each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both R$_a$ and R$_b$ groups are not H; or (b) R$_a$ and R$_b$ are joined together with the nitrogen atom to form a heterocyclic or substituted heterocyclic ring.

"Acylamino" refers to the group —C(O)NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or R$_a$ and R$_b$ groups can be joined together with the nitrogen atom to form a heterocyclic or substituted heterocyclic ring.

"Aminocarbonylalkoxy" refers to the group —NR$_a$C(O)OR$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Aminoacyl" refers to the group —NR$_a$C(O)R$_b$, where each R$_a$ and R$_b$ group is independently selected from the group consisting of H, alkyl, substituted alkyl, alkenyl, substituted alkenyl, alkynyl, substituted, alkynyl, aryl, substituted aryl, heteroaryl, substituted heteroaryl, heterocyclic or substituted heterocyclic. Preferably, R$_a$ is H or alkyl.

"Aminosulfonyl" refers to the groups —NRSO$_2$-alkyl, —NRSO$_2$ substituted alkyl, —NRSO$_2$-alkenyl, —NRSO$_2$-substituted alkenyl, —NRSO$_2$-alkynyl, —NRSO$_2$-substituted alkynyl, —NRSO$_2$-aryl, —NRSO$_2$-substituted aryl, —NRSO$_2$-heteroaryl, —NRSO$_2$-substituted heteroaryl, —NRSO$_2$-heterocyclic, and —NRSO$_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —SO$_2$NH$_2$, —SO$_2$NR-alkyl, —SO$_2$NU-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, where the two R groups are taken together and with the nitrogen atom to which they are attached to form a heterocyclic or substituted heterocyclic ring.

"Sulfonyl" refers to the groups —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic.

"Carbonylalkylenealkoxy" refers to the group —C(=O)—(CH$_2$)$_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.
"Cyano" refers to the group —CN.
"Oxo" refers to the moiety =O.
"Nitro" refers to the group —NO$_2$.
"Thioalkyl" refers to the groups —S-alkyl.

"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group, "Carbonylalkoxy" refers to as used herein refers to the groups —C(O)OH, —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure S compound means that the composition contains no more than 15% or no more than 10% or no more than 5% or no more than 3% or no more than 1% of the R form of the compound.

Compounds of the Invention

Compounds are detailed herein, including in the Brief Summary of the Invention and the appended claims. The invention includes the use of all of the compounds described herein, including any and all stereoisomers, salts and solvates of the compounds described as histamine receptor modulators.

The invention embraces compounds of the formula (I):

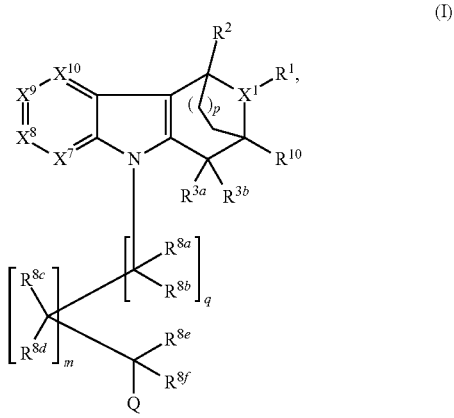

where:
R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

R$^2$ is H, substituted or unsubstituted C$_1$-C$_8$ alkyl, halo, hydroxyl, alkoxy, cyano, nitro;

each R$^{3a}$ and R$^{3b}$ is independently H, substituted or unsubstituted C$_1$-C$_8$ alkyl, halo, cyano, nitro, hydroxyl, alkoxy, amino, substituted amino, cycloalkyl, acylamino or acyloxy or R$^{3a}$ and R$^{3b}$ are taken together to form a carbonyl moiety;

each X$^7$, X$^8$, X$^9$ and X$^{10}$ is independently N or CR$^4$;
m and q are independently 0 or 1;
p is 1 or 2;
X$^1$ is N or CH;

each R$^4$ is independently H, hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$ and R$^{8f}$ is independently H, hydroxyl, C$_1$-C$_8$ alkyl or is taken together with the carbon to which it is attached and a geminal R$^8$ to form a cycloalkyl moiety or a carbonyl moiety;

R$^{10}$ is H, halo, a substituted or unsubstituted C$_1$-C$_8$ alkyl, hydroxyl or alkoxyl;

Q is a substituted or unsubstituted, aryl, substituted or unsubstituted heteroaryl, substituted or unsubstituted C$_{3-8}$ cycloalkyl, substituted or unsubstituted C$_{3-8}$ cycloalkenyl, substituted or unsubstituted heterocyclyl, amino, substituted amino, alkoxy, aminoacyl, acyloxy, carbonylalkoxy, aminocarbonylalkoxy or acylamino, provided that the compound is other than any of 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-(phenylmethyl)-7,10-iminocyclohept[b]indole. In another variation, the compounds of the invention, and methods of using the compounds detailed herein, encompass any of the compounds of formula (I), including 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-(phenylmethyl)-7,10-iminocyclohept[b]indole.

In one variation, the compound is of the formula (I) wherein R$^4$ is other than a substituted or unsubstituted aryl, substituted or unsubstituted heteroaryl, an aryloxy or an aralkyl. In one variation the compound is of the formula (I) wherein R$^4$ is other than a substituted or unsubstituted aryl.

In one variation, a compound of the invention is of the formula (I) where: R$^1$ is a substituted or unsubstituted C$_1$-C$_8$ alkyl, acyl, acyloxy, carbonylalkoxy, substituted or unsubstituted heterocyclyl or substituted or unsubstituted aryl; R$^2$ is H, methyl or fluoro; each R$^{3a}$ and R$^{3b}$ is independently H or fluoro; and R$^{10}$ is H, halo, hydroxyl or methyl. This variation of formula (I) is referred to herein as formula "(Ia)". All variations referring to formula (I), where applicable, may apply equally to any of formula (A)-(D) the same as if each and every variation were specifically and individually listed.

In a particular embodiment, the compound is of the formula (I) or (Ia) where X$^7$, X$^8$, X$^9$ and X$^{10}$ are CR$^4$. In another embodiment, the compound is of the formula (I) or (Ia) where at least one of X$^7$, X$^8$, X$^9$ and X$^{10}$ is N. Another variation provides a compound of the formula (I) or (Ia) where at least two of X$^7$, X$^8$, X$^9$ and X$^{10}$ are N. A further variation provides a compound of the formula (I) or (Ia) where 2 of X$^7$, X$^8$, X$^9$ and X$^{10}$ are N and 2 of X$^7$, X$^8$, X$^9$ and X$^{10}$ are CR$^4$. A compound of the formula (I) or (Ia) where 1 of X$^7$, X$^8$, X$^9$ and X$^{10}$ is N and 3 of X$^7$, X$^8$, X$^9$ and X$^{10}$ are CR$^4$ is also embraced by this invention.

In another variation, the invention embraces compounds of the formula (A):

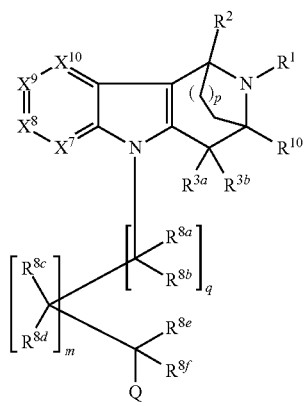

(A)

wherein:
R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

R$^2$ is H, substituted or unsubstituted C$_1$-C$_8$ alkyl, halo, hydroxyl, alkoxy, cyano or nitro;

each R$^{1a}$ and R$^{3b}$ is independently H, substituted or unsubstituted C$_1$-C$_8$ alkyl, halo, cyano, nitro, hydroxyl, alkoxy, unsubstituted amino, substituted amino, cycloalkyl, acylamino or acyloxy or R$^{3a}$ and R$^{3b}$ are taken together to form a carbonyl moiety;

each X$^7$, X$^8$, X$^9$ and X$^{10}$ is independently N or CR$^4$;
m and q are independently 0 or 1;
p is 1 or 2;
each R$^4$ is independently H, hydroxyl, nitro, cyano, halo, C$_1$-C$_8$ perhaloalkyl, substituted or unsubstituted C$_1$-C$_8$ alkyl substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$ and R$^{8f}$ is independently H, hydroxyl, C$_1$-C$_8$ alkyl or is taken together with the carbon to which it is attached and a geminal R$^8$ to form a cycloalkyl moiety or a carbonyl moiety;

R$^{10}$ is H, halo, a substituted or unsubstituted C$_1$-C$_8$ alkyl, hydroxyl or alkoxyl; and Q is a substituted or unsubstituted aryl, substituted or unsubstituted heteroaryl, substituted or unsubstituted C$_{3-8}$ cycloalkyl, substituted or unsubstituted C$_{3-8}$ cycloalkenyl, substituted or unsubstituted, heterocyclyl, unsubstituted amino, substituted, amino, alkoxy, aminoacyl, acyloxy, carbonylalkoxy, aminocarbonylalkoxy or acylamino, provided that the compound is other than any of 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-(phenylmethyl)-7,10-iminocyclohept[b]indole. In another variation, the compounds of the invention, and methods of using the compounds detailed herein, encompass any of the compounds of formula (A), including 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-(phenylmethyl)-7,10-iminocyclohept[b]indole.

In one variation the compound is of the formula (A-1):

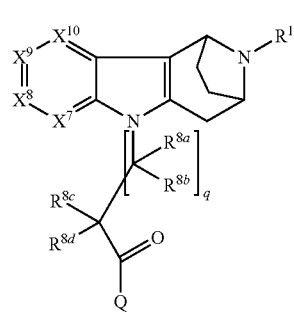

(A-1)

wherein:
q is 0 or 1;
Q is a substituted or unsubstituted aryl, substituted, or unsubstituted heteroaryl, substituted or unsubstituted C$_{3-8}$ cycloalkyl, substituted or unsubstituted C$_{3-8}$ cycloalkenyl, substituted or unsubstituted heterocyclyl, unsubstituted amino, substituted amino or alkoxy; and R$^1$, X$^7$, X$^8$, X$^9$, X$^{10}$, R$^{8a}$, R$^{8b}$, R$^{8c}$ and R$^{8d}$ are as defined in one variation for formula (A) and in another variation for formula (E).

In another variation, the compound is of the formula (A-1) where X$^9$ is N. In another variation, the compound is of the formula (A-1) where X$^9$ is CR$^4$ where R$^4$ is H, halo or methyl. In one such variation, each X$^7$, X$^8$ and X$^{10}$ is CH. In another such variation, R$^1$ methyl.

In one variation, the compound is of the formula (A-1), where Q is a substituted or unsubstituted aryl or a substituted or unsubstituted heteroaryl. In another variation, the compound is of the formula (A-1) where Q is substituted amino. In one variation, the compound is of the formula (A-1), where Q is substituted or unsubstituted heterocyclyl. In one such variation, each R$^{8a}$ and R$^{8b}$ is H when present and each R$^{8c}$ and R$^{8d}$ is H. In another such variation, R$^1$ is methyl.

In another variation, the compound is of the formula (A-1) where Q is a substituted or unsubstituted heterocyclyl comprising at least one nitrogen atom that is directly attached to a carbonyl group. In one such variation, Q is a substituted or unsubstituted heterocyclyl comprising two nitrogen atoms each is directly attached to a carbonyl group.

In one variation, the compound is of the formula (A-1), where Q is selected from the group consisting of:

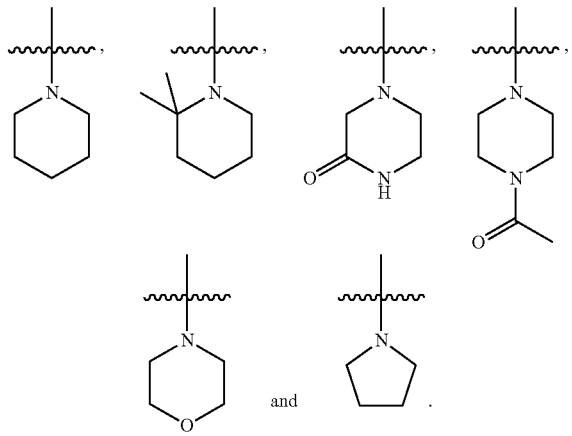

In another variation, the compound is of the formula (A-1) where $X^9$ is $CR^4$ where $R^4$ is H, halo or methyl, $R^1$ is methyl, each $R^{8a}$ and $R^{8b}$ is H when present, each $R^{8c}$ and $R^{8d}$ is H and Q is a substituted or unsubstituted heterocyclyl. In one such variation, Q is selected from the group consisting of:

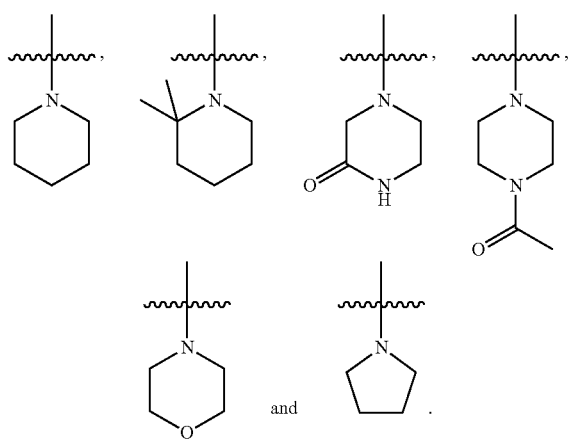

In one variation, the compound is of the formula (A-2):

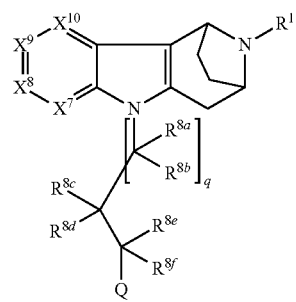

(A-2)

wherein:
q is 0 or 1;
Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or a unsubstituted heterocyclyl, unsubstituted amino, substituted amino, alkoxy, aminoacyl, acyloxy, carbonylalkoxy, aminocarbonylalkoxy or acylamino; and $R^1$, $X^7$, $X^8$, $X^9$, $X^{10}$, $R^{8a}$, $R^{8b}$, $R^{8c}$, $R^{8d}$, $R^{8e}$ and $R^{8f}$ are as defined in one variation for formula (A) and in another variation for formula (E).

In another variation, the compound is of the formula (A-2) where at least one of $X^7$, $X^8$, $X^9$ and $X^{10}$ is N. In yet another variation, the compound is of the formula (A-2) where two of $X^7$, $X^8$, $X^9$ and $X^{10}$ are N. In one variation, the compound is of the formula (A-2) where $X^9$ is N. In another variation, the compound is of the formula (A-2) where each $X^7$ and $X^{10}$ is N. In one variation, the compound is of the formula (A-2) where each $X^8$ and $X^9$ is independently $CR^4$ where $R^4$ is H, halo or methyl. In one such variation, each $X^7$ and $X^{10}$ is CH. In another such variation $R^1$ is methyl.

In one variation, the compound is of the formula (A-2), where Q is substituted or unsubstituted heterocyclyl. In another variation, the compound is of the formula (A-2) where Q is aminoacyl. In one variation, the compound is of the formula (A-2), where Q is a substituted or unsubstituted aryl or a substituted or unsubstituted heteroaryl. In one such variation, each $R^{8a}$ and $R^{8b}$ is H when present, each $R^{8c}$ and $R^{8d}$ is H and each $R^{8e}$ and $R^{8f}$ is independently H, hydroxy or methyl. In another such variation, $R^1$ is methyl.

In another variation, the compound is of the formula (A-2) where Q is a substituted phenyl or a substituted or unsubstituted heteroaryl comprising at least one nitrogen atom in the ring. In one such variation, Q is a substituted or unsubstituted heteroaryl comprising two nitrogen atoms in the ring. In another such, variation, Q is a substituted phenyl substituted with one or more of halo, methyl and methoxy. In another such variation, Q is unsubstituted pyridyl, substituted pyridyl or substituted pyrimidyl.

In one variation, the compound is of the formula (A-2), where Q is selected from the group consisting of:

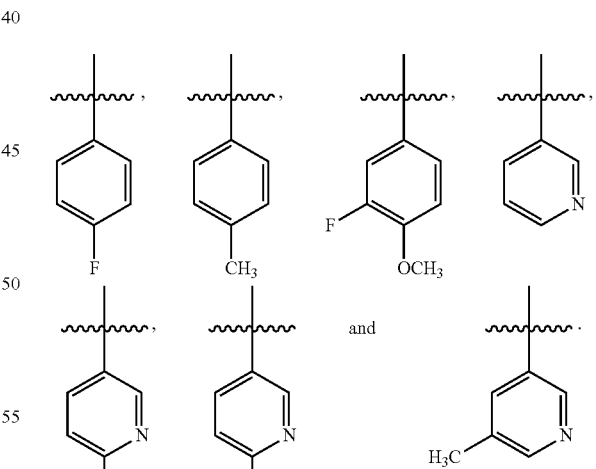

In another variation, the compound is of the formula (A-2) where each $X^8$ and $X^9$ is independently $CR^4$ where $R^4$ is H, halo or methyl, each $X^7$ and $X^{10}$ is CH, $R^1$ is methyl, each $R^{8a}$ and $R^{8b}$ is H when present, each $R^{8c}$ and $R^{8d}$ is H, each $R^{8e}$ and $R^{8f}$ is independently H, hydroxy or methyl and Q is a substituted phenyl or a substituted or unsubstituted heteroaryl. In one such variation, Q is selected from the group consisting of:

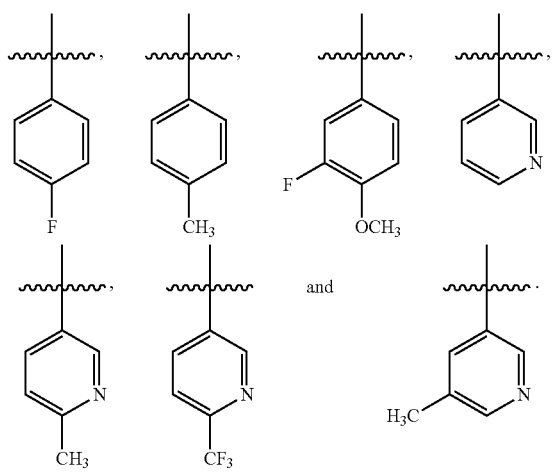

In any one of the variations of compounds of the formula (A-1) or (A-2), all stereo isomers are intended. For example, the ring bearing the $R^1$ group of the compound in the formula (A-1) or (A-2) can be either

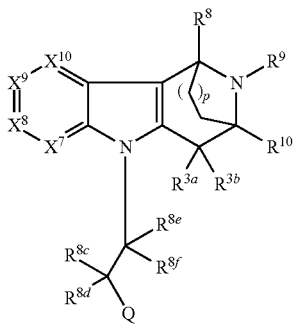

Mixtures of more than one stereo isomers are also intended.

The invention also embraces compound of the formula (B):

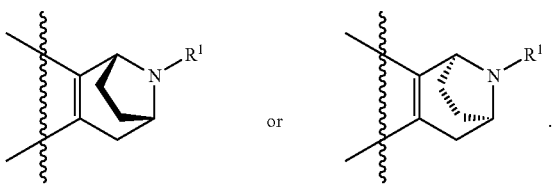

(B)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, substituted or unsubstituted $C_1$-$C_8$ alkyl, halo, hydroxyl, alkoxy, cyano, nitro;

each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

each $X^7$, $X^8$, $X^9$ and $X^{10}$ is independently N or $CR^4$;

p is 1 or 2;

$X^1$ is N or CH;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ alkyl or is taken together with the carbon to which it is attached and a geminal $R^8$ to form a cycloalkyl moiety or a carbonyl moiety;

$R^{10}$ is H, a substituted or unsubstituted $C_1$-$C_8$ alkyl, hydroxyl or alkoxyl; and Q is substituted or unsubstituted aryl, substituted or unsubstituted heterocyclyl, substituted or unsubstituted $C_{3-8}$ cycloalkyl, substituted or unsubstituted $C_{3-8}$ cycloalkenyl, substituted or unsubstituted heterocyclyl, unsubstituted amino, substituted amino, alkoxy, aminoacyl, acyloxy, carbonylalkoxy, aminocarbonylalkoxy or acylamino, or a salt or solvate thereof.

In another variation, the compound is of the formula (B) where Q is a substituted or unsubstituted $C_{3-8}$ cycloalkyl, substituted or unsubstituted $C_{3-8}$ cycloalkenyl or substituted or unsubstituted heterocyclyl, or a salt or solvate thereof. In one variation, the compound is of the formula (B) or any variation thereof detailed herein, where Q is a carbocycle, such as a 5, 6 or 7 membered carbocycle. In one variation, the compound is of the formula (B) or any variation thereof detailed herein, where Q is a heterocycle, such as a 5, 6 or 7 membered carbocycle.

In another variation, the compound is of the formula (B) where Q is substituted or unsubstituted aryl or a substituted or unsubstituted heteroaryl, provided that Q is other than phenyl, or a salt or solvate thereof.

The invention also embraces compounds of the formula (C):

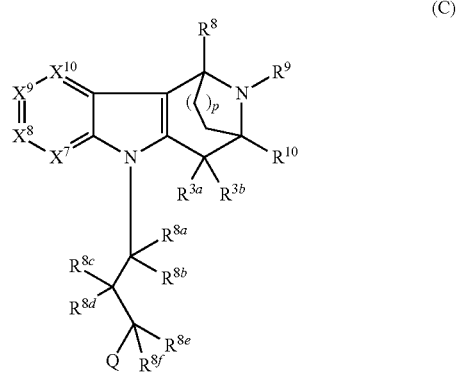

(C)

wherein:

R¹ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

R² is H, substituted or unsubstituted $C_1$-$C_8$ alkyl, halo, hydroxyl, alkoxy, cyano, nitro;

each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

each $X^7$, $X^8$, $X^9$ and $X^{10}$ is independently N or $CR^4$;

p is 1 or 2;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, or is taken together with the carbon to which it is attached and a geminal, $R^8$ to form a cycloalkyl moiety or a carbonyl moiety;

$R^{10}$ is H, halo a substituted or unsubstituted $C_1$-$C_8$ alkyl, hydroxy or alkoxyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or an unsubstituted heterocyclyl, unsubstituted amino, substituted amino, alkoxy, aminoacyl, acyloxy, carbonylalkoxy, aminocarbonylalkoxy or acylamino, or a salt or solvate thereof.

In another variation, the compound is of the formula (C) where Q is a substituted or unsubstituted $C_{3-8}$ cycloalkyl, substituted or unsubstituted $C_{3-8}$ cycloalkenyl, or substituted or unsubstituted heterocyclyl, or a salt or solvate thereof. In one variation, the compound is of the formula (C) where Q is a carbocycle, such as a 5, 6 or 7 membered carbocycle. In another variation, the compound is of the formula (C) where Q is a heterocycle, such as a 5, 6 or 7 membered heterocycle.

In another variation, the compound is of the formula (C) where Q is a substituted or unsubstituted aryl, such as a 5, 6 or 7 membered aryl group. In another variation, the compound is of the formula (C) where Q is a substituted or unsubstituted heteroaryl, such as a 5, 6 or 7 membered heteroaryl group provided that Q is other than phenyl.

The invention also embraces compounds of the formula (D):

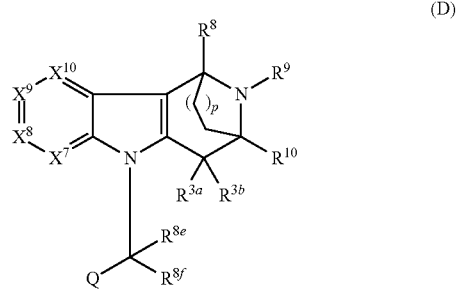

wherein:

R¹ is H, hydroxyl, nitro, cyan, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

R² is H, substituted or unsubstituted $C_1$-$C_8$ alkyl, halo, hydroxyl, alkoxy, cyano, nitro;

each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

each $X^7$, $X^8$, $X^9$ and $X^{10}$ is independently N or $CR^4$;

p is 1 or 2;

each $R^4$ is independently H, hydroxyl, nitro, cyano, halo, $C_1$-$C_8$ substituted or unsubstituted $C_1$-$C_8$ alkyl, substituted or unsubstituted $C_2$-$C_8$ alkenyl, substituted of unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8e}$ and $R^{8f}$ is independently H, hydroxyl, $C_1$-$C_8$ alkyl or is taken together with the carbon to which it is attached and a geminal $R^8$ to form a cycloalkyl moiety or a carbonyl moiety;

$R^{10}$ is H, halo, a substituted or unsubstituted $C_1$-$C_8$ alkyl, hydroxyl or alkoxyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted heterocyclyl, unsubstituted amino, substituted amino, alkoxy, aminoacyl, acyloxy, carbonylalkoxy, aminocarbonylalkoxy or acylamino, provided that the compound is other than any of 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-(phenylmethyl-7,10-iminocyclohept[b] indole, or a salt or solvate thereof. In another variation, the compounds of the invention, and methods of using the compounds detailed herein, encompass any of the compounds of formula (D), including 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-(phenylmethyl)-7,10-iminocyclohept[b]indole. In one variation, the compound is of the formula (D) where Q is a carbocycle or a heterocycle, such as a 5, 6 or 7 membered carbocycle or heterocycle.

In still another variation, the compound is of the formula (D) where Q is substituted or unsubstituted aryl or a substituted or unsubstituted heteroaryl, provided that Q is other than phenyl, or a salt or solvate thereof.

In one variation, the compound is of the formula (E):

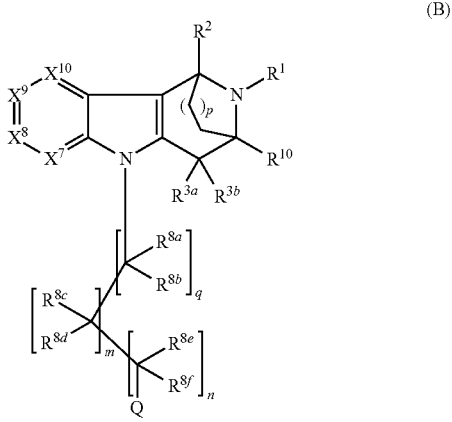

(E)

where:

$R^1$ is H, hydroxyl, nitro, cyano, halo, substituted or unsubstituted $C_1$-$C_8$ alkyl, substituted or unsubstituted $C_2$-$C_8$alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, substituted or unsubstituted $C_1$-$C_8$ alkyl, halo, cyano, hydroxyl, alkoxy or nitro each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together to form a cycloalkyl moiety or a carbonyl moiety;

each $X^7$, $X^8$, $X^9$ and $X^{10}$ is independently N or $CR^4$;

m and q are independently 0 or 1;

p is 1 or 2;

n is 1 or 0, provided that n is 0 only when Q is a substituted heterocycle wherein the substituted heterocycle is a lactam;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a\text{-}f)}$ to form a cycloalkyl moiety or a carbonyl moiety, is taken together with a geminal $R^8$ to form a methylene or a substituted methylene, is taken together with a vicinal $R^{8(a\text{-}f)}$ and the carbon atoms to which they are attached to form a substituted or unsubstituted $C_{3\text{-}8}$ cycloalkyl, substituted or unsubstituted $C_{3\text{-}8}$ cycloalkenyl or substituted or unsubstituted heterocyclyl moiety or is taken together with a vicinal $R^{8(a\text{-}f)}$ to form a bond, provided that when an $R^{8(a\text{-}f)}$ is taken together with a vicinal $R^8$ to form a bond, the geminal $R^{8(a\text{-}f)}$ is other than hydroxyl;

$R^{10}$ is H, halo, a substituted or unsubstituted $C_1$-$C_8$ alkyl, hydroxyl, alkoxyl, cyano or nitro;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, unsubstituted amino, substituted amino, alkoxy, aminoacyl, acyloxy, carbonylalkoxy, aminocarbonylalkoxy, acylamino, carboxy, alkynyl or cyano;

provided that the compound is other than any of 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-(phenylmethyl)-7,10-iminocyclohept[b]indole, or a slate or solvate thereof. In another variation, the compounds of the invention, and methods of using the compounds detailed herein, encompass any of the compounds of formula (E), including 5,6,7,8,9,10-hexahydro-11-(4-phenylbutyl)-5-(phenylmethyl)-7,10-iminocyclohept[b]indole and 5,6,7,8,9,10-hexahydro-11-(2-phenylethyl)-5-phenylmethyl)-7,10-iminocyclohept[b]indole.

In one embodiment, "alkyl" refers to and includes saturated linear, branched, or cyclic univalent hydrocarbon structures and combinations thereof provided that when the alkyl is a cyclic alkyl having more than one ring, all rings are saturated rings. In this embodiment, which may be applied as a further variation in each instance in which the term "alkyl" (e.g., "alkyl" and $C_1$-$C_8$ alkyl") is used herein (including but not limited to compounds of the formula E or any variation thereof), a cyclic alkyl having more than one ring in which a first ring is fused to a second or subsequent ring cannot have an aryl or heteroaryl group as the second or subsequent ring. Particular alkyl groups of this embodiment are those having 1 to 20 carbon atoms. More particular alkyl groups of this embodiment are those having 1 to 8 carbon atoms.

In one variation of formula (E), each $R^2$ and $R^{10}$ is independently H, halo, hydroxyl, alkoxyl or substituted or unsubstituted $C_1$-$C_8$ alkyl and $R^1$, $R^{3a}$, $R^{3b}$, p, q, m, n, $R^{8a}$, $R^{8b}$, $R^{8c}$, $R^{8d}$, $R^{8e}$, $R^{8f}$, $X^7$, $X^8$, $X^9$, $X^{10}$ and Q are as defined for formula (E). In one such variation, each $R^2$ and $R^{10}$ is independently H, hydroxyl, alkoxyl or substituted or unsubstituted $C_1$-$C_8$ alkyl. In one such variation, each $R^2$ and $R^{10}$ is independently H, halo or substituted or unsubstituted $C_1$-$C_8$ alkyl. In one such variation, each $R^2$ and $R^{10}$ is independently H or substituted or unsubstituted $C_1$-$C_8$ alkyl. In another such variation, each $R^2$ and $R^{10}$ is H. Where applicable, any variation of formula (E) detailed herein may in additional variations be further defined by the $R^2$ and $R^{10}$ moieties of this paragraph.

In another variation of formula (E), $R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, provided that when $R^1$ is other than a $C_1$-$C_8$ alkyl substituted with phenyl and $R^2$, $R^{3a}$, $R^{3b}$, p, q, m, n, $R^{8a}$, $R^{8b}$, $R^{8c}$, $R^{8d}$, $R^{8e}$, $R^{8f}$, $X^7$, $X^8$, $X^9$, $X^{10}$ and Q are as defined for formula (E). In one such variation, $R^1$ is H, hydroxyl, unsubstituted $C_1$-$C_8$ alkyl, substituted $C_1$-$C_8$ alkyl other than alkyl substituted with phenyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another such variation, $R^1$ is H, unsubstituted $C_1$-$C_8$ alkyl, substituted $C_1$-$C_8$ alkyl other than alkyl substituted with phenyl, substituted or unsubstituted $C_2$-$C_8$ alkenyl, substituted or unsubstituted $C_2$-$C_8$ alkynyl, perhaloalkyl, acyl, carbonylalkoxy, substituted or unsubstituted heterocyclyl, substituted or unsubstituted aryl, substituted or unsubstituted heteroaryl, substituted or unsubstituted aralkyl, acylamino, sulfonylamino, sulfonyl or carbonylalkylenealkoxy. In another such variation, $R^1$ is H, hydroxyl, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another such variation, $R^1$ is H, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, carbonylalkoxy, substituted or unsubstituted heterocyclyl, substituted or unsubstituted aryl, substituted or unsubstituted heteroaryl, substituted or unsubstituted aralkyl, acylamino or carbonylalkylenealkoxy. In another such variation, $R^1$ is H, acyl, unsubstituted $C_1$-$C_8$ alkyl or substituted $C_1$-$C_8$ alkyl other than alkyl substituted with phenyl. In yet another such variation, $R^1$ is unsubstituted $C_1$-$C_8$ alkyl or acyl. In a particular such variation, $R^1$ is unsubstituted $C_1$-$C_8$ alkyl (e.g. methyl). Where applicable, any variation of formula (E) detailed herein may in additional In yet another variation of formula (E), $R^1$ is H, hydroxyl, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, each $R^2$ and $R^{10}$ is independently H, hydroxyl, alkoxyl or substituted or unsubstituted $C_1$-$C_8$ alkyl and $R^{3a}$, $R^{3b}$, p, q, m, n, $R^{8a}$, $R^{8b}$, $R^{8c}$, $R^{8d}$, $R^{8e}$, $R^{8f}$, $X^7$, $X^8$, $X^9$, $X^{10}$ and Q are as defined for formula (E). In one such variation, $R^1$ is H, unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, carbonylalkoxy, substitute or unsubstituted heterocyclyl, substituted or unsubstituted aryl, substituted or unsubstituted heteroaryl, substituted or unsubstituted aralkyl, acylamino, sulfonylamino, sulfonyl or carbonylalkylenealkoxy. In another such variation, $R^1$ is unsubstituted $C_1$-$C_8$ alkyl or acyl. In another such variation, each $R^2$ and $R^{10}$ is independently H or substituted or unsubstituted $C_1$-$C_8$ alkyl.

In another variation of formula (E), Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, unsubstituted amino, substituted amino, alkoxy, aminoacyl, acyloxy, carbonylalkoxy, aminocarbonylalkoxy, acylamino, carboxy, alkynyl and cyano, m and q are independently 0 or 1, and n is 1 or 0, provided that: (i) n is 0 only when Q is a substituted heterocycle wherein the substituted heterocycle is a lactam; and (ii) when n is 1 and each m and q is 0, Q is other than phenyl, and $R^1$, $R^2$, $R^{3a}$, $R^{3b}$, $R^{10}$, p, $R^{8a}$, $R^{8b}$, $R^{8c}$, $R^{8d}$, $R^{8e}$, $R^{8f}$, $X^7$, $X^8$, $X^9$, and $X^{10}$ are as defined for formula (E). In one such variation, the sum of the integers defining q, m and n is 0, 2 or 3. In another variation, n is 0 and Q is a substituted heterocycle wherein the substituted heterocycle is a lactam. In another such variation, n is 1 and at least one of m and q is 1. In another such variation, n is 1 and one of m and q is 1 and the other is 0. In another such variation, n is 1 and each of m and q is 1. In yet another such variation, Q is a substituted aryl, substituted or unsubstituted heteroaryl, substituted or unsubstituted cycloalkyl, substituted or unsubstituted cycloalkenyl, substituted or unsubstituted heterocyclyl, unsubstituted amino, substituted amino, alkoxy, aminoacyl, acyloxy, carbonylalkoxy, aminocarbonylalkoxy, acylamino, carboxy, alkynyl and cyano. Where applicable, any variation of formula (E) detailed herein may in additional variations be further defined by the Q moieties of this paragraph.

In one variation of formula (E), Q is a substituted heterocyclyl wherein the substituted heterocyclyl group is a substituted or unsubstituted lactam, q, m and n are each 0 and the compound is of the formula (E-1):

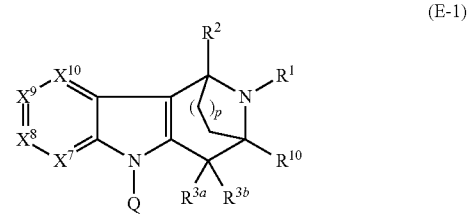

(E-1)

or a salt thereof, wherein $R^1$, $R^2$, $R^{3a}$, $R^{3b}$, $R^{10}$, p, $X^7$, $X^8$, $X^9$ and $X^{10}$ are as defined for formula (E).

In certain variations of formula (E-1), Q is of the formula:

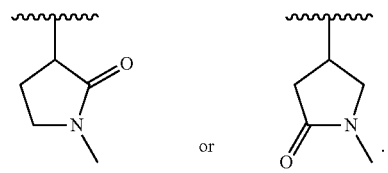

In one embodiment, the compound is of formula (E-1a):

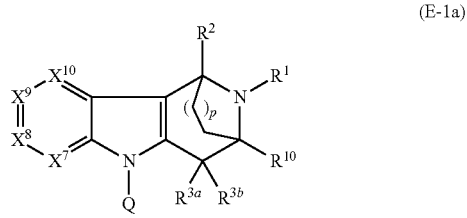

(E-1a)

or a salt thereof,
wherein $R^1$, $R^2$, $R^{3a}$, $R^{3b}$, $R^{10}$, p, $X^7$, $X^8$, $X^9$, and $X^{10}$ are as defined for formula (E) and Q is a substituted or unsubstituted $C_3$-$C_7$ cycloalkyl. In one variation, Q is 2-hydroxycyclohexyl.

In other variations of formula (E), q is 0, Q is a cyano and the compound is of the formula (E-2):

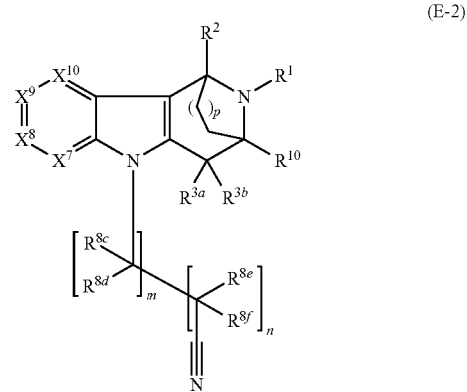

(E-2)

or a salt thereof,
wherein $R^1$, $R^2$, $R^{3a}$, $R^{3b}$, $R^{10}$, p, m, n, $R^{8c}$, $R^{8d}$, $R^{8e}$, $R^{8f}$, $X^7$, $X^8$, $X^9$, $X^{10}$ and Q are as defined for formula (E).

In one embodiment, the compound is of the formula (E) or any variation of formula (E) detailed herein where $X^7$, $X^8$, $X^9$ and $X^{10}$ are $CR^4$. In another embodiment, the compound is of the formula (E) or any variation of formula (E) detailed herein where at least one of $X^7$, $X^8$, $X^9$ and $X^{10}$ is N. In one variation, at least two of $X^7$, $X^8$, $X^9$ and $X^{10}$ are N. In another variation, two of $X^7$, $X^8$, $X^9$ and $X^{10}$ are N and two of $X^7$, $X^8$, $X^9$ and $X^{10}$ are $R^4$. In yet another variation, one of $X^7$, $X^8$, $X^9$ and $X^{10}$ is N and three of $X^7$, $X^8$, $X^9$ and $X^{10}$ are $CR^4$. In a particular variation, $X^9$ is N and $X^7$, $X^8$ and $X^{10}$ are $CR^4$. In another particular variation, $X^7$ and $X^{10}$ are N and $X^8$ and $X^9$ are $CR^4$.

In one embodiment, "alkyl" refers to and includes saturated linear, branched, or cyclic univalent hydrocarbon structures and combinations thereof provided that when the alkyl is a cyclic alkyl having more than one ring, all rings are saturated rings. In this embodiment, which may be applied as a further variation in each instance in which the term "alkyl" (e.g., "alkyl" and $C_1$-$C_8$ alkyl") is used herein (including but not limited to compounds of the formula (E) or any variation thereof), a cyclic alkyl having more than one ring in which a first ring is fused to a second or subsequent ring cannot have an aryl or heteroaryl group as the second or subsequent ring. Particular alkyl groups of this embodiment are those having 1 to 20 carbon atoms. More particular alkyl groups of this embodiment are those having 1 to 8 carbon atoms.

In one variation, the compound is of the formula (F):

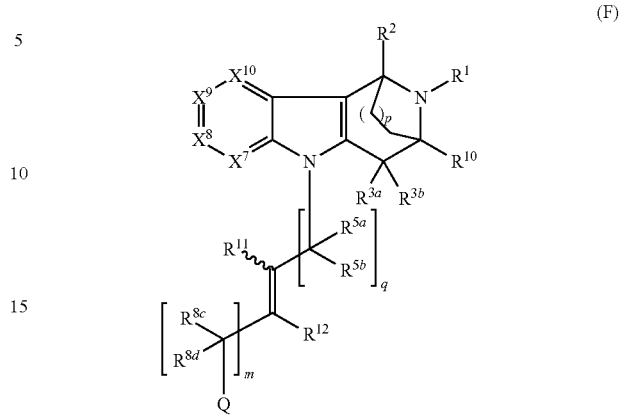

(F)

where:
$R^1$ is H, hydroxyl, nitro, cyano, halo, substituted or unsubstituted $C_1$-$C_8$ alkyl, substituted or unsubstituted $C_2$-$C_8$ alkenyl substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^2$ is H, substituted or unsubstituted $C_1$-$C_8$ alkyl, halo, cyano, hydroxyl, alkoxy or nitro;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together to form a cycloalkyl or a carbonyl moiety;

each $X^7$, $X^8$, $X^9$ and $X^{10}$ is independently N or $CR^4$;

m and q are independently 0 or 1;

p is 1 of 2;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-d)}$ for form a cycloalkyl moiety or a carbonyl moiety, or is taken together with a geminal $R^8$ to form a methylene or a substituted methylene;

$R^{10}$ is H, halo, a substituted or unsubstituted $C_1$-$C_8$ alkyl, hydroxyl, alkoxyl, cyano or nitro;

$R^{11}$ and $R^{12}$ are independently H, $C_1$-$C_8$ alkyl, $C_1$-$C_8$ perhaloalkyl, carboxy, carbonylalkoxy, or taken together with the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or are taken together to form a bond, thereby providing an acetylenyl moiety;

⌇ indicates the presence of either an E or Z double bond configuration when $R^{11}$ and $R^{12}$ are independently H or $C_1$-$C_8$ alkyl;

Q is a substituted or unsubstituted aryl, substituted or unsubstituted heteroaryl, substituted or unsubstituted cycloalkyl, substituted of unsubstituted cycloalkenyl, substituted or an unsubstituted heterocyclyl, unsubstituted amino, substituted amino, alkoxy, aminoacyl, acyloxy, carbonylalkoxy, aminocarbonylalkoxy, acylamino, carboxy, alkynyl or cyano.

In one variation of formula (F), $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another variation of formula (F), $R^1$ is H, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, carbonylalkoxy, substituted or unsubstituted heterocyclyl, substituted or unsubstituted aryl, substituted or unsubstituted heteroaryl, substituted or unsubstituted aralkyl, acylamino or carbonylalkylenealkoxy. In another variation of formula (F), each $R^2$ and $R^{10}$ is independently H or substituted or unsubstituted $C_1$-$C_8$ alkyl. In another variation of formula (F), each $R^2$ and $R^{10}$ is independently H, halo or substituted or unsubstituted $C_1$-$C_8$ alkyl.

In another variation of formula (F), q and n are 0, $R^{11}$ and $R^{12}$ are independently H, $C_1$-$C_8$ alkyl, $C_1$-$C_8$ perhaloalkyl, carboxy or carbonylalkoxy and the compound is of the formula (F-1):

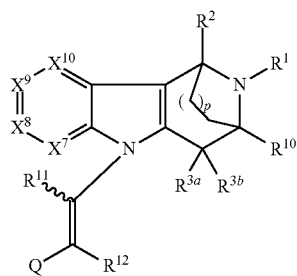

(F-1)

or a salt thereof, wherein $R^1$, $R^2$, $R^{3a}$, $R^{3b}$, $R^{10}$, p, $X^7$, $X^8$, $X^9$, $X^{10}$ and Q are as defined for formula (F).

In a particular variation of formula (F-1), $R^{11}$ is H and Q is a substituted or unsubstituted aryl or heteroaryl e.g., a substituted or unsubstituted phenyl or pyridyl. In a more particular variation of formula (F-1), $R^{11}$ is H, $R^{12}$ is H or methyl and Q is a substituted or unsubstituted aryl or heteroaryl. Examples of substituted or unsubstituted phenyl or pyridyl Q groups include, but are not limited to, 3-pyridyl, 4-pyridyl, 4-methoxyphenyl, 4-chlorophenyl, 4-fluorophenyl, 3-fluoro-4-methoxyphenyl, 3,4-dichlorophenyl, 3,4-difluorophenyl, 4-methyl-3-pyridyl, 4-fluorophenyl and 2-methyl-5-pyrimidyl. In another particular variation, the compound is of the formula (F-1) where $R^1$ is methyl, p is 1, $X^9$ is $CR^4$ where $R^4$ is halo or methyl, $R^{11}$ is H, $R^{12}$ is H or methyl and Q is substituted phenyl. In another particular variation, the compound is of the formula (F-1) where $R^1$ is methyl, each $R^2$, $R^{3a}$, $R^{3b}$ and $R^{10}$ is H, p is 1, $X^9$ is $CR^4$ where $R^4$ is halo or methyl, each $X^7$, $X^8$ and $X^{10}$ is CH, $R^{11}$ is H, $R^{12}$ is methyl and Q is substituted phenyl, e.g. 4-fluorophenyl and 3-fluoro-4-methoxyphenyl.

In another variation of formula (F), q and n are 0, $R^{11}$ and $R^{12}$ are taken together to form a bond and the compound is of the formula (F-2):

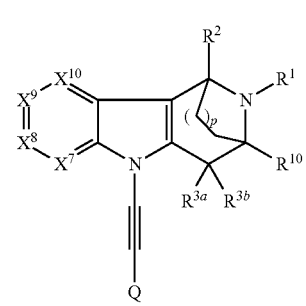

(F-2)

or a salt thereof, wherein $R^1$, $R^2$, $R^{3a}$, $R^{3b}$, $R^{10}$, p, $X^7$, $X^8$, $X^9$, $X^{10}$ and Q are as defined for formula (F). In one variation of formula (F-2), Q is a substituted or unsubstituted aryl, substituted or unsubstituted heteroaryl, substituted or unsubstituted cycloalkyl, substituted or unsubstituted cycloalkenyl or substituted or unsubstituted heterocyclyl.

In a particular variation of formula (F-2), Q is a substituted or unsubstituted aryl or heteroaryl, e.g., a substituted or unsubstituted phenyl or pyridyl. Examples of Q include, but are not limited to, 4-methoxyphenyl, 4-chlorophenyl, 4-fluorophenyl, 3-fluoro-4-methoxyphenyl, 3,4-dichlorophenyl, 3,4-difluorophenyl, 3-pyridyl, 4-pyridyl, 4-trifluoromethyl-3-pyridyl and 4-methyl-3-pyridyl. In another particular variation, the compound is of the formula (F-2) where $R^1$ is methyl, p is 1, $X^9$ is $CR^4$ where $R^4$ is halo or methyl and Q is substituted or unsubstituted aryl or heteroaryl. In another particular variation, the compound is of the formula (F-2) where $R^1$ is methyl, each $R^2$, $R^{3a}$, $R^{3b}$ and $R^{10}$ is H, p is 1, $X^9$ is $CR^4$ where $R^4$ is halo or methyl, each $X^7$, $X^8$ and $X^{10}$ is CH and Q is substituted pyridyl, e.g. 6-methyl-3-pyridyl.

In another variation, a compound of the invention is of the formula (I) or (Ia) where $X^7$, $X^8$, $X^9$ and $X^{10}$ are taken together to provide an aromatic moiety selected from the following structures:

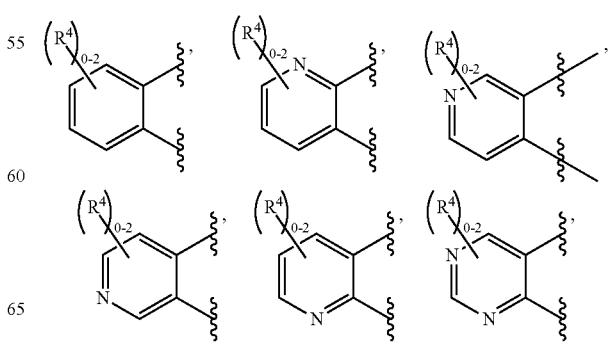

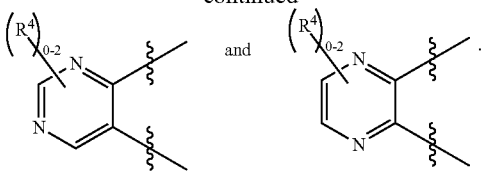 and where each $R^4$ is as defined for formula (I) or (Ia); or in a particular variation, where each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where $R^4$ is independently halo, unsubstituted $C_1$-$C_4$ alkyl or $C_1$-$C_4$ perhaloalkyl.

In another variation, a compound of the invention is of the formula (I) or (Ia) where $X^7$, $X^8$, $X^9$ and $X^{10}$ are taken together to provide an aromatic moiety selected from the following structures:

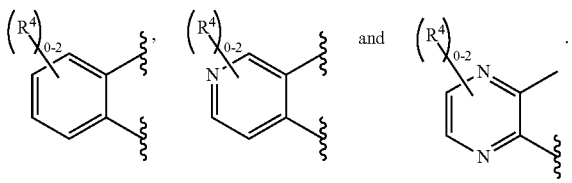

where each $R^4$ is as defined for formula (I) or (Ia); or in a particular variation, where each $R^4$ is independently alkyl, perhaloalkyl or halo or in an even more particular variation, where each $R^4$ is independently methyl, trifluoromethyl, chloro or fluoro.

In still a further variation, a compound of the invention is of the formula (I) or (Ia) where $X^7$, $X^8$, $X^9$ and $X^{10}$ are taken together provide an aromatic moiety selected from the following structures:

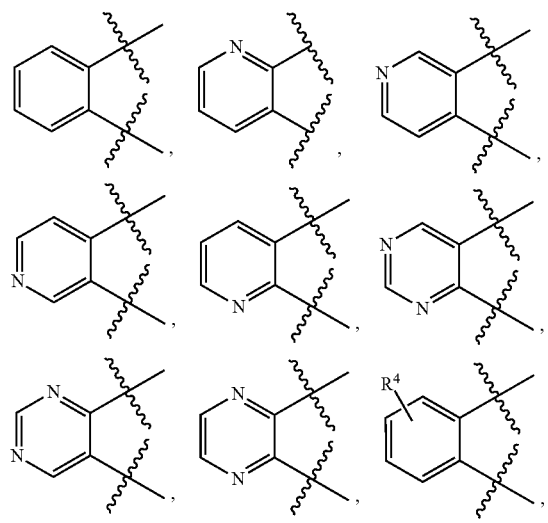

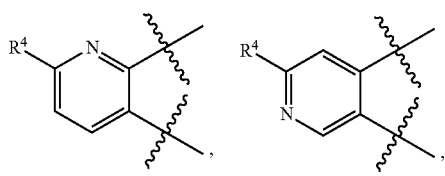

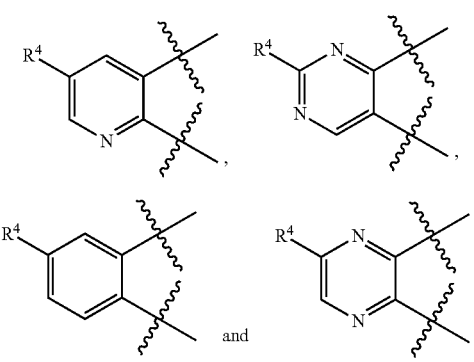

wherein $R^4$ is as defined in formula (I); or in a particular variation, where $R^4$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where each $R^4$ is independently halo, unsubstituted $C_1$-$C_4$ alkyl or $C_1$-$C_4$ perhaloalkyl.

In still a further variation, a compound of the invention is of the formula (I) or (Ia) where $X^7$, $X^8$, $X^9$ and $X^{10}$ are taken together provide an aromatic moiety selected from the following structures:

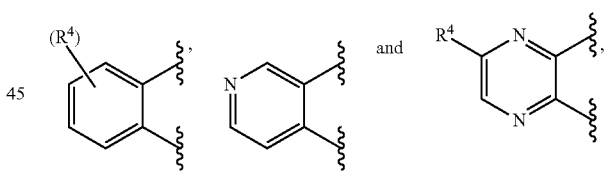

wherein $R^4$ is as defined in formula (I) or in any particular variation herein, such as when each $R^4$ is independently alkyl or halo or in an even more particular variation, where each $R^4$ is independently methyl, chloro, iodo or fluoro. In yet another variation, a compound of the invention is of the formula (I) or (Ia) where $X^7$, $X^8$, $X^9$ and $X^{10}$ are taken together provide an aromatic moiety selected from the following structures:

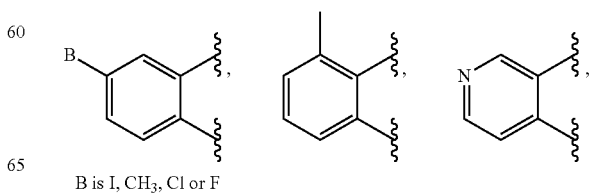

B is I, $CH_3$, Cl or F

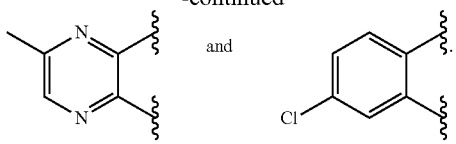

Any formula detailed herein, where applicable, may in one variation have $X^7$, $X^8$, $X^9$ and $X^{10}$ taken together to provide an aromatic moiety detailed herein above. It is understood that by "where applicable" it is intended that in one variation such $X^7$, $X^8$, $X^9$ and $X^{10}$ groups are taken together to provide a moiety hereinabove if the formula encompasses such a structure. For example, if a given formula does not encompass structures wherein $X^7$, $X^8$, $X^9$ and $X^{10}$ groups are taken together provide a pyridyl moiety, then a pyridyl moiety as detailed hereinabove is not applicable to that particular formula, but remains applicable to formulae that do encompass structures where $X^7$, $X^8$, $X^9$ and $X^{10}$ groups are taken together provide a pyridyl moiety.

In another embodiment, a compound of the invention is of the formula (I), wherein $X^7$-$X^{10}$ are as defined in formula (I) or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is of the formula (I), wherein $X^7$-$X^{10}$ are as defined in formula (I) or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is of the formula (I), wherein $X^7$-$X^{10}$ are as defined in formula (I) or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In another variation, the compound of the invention is of the formula (I), where $X^7$-$X^{10}$ and $R^1$ are as defined in formula (I) or as detailed in any variation herein, where $R^2$ is H, substituted or unsubstituted $C_1$-$C_8$ alkyl, halo, cyano or nitro and each $R^{3a}$ and $R^{3b}$ is independently H, substituted or unsubstituted $C_1$-$C_8$ alkyl, halo, cyano or nitro. In another variation, the compound of the invention is of the formula (I), where $X^7$-$X^{10}$ and $R^1$ are as defined in formula (I) or as detailed in any variation herein, where $R^2$ is H, unsubstituted $C_1$-$C_8$ alkyl or halo and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, the compound of the invention is of the formula (I), where $X^7$-$X^{10}$ and $R^1$ are as defined in formula (I) or as detailed in any variation herein, where $R^2$ is H, unsubstituted $C_1$-$C_8$ alkyl or halo; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention according to formula (I), where $X^7$-$X^{10}$ and $R^1$ are as defined in formula (I) or as detailed in any variation herein, where $R^2$ is H, methyl or halo and each $R^{3a}$ and $R^{3b}$ is independently H, methyl, halo or $R^{3a}$ and $R^{3b}$ are taken together to form a carbonyl moiety. The invention further embraces compounds of the invention according to formula (I), where $X^7$-$X^{10}$ and $R^1$ are as defined in formula (I) or as detailed in any variation herein, where each of $R^2$, $R^{3a}$ and $R^{3b}$ is H. In one variation, a compound of the invention is of the formula (I) where $X^7$-$X^{10}$ and $R^1$ are as defined in formula (I) or as detailed in any variation herein, where at least one of $R^2$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In another variation, a compound of the invention is of the formula (I) where $X^7$-$X^{10}$ and $R^1$ are as defined in formula (I) or as detailed in any variation herein, where at least two of $R^2$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In yet another variation, a compound of the invention is of the formula (I) where $X^7$-$X^{10}$ and $R^1$ are as defined in formula (I) or as detailed in any variation herein, where at least one of $R^2$, $R^{3a}$ and $R^{3b}$ is fluoro or methyl or is taken together with a geminal $R^2$ or $R^3$ to form a carbonyl moiety. In still another variation, a compound of the invention is of the formula (I) where $X^7$-$X^{10}$ and $R^1$ are as defined in formula (I) or as detailed in any variation herein, where $R^2$ or either $R^{3a}$ and $R^{3b}$ are each methyl or fluoro (e.g., both $R^{3a}$ and $R^{3b}$ are methyl or one is fluoro and one is methyl) or are taken together to form a carbonyl moiety. In another variation, $R^2$ is hydroxyl or alkoxyl. In a particular variation, $R^2$ is H, substituted or unsubstituted $C_1$-$C_8$ alkyl, halo, cyano or nitro. In another variation, when $X^1$ is N, $R^2$ is H, substituted or unsubstituted $C_1$-$C_8$ alkyl, halo, cyano or nitro.

The invention also embraces compounds according to formula (I), where $X^7$-$X^{10}$, $R^1$, $R^2$, $R^{3a}$ and $R^{3b}$ are as defined in formula (I) or as detailed in any variation herein, where $R^{10}$ is H, halo, an unsubstituted $C_1$-$C_8$ alkyl or hydroxyl. Also embraces are compounds according to formula (I), where $X^7$-$X^{10}$, $R^1$, $R^2$, $R^{3a}$ and $R^{3b}$ are as defined in formula (I) or as detailed in any variation herein, where each $R^{10}$ is H, halo, an unsubstituted $C_1$-$C_4$ alkyl or hydroxyl. In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is H, bromo, methyl or hydroxyl. In yet another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is an unsubstituted $C_1$-$C_8$ alkyl, hydroxyl, or halo. In still a further variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is methyl, bromo or hydroxyl. In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is methyl. In another variation, a compound of the invention is of the formula (I), where $X^7$-$X^{10}$, $R^1$, $R^2$, $R^{3a}$ and $R^{3b}$ are as defined in formula (I). In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is H or methyl. In another variation, a compound of the invention is of the formula (I), where $X^7$-$X^{10}$, $R^1$, $R^2$, $R^{3a}$ and $R^{3b}$ are as defined in formula (I) or as detailed in any variation herein, where $R^{10}$ is H or bromo. When the carbon of formula (I) bearing $R^{10}$ is optically active, it may be in the S or R configuration and compositions comprising substantially pure R or S compound or mixtures thereof in any amount are embraced by this invention.

In a particular variation, a compound of the invention is of the formula (I) where $R^2$, $X^1$, $R^{10}$, $R^{3a}$ and $R^{3b}$ are taken together to form a ring selected from the structures:

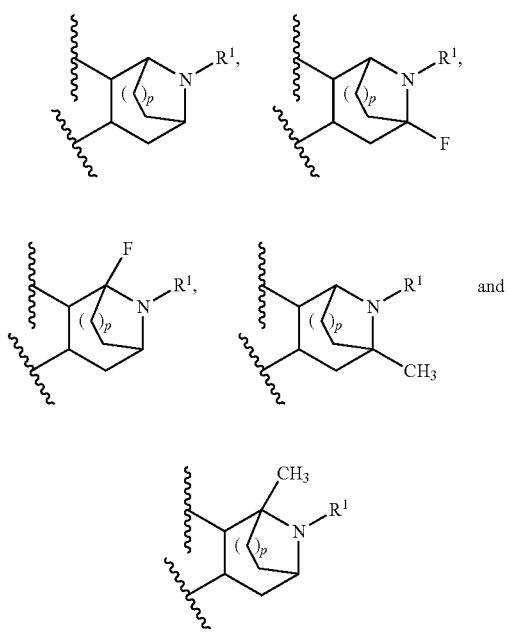

where $R^1$ in the structures above is as defined for formula (I) or any particular variation detailed herein.

In another variation, a compound of the invention is of the formula (I) where $R^2$, $X^1$, $R^{10}$, $R^{3a}$ and $R^{3b}$ are taken together to form a ring of the formula:

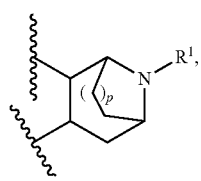

where p is 1 or 2 and $R^1$ is as defined in formula (I) or any variation detailed herein. In one such variation, $R^2$, $X^1$, $R^{10}$, $R^{3a}$ and $R^{3b}$ are taken together to form a ring of the formula:

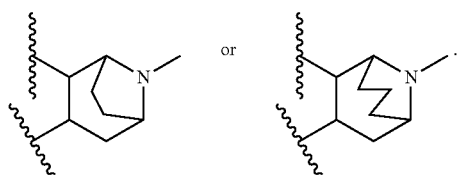

In yet another variation, a compound of the invention is of the formula (I) where $R^2$, $X^1$, $R^{10}$, $R^{3a}$ and $R^{3b}$ are taken together to form a ring of the formula:

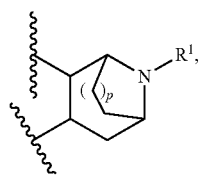

and where $X^7$, $X^8$, $X^9$ and $X^{10}$ are taken together provide an aromatic moiety selected from the following structures:

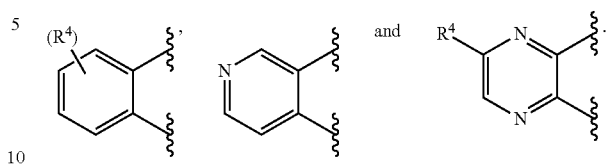

where $R^1$ is as defined in formula (I) or any variation detailed herein and $R^4$ is as defined in formula (I) or in any particular variation herein, such as when each $R^4$ is independently alkyl or halo or in an even more particular variation, where each $R^4$ is independently methyl, chloro, iodo or fluoro.

Any formula detailed herein, where applicable, may in one variation have $R^2$, $X^1$, $R^{10}$, $R^{3a}$ and $R^{3b}$ taken together to provide a moiety detailed herein above. It is understood that by "where applicable" it is intended that in one variation such $R^2$, $X^1$, $R^{10}$, $R^{3a}$ and $R^{3b}$ groups are taken together to provide a moiety hereinabove if the formula encompasses such a structure. For example, if a given formula does not encompass structures wherein $R^2$, $X^1$, $R^{10}$, $R^{3a}$ and $R^{3b}$ are taken together provide a

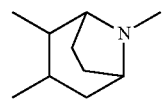

moiety, then a

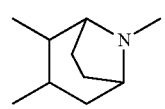

moiety as detailed hereinabove is not applicable to that particular formula, but remains applicable to formulae that do encompass structures where $R^2$, $X^1$, $R^{10}$, $R^{3a}$ and $R^{3b}$ are taken together provide a

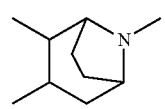

moiety.

Compounds of the formulae (IIa), (IIb), (I), (IId), (IIe), (IIf), (IIg), (IIh), (IIi), (IIj), (IIk), (III), (IIm) and (IIn) are also embraced by this invention:

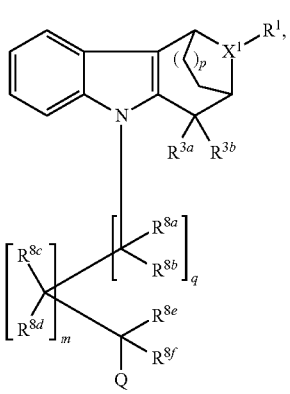

(IIa)

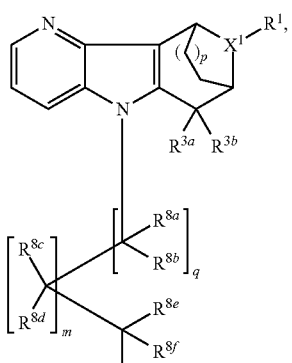 (IIb)
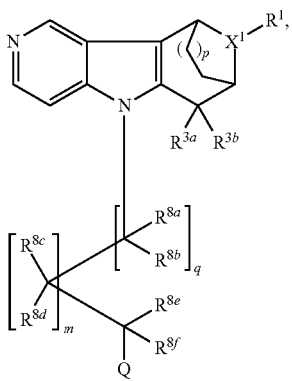 (IIc)
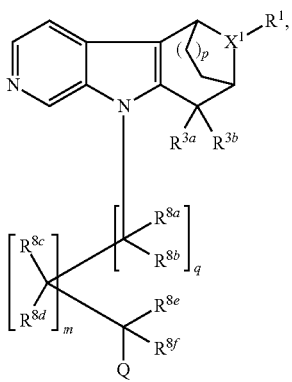 (IId)
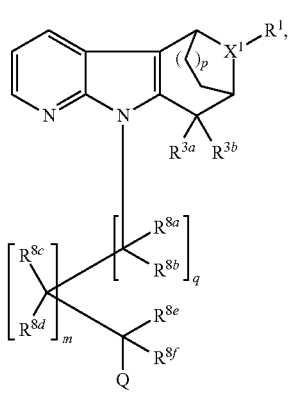 (IIe)
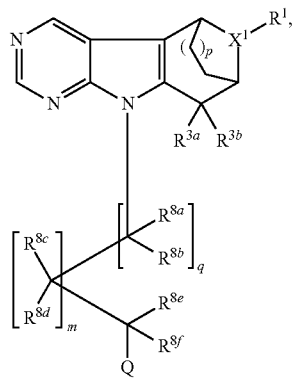 (IIf)
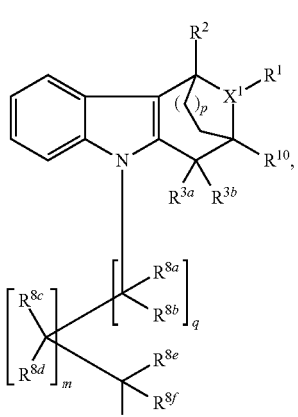 (IIg)
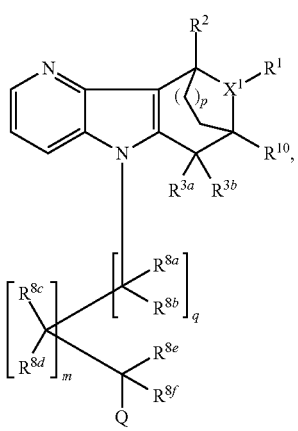 (IIh)
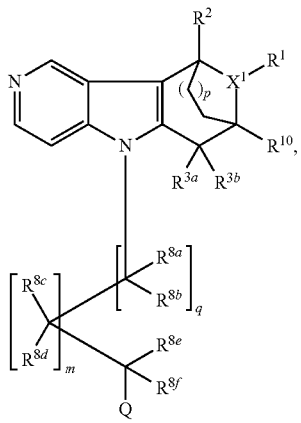 (IIi)

-continued (IIj)
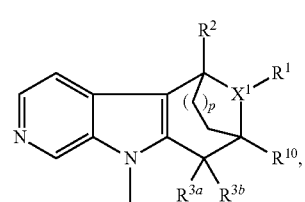

(IIk)
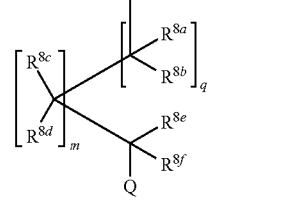

(III)
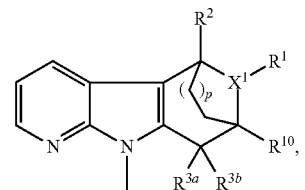

(IIm)
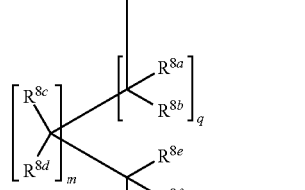

-continued (IIn)
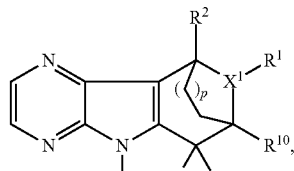

where in each of (IIa), (IIb), (IIc), (IId), (IIe), (IIf), (IIg), (IIh), (IIi), (IIj), (IIk), (IIl), (IIm) and (IIn), $R^1$, $R^2$, $R^{3a}$, $R^{3b}$, $R^{10}$, $R^{8a}$-$R^{8f}$, m, q, p and Q are as described for formula (I) or any applicable variation thereof. In one variation, a compound of the invention is of the formula (IIc). Where applicable, in each of (IIa), (IIb), (IIc), (IId), (IIe), (IIf), (IIg), (IIh), (IIi), (IIj), (IIk), (IIl), (IIm) and (IIn), $R^1$, $R^2$, $R^{3a}$, $R^{3b}$, $R^{10}$, $R^{8a}$-$R^{8f}$, m, q and Q may also be as described for any formulae or any applicable variation thereof detailed herein, including but not limited to formulae (A)-(F).

Compounds of the formulae (IIIa)-(IIIx) are further embraced by this invention:

(IIIa)
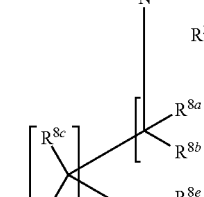

(IIIb)
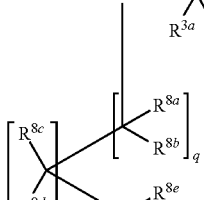

-continued
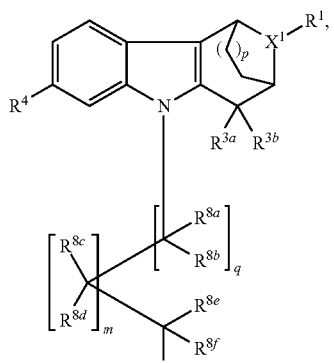
(IIIc)
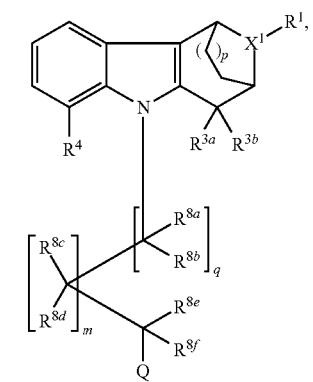
(IIId)
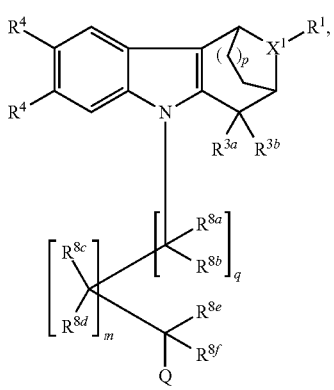
(IIIe)
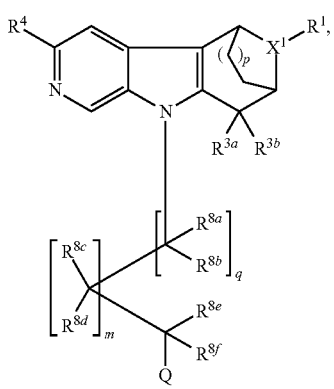
(IIIf)
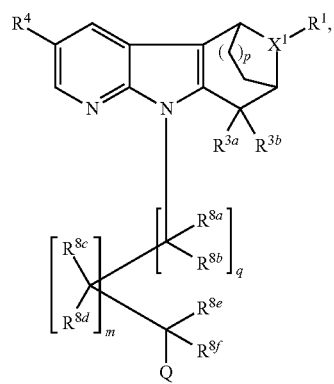
(IIIg)
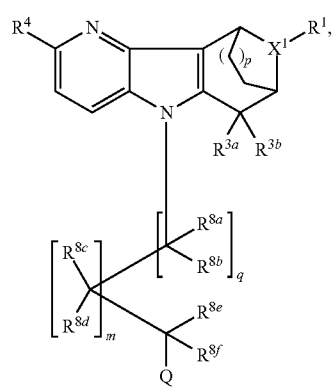
(IIIh)
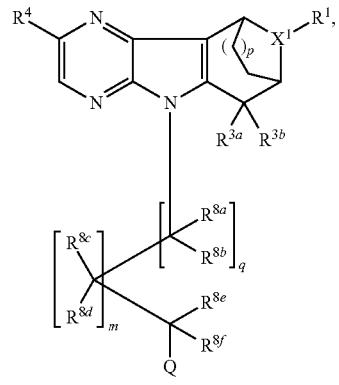
(IIIi)
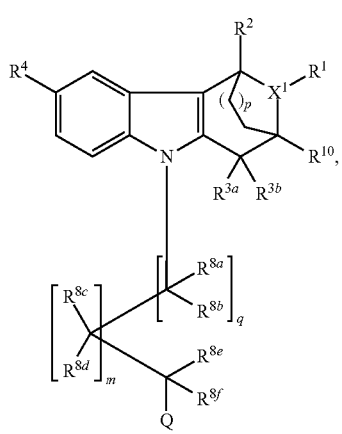
(IIIj)

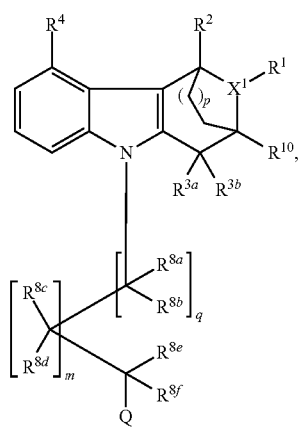
(IIIk)
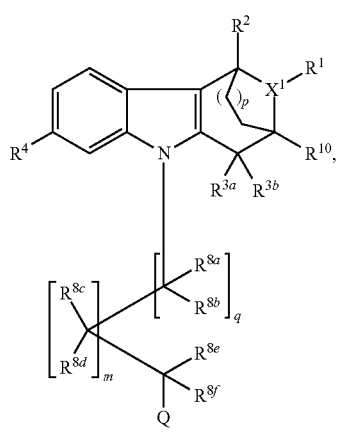
(IIIl)
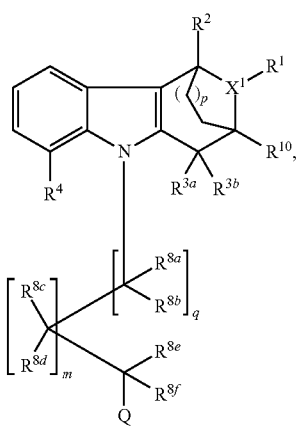
(IIIm)
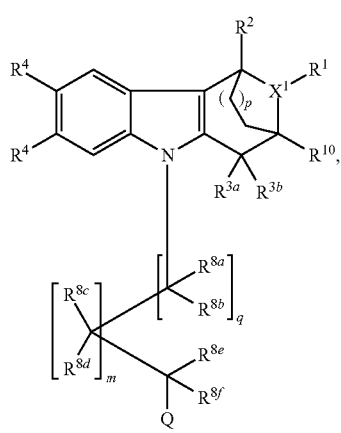
(IIIn)
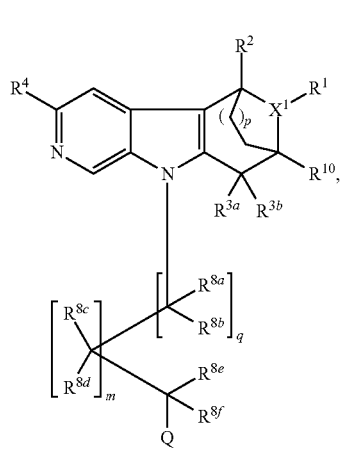
(IIIo)
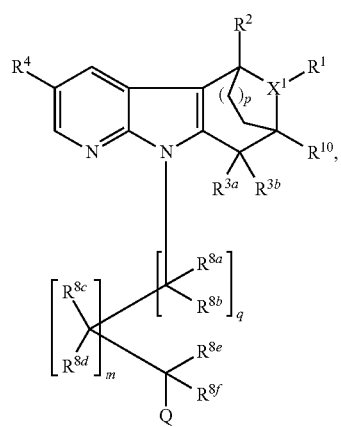
(IIIp)

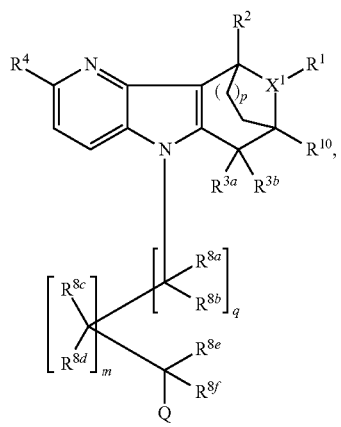
(IIIq)
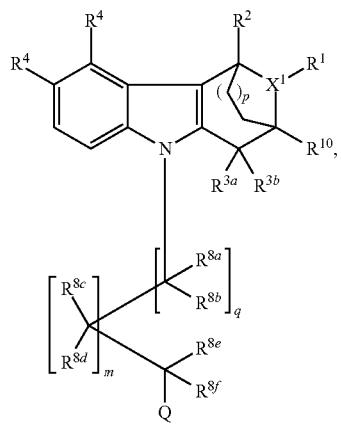
(IIIt)
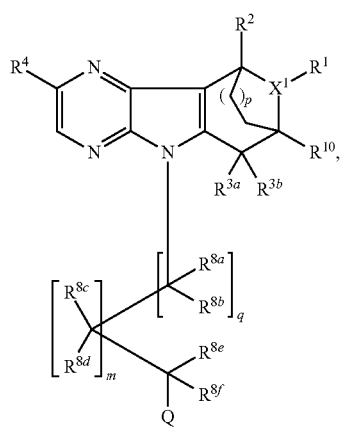
(IIIr)
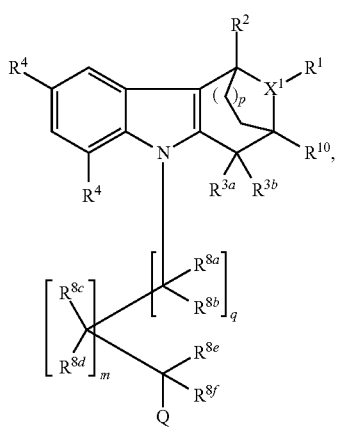
(IIIu)
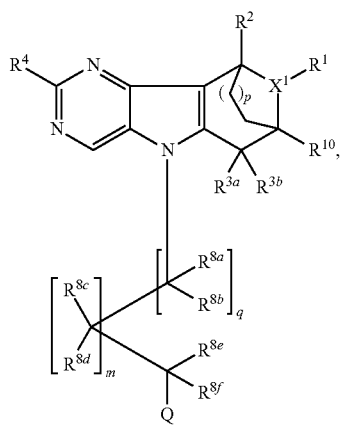
(IIIs)
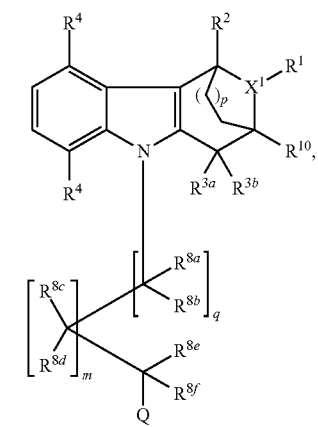
(IIIv)

-continued (IIIw)
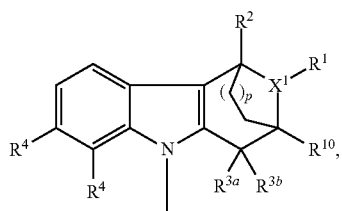

(IIIx)
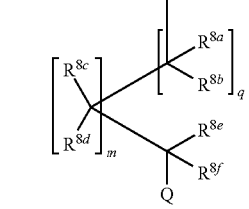

where in each of (IIIa)-(IIIx), $R^1$, $R^4$, $R^2$, $R^{3a}$, $R^{3b}$, $R^{10}$, $R^{8a}$-$R^{8f}$, m, q, p and Q are as described for formula (I) or any applicable variation thereof. In one variation, the invention relates to a compound of the formula (IIIa), (IIIb), (IIIc) or (IIIi). Where applicable, in each of formulae (IIIa)-(IIIx), $R^1$, $R^2$, $R^{3a}$, $R^{3b}$, $R^{10}$, $R^4$, $R^{8a}$-$R^{8f}$, m, q and Q may also be as described for any formulae or any applicable variation thereof detailed herein, including but not limited to formulae (A)-(F).

Compounds of the formulae (IVa), (IVb), (IVc), (IVd), (IVe) and (IVf) are further embraced by this invention:

(IVa)
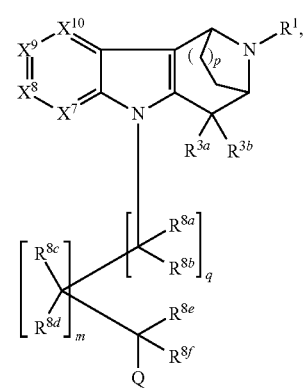

(IVb)
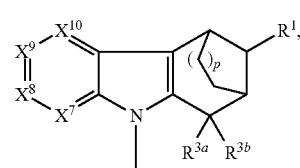

(IVc)
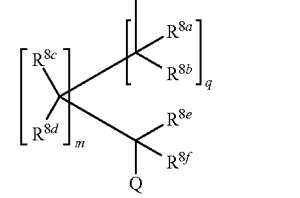

(IVd)
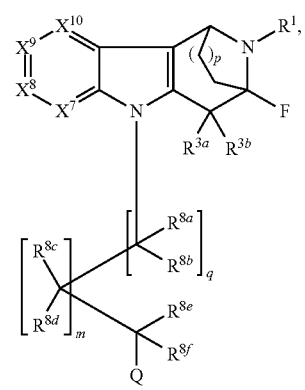

(IVe)
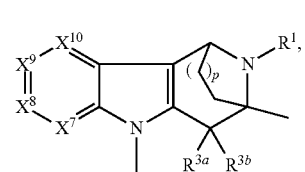

-continued

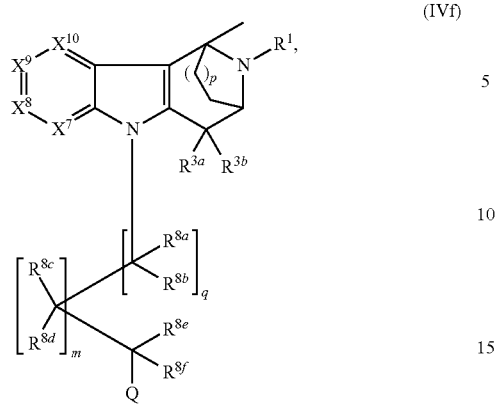
(IVf)

where in each of (IVa), (IVb), (IVc), (IVd), (IVe) and (IVf), $R^1$, $X^7$, $X^8$, $X^9$, $X^{10}$, $R^{8a}$-$R^{8f}$, m, q, p and Q are as described for formula (I) or any applicable variation thereof. In one variation, a compound of the invention is of the formula (IVa). Where applicable, in each of (IVa)-(IVf), $R^1$, $R^{3a}$, $R^{3b}$, $X^7$-$X^{10}$ $R^{8a}$-$R^{8f}$, m, q and Q may also be as described for any formulae or any applicable variation thereof detailed herein, including but not limited to formulae (A)-(F).

The invention also embraces compounds of the formulae (Va)-(Vu):

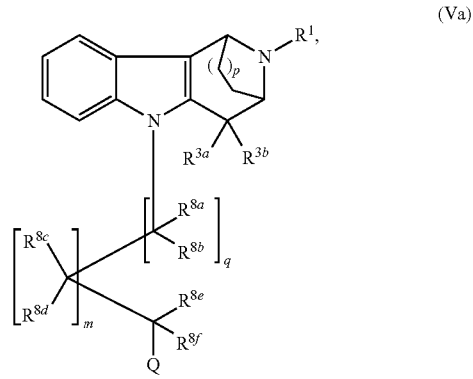
(Va)

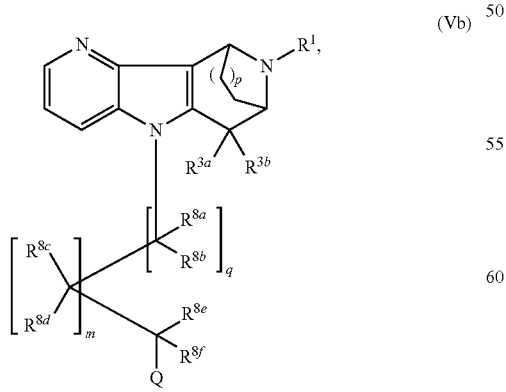
(Vb)

(Vc)

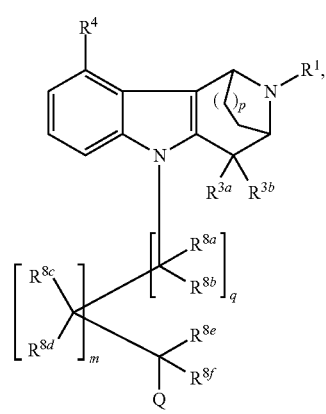
(Vd)

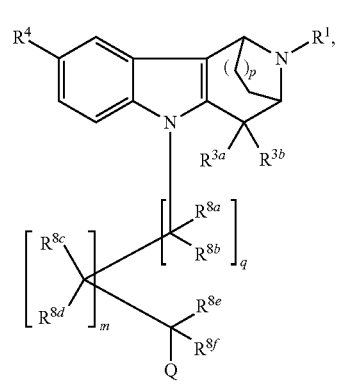
(Ve)

(Vf)

-continued
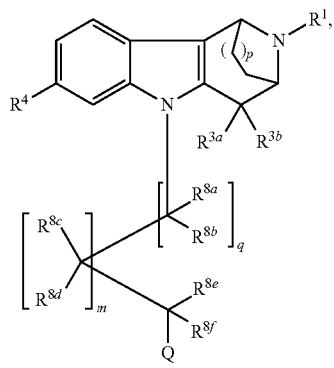
(Vg)
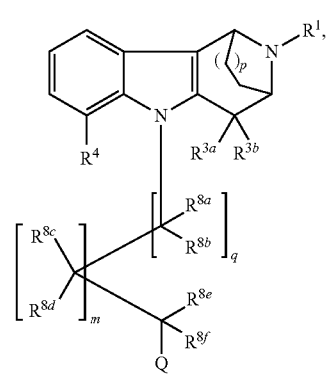
(Vh)
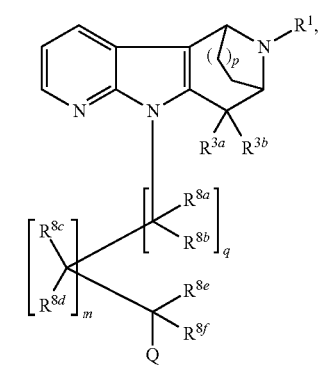
(Vi)
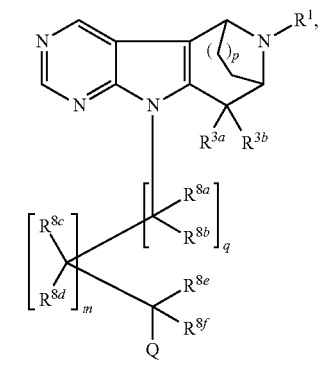
(Vj)
-continued
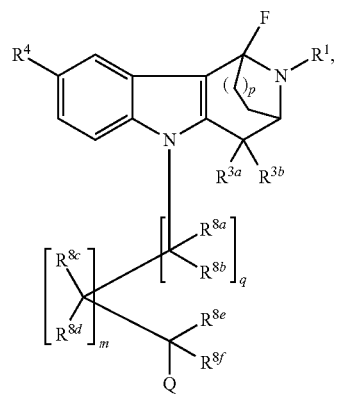
(Vk)
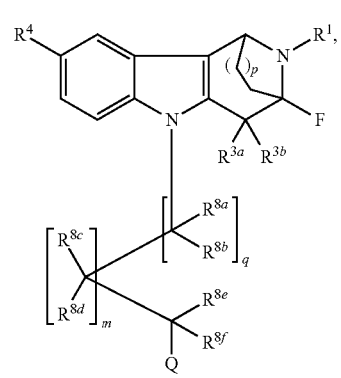
(Vl)
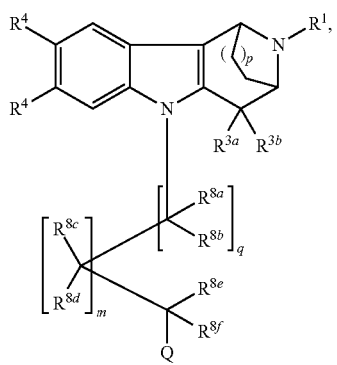
(Vm)
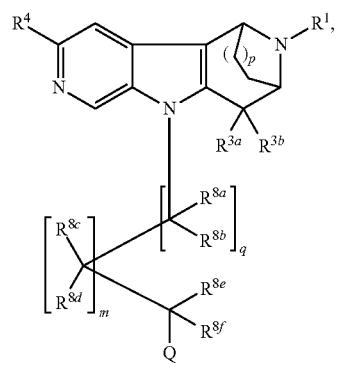
(Vn)

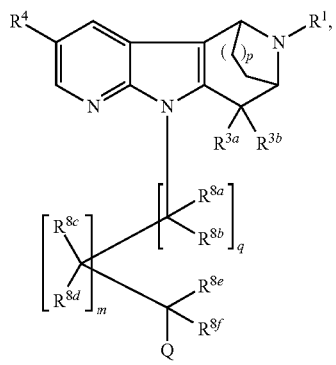 (Vo)

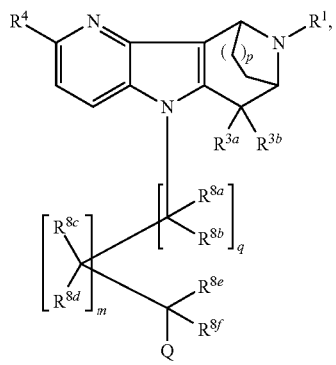 (Vp)

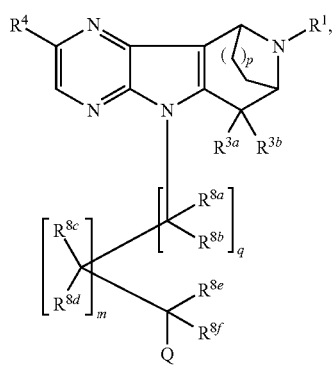 (Vq)

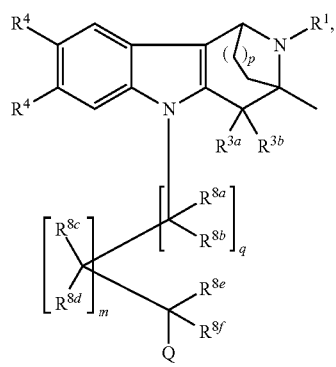 (Vr)

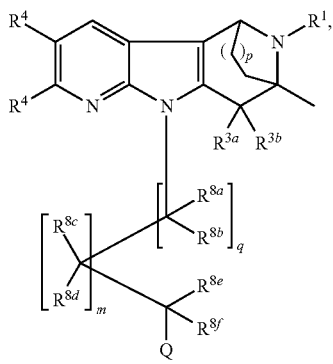 (Vs)

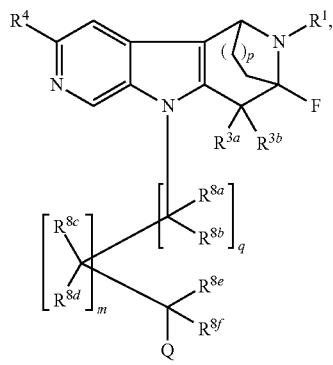 (Vt)

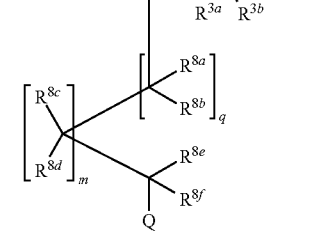 (Vu)

where in each of (Va)-(Vu), $R^1$, $R^4$, $R^{8a}$-$R^{8f}$, m, q, p and Q are as described for formula (I) or any applicable variation thereof. In one variation, the invention relates to compounds of the formula (Vc), (Ve), (Vf), (Vg) or (Vq). Where applicable, in each of (Va)-(Vu), $R^1$, $R^{3a}$, $R^{3b}$, $R^4$, $R^{8a}$-$R^{8f}$, m, q and Q may also be as described for any formulae or any applicable variation thereof detailed herein, including but not limited to formulae (A)-(F).

In one variation, a compound of the invention is of the formula (I) or (Ia) or any variation of the foregoing detailed herein, or is of any one of the formula (IIa)-(IIn), (IIIa)-(IIIx), (IVa)-(IVf) or (Va)-(Vu), where each $R^{8a}$, $R^{8b}$, $R^{8c}$, $R^{8d}$, $R^{8e}$ and $R^{8f}$ is independently H, hydroxyl, unsubstituted $C_1$-$C_4$ alkyl or is taken together with the carbon to which it is attached and a geminal $R^8$ to form a cycloalkyl moiety. In one variation, a compound of the invention is of the formula (I) or (Ia) or any variation of the foregoing detailed herein, or is of any one of the formulae (IIa)-(IIn), (IIIa)-(IIIx), (IVa)-(IVf) or (Va)-(Vu), where at least $R^{8a}$, $R^{8b}$, $R^{8c}$, $R^{8d}$, $R^{8e}$ and $R^{8f}$ is taken together with the carbon to which it is attached and a geminal $R^8$ to form a carbonyl moiety. In another variation, a compound of the invention is of the formula (I) or (Ia) or any variation of the foregoing detailed herein, or is of any one of the formulae (IIa)-(IIn), (IIIa)-(IIIx), (IVa)-(IVf) or (Va)-(Vu), where each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^8$ to form a cyclopropyl moiety. In yet another variation, a compound of the invention is of the formula (I) or (Ia) or any variation of the foregoing detailed herein, or is any one of the formulae (IIa)-(IIn), (IIIa)-(IIIx), (IVa)-(IVf) or (Va)-(Vu), where wherein q is 0 and m is 1. The invention also embraces a compound of the invention according to formula (I) or (Ia) or any variation of the foregoing detailed herein, or a compound according to any one of the formulae (IIa)-(IIn), (IIIa)-(IIIx), (IVa)-(IVf) or (Va)-(Vu), where q and m are both 0. The invention further embraces a compound according to formula (I) or (Ia) or any variation of the foregoing detailed herein, or a compound according to any one of the formulae (IIa)-(IIn), (IIIa)-(IIIx), (IVa)-(IVf) or (Va)-(Vu), where q, m, $R^{8a}$, $R^{8b}$, $R^{8c}$, $R^{8d}$, $R^{8e}$ and $R^{8f}$ are taken together to form a moiety selected from the group consisting of: —$CH_2$—, —$CH_2CH_2$—, —$CH_2CH_2CH_2$—$CH_2CH_2CH_2$—, —$CH_2$—$C(H)(OH)$—, —$C(H)(OH)$—$CH_2$—, —$CH_2$—$C(OH)(CH_3)$—, —$C(OH)(CH_3)$—$CH_2$—, —$CH_2$—$C(H)(CH_3)$—, —$C(H)(CH_3)$—$CH_2$—, —$CH_2$—$C(CH_3)(CH_3)$—, —$C(CH_2CH_2)$—$CH_2$— and —$CH_2$—$C(CH_2CH_2)$—.

The invention embraces a compound according to formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where each $R^{8a}$, $R^{8b}$, $R^{8c}$, $R^{8d}$, $R^{8e}$ and $R^{8f}$, where present, is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^8$ to form a bond, provided that when an $R^8$ is taken together with a vicinal $R^8$ to form a bond, the geminal $R^8$ is other than hydroxyl. In one variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where each $R^{8a}$, $R^{8b}$, $R^{8c}$, $R^{8d}$, $R^{8e}$ and $R^{8f}$, where present, is independently H, hydroxyl, unsubstituted $C_1$-$C_4$ alkyl or is taken together with the carbon to which it is attached and a geminal $R^8$ to form a cycloalkyl moiety. In one variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where at least one of $R^{8a}$, $R^{8b}$, $R^{8c}$, $R^{8d}$, $R^{8e}$ and $R^{8f}$ is taken together with the carbon to which it is attached and a geminal $R^8$ to form a carbonyl moiety. In another variation, a compound of the invention is of the formulae (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^8$ to form a cyclopropyl moiety. In one variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where at least one of $R^{8a}$, $R^{8b}$, $R^{8c}$, $R^{8d}$, $R^{8e}$ and $R^{8f}$ is taken together with a geminal $R^8$ to form a methylene ($CH_2$=) or a substituted methylene such as $CH_3CH$= or the like. In another variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where at least one of $R^{8a}$, $R^{8b}$, $R^{8c}$, $R^{8d}$, $R^{8e}$ and $R^{8f}$ is taken together with a vicinal $R^8$ to form a bond, where the resultant double bond is in E- or Z-configuration. In one variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where at least one of $R^{8a}$, $R^{8b}$, $R^{8c}$, $R^{8d}$, $R^{8e}$ and $R^{8f}$ is taken together with a vicinal $R^8$ and the carbons to which they are attached to form a substituted or unsubstituted $C_{3-8}$ cycloalkyl, substituted or unsubstituted $C_{3-8}$ cycloalkenyl or substituted or unsubstituted heterocyclyl moiety. In one variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where at least one of $R^{8a}$, $R^{8b}$, $R^{8c}$, $R^{8d}$, $R^{8e}$ and $R^{8f}$ is taken together with a vicinal $R^8$ and the carbons to which they are attached to form a $C_{3-8}$ cycloalkyl. In one variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where $R^{8e}$, $R^{8d}$ and the carbon to which they are attached are taken together with two other $R^8$ groups that are geminal to each other and the carbon to which they are attached to form a $C_{3-8}$ cycloalkenyl. In yet another variation, a compound of the invention is of the formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where wherein q is 0 and m is 1. The invention also embraces a compound of the invention according to formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where q and m are both 0.

The invention further embraces a compound according to formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where q, m, $R^{8a}$, $R^{8b}$, $R^{8c}$, $R^{8d}$, $R^{8e}$ and $R^{8f}$ are taken together to form a moiety selected from the group consisting of the structures:

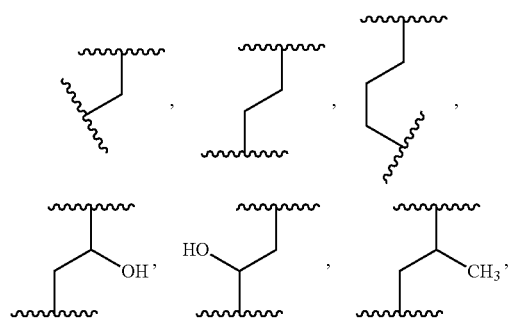

-continued

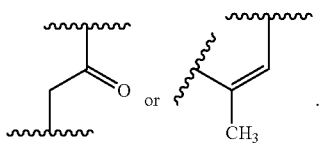

In a further variation and where applicable, a compound of the formulae detailed herein is provided where q, m, $R^{8a}$, $R^{8b}$, $R^{8c}$, $R^{8d}$, $R^{8e}$ and $R^{8f}$ are taken together to form a moiety of the formula:

When the above structures are applied to formula (E) or any variation thereof, it is understood that q, m, n, $R^{8a}$, $R^{8b}$, $R^{8c}$, $R^{8d}$, $R^{8e}$ and $R^{8f}$ where applicable are taken together to form the structures of this paragraph. Likewise, any formula detailed herein, where applicable, may in one variation have q, m, n, $R^{8a}$, $R^{8b}$, $R^{8c}$, $R^{8d}$, $R^{8e}$ and $R^{8f}$ taken together to form a moiety selected from the group consisting of the foregoing structures of this paragraph.

The invention further embraces a compound according to formula (I), (A), (B), (C), (D) or (E) or any variation thereof detailed herein, or a compound according to any one of the formulae (IIa)-(IIn), (IIIa)-(IIIx), (IVa)-(IVf) or (Va)-(Vu), where $R^{8c}$, $R^{8d}$ and the carbon to which they are attached are taken together with $R^{8e}$, $R^{8f}$ and the carbon to which they are attached or $R^{8a}$, $R^{8b}$ and the carbon to which they are attached to form a moiety selected from the group consisting of the structures, each of which may be optionally substituted, where each $R^8$ is independently H, hydroxyl, $C_1$-$C_8$ alkyl, $C_1$-$C_8$ perhaloalkyl, carboxy or carbonylalkoxy:

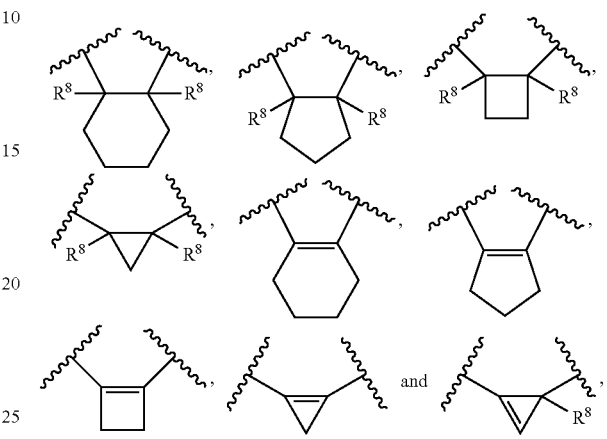

In another variation, a compound of the invention is of the formula (I) or (Ia) or any variation of the foregoing detailed herein, or a compound according to any one of the formulae (IIIa)-(IIIx), (IVa)-(IVf) or (Va)-(Vu), where each $R^4$ is independently H, halo, substituted or unsubstituted $C_1$-$C_8$ alkyl, $C_1$-$C_8$ perhaloalkyl, substituted or unsubstituted heterocyclyl or a substituted or unsubstituted aryl. In yet another variation, a compound of the invention is of the formula (I) or (Ia) or any variation of the foregoing detailed herein, or a compound according to any one of the formulae (IIIa)-(IIIx), (IVa)-(IVf) or (Va)-(Vu), where each $R^4$ is independently H or a substituted or unsubstituted $C_1$-$C_8$ alkyl. In still another variation, a compound of the invention is of the formula (I) or (Ia) or any variation of the foregoing detailed herein, or a compound according to any one of the formulae (IIIa)-(IIIx), (IVa)-(IVf) or (Va)-(Vu), where each $R^4$ is H. The invention also embraces compounds of the formula (I) or (Ia) or any variation of the foregoing detailed herein, or a compound according to any one of the formulae (IIIa)-(IIIx), (IVa)-(IVf) or (Va)-(Vu), where each $R^4$ is independently H, halo, unsubstituted $C_1$-$C_4$ alkyl, $C_1$-$C_4$ perhaloalkyl or a substituted or unsubstituted aryl. The invention further embraces compounds of the formula (I) or (Ia) or any variation of the foregoing detailed herein, or a compound according to any one of the formulae (IIIa)-(IIIx), (IVa)-(IVf) or (Va)-(Vu), where each $R^4$ is independently H, halo, methyl, perfluoromethyl or cyclopropyl.

The invention also embraces compounds of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a substituted or unsubstituted aryl or a substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu), where Q is a substituted or unsubstituted phenyl or pyridyl group. In a particular variation, Q is a phenyl or pyridyl group substituted with at least one methyl group. In another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In still another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu), where Q is a substituted or unsubstituted $C_{3-8}$ cycloalkyl or a substituted or unsubstituted heterocyclyl. In yet another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a substituted or unsubstituted pyridyl, phenyl, pyrazinyl, piperazinyl, pyrrolidinyl or thiomorpholinyl group. In a particular variation, Q is a pyridyl, phenyl, pyrazinyl, piperazinyl, pyrrolidinyl, or thiomorpholinyl group substituted with at least one methyl or halo group. In one variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is an unsubstituted $C_{3-8}$ cycloalkyl or an unsubstituted heterocyclyl. In another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a substituted or unsubstituted cyclohexyl, morpholinyl, piperazinyl, thiomorpholinyl, cyclopentyl or pyrrolidinyl moiety. In yet another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group.

In still another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a moiety selected from the structures:

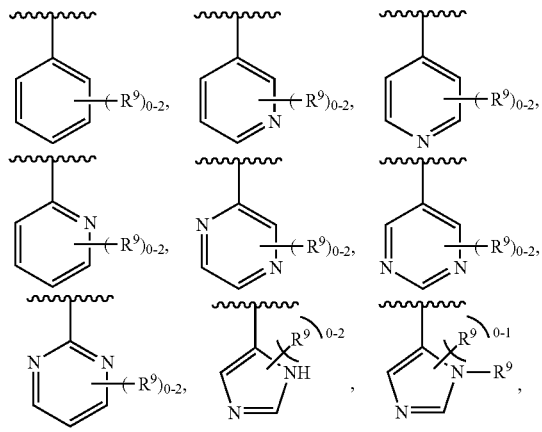

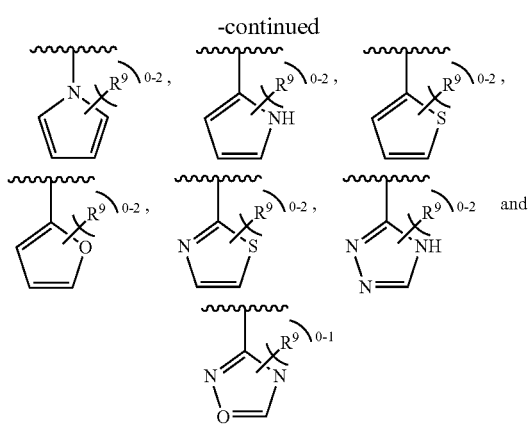

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In still another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a moiety selected from the structures:

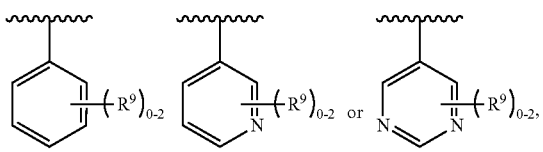

wherein each $R^9$ is independently alkyl, perhaloalkyl or halo.

In another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a moiety selected from the structures:

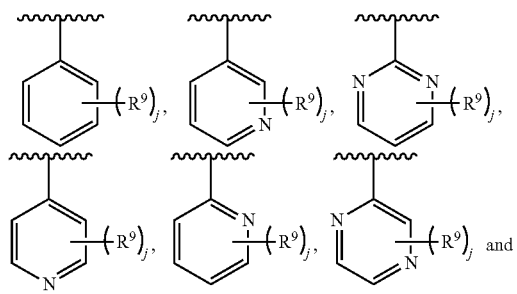

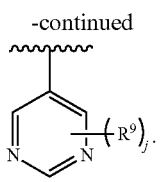

and wherein $R^9$ is connected to Q ortho or para to the position at which Q is connected to the carbon bearing $R^{8e}$ and $R^{8f}$. In a particular variation, Q is a structure of the formula:

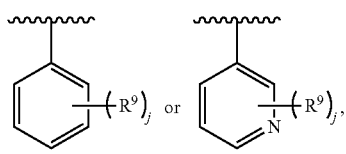

and $R^9$ is connected to Q para to the position at which Q is connected to the carbon bearing $R^{8e}$ and $R^{8f}$. In another particular variation, Q is a structure of the formula

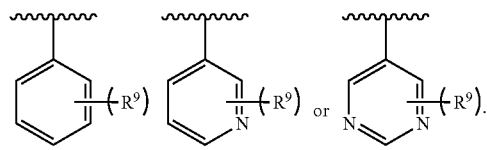

where each $R^9$ is independently alkyl, perhaloalkyl or halo.

In another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a moiety selected from the structures:

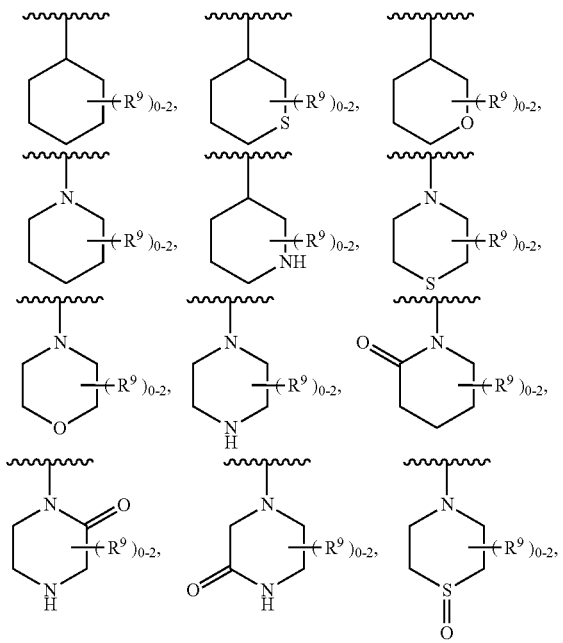

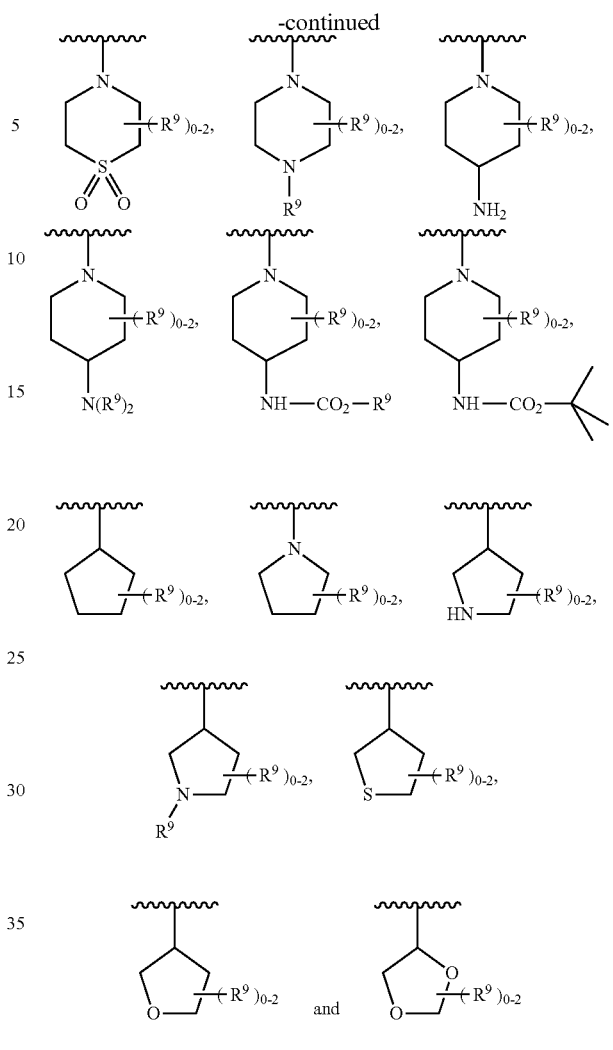

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In yet another variation, Q is substituted with two $R^9$ groups. In a particular variation, Q is selected from the carbocyclic and heterocyclic structures detailed where the residue has the moiety $(R^9)_0$ such that Q either contains no $R^9$ functionality or a moiety of the formula N—$R^9$.

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a moiety selected from the structures:

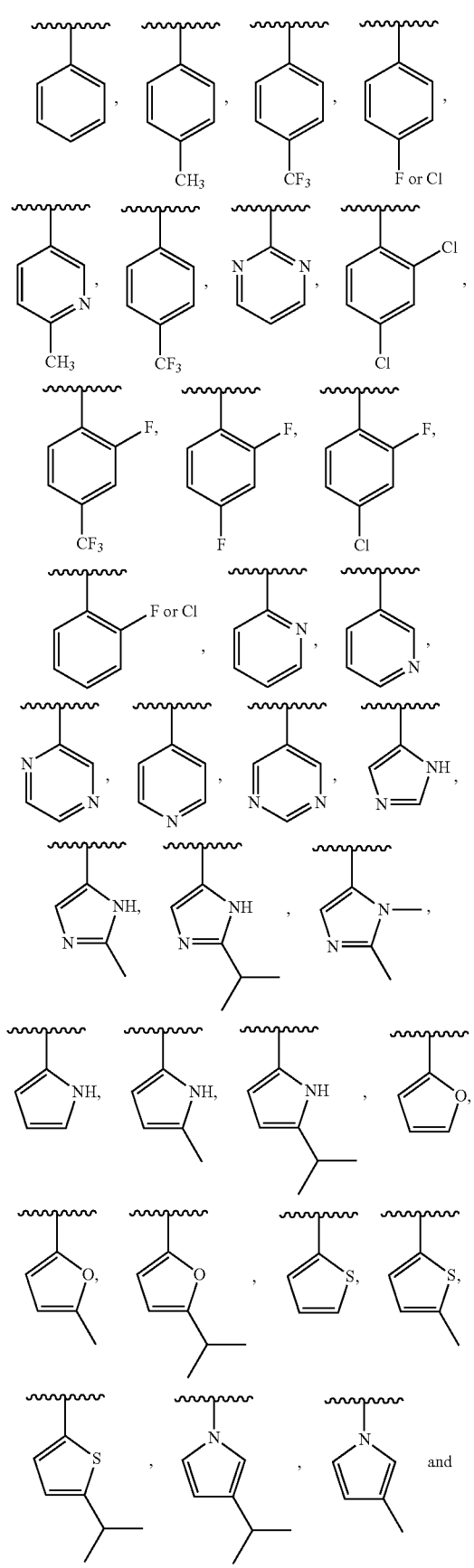
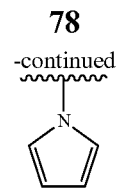
In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIn), (IIIa)-(IIIx), (IVa)-(IVf) or (Va)-(Vu) where Q is a 6-membered ring heteroaryl or substituted heteroaryl selected from the structures:
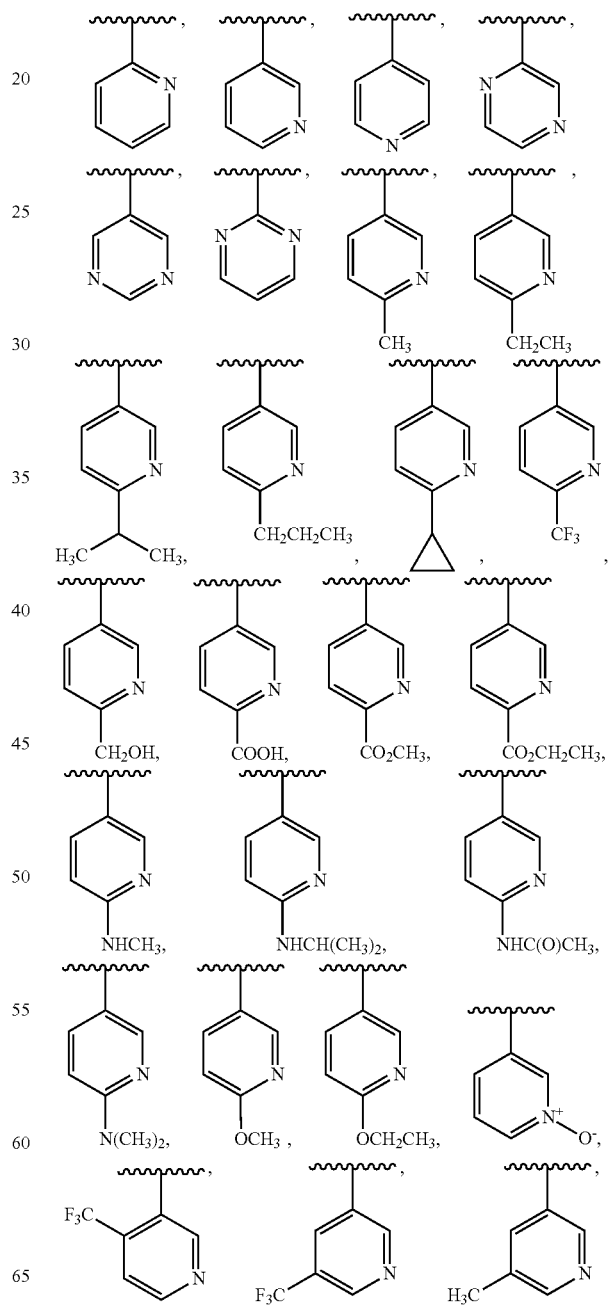

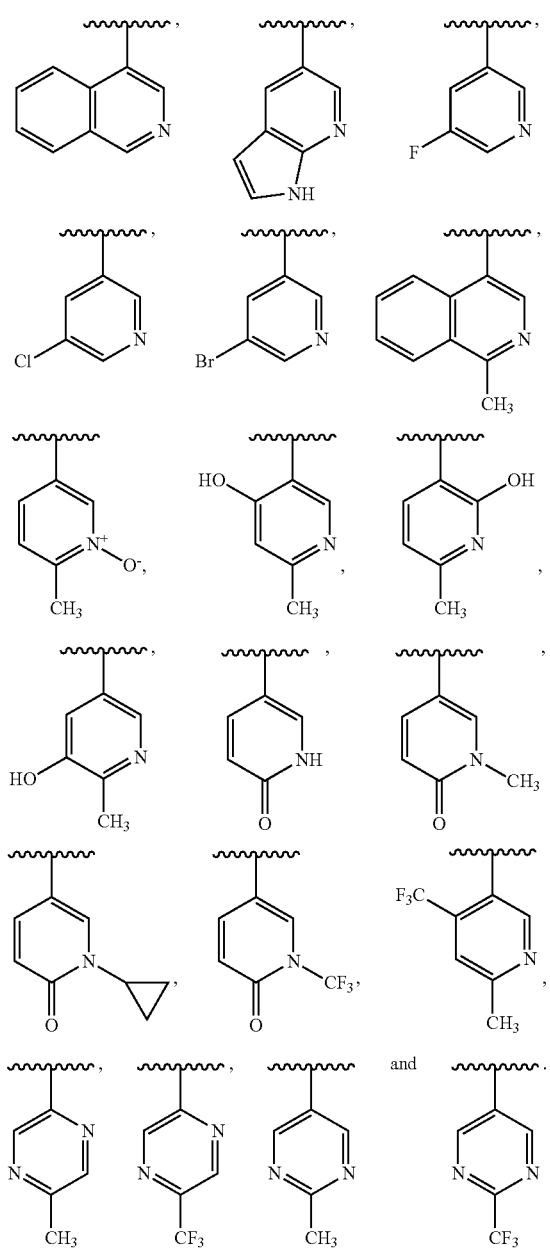

In another variation, a compound of the invention is of a formulae detailed herein, e.g., formula (I), (A), (B), (C), (D), (E) or (F) or any variation of the foregoing detailed herein, or a compound according to any one of the formulae (IIa)-(IIn), (IIIa)-(IIIx), (IVa)-(IVf) or (Va)-(Vu) where Q is a phenyl or substituted phenyl selected from the structures:

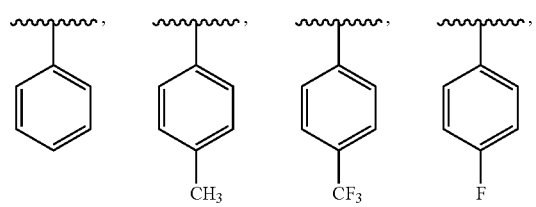

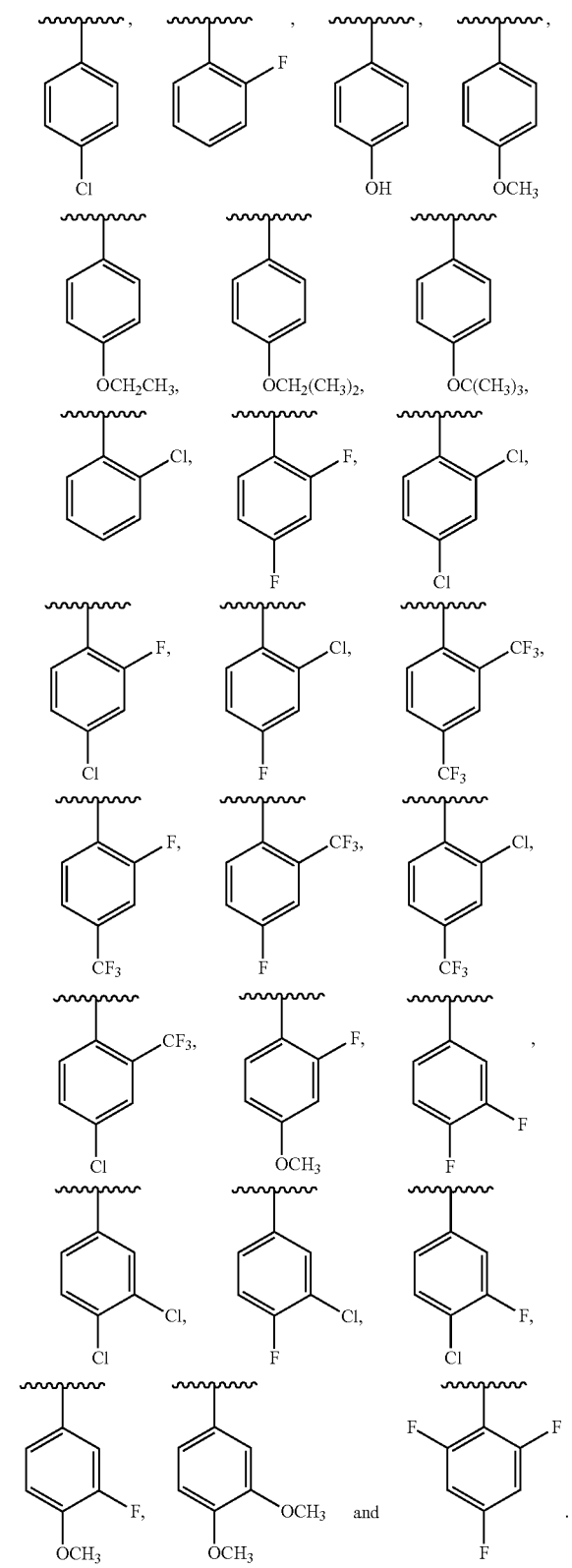

In another variation, a compound of the invention is of a formulae detailed herein e.g., formula (I), (A), (B), (C), (D), (E) or (F) or any variation of the foregoing detailed herein, or a compound according to any one of the formulae (IIa)-(IIn), (IIIa)-(IIIx), (IVa)-(IVf) or (Va)-(Vu) where Q is a 5-membered ring heteroaryl or substituted heteroaryl selected from the structures:

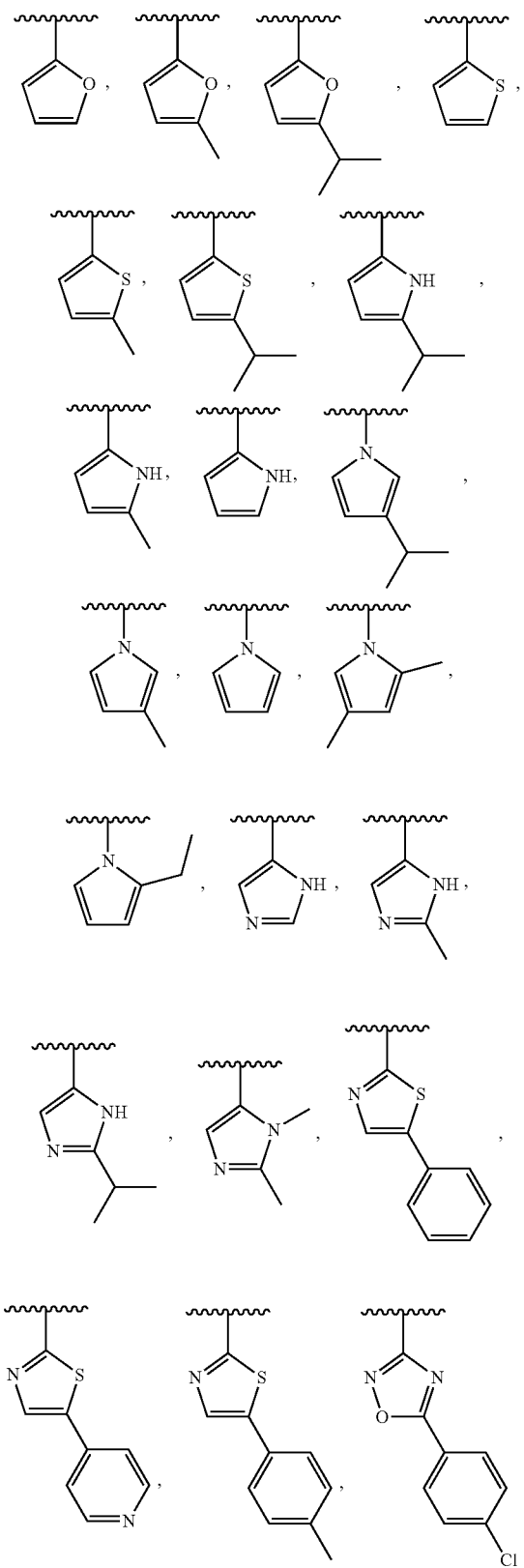

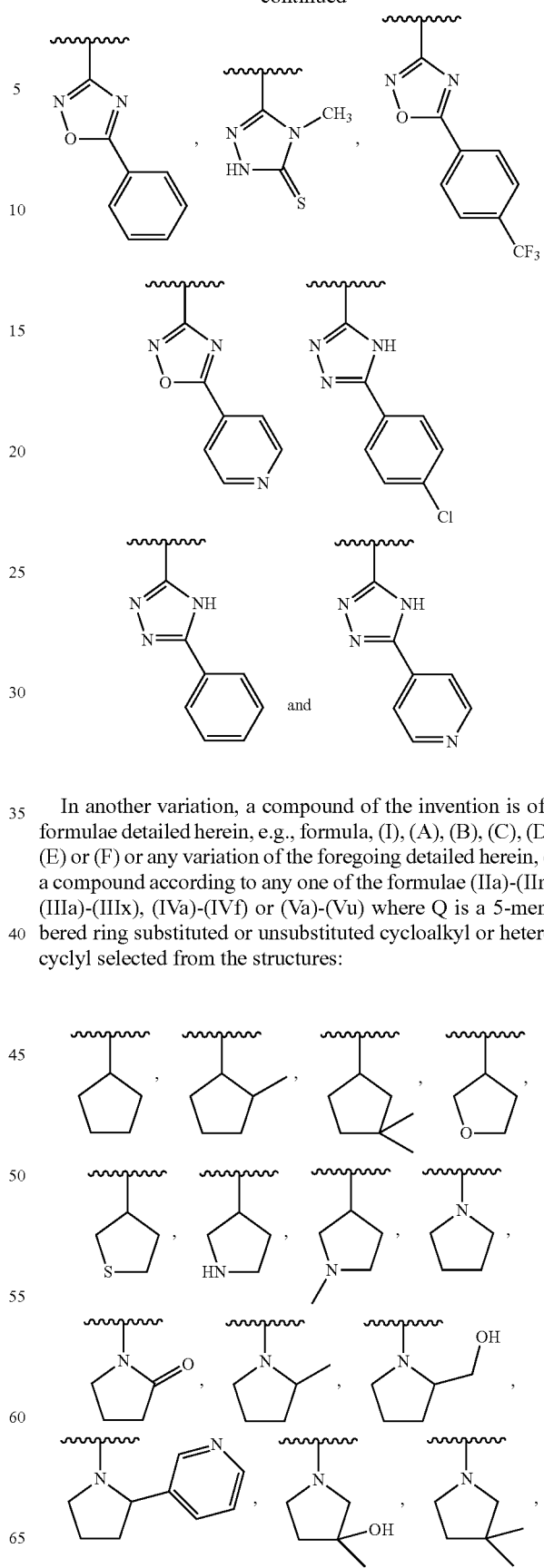

In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIn), (IIIa)-(IIIx), (IVa)-(IVf) or (Va)-(Vu) where Q is a 5-membered ring substituted or unsubstituted cycloalkyl or heterocyclyl selected from the structures:

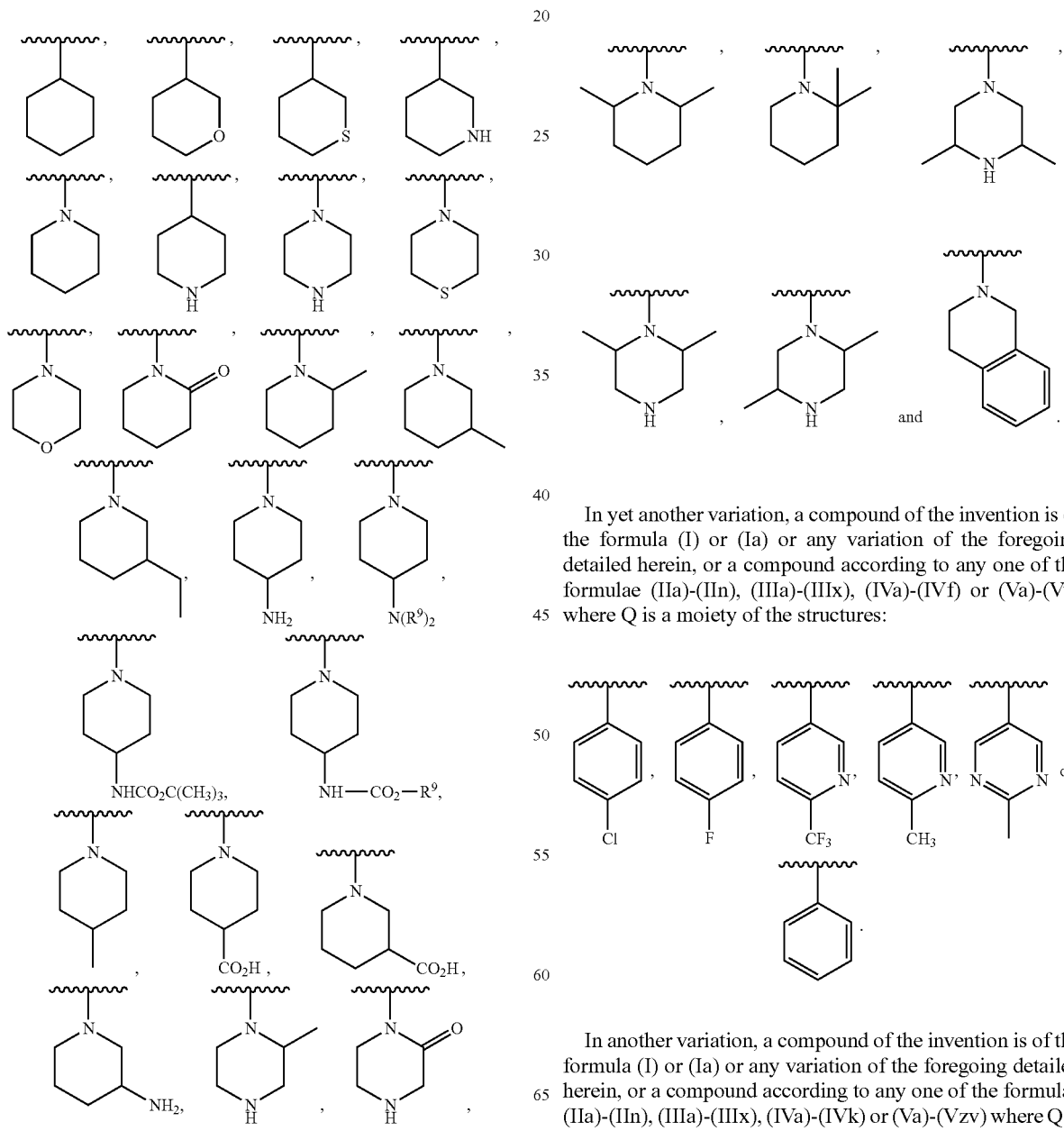

In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIn), (IIIa)-(IIIx), (IVa)-(IVf) or (Va)-(Vu) where Q is a 6-membered ring substituted or unsubstituted cycloalkyl or heterocyclyl selected from the structures:

In yet another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a moiety of the structures:

In another variation, a compound of the invention is of the formula (I) or (Ia) or any variation of the foregoing detailed herein, or a compound according to any one of the formulae (IIa)-(IIn), (IIIa)-(IIIx), (IVa)-(IVk) or (Va)-(Vzv) where Q is a moiety selected from the structures:

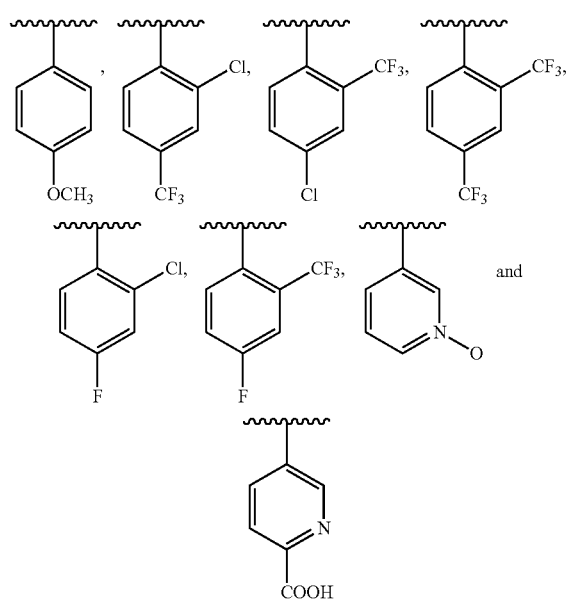

In yet another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is a moiety selected from the structures:

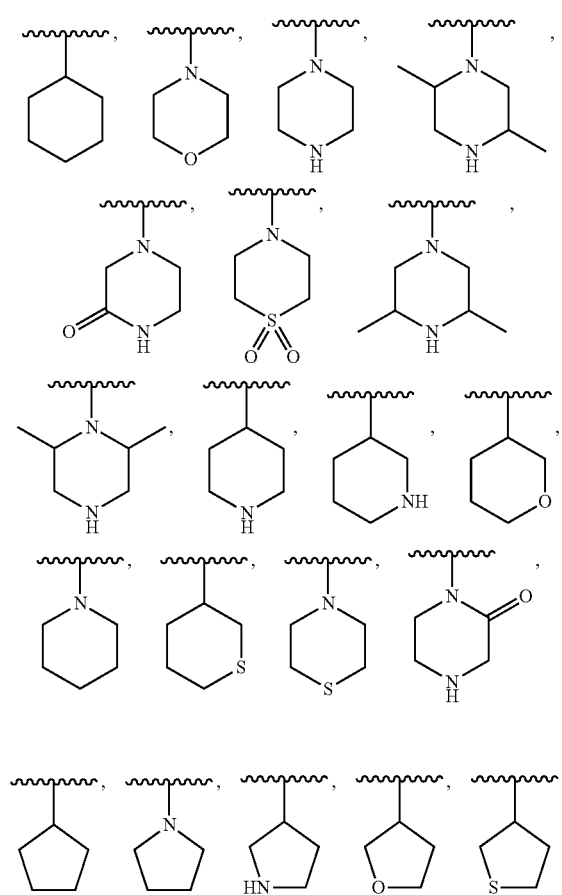

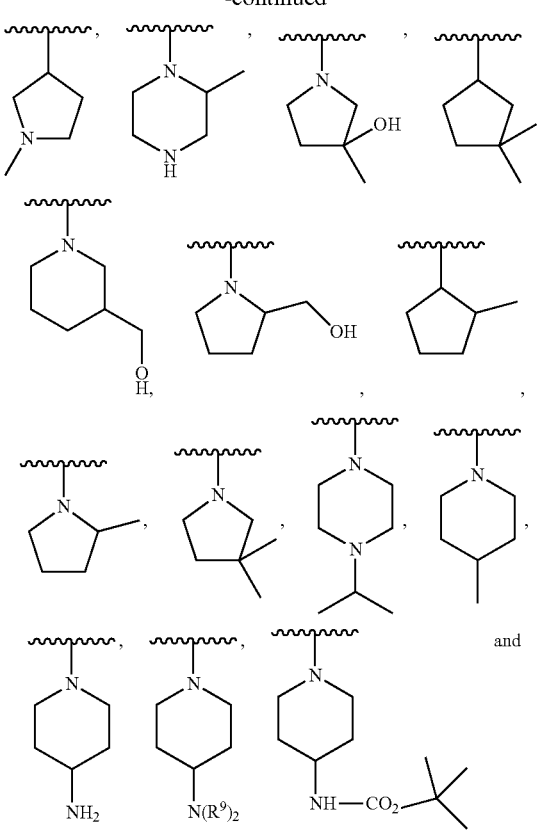

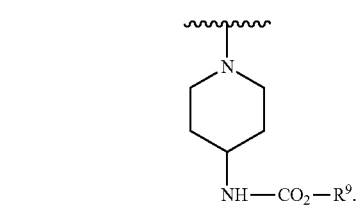

In yet another variation, a compound of the invention is of the formula (I) or (Ia) or any variation of the foregoing detailed herein, or a compound according to any one of the formalae (IIa)-(IIn), (IIIa)-(IIIx), (IVa)-(IVf) or (Va)-Vu) where Q is a moiety selected from the structures:

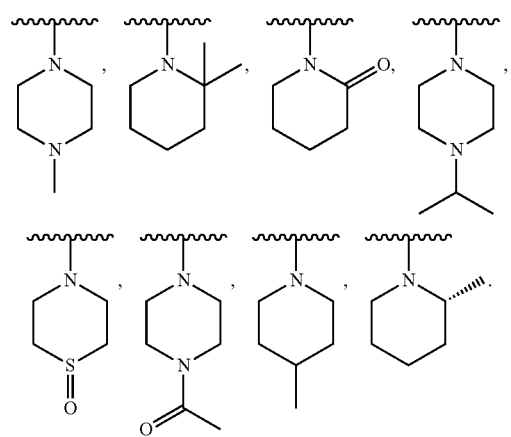

In a further variation of the formulae detailed herein, Q is a moiety of the formula:

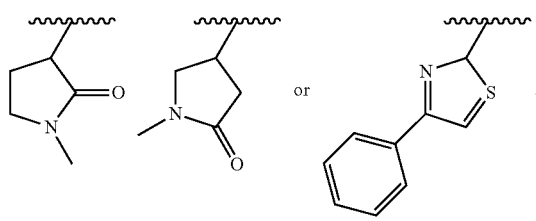

In another variation, a compound of the invention is of the formula (I) or (Ia) or any variation of the foregoing detailed herein, or a compound according to any one of the formulae (IIa)-(IIn), (IIIa)-(IIIx), (IVa)-(IVf) or (Va)-(Vu) where Q is an unsubstituted amino, substituted amino, alkoxy, aminoacyl, acyloxy, carbonylalkoxy, aminocarbonylalkoxy or acylamino moiety. In a particular variation, Q is an unsubstituted amino. In another variation, Q is substituted amino of the formula $—N(C_1-C_8alkyl)_2$ such as the moiety $—N(Me)_2-N(CH_3)(CH_2CH_3)$. In another variation, Q is a substituted amino of the formula $—N(H)(cycloalkyl$ or substituted cycloalkyl), such as a moiety of the formula:

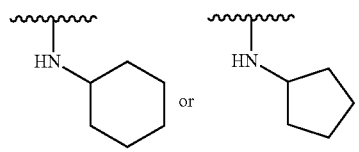 [SMILES: *NC1CCCCC1 ; *NC1CCCC1]

In another variation, Q is a substituted amino of the formula —N(H)(aryl or substituted aryl), such as a moiety of the formula

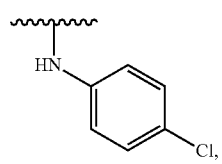 [SMILES: *Nc1ccc(Cl)cc1]

In a particular variation, Q is an amino or substituted amino and $R^{8e}$ and $R^{8f}$ are taken together to form a carbonyl moiety. In yet another variation, Q is an acylamino moiety. In still another variation, Q is an acylamino moiety and $R^{8e}$ and $R^{8f}$ are both hydrogen.

In another variation, Q is an alkoxy group of the formula $—O—C_1-C_8alkyl$, such as the moiety $—O—CH_2CH_3$. In yet another variation, Q is an alkoxy group and $R^{8e}$ and $R^{8f}$ are taken together to form a carbonyl moiety. In still a further variation, Q is a carbonylalkoxy moiety. In yet another variation, Q is a carbonylalkoxy moiety and $R^{8e}$ and $R^{8f}$ are both hydrogen.

In still another variation, Q is an acyloxy, aminocarbonylalkoxy or acylamino moiety. In one variation, Q is an acyloxy, aminocarbonylalkoxy or acylamino moiety and $R^{8e}$ and $R^{8f}$ are both hydrogen.

In one variation, Q is a moiety selected from the structures:

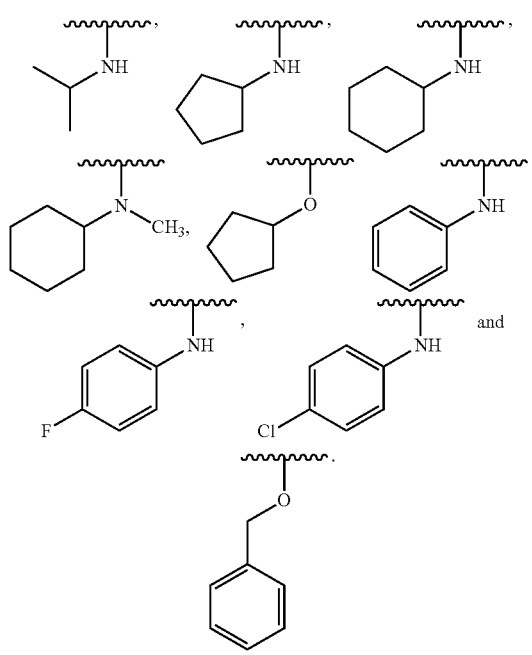

The invention also embraces compounds of the formula (I) or (Ia) or any variation of the foregoing detailed herein or a compound according to any one of the formulae (IIa)-(IIn), (IIIa)-(IIIx), (IVa)-(IVk) or (Va)-(Vu) where Q is an aminoacyl moiety. In one variation, Q is an aminoacyl group where at least one of $R_a$ and $R_b$ is H, such as when Q is of the formula $—NHC(O)R_b$. In one variation, Q is aminoacyl moiety selected from the group consisting of: —NHC(O)-heterocyclyl, —NHC(O)-substituted heterocyclyl, —NHC(O)-alkyl, —NHC(O)-cycloalkyl, —NHC(O)-alkaryl and —NHC(O)-substituted aryl. In another variation, Q is an aminoacyl moiety selected from the group consisting of: —NHC(O)—$C_5$-$C_7$heterocyclyl, —NHC(O)—$C_1$-$C_6$alkyl, —NHC(O)—$C_3$-$C_7$cycloalkyl, —NHC(O)—$C_1$-$C_3$alkaryl and —NHC(O)-substituted phenyl. In a particular variation, Q is a moiety of the formula:

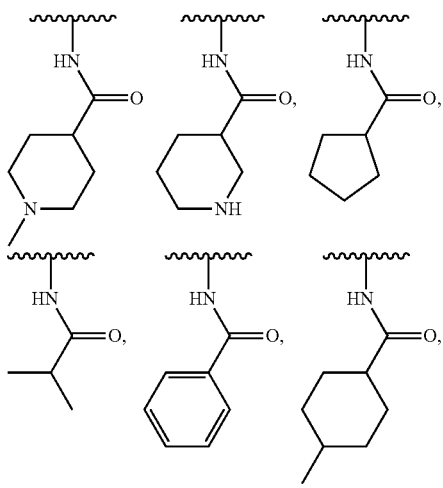

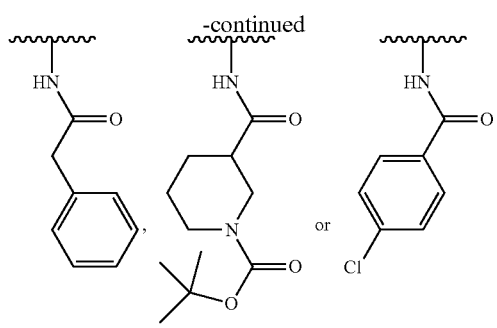

In one variation, a compound of the invention is of the formula (I) or (Ia) or any variation of the foregoing detailed herein, or a compound according to any one of the formulae (IIa)-(IIn), (IIIa)-(IIIx), (IVa)-(IVk) or (Va)-(Vu) where Q is acyloxy.

In one variation, a compound of the invention is of the formula (I) or (Ia) or any variation of the foregoing detailed herein, or a compound according to any one of the formulae (IIa)-(IIn), (IIIa)-(IIIx), (IVa)-(IVk) or (Va)-(Vu) where Q is a carbonylalkoxy moiety. In one variation, Q is a carbonylalkoxy moiety of the formula —C(O)—O—R where R is H, alkyl, substituted alkyl or alkaryl. In one variation, Q is carbonylalkoxy moiety of the formula —C(O)—O—$C_1$-$C_6$alkyl. In a particular variation, Q is a carbonylalkoxy moiety of the formula —C(O)—O—$C_2H_5$. In one variation, Q is a carbonylalkoxy moiety selected from the group consisting of: —C(O)—O—$C_1$-$C_{10}$alkyl, —C(O)—O—$C_1$-$C_3$alkaryl, —C(O)—O—$C_1$-$C_3$substituted alkyl and —C(O)—OH. In another variation, Q is —C(O)—O—$C_1$-$C_6$alkyl. In a particular variation, Q is a moiety of the formula:

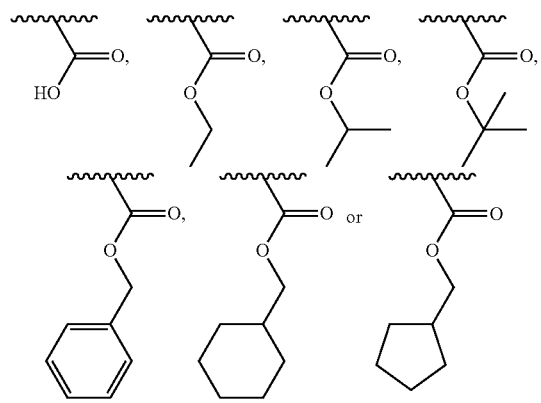

In another variation, a compound of the invention is of the formula (I) or (Ia) or any variation of the foregoing detailed herein, or a compound according to any one of the formulae (IIa)-(IIn), (IIIa)-(IIIx), (Iva)-(IVk) Or (Va)-(Vzv) where Q is an aminocarbonylalkoxy moiety. In one variation, Q is an aminocarbonylalkoxy moiety of the formula —NHC(O)—O—$R_b$. In another variation, Q is an aminocarbonylalkoxy moiety of the formula —NHC(O)—O—$R_b$ where $R_b$ is a substituted alkyl group. In a particular variation, Q is a moiety of the formula —NH—C(O)—O—$CH_2$—$C(Cl)_3$.

The invention also embraces compounds of the formula (I) or (Ia) or any variation of the foregoing detailed herein, or a compound according to any one of the formulae (IIa)-(IIn), (IIIa)-(IIIx), (Iva)-(IVk or (Va)-(Vzv) where Q is an acylamino moiety. In one variation, Q is an acylamino group where at least one of $R_a$ and $R_b$ is H, such as when Q is of the formula —C(O)N(H)($R_b$). In another variation, Q is an acylamino group where both $R_a$ and $R_b$ alkyl. In one variation, Q is an acylamino moiety selected from the group consisting of: —C(O)—N(H)(alkyl), —C(O)—N(alkyl)$_2$, —C(O)—N(H)(alkaryl) and —C(O)—N(H)(aryl). In another variation, Q is an acylamino moiety selected from the group consisting of: —C(O)—N(H)$_2$, —C(O)—N(H)($C_1$-$C_8$alkyl), —C(O)—N($C_1$-$C_6$alkyl)$_2$ and —C(O)—N(H)($C_1$-$C_3$alkaryl). In a particular variation, Q is a moiety of the formula:

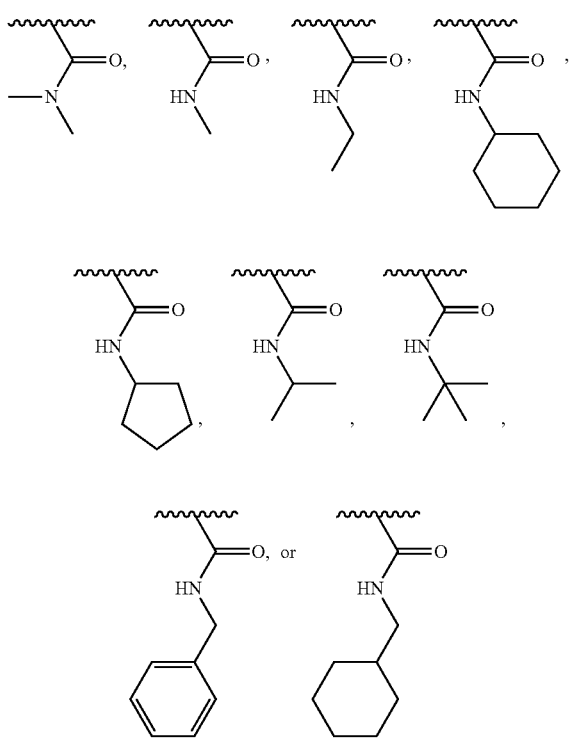

In a further variation of the formulae detailed herein, Q is a moiety of the formula:

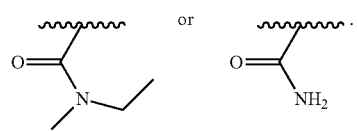

In still a further variation of the formulae detailed herein, Q is a cyano. In one variation of the formula (E) or any variation detailed herein, Q is other than carboxy or alkynyl.

Any formula detailed herein, where applicable, may in one variation has as Q the moieties detailed herein above. It is understood that by "where applicable" it is intended that such Q moieties be a variation if the formula encompasses such a structure. For example, if a given formula does not encompass structures wherein Q is a phenyl moiety, then a phenyl moiety is not applicable to that particular formula, but remains applicable to formulae that do encompass structures where Q is a phenyl moiety.

In a further variation, a compound of the invention is of the formula (I) where $R^1$ is an unsubstituted alkyl, $R^2$, $R^{3a}$, $R^{3b}$, $R^{10}$ is H, each $X^7$, $X^8$, $X^9$ and $X^{10}$ is independently N or CH, each $R^{8a}$, $R^{8b}$, $R^{8c}$, $R^{8d}$, $R^{8e}$ and $R^{8f}$ is independently H or hydroxyl, and Q is a substituted or unsubstituted aryl, substituted or unsubstituted heteroaryl, including but not limited to a substituted or unsubstituted phenyl or pyridyl group. Where Q is a substituted phenyl or pyridyl group, in one variation it is substituted with at least one methyl group.

In yet a further variation, a compound of the invention is of the formula (I) where $R^1$ is a substituted or unsubstituted $C_1$-$C_8$ alkyl, acyl, acyloxy, carbonylalkoxy, substituted or unsubstituted heterocyclyl, substituted or unsubstituted aryl; $R^2$ is H, unsubstituted $C_1$-$C_8$ alkyl or halo; each $R^{3a}$ and $R^{3b}$ is independently H or halo; each $X^7$, $X^8$, $X^9$ and $X^{10}$ is $CR^4$, where $R^4$ is as defined in formula (I) or in a particular variation, $R^4$ is H, halo, pyridyl, methyl or trifluoromethyl; $R^{10}$ is H, and Q is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is of the formula (I) where $R^1$ is a substituted or unsubstituted $C_1$-$C_8$ alkyl; each $R^2$, $R^{3a}$ and $R^{3b}$ is independently H or halo; $X^1$ is N; each $R^4$ is independently H, halo, $C_1$-$C_8$ perhaloalkyl, substituted or a unsubstituted $C_1$-$C_8$ alkyl; each $R^{8a}$, $R^{8b}$, $R^{8c}$, $R^{8d}$, $R^{8e}$ and $R^{8f}$ is H; and Q is a substituted or unsubstituted cyclohexyl, morpholinyl, piperazinyl, thiomorpholinyl, cyclopentyl or pyrrolidinyl moiety. The invention also embraces a compound of the formula (I) where $R^1$ is a methyl; at least one of $X^7$, $X^8$, $X^9$ and $X^{10}$ is $CR^4$ and each $R^4$ is independently H, halo, methyl or trifluoromethyl. The invention embraces compounds where Q in any variation detailed is substituted with at least one carbonyl, hydroxymethyl, methyl or hydroxyl group.

In a particular variation, the compound is of the formula (I) where $R^1$ is a substituted or unsubstituted $C_1$-$C_8$ alkyl; $R^2$ is H, a substituted or unsubstituted $C_1$-$C_8$ alkyl; $R^{3a}$ and $R^{3b}$ are both H; $X^1$ is N, each $R^4$ is independently H, halo or substituted or unsubstituted $C_1$-$C_8$ alkyl; each $R^{8a}$, $R^{8b}$, $R^{8c}$, $R^{8d}$, $R^{8e}$ and $R^{8f}$ is H; $R^{10}$ is H, halo, a substituted or unsubstituted $C_1$-$C_8$ alkyl, hydroxyl, alkoxyl. In one aspect of this variation, Q may be a substituted or unsubstituted pyridyl, phenyl, pyrazinyl, piperazinyl, pyrrolidinyl or thiomorpholinyl group. In another aspect of this variation, Q is a pyridyl, phenyl, pyrazinyl, piperazinyl, pyrrolidinyl or thiomorpholinyl group substituted with at least one methyl or halo group. In yet another aspect of this variation, $X^7$, $X^8$, $X^9$ and $X^{10}$ are $CR^4$ and each $R^4$ is independently H, halo or methyl.

In another variation, a compound of the invention is of the formula (I), (E) or (Ia) or any variation of the foregoing detailed herein, or a compound according to any one of the formulae (IIa)-(IIn), (IIIa)-(IIIx), (IVa)-(IVf) or (Va)-(Vu) where q, m, Q and $R^{8a}$-$R^{8f}$ are taken together to form a moiety of the structure:

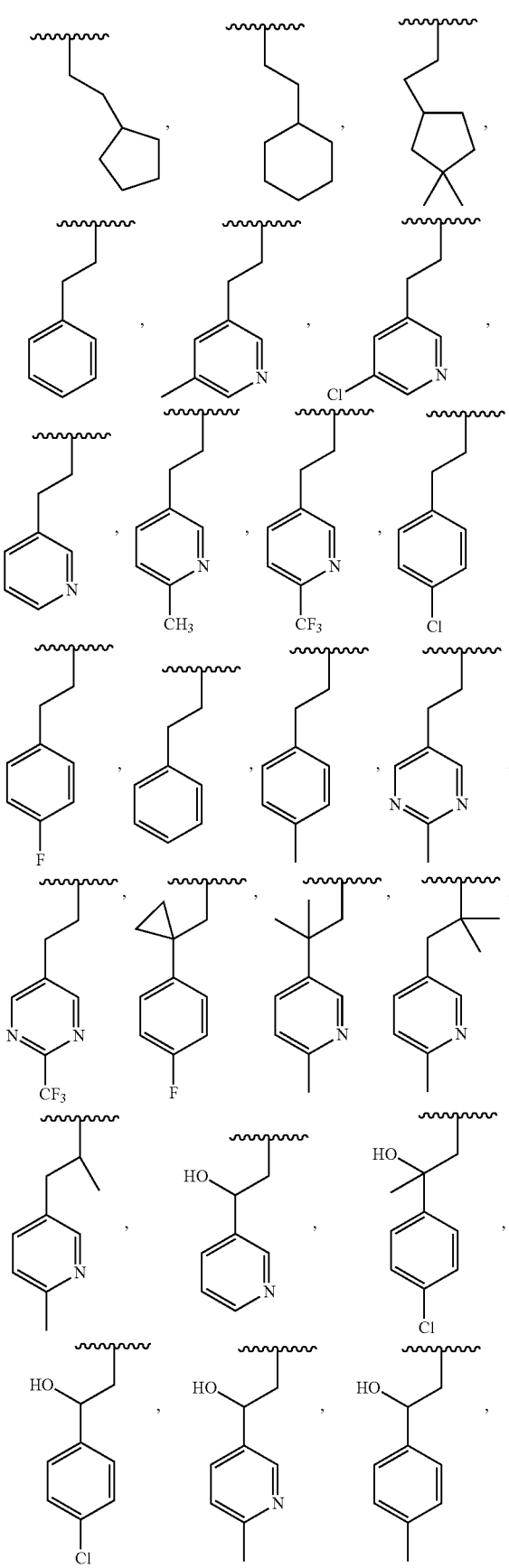

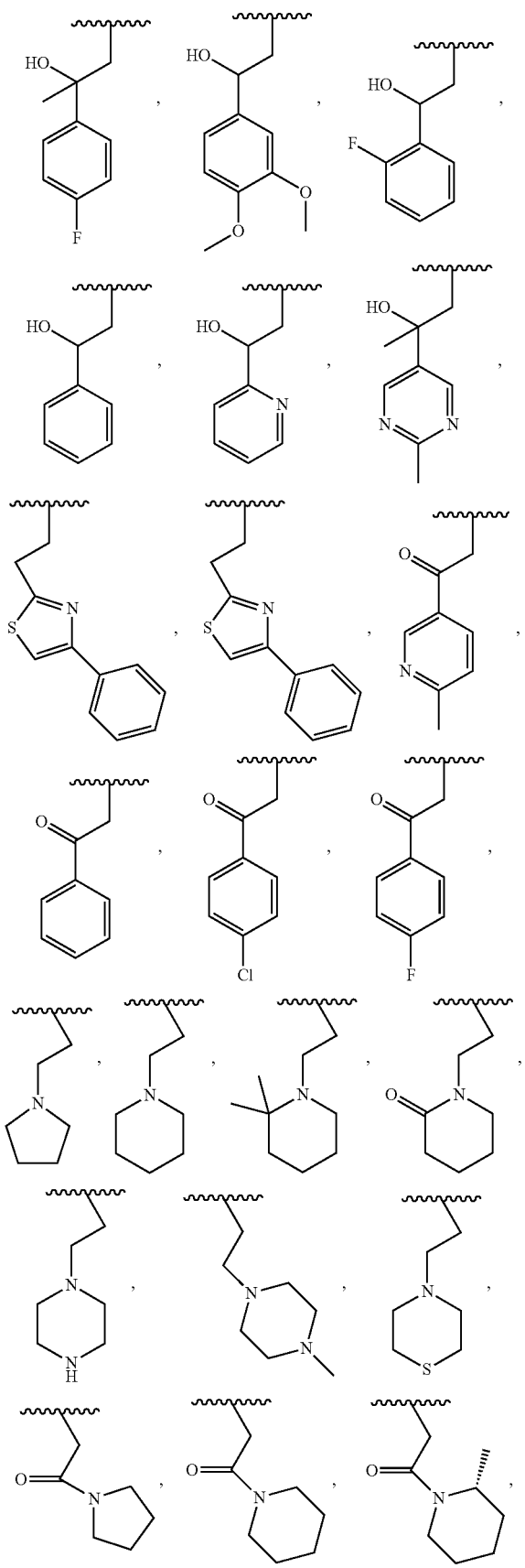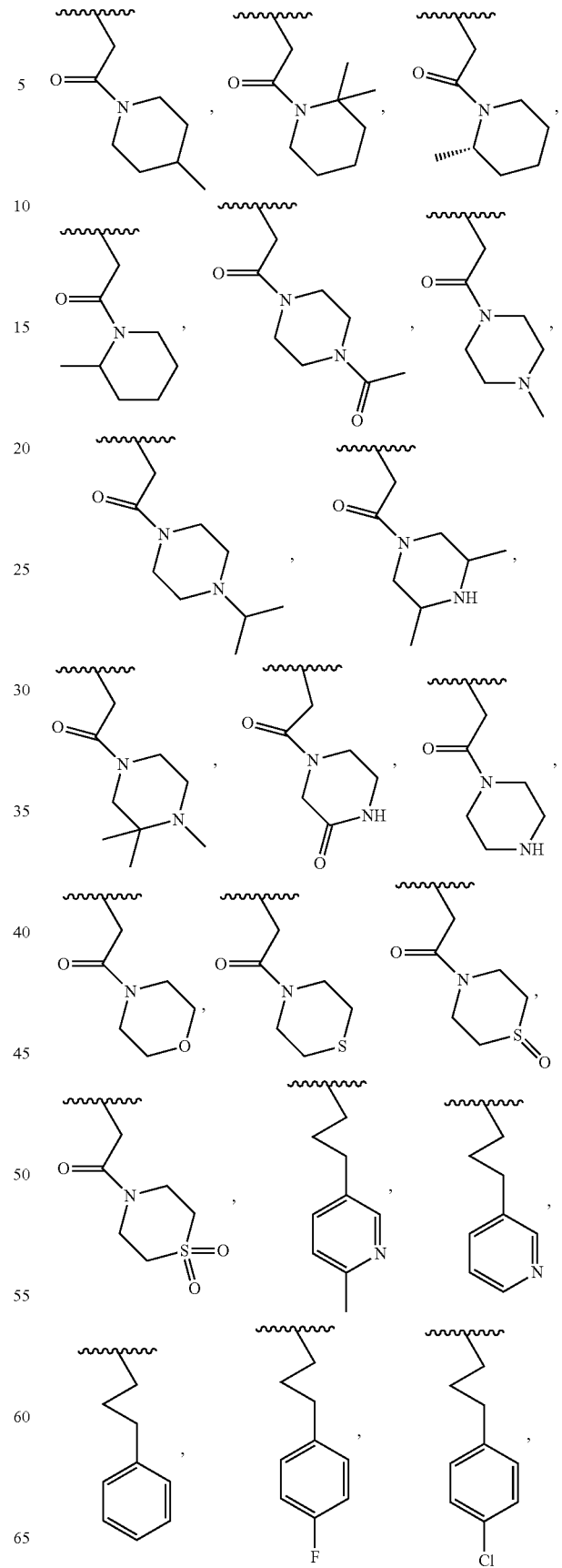

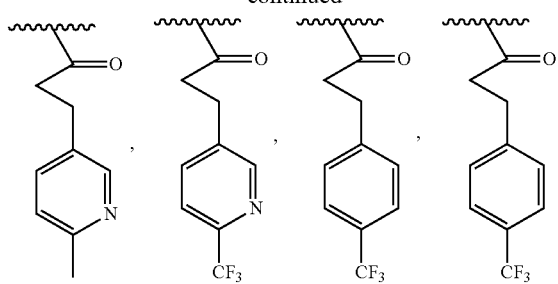
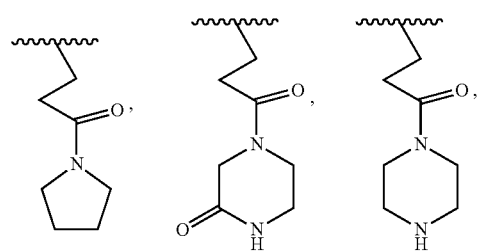
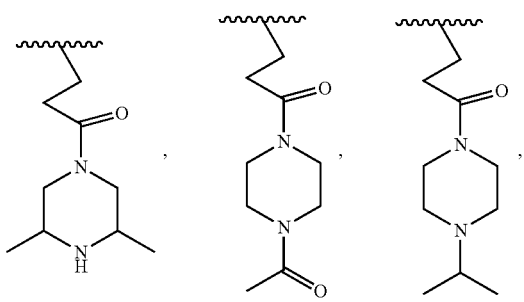
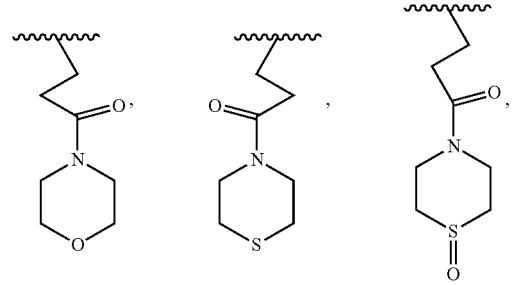
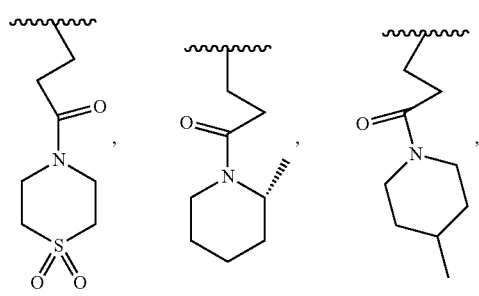
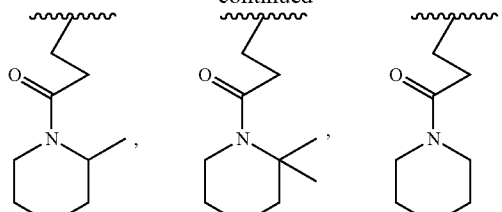
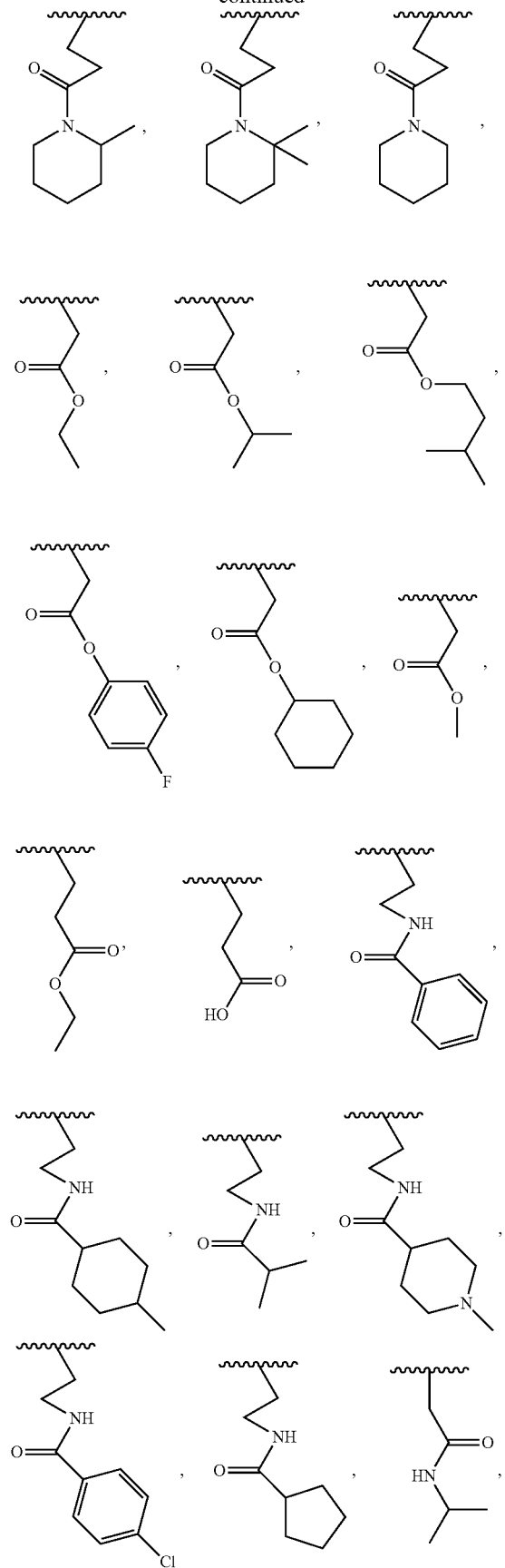

-continued

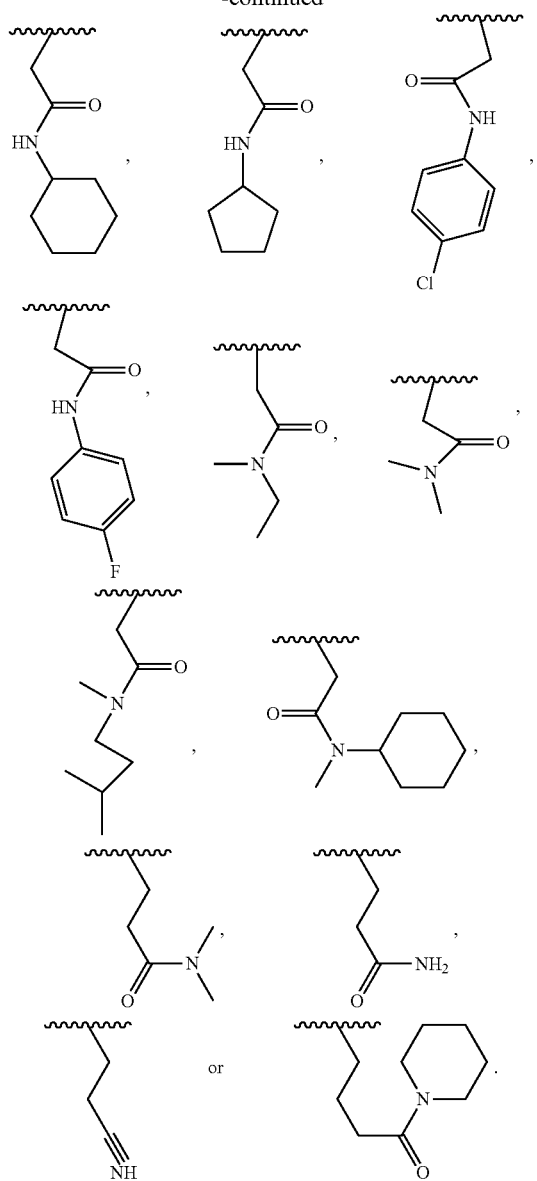

In another variation, a compound of the invention is of the formula (I), (E) or (Ia) or any variation of the foregoing detailed herein, or a compound according to any one of the formulae (IIa)-(IIn), (IIIa)-(IIIx), (IVa)-(IVf) or (Va)-(Vu) where q, m, Q and $R^{8a}$-$R^{8f}$ are taken together to form any of the moieties listed here or a moiety of the structure:

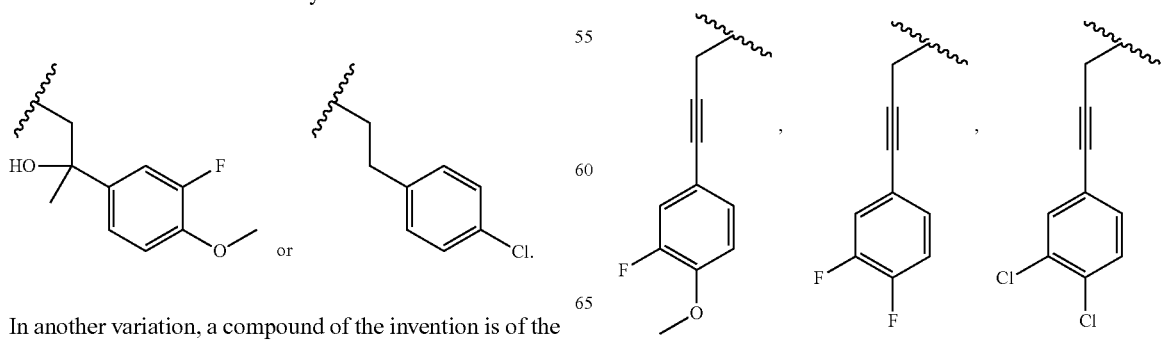

In another variation, a compound of the invention is of the formula (E) or (F) or any applicable variation of the foregoing detailed herein, where q, m, n, Q, $R^{8a}$-$R^{8f}$, $R^{11}$ and $R^{12}$ where applicable are taken together to form a moiety of the structure:

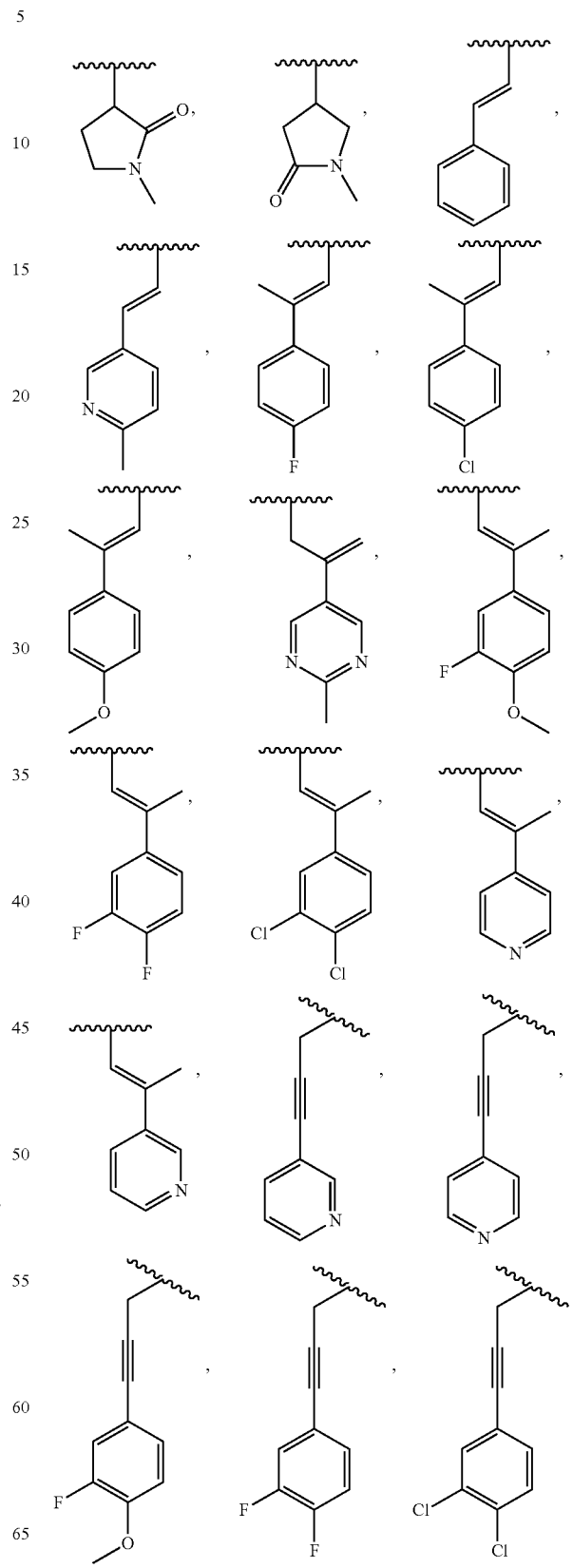

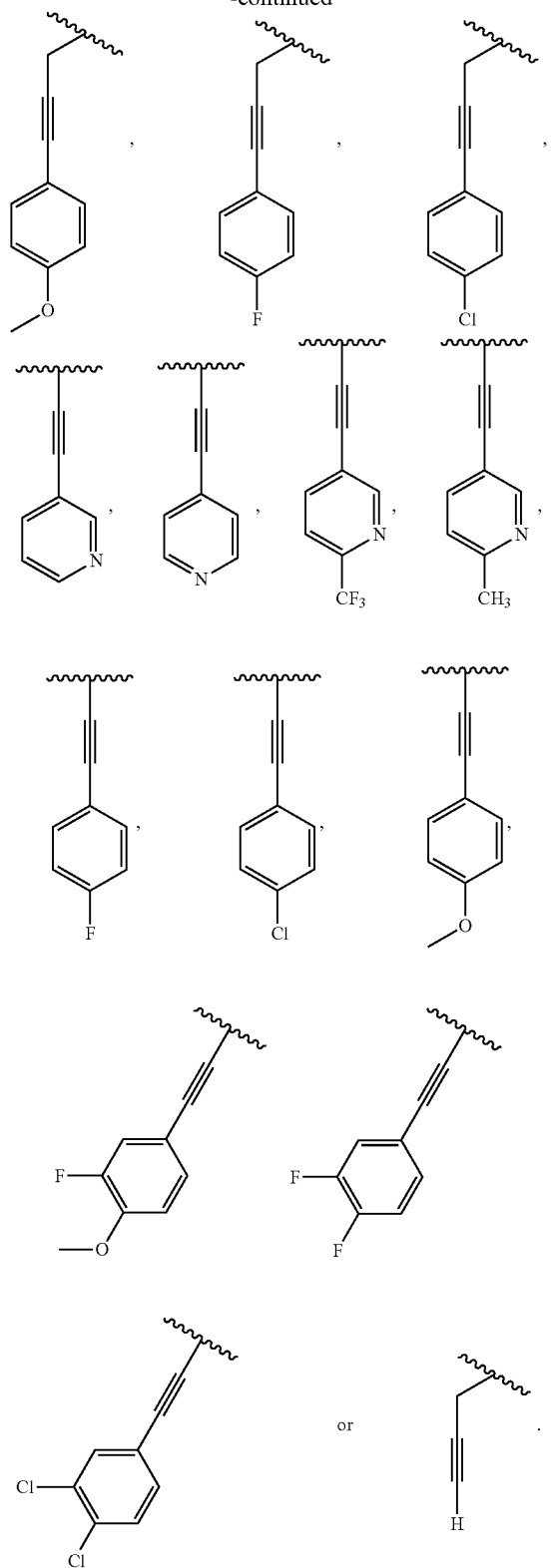

Examples of compounds according to the invention are depicted in Table 1. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE I

Representative Compounds According to the Invention

| Compound # | Structure |
|---|---|
| 1 | 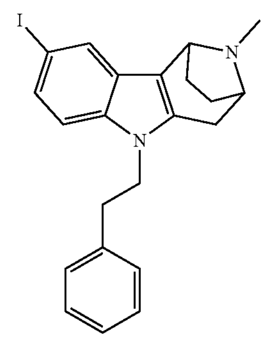 [SMILES: CN1C2CCC1c1c(n(CCc3ccccc3)c3ccc(I)cc13)C2] |
| 2 | 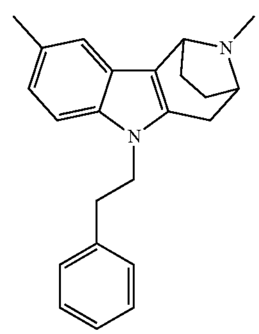 |
| 3 | 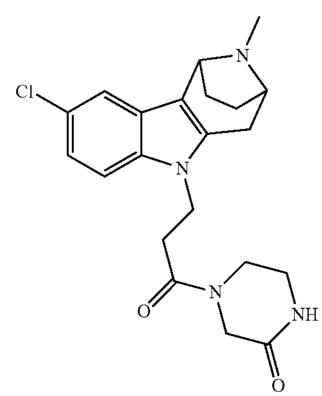 [SMILES: CN1C2CCC1c1c(n(CCC(=O)N3CCNC(=O)C3)c3ccc(Cl)cc13)C2] |

In another variation, a compound of the invention is of the formula (E) or (F) or any applicable variation of the foregoing detailed herein, where q, m, n, Q, $R^{8a}$-$R^{8f}$, $R^{11}$ and $R^{12}$ where applicable are taken together to form any of the moieties listed here or a moiety of the structure:

TABLE I-continued
Representative Compounds According to the Invention
| Compound # | Structure |
|---|---|
| 4 | 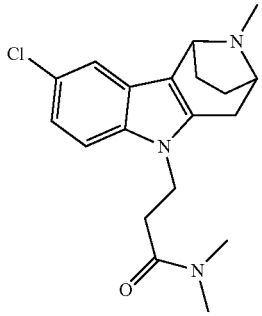 [SMILES: CN(C)C(=O)CCn1c2c(c3cc(Cl)ccc31)C1CCC(C2)N1C] |
| 5 | 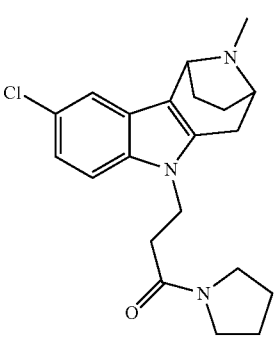 [SMILES: CN1C2CCC1c1c(n(CCC(=O)N3CCCC3)c3ccc(Cl)cc13)C2] |
| 6 | 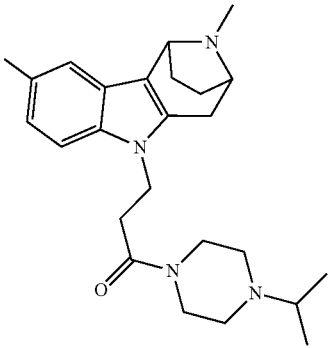 |
| 7 | 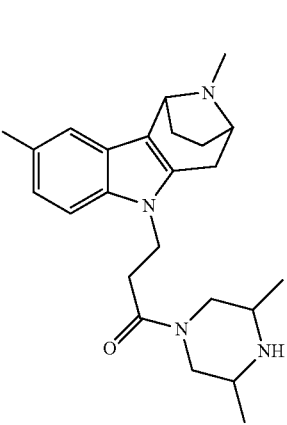 |
| 8 | 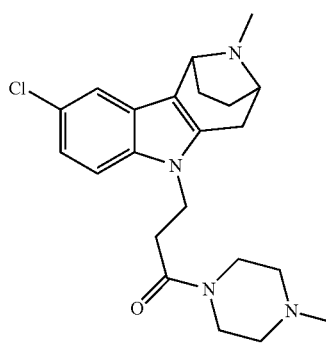 |
| 9 | 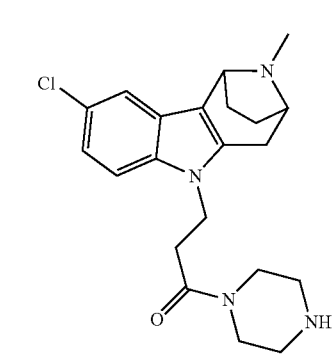 [SMILES: CN1C2CCC1c1c(n(CCC(=O)N3CCNCC3)c3ccc(Cl)cc13)C2] |
| 10 | 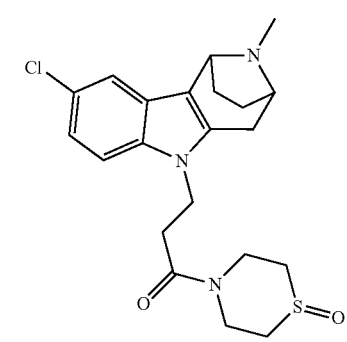 [SMILES: CN1C2CCC1c1c(n(CCC(=O)N3CCS(=O)CC3)c3ccc(Cl)cc13)C2] |
| 11 | 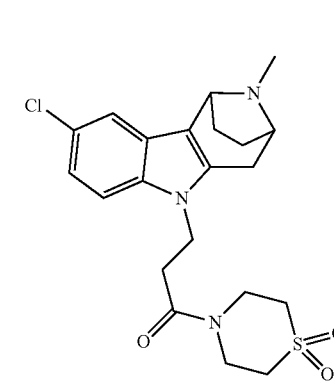 |

TABLE I-continued

Representative Compounds According to the Invention

| Compound # | Structure |
|---|---|
| 12 | (structure) |
| 13 | (structure) |
| 14 | (structure) |
| 15 | (structure) |
| 16 | (structure) |
| 17 | (structure) |
| 18 | (structure) |
| 19 | (structure) |

TABLE I-continued

Representative Compounds According to the Invention

| Compound # | Structure |
|---|---|
| 20 | *(structure)* |
| 21 | *(structure)* |
| 22 | *(structure)* |
| 23 | *(structure)* |
| 24 | *(structure)* |
| 25 | *(structure)* |
| 26 | *(structure)* |

TABLE I-continued

Representative Compounds According to the Invention

| Compound # | Structure |
|---|---|
| 27 | (structure) |
| 28 | (structure) |
| 29 | (structure) |
| 30 | (structure) |
| 31 | (structure) |
| 32 | (structure) |
| 33 | (structure) |
| 34 | (structure) |

TABLE I-continued

Representative Compounds According to the Invention

| Compound # | Structure |
|---|---|
| 35 | 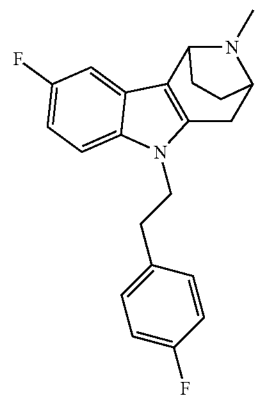 [SMILES: CN1C2CCC1c1c(n(CCc3ccc(F)cc3)c3ccc(F)cc13)C2] |
| 36 | 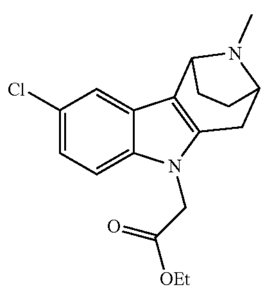 [SMILES: CCOC(=O)Cn1c2c(c3cc(Cl)ccc31)C1CCC(C2)N1C] |
| 37 | 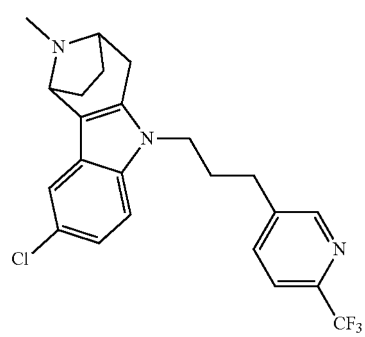 |
| 38 | 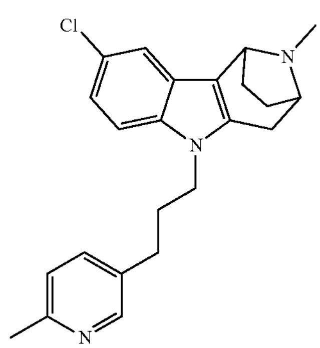 |
| 39 | |
| 40 | |
| 41 | |
| 42 | |

TABLE I-continued
Representative Compounds According to the Invention
| Compound # | Structure |
|---|---|
| 43 | 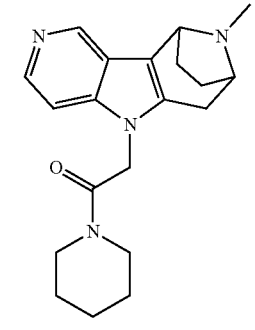 [SMILES: CN1C2CCC1c1c(n(CC(=O)N3CCCCC3)c3ccncc13)C2] |
| 44 | 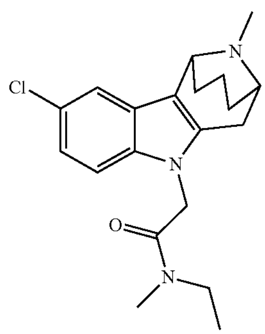 [SMILES: CCN(C)C(=O)Cn1c2c(c3cc(Cl)ccc31)C1CCCC(C2)N1C] |
| 45 | 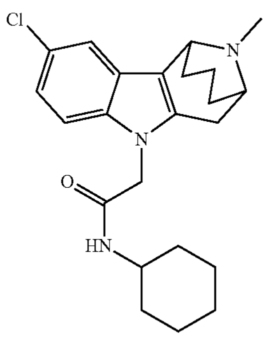 [SMILES: CN1C2CCCC1c1c(n(CC(=O)NC3CCCCC3)c3ccc(Cl)cc13)C2] |
| 46 | 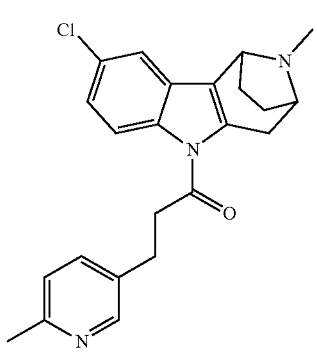 |
TABLE I-continued
Representative Compounds According to the Invention
| Compound # | Structure |
|---|---|
| 47 | 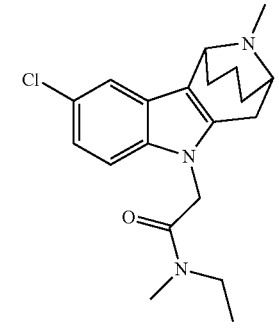 |
| 48 | 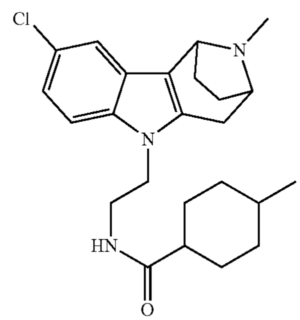 [SMILES: CC1CCC(C(=O)NCCn2c3c(c4cc(Cl)ccc42)C2CCC(C3)N2C)CC1] |
| 49 | 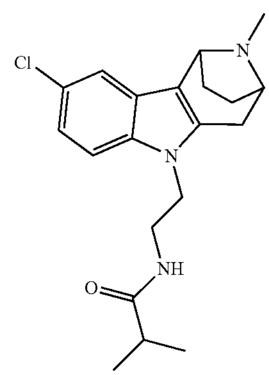 [SMILES: CC(C)C(=O)NCCn1c2c(c3cc(Cl)ccc31)C1CCC(C2)N1C] |
| 50 | 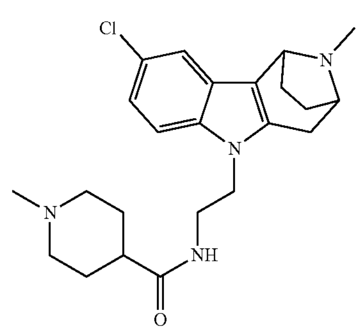 |

TABLE I-continued
Representative Compounds According to the Invention
| Compound # | Structure |
|---|---|
| 51 | 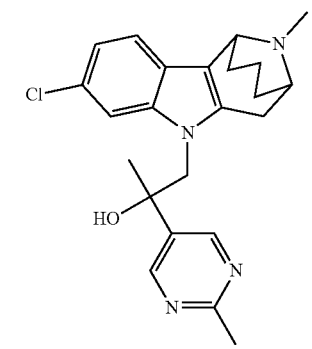 |
| 52 | 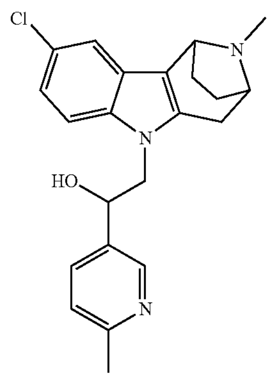 [SMILES: Cc1ccc(C(O)Cn2c3c(c4cc(Cl)ccc42)C2CCC(C3)N2C)cn1] |
| 53 | 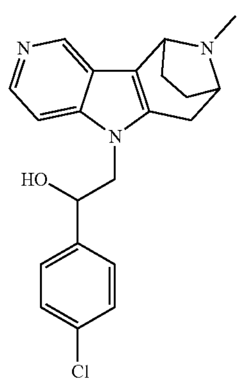 [SMILES: CN1C2CCC1c1c(n(CC(O)c3ccc(Cl)cc3)c3ccncc13)C2] |
| 54 | 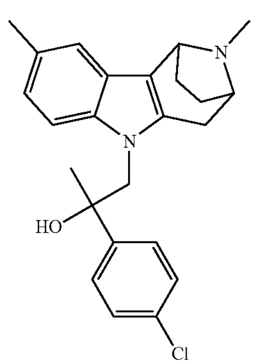 |
| 55 | 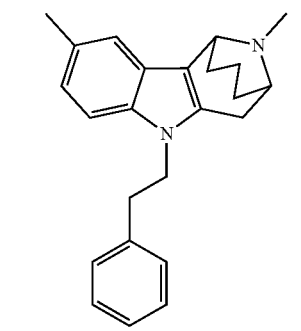 |
| 56 | 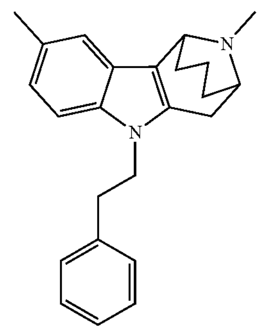 |
| 57 | 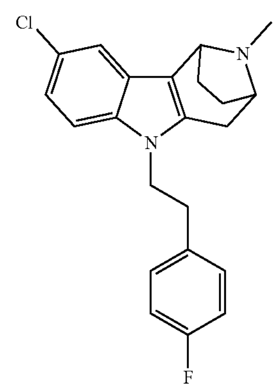 [SMILES: CN1C2CCC1c1c(n(CCc3ccc(F)cc3)c3ccc(Cl)cc13)C2] |
| 58 | 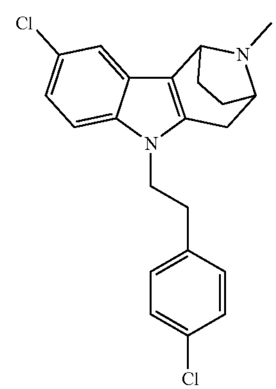 [SMILES: CN1C2CCC1c1c(n(CCc3ccc(Cl)cc3)c3ccc(Cl)cc13)C2] |

TABLE I-continued
Representative Compounds According to the Invention
| Compound # | Structure |
|---|---|
| 59 | 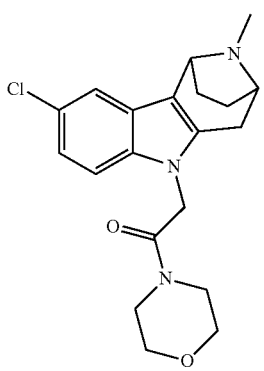 [SMILES: CN1C2CCC1c1c(n(CC(=O)N3CCOCC3)c3ccc(Cl)cc13)C2] |
| 60 | 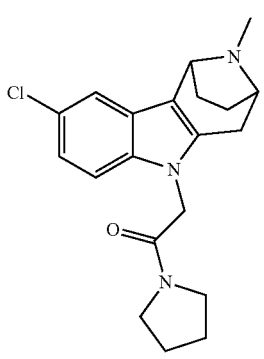 [SMILES: CN1C2CCC1c1c(n(CC(=O)N3CCCC3)c3ccc(Cl)cc13)C2] |
| 61 | 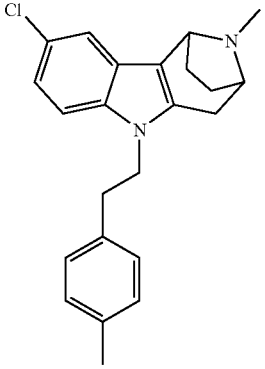 [SMILES: Cc1ccc(CCn2c3c(c4cc(Cl)ccc42)C2CCC(C3)N2C)cc1] |
| 62 | 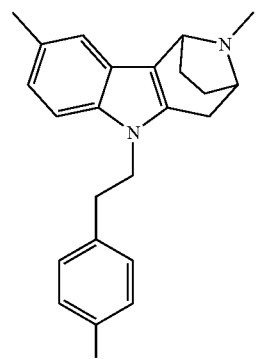 |
| 63 | 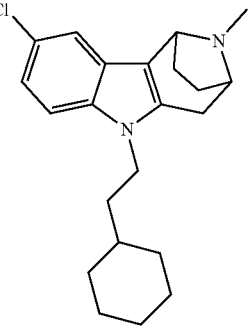 |
| 64 | 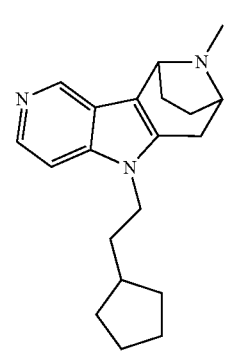 [SMILES: CN1C2CCC1c1c(n(CCC3CCCC3)c3ccncc13)C2] |
| 65 | 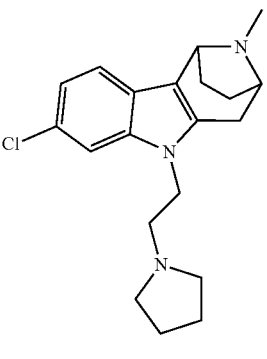 [SMILES: CN1C2CCC1c1c(n(CCN3CCCC3)c3cc(Cl)ccc13)C2] |
| 66 | 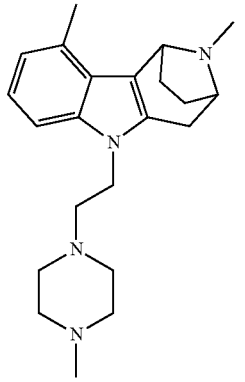 [SMILES: Cc1cccc2c1c1c(n2CCN2CCN(C)CC2)CC2CCC1N2C] |

TABLE I-continued

Representative Compounds According to the Invention

| Compound # | Structure |
|---|---|
| 67 | |
| 68 | |
| 69 | |
| 70 | |
| 71 | 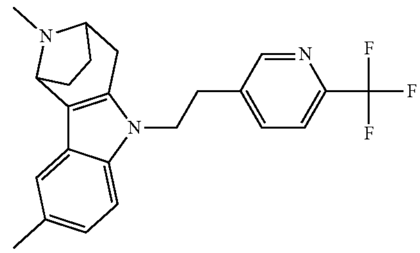 [SMILES: Cc1ccc2c(c1)c1c(n2CCc2ccc(C(F)(F)F)nc2)CC2CCC1N2C] |
| 72 | 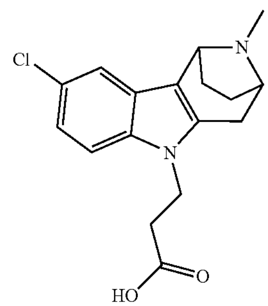 [SMILES: CN1C2CCC1c1c(n(CCC(=O)O)c3ccc(Cl)cc13)C2] |
| 73 | 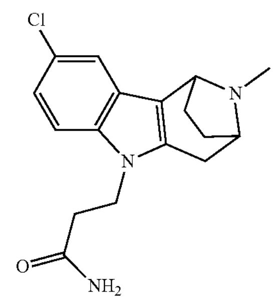 [SMILES: CN1C2CCC1c1c(n(CCC(N)=O)c3ccc(Cl)cc13)C2] |
| 74 | 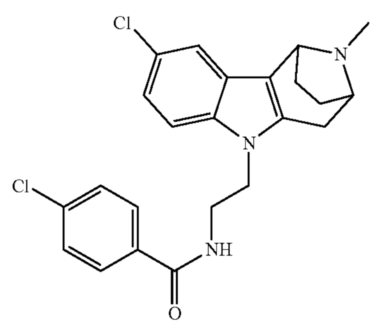 [SMILES: CN1C2CCC1c1c(n(CCNC(=O)c3ccc(Cl)cc3)c3ccc(Cl)cc13)C2] |
| 75 | 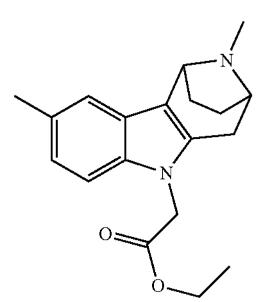 [SMILES: CCOC(=O)Cn1c2c(c3cc(C)ccc31)C1CCC(C2)N1C] |

TABLE I-continued
Representative Compounds According to the Invention
| Compound # | Structure |
|---|---|
| 76 | 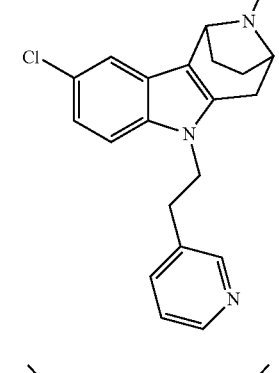 |
| 77 | 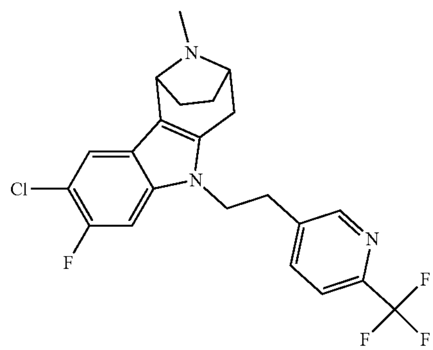 [SMILES: CN1C2CCC1c1c(n(CCc3ccc(C(F)(F)F)nc3)c3cc(F)c(Cl)cc13)C2] |
| 78 | 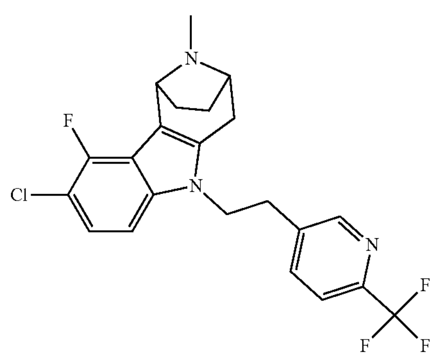 [SMILES: CN1C2CCC1c1c(n(CCc3ccc(C(F)(F)F)nc3)c3ccc(Cl)c(F)c13)C2] |
| 79 | 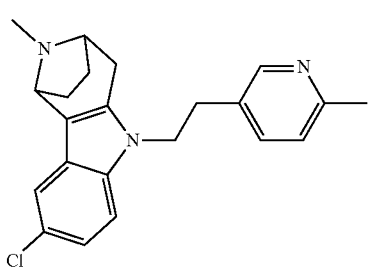 |
| 80 | 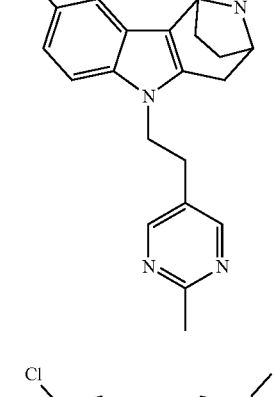 |
| 81 | |
| 82 | 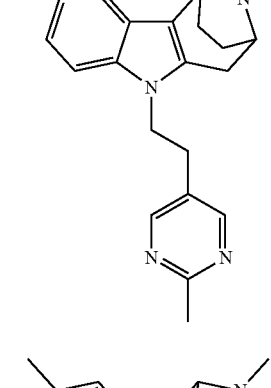 |
| 83 | 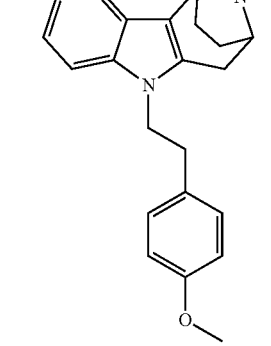 |

TABLE I-continued

Representative Compounds According to the Invention

| Compound # | Structure |
|---|---|
| 84 | 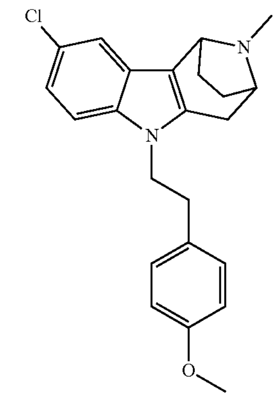 [SMILES: COc1ccc(CCn2c3c(c4cc(Cl)ccc42)C2CCC(C3)N2C)cc1] |
| 85 | 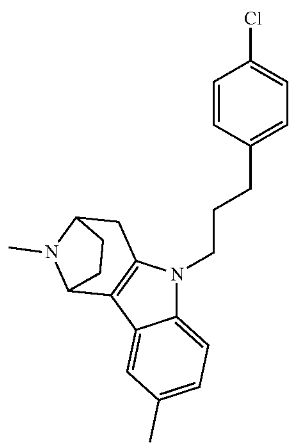 [SMILES: Cc1ccc2c(c1)c1c(n2CCCc2ccc(Cl)cc2)CC2CCC1N2C] |
| 86 | 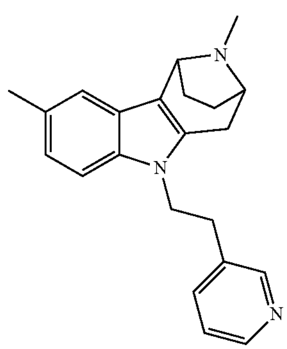 [SMILES: Cc1ccc2c(c1)c1c(n2CCc2cccnc2)CC2CCC1N2C] |
| 87 | 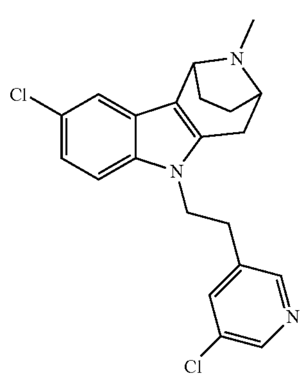 [SMILES: CN1C2CCC1c1c(n(CCc3cncc(Cl)c3)c3ccc(Cl)cc13)C2] |
| 88 | |
| 89 | |
| 90 | |
| 91 | |

TABLE I-continued

Representative Compounds According to the Invention

| Compound # | Structure |
|---|---|
| 92 | 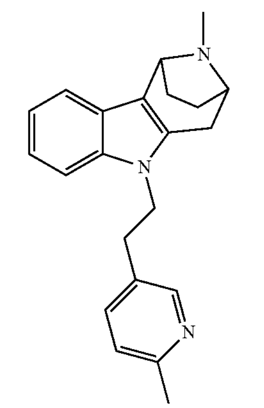 [SMILES: Cc1ccc(CCn2c3c(c4ccccc42)C2CCC(C3)N2C)cn1] |
| 93 | 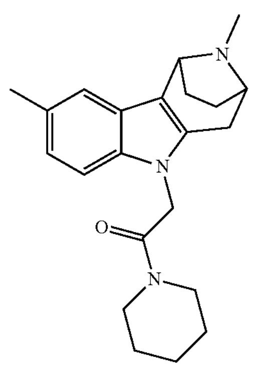 [SMILES: Cc1ccc2c(c1)c1c(n2CC(=O)N2CCCCC2)CC2CCC1N2C] |
| 94 | 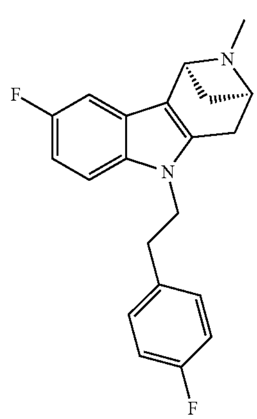 [SMILES: CN1[C@H]2Cc3c(c4cc(F)ccc4n3CCc3ccc(F)cc3)[C@@H]1C2] |
| 95 | 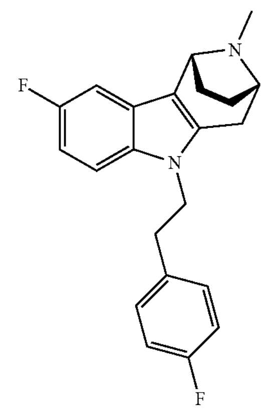 |
| 96 | 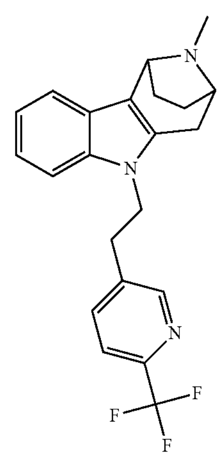 [SMILES: CN1C2CCC1c1c(n(CCc3ccc(C(F)(F)F)nc3)c3ccccc13)C2] |
| 97 | 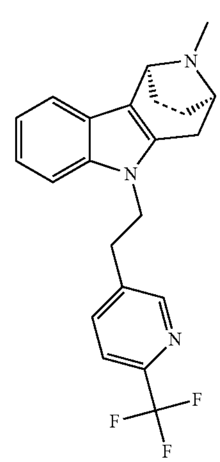 |

TABLE I-continued
Representative Compounds According to the Invention
| Compound # | Structure |
|---|---|
| 98 | 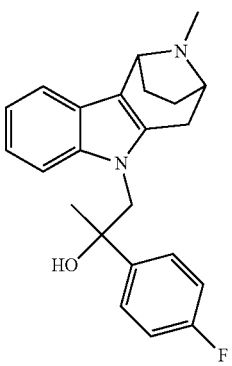 [SMILES: CN1C2CCC1c1c(n(CC(C)(O)c3ccc(F)cc3)c3ccccc13)C2] |
| 99 | 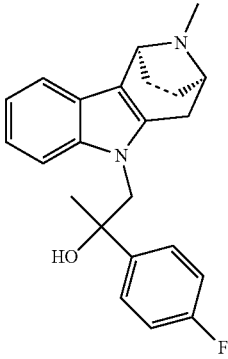 |
| 100 | 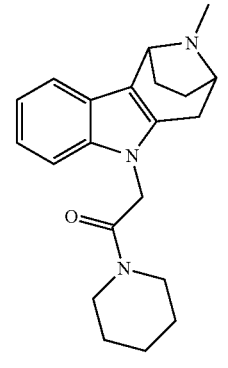 [SMILES: CN1C2CCC1c1c(n(CC(=O)N3CCCCC3)c3ccccc13)C2] |
| 101 | 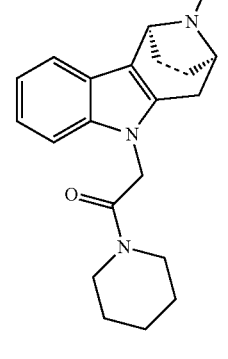 |
| 102 | 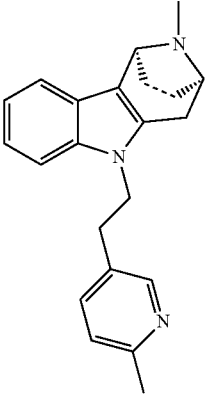 |
| 103 | 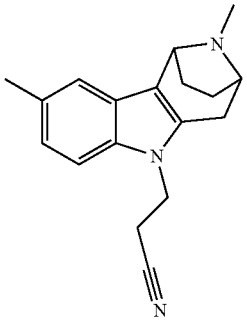 [SMILES: Cc1ccc2c(c1)c1c(n2CCC#N)CC2CCC1N2C] |
| 104 | 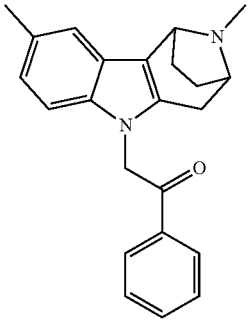 |
| 105 | 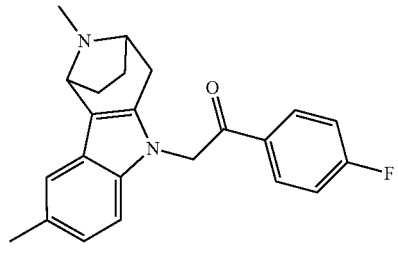 [SMILES: Cc1ccc2c(c1)c1c(n2CC(=O)c2ccc(F)cc2)CC2CCC1N2C] |

TABLE I-continued
Representative Compounds According to the Invention
| Compound # | Structure |
|---|---|
| 106 | 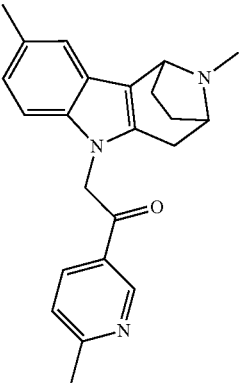 |
| 107 | 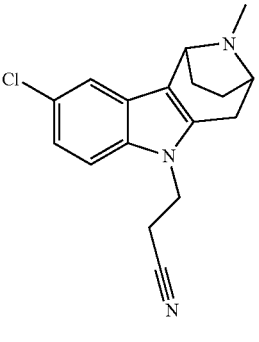 [SMILES: CN1C2CCC1c1c(n(CCC#N)c3ccc(Cl)cc13)C2] |
| 108 | 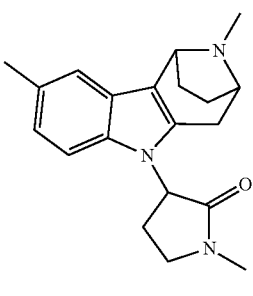 |
| 109 | 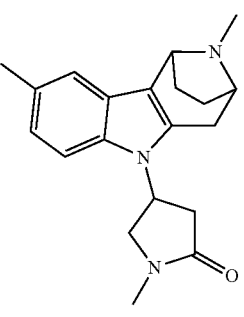 |
TABLE I-continued
Representative Compounds According to the Invention
| Compound # | Structure |
|---|---|
| 110 | 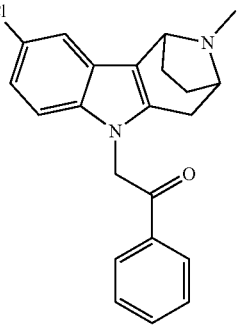 |
| 111 | 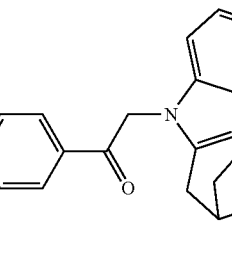 |
| 112 | 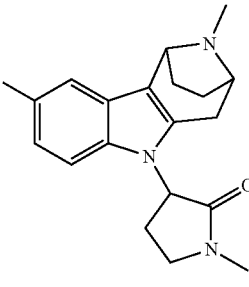 |
| 113 | 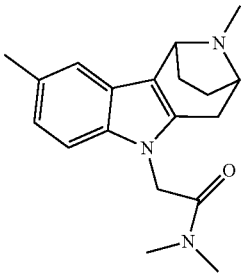 |
| 114 | 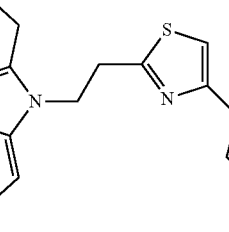 |

TABLE I-continued
Representative Compounds According to the Invention
| Compound # | Structure |
|---|---|
| 115 | 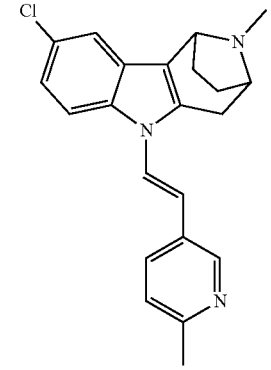 [SMILES: Cc1ccc(/C=C/n2c3c(c4cc(Cl)ccc42)C2CCC(C3)N2C)cn1] |
| 116 | 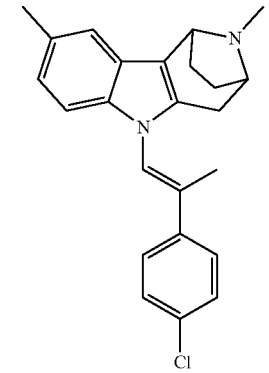 |
| 117 | 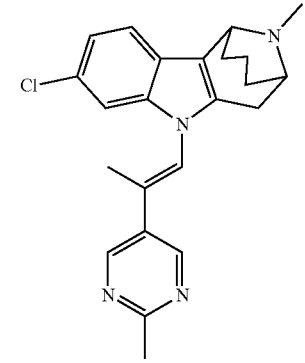 [SMILES: C/C(=C\n1c2c(c3ccc(Cl)cc31)C1CCCC(C2)N1C)c1cnc(C)nc1] |
| 118 | 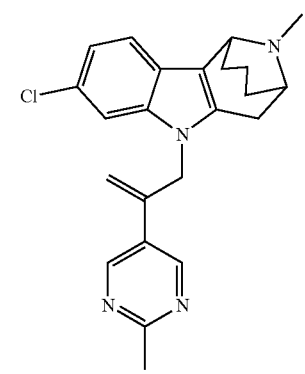 [SMILES: C=C(Cn1c2c(c3ccc(Cl)cc31)C1CCCC(C2)N1C)c1cnc(C)nc1] |
| 119 | 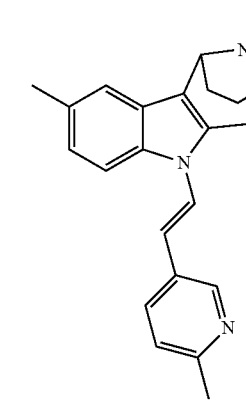 |
| 120 | 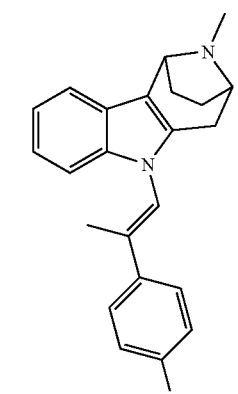 |
| 121 | 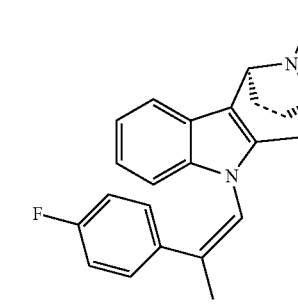 |
| 122 | 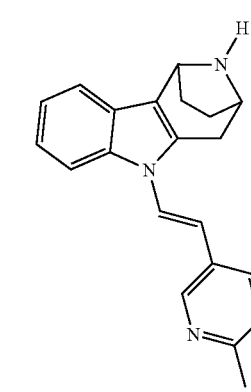 |

TABLE I-continued
Representative Compounds According to the Invention
| Compound # | Structure |
|---|---|
| 123 | 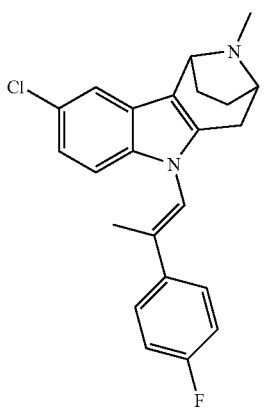 [SMILES: C/C(=C\n1c2c(c3cc(Cl)ccc31)C1CCC(C2)N1C)c1ccc(F)cc1] |
| 124 | 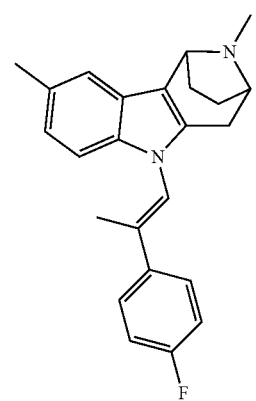 |
| 125 | 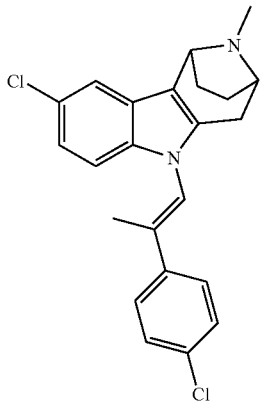 [SMILES: C/C(=C\n1c2c(c3cc(Cl)ccc31)C1CCC(C2)N1C)c1ccc(Cl)cc1] |
| 126 | 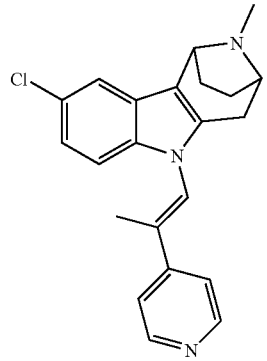 [SMILES: C/C(=C\n1c2c(c3cc(Cl)ccc31)C1CCC(C2)N1C)c1ccncc1] |
| 127 | 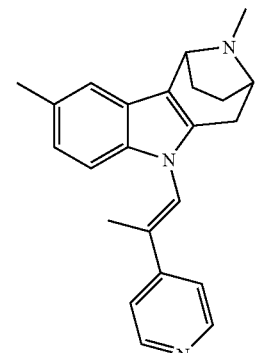 [SMILES: C/C(=C\n1c2c(c3cc(C)ccc31)C1CCC(C2)N1C)c1cccnc1] |
| 128 | 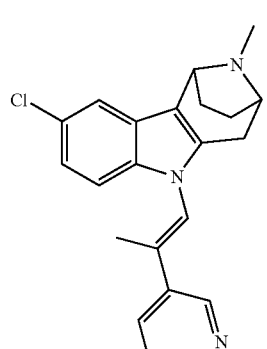 |
| 129 | 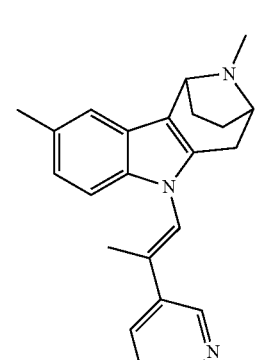 |

TABLE I-continued
Representative Compounds According to the Invention
| Compound # | Structure |
|---|---|
| 130 | 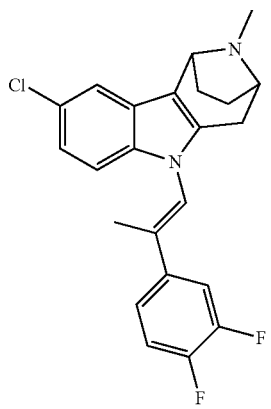 [SMILES: C/C(=C\n1c2c(c3cc(Cl)ccc31)C1CCC(C2)N1C)c1ccc(F)c(F)c1] |
| 131 | 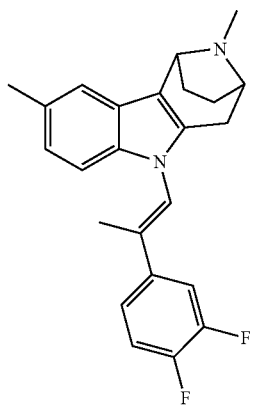 [SMILES: C/C(=C\n1c2c(c3cc(C)ccc31)C1CCC(C2)N1C)c1ccc(F)c(F)c1] |
| 132 | 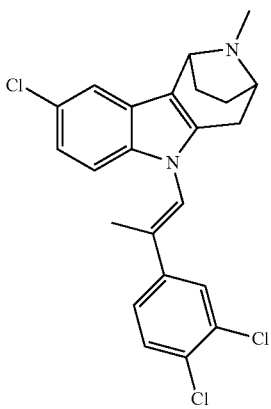 [SMILES: C/C(=C\n1c2c(c3cc(Cl)ccc31)C1CCC(C2)N1C)c1ccc(Cl)c(Cl)c1] |
TABLE I-continued
Representative Compounds According to the Invention
| Compound # | Structure |
|---|---|
| 133 | 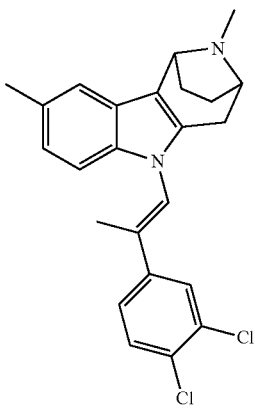 [SMILES: C/C(=C\n1c2c(c3cc(C)ccc31)C1CCC(C2)N1C)c1ccc(Cl)c(Cl)c1] |
| 134 | 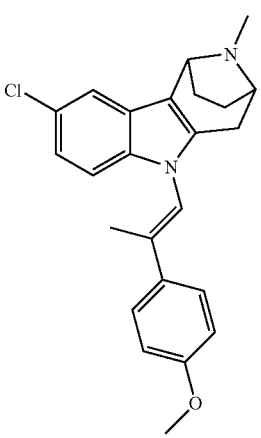 [SMILES: COc1ccc(/C(C)=C/n2c3c(c4cc(Cl)ccc42)C2CCC(C3)N2C)cc1] |
| 135 | 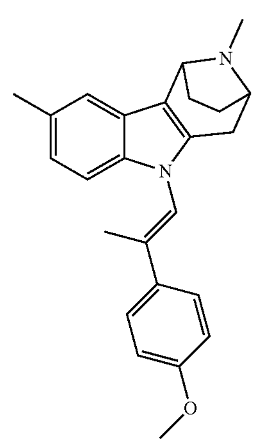 [SMILES: COc1ccc(/C(C)=C/n2c3c(c4cc(C)ccc42)C2CCC(C3)N2C)cc1] |

TABLE I-continued

Representative Compounds According to the Invention

| Compound # | Structure |
|---|---|
| 136 | 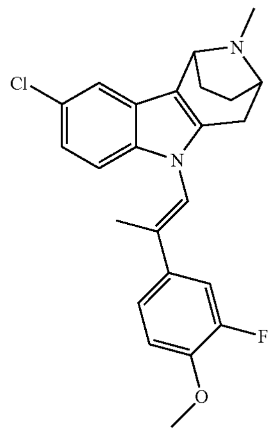 [SMILES: COc1ccc(/C(C)=C/n2c3c(c4cc(Cl)ccc42)C2CCC(C3)N2C)cc1F] |
| 137 | 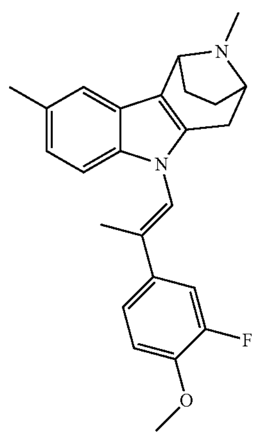 [SMILES: COc1ccc(/C(C)=C/n2c3c(c4cc(C)ccc42)C2CCC(C3)N2C)cc1F] |
| 138 | 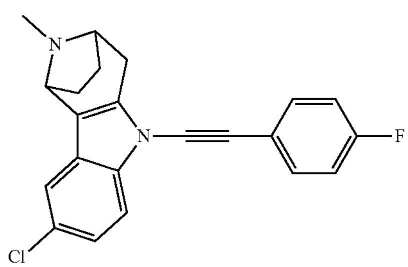 [SMILES: CN1C2CCC1c1c(n(C#Cc3ccc(F)cc3)c3ccc(Cl)cc13)C2] |
| 139 | 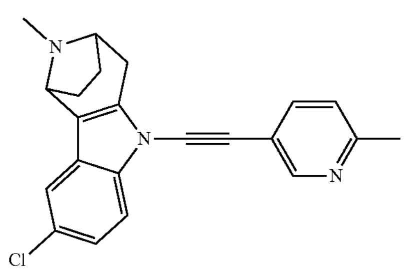 |
| 140 | |
| 141 | |
| 142 | |
| 143 | |

TABLE I-continued

Representative Compounds According to the Invention

| Compound # | Structure |
|---|---|
| 144 | 5-Cl, pyridin-4-yl alkyne |
| 145 | 5-methyl, pyridin-4-yl alkyne |
| 146 | 5-Cl, pyridin-3-yl alkyne |
| 147 | 5-methyl, pyridin-3-yl alkyne |
| 148 | 5-Cl, 3,4-difluorophenyl alkyne |
| 149 | 5-methyl, 3,4-difluorophenyl alkyne |
| 150 | 5-Cl, 3,4-dichlorophenyl alkyne |

TABLE I-continued
Representative Compounds According to the Invention
| Compound # | Structure |
|---|---|
| 151 | 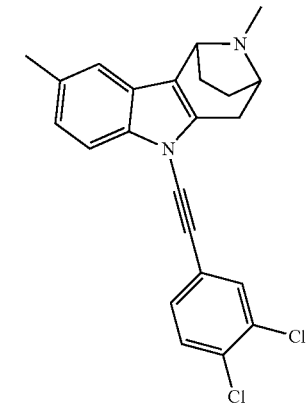 [SMILES: Cc1ccc2c(c1)c1c(n2C#Cc2ccc(Cl)c(Cl)c2)CC2CCC1N2C] |
| 152 | |
| 153 | |
| 154 | 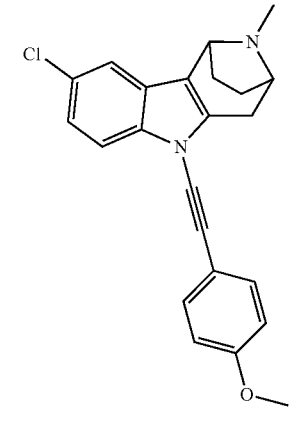 [SMILES: COc1ccc(C#Cn2c3c(c4cc(Cl)ccc42)C2CCC(C3)N2C)cc1] |
| 155 | 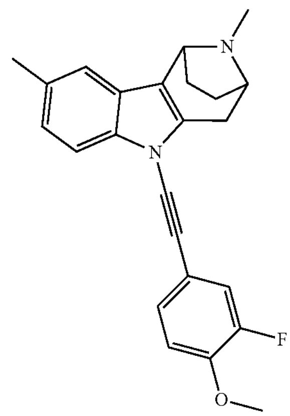 |
| 156 | 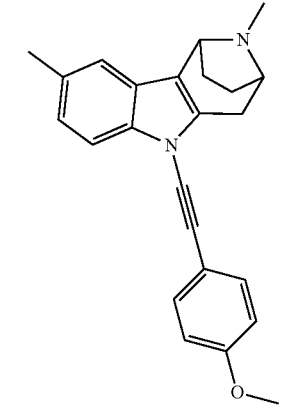 |
| 157 | 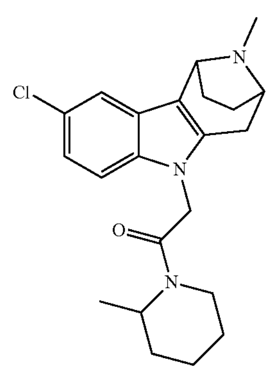 [SMILES: CC1CCCCN1C(=O)Cn1c2c(c3cc(Cl)ccc31)C1CCC(C2)N1C] |

TABLE I-continued

Representative Compounds According to the Invention

| Compound # | Structure |
|---|---|
| 158 | 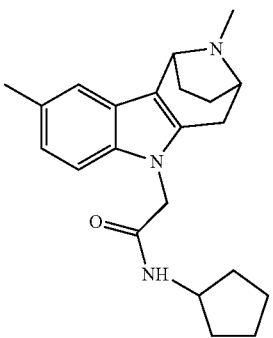 [SMILES: Cc1ccc2c(c1)c1c(n2CC(=O)NC2CCCC2)CC2CCC1N2C] |
| 159 | 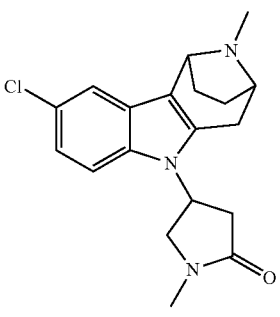 [SMILES: CN1CC(n2c3c(c4cc(Cl)ccc42)C2CCC(C3)N2C)CC1=O] |
| 160 | 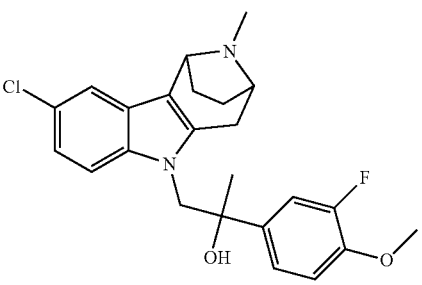 [SMILES: COc1ccc(C(C)(O)Cn2c3c(c4cc(Cl)ccc42)C2CCC(C3)N2C)cc1F] |
| 161 | 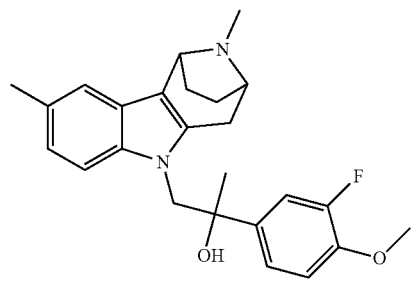 |
| 162 | 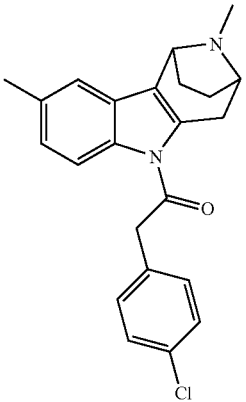 [SMILES: Cc1ccc2c(c1)c1c(n2C(=O)Cc2ccc(Cl)cc2)CC2CCC1N2C] |
| 163 | 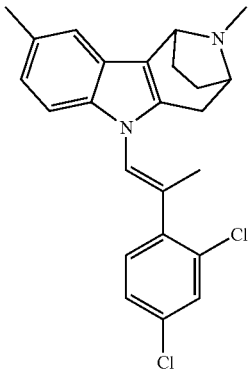 |
| 164 | 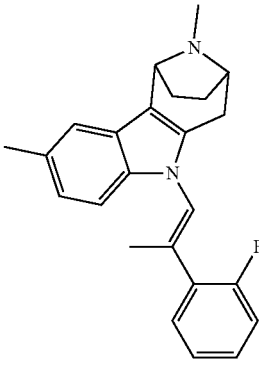 |
| 165 | 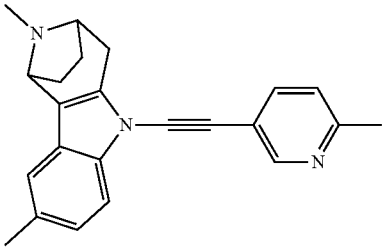 |

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. Pharmaceutical compositions according to the invention may take a form suitable for oral buccal, parenteral, nasal, topical or rectal administration or a form suitable for administration by inhalation.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms pharmaceutical compositions and methods of administering the compounds are suitable for any compound or form thereof detailed herein.

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha 1D$, $\alpha 2A$ and $\alpha 2B$), inhibition of binding of a ligand to a serotonin receptor (e.g., 5-HT2A, 5-HT2C, 5-HT6 and 5-HT7), inhibition of binding of a ligand to a dopamine receptor (e.g., D2L), and inhibition of binding of a ligand to a histamine receptor (e.g., H1, $H_2$ and H3); agonist/antagonist activity to a serotonin receptor (e.g., 5-HT2A, 5-HT6); agonist/antagonist activity to a dopamine receptor (e.g., D2L, D2S); agonist/antagonist activity to a histamine receptor (e.g., H1); activity in a neurite outgrowth assay; efficacy in a preclinical model of memory dysfunction associated with cholinergic dysfunction/hypofunction; and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85-95% or between about 90100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g. $\alpha 1D$, $\alpha 2A$, $\alpha 2B$, 5-HT2A, 5-HT2C, 5-HT6, 5-HT7, D2L, H1, H2, H3). In one variation, a compound of the invention inhibits binding of a ligand to at least one and as many as eleven receptors detailed herein and further displays agonist or antagonist activity to one or more receptors detailed herein (e.g., serotonin receptor 5HT2A, serotonin receptor 5-HT6, dopamine receptor D2L, and dopamine receptor D2S, histamine receptor H1) as measured in the assays described herein. In one variation, agonist response of serotonin receptor 5-HT2A is inhibited by compounds of the invention by at least about any one of 50%, 50%, 70%, 80%, 90%, 100%, 110%; 120%, 130%, 140%, 150% as determined in a suitable assay such as the assay described herein.

In one variation, a compound of the invention displays the above described neurotransmitter receptor binding profile i.e. inhibits binding of a ligand to at least one receptor and as many as eleven as detailed herein and further stimulates neurite outgrowth, e.g. as measured by the assays described herein. Certain compounds of the invention showed activity in neurite outgrowth assays using primary neurons in culture (see Example 11B). Data is presented indicating that a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention: inhibits binding of a ligand to at least one receptor and as many as eleven as detailed herein, further displays agonist or antagonist activity to one or more receptors detailed herein and further stimulates neurite outgrowth.

In a further variation, a compound of the intention inhibits binding of a ligand to at least one and as many as eleven receptors as detailed herein and/or display the above described neurotransmitter receptor binding profile and further shows efficacy in a preclinical model of memory dysfunction associated with cholinergic dysfunction/hypofunction, i.e. shows pro-cognitive effects in a preclinical model of memory dysfunction. As HI antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a 5-HT6 antagonist may have cognition-enhancing effects as serotonin acting through this receptor may impair memory.

In another variation, a compound of the invention inhibits at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction and further stimulates neurite outgrowth.

In another variation, a compound of the invention inhibits at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, further displays agonist or antagonist activity to one or more receptor detailed herein and further stimulates neurite outgrowth.

In a further variation, a compound of the invention inhibits binding of a ligand to at least one and as many as eleven receptors and further possesses anti-psychotic effects as measured in a preclinical model of schizophrenia, i.e., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic dysfunction/hypofunction such as enhancement of memory retention and reduction of memory impairment, and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic dysfunction/hypofunction such as enhancement of memory retention and reduction of memory impairment.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment.

In a further variation, a compound of the invention inhibits binding to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic dysfunction/hypofunction such as enhancement of memory retention and reduction of memory impairment.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic dysfunction/hypofunction such as enhancement of memory retention and reduction of memory impairment. In another variation, a compound of the invention shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment.

In one aspect, compounds of the invention inhibit binding of a ligand to adrenergic receptors α1D, α2A, α2B and inhibit binding of a ligand to serotonin receptor 5-HT6. In another variation, compounds of the invention inhibit binding of a ligand to adrenergic receptors α1D, α2A, α2B, to serotonin receptor 5-HT6 and to any one or more of the following receptors: serotonin receptor 5-HT7, 5-HT2A and 5-HT2C. In another variation, compounds of the invention inhibit binding of a ligand to adrenergic receptors α1D, α2A, α2B, to serotonin receptor 5-HT6 and to any one or more of the following receptors: serotonin receptor 5-HT7, 5-HT2A and 5-HT2C and further show weak inhibition of binding of a ligand to histamine receptor H1 and/or H2. In one variation, compounds of the invention that also display strong inhibition of binding of a ligand to the serotonin receptor 5-HT7 are particularly desired. In another variation, compounds of the invention inhibit binding of a ligand to adrenergic receptors α1D, α2A, α2B, to serotonin receptor 5-HT6 and further show weak inhibition of binding of a ligand to histamine receptor H1 and/or H2. Weak inhibition of binding of a ligand to the histamine H1 receptor is permitted as agonists of this receptor have been implicated in stimulating memory as well as weight gain. In one variation, binding to histamine receptor H1 is inhibited by less than about 80%. In another variation, binding of a ligand to histamine receptor H1 is inhibited by less than about any of 75%, 0%, 65%, 60%, 55%, or 50% as determined by a suitable assay known in the art such as the assays described herein.

In another variation, compounds of the invention inhibit binding of a ligand to dopamine receptor D2L. In another variation, compounds of the invention inhibit binding of a ligand to dopamine receptor D2L and to serotonin receptor 5-HT2A. In another variation, compounds of the invention inhibit binding of a ligand to histamine receptor H1. In certain aspects, compounds of the ligand to the serotonin 5-HT7 receptor, strong inhibition of binding of a ligand to the serotonin 5-HT2A receptor, strong inhibition of binding of a ligand to the serotonin 5-HT2C receptor, weak inhibition of binding of a ligand to the histamine H1 receptor, weak inhibition of binding of ligands to the histamine H2 receptor, and antagonist activity to serotonin receptor 5-HT2A.

In one variation, compounds of the invention show any of the receptor binding aspects detailed herein and further display agonist/antagonist activity to one or more of the following receptors: serotonin receptor 5-HT2A, serotonin receptor 5-HT6, dopamine receptor D2L, dopamine receptor D2S and histamine receptor H1. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic dysfunction/hypofunction. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-HT2A, 5-HT6, dopamine receptor D2L, dopamine receptor D2S and histamine receptor H1), neurite outgrowth, a preclinical model of memory dysfunction associated with cholinergic dysfunction; hypofunction and a preclinical model of schizophrenia.

In some aspects, compounds of the invention inhibit binding of a ligand to adrenergic receptors α1D, α2A, α2B, serotonin receptor 5-HT6 and dopamine receptor D2L by at least about 80% as determined in a suitable assay known in the art such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85% and about 95%, or between about 90% and about 100% as determined in a suitable assay known in the art such as the assays described herein.

In some aspects, compounds of the invention display the above described neurotransmitter receptor binding profile and further show antipsychotic effects. It is recognized that compounds of the invention have binding profiles similar to compounds with antipsychotic activity. In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show pro-cognitive effects in a preclinical model of memory dysfunction such as enhancement of memory retention and reduction of memory impairment due to cholinergic hypofunction in preclinical animal models. In another variation, compounds of the invention display the above described neurotransmitter receptor binding profile and do not show pro-cognitive effects in a preclinical model of memory dysfunction, learning and memory.

In one variation, compounds of the invention demonstrate pro-cognitive effects in a preclinical model of memory dysfunction, learning and memory. In a further variation, compounds of the invention possess anti-psychotic effects in a preclinical model of schizophrenia. In a further variation, compounds of the invention demonstrate pro-cognitive effects in a preclinical model of memory dysfunction, learning and memory and further possess anti-psychotic effects in a preclinical model of schizophrenia.

Overview of the Methods

The compounds described herein may be used to treat, prevent, delay and onset and/or delay the development of cognitive disorders, psychotic disorders, neurotransmitter-mediated disorders and/or neuronal dividers in individuals, such as humans. In one aspect, the compounds described herein may be used to treat, prevent, delay the onset and/or delay the development of a cognitive disorder. In another aspect, the compounds described herein may be used to treat, prevent, delay the onset and/or delay the development of a psychotic disorder. In yet another aspect, the compounds described herein may be used to treat, prevent, delay the onset and/or delay the development of a neurotransmitter-mediated disorders disorder. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, Guillain-Barré syndrome, mild cognitive impairment, multiple sclerosis, stroke and traumatic brain injury. In yet another embodiment, the neurotransmitter-mediate disorder includes schizophrenia, anxiety, bipolar disorders, psychosis and depression. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor α1D, α2A, α2B, serotonin receptor 5-HT2A, 5-HT6, 5HT7, histamine receptor H1 and/or H2 is expected to be or is beneficial for the cognitive disorders, psychotic disorders, neurotransmitter-mediated disorders and/or neuronal disorders. In some variation, modulation adrenergic receptor α1D, α2A, α2B and a serotonin receptor 5-HT6 receptor is expected to be or is beneficial for the cognitive disorders, psychotic disorders, neurotransmitter-mediated disorders and/or neuronal disorders. In some variations, modulation of adrenergic receptor α1D, α2A, α2B, and a serotonin receptor 5-HT6 receptor and modulation of one or more of the following receptors serotonin 5-HT7, 5-HT2A, 5-HT2C and histamine H1 and H2 is expected to be or is beneficial for the cognitive disorders, psychotic disorders, neurotransmitter-mediated disorders and/or neuronal disorders. In some variations, modulation of dopamine receptor D2L is expected to be or is beneficial for the cognitive disorders, psychotic disorders, neurotransmitter-mediated disorders and/or neuronal disorders. IN certain variations, modulation of a dopamine D2L receptor and serotonin receptor 5-HT2A is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor α1D, α2A, α2B, serotonin receptor 5-HT2A, 5-HT6, 5HT7, histamine receptor H1 and/or H2 is desirable or expected to be desirable to improve cognitive functions. In some variations modulation of α1, α2A, α2B adrenergic receptors and a serotonin 5-HT6 receptor is desirable or expected to be desirable to improve cognitive functions. IN some variations, modulation of α1D, α2A, α2B adrenergic receptors and serotonin receptor 5-HT6 and modulation of one or more of the following receptors: serotonin receptor 5-HT7, 5-HT2A, 5-HT2C and histamine receptor H1 and H2, is desirable or expected to be desirable to improve cognitive functions. In another aspect, the invention encompasses methods to reduce psychotic effects by administering a compound of the invention to an individual in need thereof. In some embodiments, modulation of a dopamine D2L receptor is expected to be or is desirable to reduce psychotic effects. In some embodiments, modulation of a dopamine D2L receptor and a serotonin 5-HT2A receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G-protein-coupled receptor is a α1D, α2A, α2B adrenergic receptor and a serotonin 5-HT6 receptor. In some variations, the aminergic G protein-coupled receptor is a α1D, α2A, α2B adrenergic receptor and a serotonin 5-HT6 and 5-HT7 receptor. In some variations, the aminergic G protein-coupled receptor is a α1D, α2A, α2B adrenergic receptor, a serotonin 5-HT6 and one or more of the following receptors: serotonin 5-HT-7, 5-HT2A, and 5-HT2C and histamine H1 and H2 receptor. In some variations, the aminergic G protein-coupled receptor is a dopamine D2L receptor. In some variations, the aminergic G protein-coupled receptor is a dopamine D2L receptor and a serotonin 5-HT2A receptor. In some variations, the aminergic G protein-coupled receptor is a histamine H1 receptor.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

By way of example only, using suitable methods such as those detailed herein, compounds of the formula (E) may be resolved to provide compounds of the formulae (Ea) and (Eb):

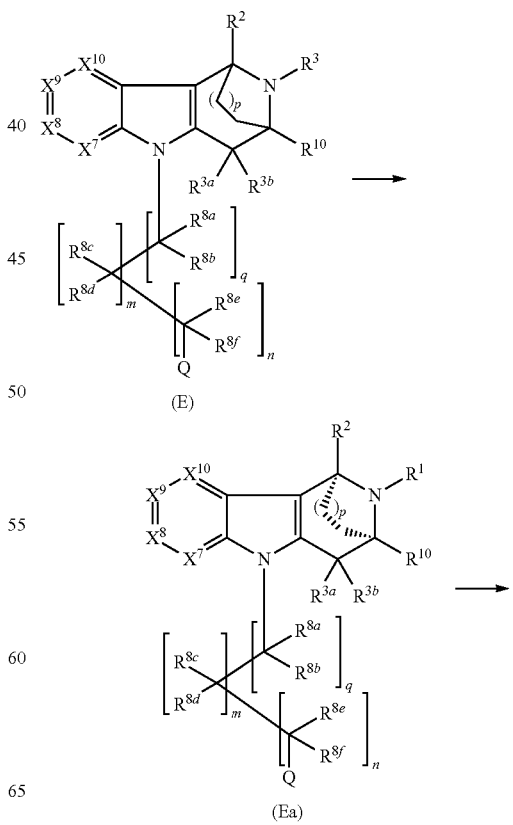

-continued

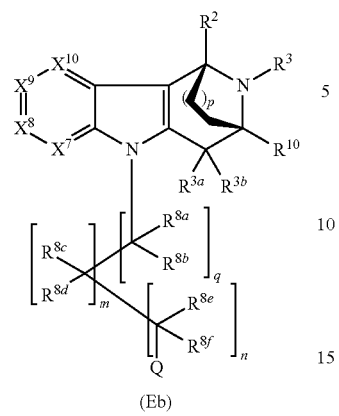

(Eb)

The following abbreviations are used herein: thin layer chromatography (TLC); Hour (h); Ethanol (EtOH); dimethylsulfoxide (DMSO); N,N-dimethylformamide (DMF); trifluoroacetic acid (TFA); teterahydrofuran (THF); Normal (N); aqueous (aq.); methanol (MeOH); dichloromethane (DCM); Retention factor (Rf).

A method of synthesizing an intermediate used in the synthesis of compounds of the invention is shown as General Method 1-12. Compounds made by General Methods 2 and 12 may also be used as intermediates for the synthesis of other compounds of the invention.

General Synthetic Method 1

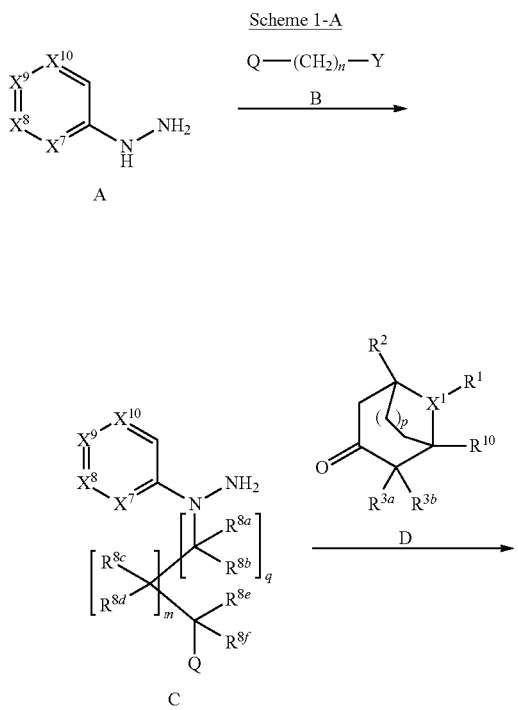

-continued

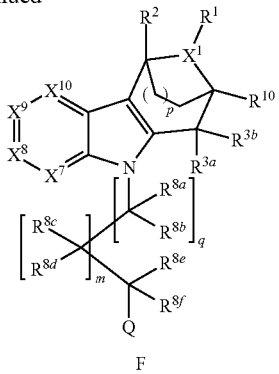

F m and q = 0 or 1
Y = Cl, Br, I, OTs, OMs, OTf, OH
p = 1 or 2

In general, a suitably substituted hydrazine A can be reacted with an appropriately substituted reagent B to generate a substituted hydrazine C, where the internal nitrogen on the hydrazine is substituted, as shown above. The reaction of intermediate C with an appropriately substituted 4-dialkylamino cyclohexanone D should provide structures of the type generally described by structure F.

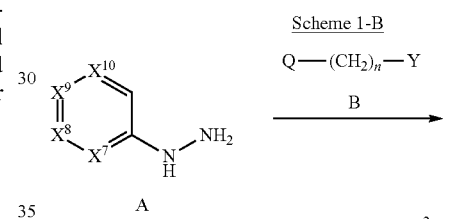

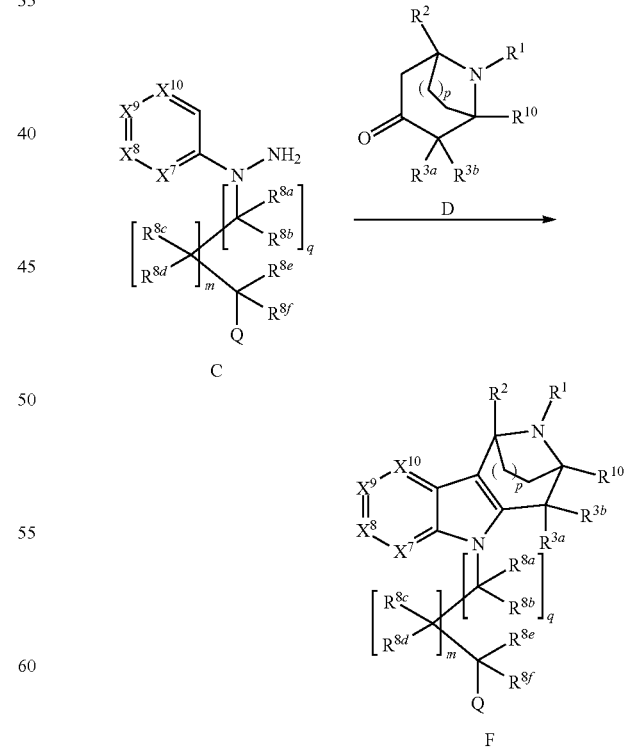

m and q = 0 or 1
Y = Cl, Br, I, OTs, OMs, OTf, OH
p = 1 or 2

Similar synthetic details may be employed for compounds made according to Scheme 1-A.

Scheme 1-C

Similar synthetic details may be employed for compounds made according to Scheme 1-A in general methods for synthesis of structures of the type generally described by structure F, wherein Q is aryl, substituted aryl, heteroaryl (five and six membered) and substituted heteroaryl (five and six membered).

Scheme 1-D

Similar synthetic details may be employed for compounds made according to Scheme 1-A in general methods for synthesis of structures of the type generally described by structure F, wherein Q is alkyl, substituted alkyl, amino, substituted amino, thio, substituted thio, alkoxy, cycloalkyl and heterocyclic (including 4, 5, 6 and 7-membered rings).

Scheme 1-E

Similar synthetic details may be employed for compounds made according to Scheme 1-A in general methods for synthesis of structures of the type generally described by structure F, wherein q and m=0, and Q is alkyl, substituted alkyl, amino, substituted amino, thio, substituted thio, alkoxy, cycloalkyl and heterocyclic including 4, 5, 6 and 7-membered rings).

Scheme 1-F

Similar synthetic details may be employed for compounds made according to Scheme 1-A in general methods for synthesis of structures of the type generally described by structure F, wherein m=0, q=1, $R^{8a}$ and $R^{8b}$ taken together with the carbon to which it is attached form a carbonyl moiety, $R^{8a}$ and $R^{8b}$ is independently H, hydroxyl or $C_1$-$C_8$ alkyl; and Q is alkyl, substituted alkyl, amino, substituted amino, thio, substituted thio, alkoxy, cycloalkyl and heterocyclic (including, 4, 5, 6 and 7-membered rings).

Scheme 1-G

Similar synthetic details may be employed for Compounds made according to Scheme 1-A in general methods for synthesis of structures of the type generally described by structure F, wherein m=0, q=1, $R^{8e}$ and $R^{8f}$ taken together with the carbon to which it is attached form a carbonyl moiety, $R^{8a}$ and $R^{8b}$ is independently H, hydroxyl or $C_1$-$C_8$ alkyl; and Q is alkyl, substituted alkyl, amino, substituted amino, thio, substituted thio, alkoxy, cycloalkyl and heterocyclic (including 4, 5, 6 and 7-membered rings).

Scheme 1-H

Similar synthetic details may be employed for compounds made according to Scheme 1-A In general methods for synthesis of structures of the type generally described by structure F, wherein m and q=1, $R^{8a}$ and $R^{8b}$ taken together with the carbon to which it is attached form a carbonyl moiety, $R^{8c}$, $R^{8d}$, $R^{8e}$ and $R^{8f}$ is independently H, hydroxyl or $C_1$-$C_8$ alkyl; and Q is alkyl, substituted alkyl, amino, substituted amino, thio, substituted thio, alkoxy, cycloalkyl and heterocyclic (including 4, 5, 6 and 7-membered rings).

Scheme 1-I

Similar synthetic details may be employed for compounds made according to Scheme 1-A in general methods for synthesis of structures of the type generally described by structure F, wherein m and q=1, $R^{8e}$ and $R^{8f}$ taken together with the carbon to which it is attached form a carbonyl moiety, $R^{8a}$, $R^{8b}$, $R^{8c}$ and $R^{8d}$ is independently H, hydroxyl or $C_1$-$C_8$ alkyl; and Q is alkyl, substituted alkyl, amino, substituted amino, thio, substituted thio, alkoxy, cycloalkyl and heterocyclic (including 4, 5, 6 and 7-membered rings).

Scheme 1-J

Similar synthetic details may be employed for compounds made according to Scheme 1-A in general methods for synthesis of structures of the type generally described by structure F, wherein q and m=0, and Q is COOR.

Scheme 1-K

Similar synthetic details may be employed for compounds made according to Scheme 1-A in general methods for synthesis of structures of the type generally described by structure F, wherein m=0, q=1, and Q is COOR.

Scheme 1-L

Similar synthetic details may be employed for compounds made according to Scheme 1-A in general methods for synthesis of structures of the type generally described by structure F, wherein m and q=1, and Q is COOR.

General Method 2

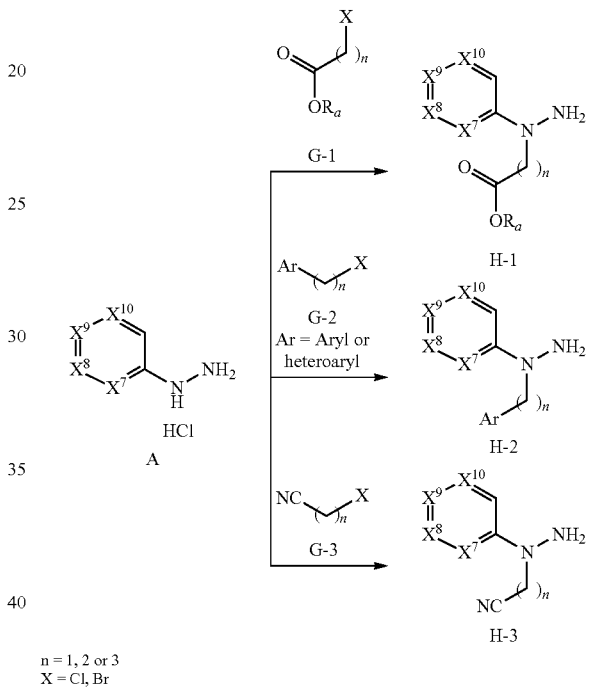

n = 1, 2 or 3
X = Cl, Br

Arylhydrazine hydrochloride (1 equiv) is mixed with triethylamine (3 equiv) and alkyl halide (1 equiv) at 25° C. The reaction mixture is stirred at RT for 1 h and subsequently heated at 90 C. for 16 h at which point the reaction is found complete by TLC and LC-MS. The reaction mixture is concentrated under reduced pressure, diluted with water and extracted with ethyl acetate. The combined organic layer is dried ($Na_2SO_4$) and concentrated to obtain crude product that is purified by column chromatography (silica gel, 100-200 mesh, eluent: ethyl acetate-hexanes gradient).

General Method 3

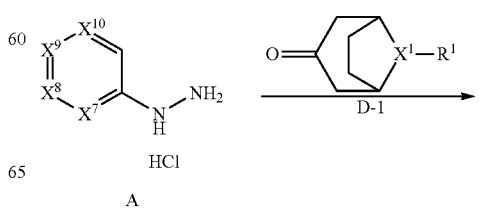

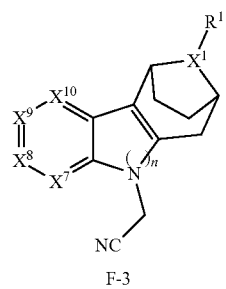

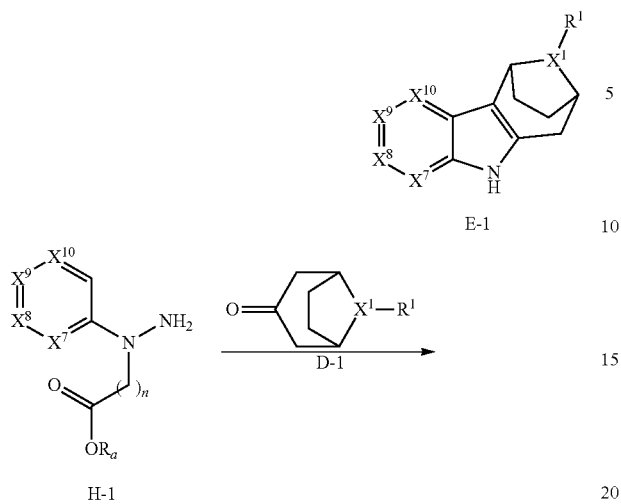

Aryl hydrazine or substituted aryl hydrazine hydrochloride (1 equiv) and appropriate hydrochloride salt of tropinone (1 equiv) are mixed in a suitable solvent such as EtOH and heated at 80-100° C. for 16 h (overnight) after which the solvent is removed in vacuo. The remaining residue is basified, e.g., with saturated aq. $NaHCO_3$. The aqueous layer is extracted with dichloromethane or ethyl acetate and the combined organic layers are dried over $Na_2SO_4$, and concentrated in vacuo. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TPA in acetonitrile, Gradient: 10% B to 80% B in 30 min, injection vol. 5 mL).

General Method 4

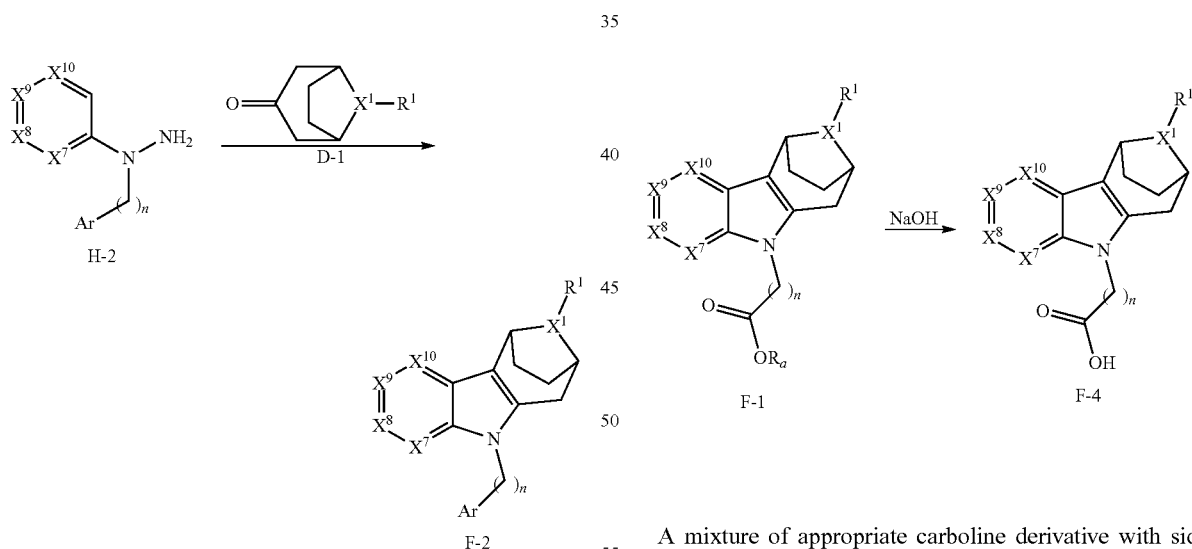

A mixture of appropriate carboline derivative with side chain carboxylate ester (1 equiv) and NaOH (3N, 5 folds w/v) in ethanol (5 folds w/v) is stirred at 50° C. for 3 h after which it was cooled to RT and neutralized with conc. HCl. The solvent is removed under reduced pressure to obtain corresponding crude carboxylic acid. The resulting crude product is purified by silica gel chromatography (100-200 mesh or 230-400 mesh) using methanol-dichloromethane gradient by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 5

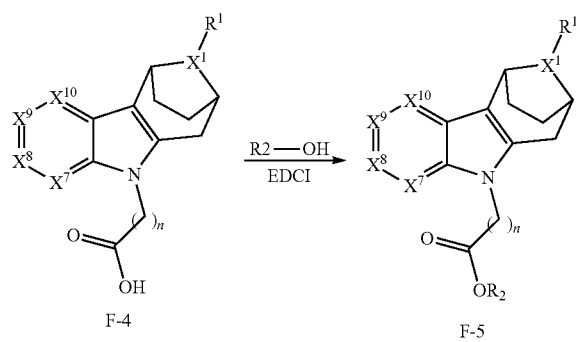

A mixture of appropriate carboline derivative with side chain carboxylic acid (1 equiv) is stirred with appropriate alcohol (1 equiv), EDCI-HCl (1 equiv) and triethylamine (1 equiv) in dichloromethane for 12-16 h. The reaction mixture is evaporated under vacuo to obtain the crude ester that is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TPA in water, B=0.05% TPA in acetonitrile, Gradient: 10% B to 80% B in 30 min, injection vol. 5 mL).

General Method 6A

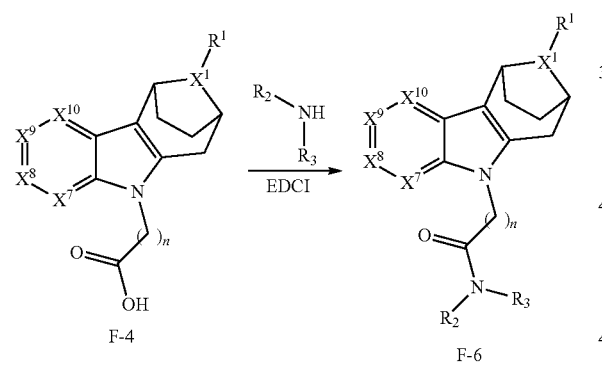

A mixture of appropriate carboline derivative with side chain carboxylic acid (1 equiv) is stirred with appropriate amine (1 equiv), EDCI (1 equiv) and triethylamine (1 equiv) in dichloromethane for 12-16 h. The reaction mixture is evaporated in vacuo to obtain the crude amide that is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min. injection vol. 5 mL).

General Method 6B

Appropriate carboxylic acid (1 equiv 0.150 g, 0.472 mmol) is dissolved in dichloromethane and cooled to 0° C. chloride (1.5 equiv) is added drop-wise followed by addition of a catalytic amount of dimethyl-formamide and the reaction mixture is stirred for 1 h at RT. Excess oxalyl chloride is distilled off under reduced pressure; a solution of appropriate amine (1.1 equiv) in dichloromethane and 4-(N,N-dimethylamino)pyridine (1.2 equiv) is added to this residue under nitrogen at RT and reaction mixture is stirred for 30 min at RT. The reaction mixture is quenched with water and neutralized with 10% NaHCO$_3$, extracted with ethyl acetate (2×10 mL). The combined organic layers are dried over sodium sulfate and concentrated under reduced pressure to provide the crude product that is purified by silica gel chromatography and/or reverse phase HPLC.

General Method 7

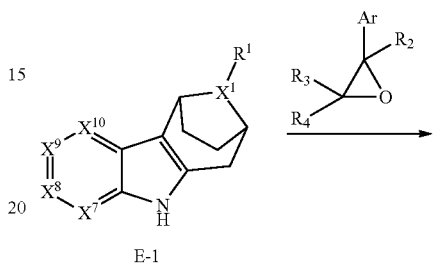

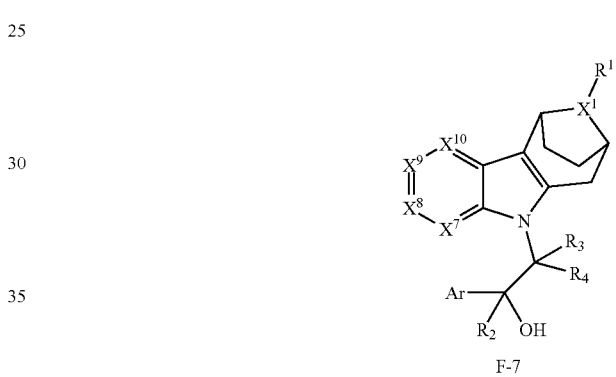

Carboline derivative (1 equiv), epoxide derivative (4-7.5 equiv) and NaH (3 equiv) are heated in DMF (3 mL/mmol) at 120° C. for 16 h. The contents are quenched by methanol and evaporated to dryness. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A-0.05% TFA in water, B=0.05% TFA in acetonitrile, Gradient: 10% B to 80% B in 30 min, injection vol. 5 mL).

General Method 8

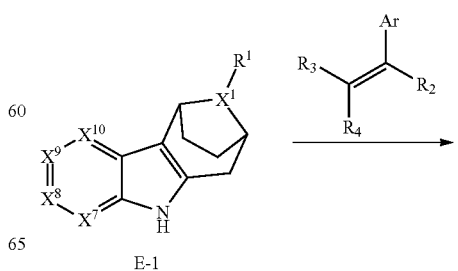

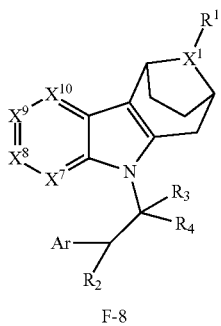

F-8

Appropriate carboline (1 equiv) is dissolved in NMP (0.6 mL/mmol). Powdered KOH (3.5 equiv) is added to this solution, and the reaction mixture is stirred for 10 min at 25° C. Appropriate vinylpyridine derivative (1.1 equiv) is added and the reaction mixture is heated in sealed tube at 45° C. for 30 min. The reaction is monitored by LCMS. After this period, the reaction mixture is cooled to 25° C. and diluted with saturated aqueous NaCl (5 mL). The product is extracted with ethyl acetate. The combined organic layer is dried over anhydrous sodium sulfate and evaporated under reduced pressure. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile Gradient: 10% B to 80% B in 30 min, injection vol. 5 mL).

General Method 9

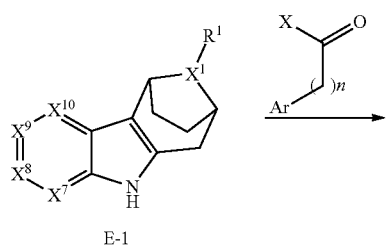

E-1

F-9 n = 1, 2, 3
X = Cl, Br

Appropriate carboline (1 equiv) is dissolved in dichloromethane (3 mL/mmol) and cooled to 0° C. Triethylamine (1 equiv) is added followed by appropriate acid chloride. The reaction mixture is slowly allowed to warm to 25° C. and stirred at 25° C. for 24 h. The reaction mixture is quenched by adding saturated aqueous NaHCO$_3$ and extracted with dichloromethane. The combined organic layer is dried over anhydrous sodium sulfate and evaporated under reduced pressure. The resulting crude product is purified by silica gel chromatography (100-200 mesh or 200-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile. Gradient: 10% B to 80% B in 30 min, injection vol. 5 mL).

General Method 10

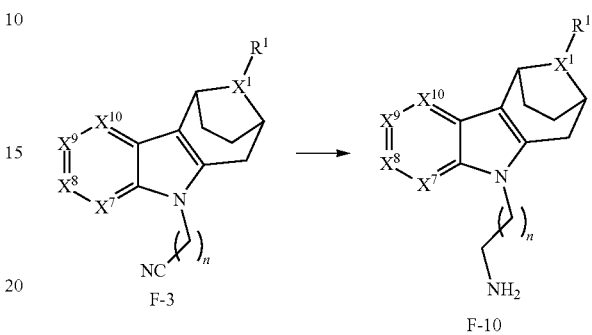

F-3

F-10

An appropriate carboline derivative with side chain nitrite (1 equiv) is treated with diisobutylaluminum hydride (3 equiv) in toluene (5 ml/mmol) at 80° C. for 1-2 h. The reaction mixture is cooled to 25° C., quenched with water and extracted ethyl acetate. The combined organic layer is dried over anhydrous sodium sulfate and evaporated under reduced pressure. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 11

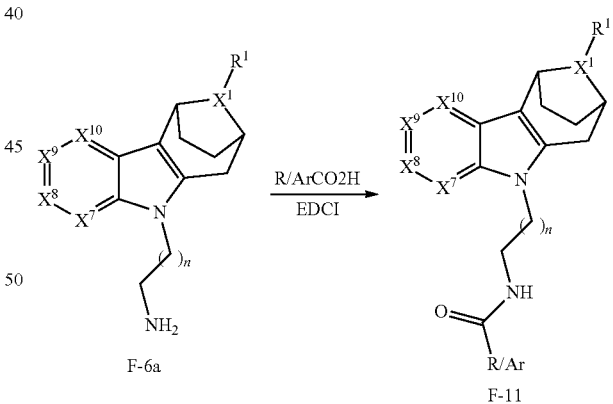

F-6a

F-11

A mixture of appropriate carboline derivative with side chain amine (1 equiv) is stirred with appropriate carboxylic acid (1 equiv), EDCI (1 equiv) and triethylamine (1 equiv) in dichloromethane for 12-16 h. The reaction mixture is evaporated in vacuo to obtain the crude amide that is purified by silica gel chromatography (100-100 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 0% B in 30 min, injection vol. 5 mL).

General Method 12

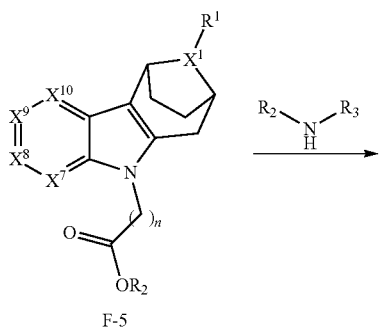

F-5

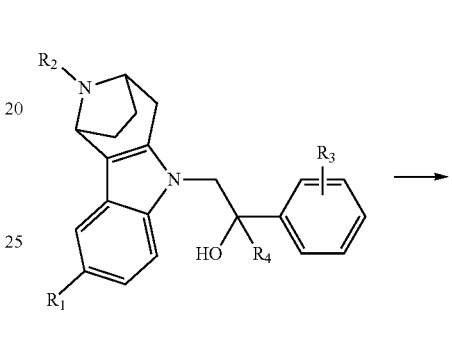

F-6

A mixture of appropriate carboline derivative with side chain carboxylate ester (1 equiv) and appropriate amine (10 fold w/v) is heated at 120° C. for 12-18 h after which the reaction mixture is evaporated to dryness and the resulting crude product was purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 13

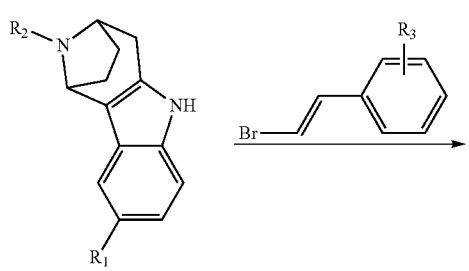

Appropriately substituted 5,6,7,8,9,10-hexahydro-7,10-iminocyclohept[b]indole (0.36 mmol) is dissolved in DMF. To this solution CuI (1 equiv), L-proline (0.02 equiv), $K_3PO_4$ (2 equiv) are added and the reaction mixture is stirred for 10 min at room temperature. This is followed by drop wise addition of (2-bromovinyl)arene (100 mg, 1.2 equiv). The reaction mixture is heated at 80° C. for overnight. DMF is evaporated under reduced pressure and the product is extracted with ethyl acetate and the organic layer is washed with brine. The organic layer is dried over anhydrous Na2SO4, and concentrated under reduced pressure. The crude compound thus obtained is purified by column chromatography on silica gel to afford the product. The general method may be modified to reach similar products, e.g., by substituting (2-bromovinyl)arene with like compounds.

General Method 14.

Appropriately substituted (5,6,7,8,9,10-hexahydro-7,10-iminocyclohept[b]indol-5-yl)ethanol derivative (1 equiv) is refluxed with 25% aqueous sulfuric acid for 2 h. The reaction mixture is cooled to 5° C. with an ice-water bath. KOH (15% aq. solution) is added drop wise to the reaction mixture till pH of 9-10. The reaction mixture is extracted with ethyl acetate. The combined organic layer is washed with water (10 ml) followed by brine, dried over sodium sulfate and evaporated under vacuum. The crude product is purified by column chromatography on silica gel (100-200 mesh).

General Method 15A.

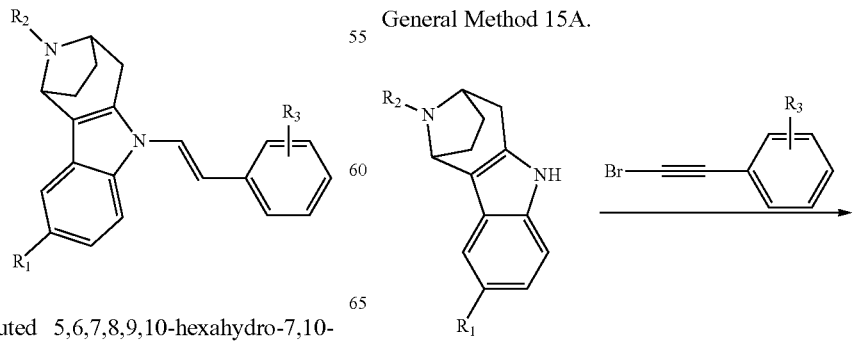

-continued

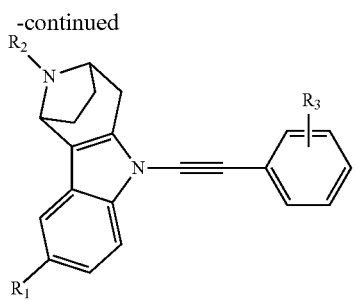

To a stirred solution of appropriately substituted 5,6,7,8,9,10-hexahydro-7,10-iminocyclohept[b]indole (1 equiv) and copper sulfate (0.01 equiv) in toluene is added potassium carbonate (2 equiv) and 1,10 phenanthroline (0.05 equiv), reaction mixture is stirred for 5 minutes at room temperature. A solution of 1-Bromoethynylarene (1 equiv) in toluene is added to the reaction mixture. The reaction mixture is stirred for 2 h at 80° C. Solvent is removed under pressure and the resulting crude product is purified by column chromatography on silica gel. The general method may be modified to reach similar products, e.g., by substituting 1-Bromoethynylarene with like compounds.

General Method 15B.

An appropriately substituted 5,6,7,8,9,10-hexahydro-7,10-iminocyclohept[b]indole (1 equiv) is added to a solution of sodium hydride (5 equiv) in THF at 0° C. and the contents are stirred at 0° C. for 30 minutes. A solution of appropriately substituted alkyl halide (2 equiv.) in THF is added dropwise to the reaction mixture which and stirred at RT for three hours. After completion of the reaction, the reaction mixture is quenched with ice cold water and product extracted with ethyl acetate, washed with water, dried over sodium sulfate and concentrated under reduced pressure to obtain crude compound. The crude product is purified to yield the desired product. The general method may be modified to reach similar products, e.g., by substituting chloroacetamide with like compounds.

General Method 15C.

I. Tetrabutylammonium chloride (0.5 equiv.) is dissolved in 50% NaOH followed by addition of appropriately substituted 5,6,7,8,9,10-hydro-7,10-iminocyclohept[b]indole (1 equiv.). The reaction mixture is stirred for 5 min at RT, and appropriate alkyl halide (1 equiv.) is added and stirred at 100° C. for 12 h. The reaction is quenched with water and extracted in dichloromethane. The combined organic layers are dried over sodium sulfate and concentrated under vacuum to yield the crude product which is purified by reverse phase chromatography.

II. An appropriately substituted 5,6,7,8,9,10-hexahydro-7,10-iminocyclohept[b]indole (1 equiv.) and appropriate alkyl halide (1 equiv.) is added to vigorously stirred mixture of tetra-n-butyl ammonium chloride (0.5 equiv.) in 50% aq NaOH solution and the resultant mixture is heated to 60° C. for 6 h. Upon completion (the reaction is monitored by LCMS), the reaction is quenched with and extracted with dichloromethane, the combined organic layers are separated, dried over $Na_2SO_4$ and concentrated, and the resultant crude is purified by reverse-phase chromatography.

III. An appropriately substituted 5,6,7,8,9,10-hexahydro-7,10-iminocyclohept[b]indole (1 equiv.) is added to a solution of tetra n-butyl ammonium chloride (0.5 equiv.) in 50% aq NaOH and stirred for 30 minutes. Appropriate alkyl halide (1 equiv.) is added and the reaction mixture is heated at 60° C. for 15 h. The progress of the reaction is monitored by LCMS, TLC. After complete reaction, the reaction mixture is quenched with water and extracted with ethyl acetate. The combined organic layers are dried over sodium sulfate and concentrated under reduced pressure and the resultant crude product is purified by chromatography.

General Methods for HPLC Analysis

Method-1

Column: YMC ODS-A 150 mm×4.6 mm×5μ, ID: E-AC-1/06/COL/013

Mobile Phase: A: 0.05% TFA in Water/B: 0.05% TFA in Acetonitrile

Inj. Vol: 10 μL, Col. Temp: 30° C., Flow rate: 1.2 ml/min

Gradient: 10% B to 80% B in 5 min, Hold for 2 min, 7.01-10 min 10% B

Method-2

Column: YMC ODS-A 150 mm×4.6 mm×5μ, ID: E-AC-1/06/COL/0.13

Mobile Phase: A: 0.05% TFA in Water/B: 0.05% TFA in Acetonitrile

Inj. Vol: 10 μL, Col. Temp: 30° C., Flow rate: 1.2 mL/min

Gradient: 50% B to 100% B in 5 min, Hold for 2 min, 7.01-10 min 50% B

Method-3

Column: YMC ODS-A 150 mm×4.6 mm×5μ, ID: E-AC-1/06/COL/013

Mobile Phase: A: 0.05% TFA in Water/B: 0.05% TFA in Acetonitrile

Inj. Vol: 10 μL, Col. Temp.: 30° C., Flow rate: 1.4 mL/min

Gradient: 5% B to 95% B in 8 min, Hold for 1.5 min, 9.51-12 min 5% B

The methods detailed above may be adapted as known by those of skill in the art. Particular examples of each General Method are provided in the Examples below.

The following Examples are provided to illustrate but not limit the invention.

All references disclosed herein are incorporated by reference in their entireties.

EXAMPLES

Example 1

Preparation of Compound 1

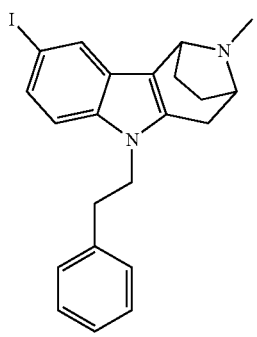 [SMILES: CN1C2CCC1c1c(n(CCc3ccccc3)c3ccc(I)cc13)C2]

The title compound is prepared according to General Methods 2 and 3 by reacting 4-iodophenyl hydrazine with phenethyl bromide or chloride (General Method 2) followed by Fischer indole cyclization with tropinone (General Method 3). The compound is purified by normal phase or reverse phase chromatography and is characterized by HPLC, LCMS and ¹H NMR.

Example 2A

Preparation of Compound 2

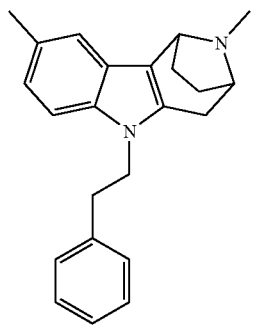

The title compound was prepared according to General Methods 2 and 3 by reacting 4-methylphenyl hydrazine with phenethyl bromide (General Method 2) followed by Fischer indole cyclization with tropinone (General Method 3). The compound was purified by normal phase or reverse phase chromatography and is characterized by HPLC, LCMS and ¹H NMR.

p-Tolylhydrazine hydrochloride (10 g) was mixed with triethylamine (28 mL) and the reaction mixture was stirred at 25° C. for 10 min after which 2-phenethyl bromide (18.6 mL) was added drop wise. The reaction mixture was heated at 80° C. for 3 h after which the solvent was evaporated under reduced pressure. The residue was basified with saturated aqueous NaHCO₃ and extracted with ethyl acetate. The combined organic layer was dried over sodium sulfate and evaporated to obtain the crude product. Purification on silica gel chromatography using hexanes-ethyl acetate eluent generated 3 g of 1-phenethyl-1-p-tolylhydrazine.

1-Phenethyl-1-p-tolylhydrazine (0.4 g) and tropinone (0.25 g) were mixed in 10 mL ethanol-HCl and heated at 90° C. for 1 h after which the solvent was removed under reduced pressure and the residue was basified with saturated aqueous NaHCO₃ and extracted with ethyl acetate. The combined organic layer was dried over sodium sulfate and evaporated to obtain the crude product. Purification on silica gel chromatography using hexanes-acetone eluent generated 40 mg of product. The free base was converted into its oxalate salt by treatment of oxalic acid (1 equiv) in anhydrous THF.

Example 2B

Preparation of Compound 2

8-Methyl-8-azabicyclo[3.2.1]octan-3-one.HCl was added to a solution of 1-phenyl-1-p-tolylhydrazine (1.5 g, 6.627 mmol) in ethanolic HCl (10 mL) at RT and stirred for 20 min. The solvent was evaporated under reduced pressure, ethanol was added and the reaction mixture was heated at 90° C. for 2 h. The reaction mixture was cooled and the solvent was evaporated under reduced pressure. Saturated aq. sodium hydrogen carbonate solution was added to the crude product at 0° C. and extracted with ethyl acetate, dried over anhydrous sodium sulfate, evaporated under reduced pressure and purified through silica column. The free base (1 g, 3.026 mmol)) was dissolved in THF (5.0 mL) and oxalic acid (381 mg, 3.026 mmol) in THF (3.0 mL) was added slowly, the mixture was stirred at RT for 20 min and the solid was filtered, washed with ether and dried to yield the product as oxalate salt. ¹H NMR (Oxalate salt, DMSO) δ 7.50-7.40 (d, 1H), 7.38-730 (d, 1H), 7.25 (s, 1H), 7.20-7.19 (t, 1H), 7.15-6.90 (m, 2H), 6.85-6.70 (m, 2H), 4.85 (s, 1H), 4.4-4.0 (m, 3H), 3.3-3.2 (m, 1H), 3.1 (s, 3H), 3.0-2.9 (m, 2H), 2.7-2.6 (m, 1H), 2.5 (s, 3H), 2.5-2.4 (m, 2H), 2.0-1.9 (m, 1H), 1.5-1.35 (m, 1H), MS m/z observed 331. HPLC (Method 3) RT 6.65 min.

Example 3A

Preparation of Compound 3

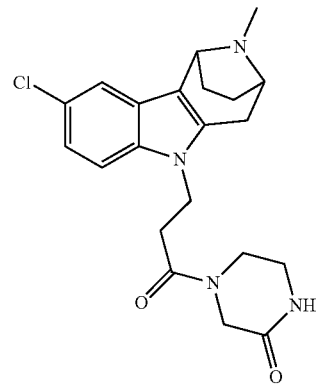 [SMILES: CN1C2CCC1c1c(n(CCC(=O)N3CCNC(=O)C3)c3ccc(Cl)cc13)C2]

Compound 3 was prepared according to a general method detailed herein.

In one method, the title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with piperazinone (General Method 6). The compound is purified by normal phase or reverse phase chromatography and is characterized by HPLC, LCMS and ¹H NMR.

Example 3B

Preparation of Compound 3

3-(2-Chloro-,11-methyl-5,6,7,8,9,10-hexahydro-7,10-iminocyclohept[b]indol-5-yl)propanoic acid (0.150 g, 0.472 mmol) was dissolved in dichloromethane (3 mL) and cooled to 0° C. Oxalyl chloride (0.061 mL, 0.708 mmol) was added drop-wise followed by addition of a catalytic amount (1 drop) of dimethyl-formamide and reaction mixture was stirred for 1 h at RT. Excess oxalyl chloride was distilled off under reduced pressure. To this residue, a solution of 2-oxopiperazine (0.052 mL, 0.519 mmol) in dichloromethane (2 mL) and 4-N,N-dimethylaminopyridine (0.069 g, 0.566 mmol) was added under nitrogen at RT and reaction mass was stirred for 30 min at RT. The reaction mixture was quenched with water and neutralized with 10% NaHCO₃, extracted with ethyl acetate (2×10 mL). The combined organic layers were dried over sodium sulfate and concentrated under reduced pressure to provide the product as a TFA salt (9 m g) after purification by reverse phase chromatography (C-18, 500 mm×50 mm. Mobile Phase A=0.05% TFA in water, B=0.05% TFA in acetonitrile. Gradient: 10% B to 80% B in 30 min, injection volume 5 mL). The NMR data for the compound is as follows: $^1$H NMR (DMSO)—10.1 (bs, 1H), 8.1 (d, 1H), 7.6 (d, 2H), 7.2 (d, 1H), 5.1 (d, 1H), 4.4-3.8 (m, 3H), 4.3 (bs, 2H), 3.4-3.3 (m, 1H), 3.0-2.9 (m, 1H), 3.5-3.4 (m, 2H), 3.2-3.0 (m, 2H), 2.9 (s, 3H), 2.6 (bs, 2H), 2.4-2.3 (m, 1H), 2.2-2.0 (m, 2H), 1.9-1.8 (m, 1H).

Example 4

Preparation of Compound 4

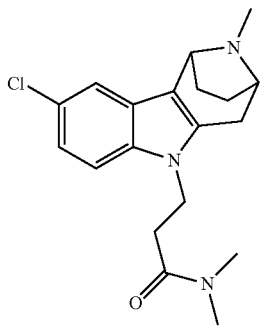 [SMILES: CN(C)C(=O)CCn1c2c(c3cc(Cl)ccc31)C1CCC(C2)N1C]

The title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with dimethylamine (General Method 6). The compound is purified by normal phase or reverse phase chromatography and is characterized by HPLC, LCMS and $^1$H NMR.

Example 5A

Preparation of Compound 5

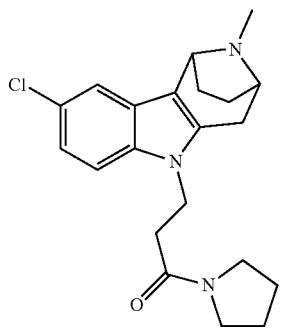 [SMILES: CN1C2CCC1c1c(n(CCC(=O)N3CCCC3)c3ccc(Cl)cc13)C2]

The title compound was prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with pyrrolidine (General Method 6). The compound was purified by normal phase or reverse phase chromatography and is characterized by HPLC, LCMS and $^1$H NMR.

Example 5B

Preparation of Compound 5

To a solution of 3-(2-Chloro-11-methyl-5,6,7,8,9,10-hexahydro-7,10-iminocyclohept[b]indol-5-yl)propanoic acid (100 mg, 0.3 mmol) in dichloromethane (5 mL), pyrrolidine (0.08 mL, 0.3 mmol), 1-ethyl-3-(3-dimethylaminopropyl)carbodiimide monohydrochloride (0.12 mg, 0.6 mmol), 1-hydroxybenzotriazole (0.085 mg, 0.6 mmol), and triethylamine (0.1 mL, 0.7 mmol) was added and stirred at 25° C. for 16 h. After completion of the reaction (the progress of the reaction was monitored by LCMS), the reaction mixture was concentrated to dryness. The crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to yield the product as TFA salt (100 mg, Yield 90%). $^1$H NMR (TFA salt, CD$_3$OD) δ 7.55 (s, 1H), 7.50-7.44 (m, 1H), 7.20-7.16 (m, 1H), 5.1-5.0 (m, 1H), 4.5-4.3 (m, 3H), 3.6-3.4 (m, 1H), 3.2-3.1 (m, 1H), 3.4-3.1 (m, 4H), 2.9 (s, 3H), 2.9-2.8 (m, 2H), 2.6-2.4 (m, 2H), 2.3-2.1 (m, 1H), 2.1-1.9 (m, 1H), 1.8-1.6 (m, 4H). MS m/z observed 372. HPLC (Method 3) RT 5.49 min.

Example 6

Preparation of Compound 6

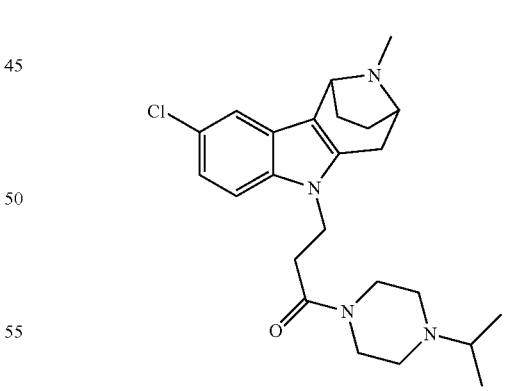

The title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with 1-isopropylpiperazine (General Method

Example 7

Preparation of Compound 7

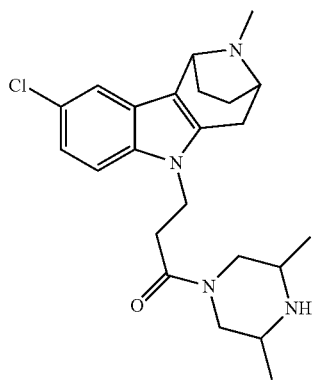 [SMILES: CC1CN(C(=O)CCn2c3c(c4cc(Cl)ccc42)C2CCC(C3)N2C)CC(C)N1]

The title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with 2,6-dimethylpiperazine (General Method 6). The compound is purified by normal phase or reverse phase chromatography and is characterized by HPLC, LCMS and $^1$H NMR.

Example 8A

Preparation of Compound 8

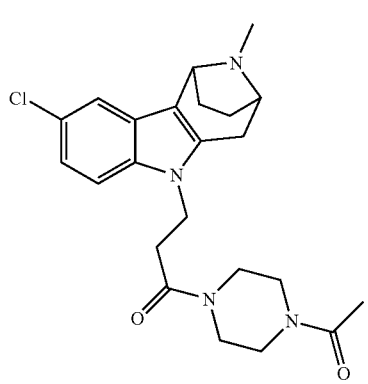 [SMILES: CC(=O)N1CCN(C(=O)CCn2c3c(c4cc(Cl)ccc42)C2CCC(C3)N2C)CC1]

Compound 8 was prepared according to a general method detailed herein.

In one method, the title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with 1-acetylpiperazine (General Method 6). The compound is purified by normal phase or reverse phase chromatography and is characterized by HPLC, LCMS and $^1$H NMR.

Example 8B

Preparation of Compound 8

3-(2-Chloro,11-methyl-5,6,7,8,9,10-hexahydro-7,10-iminocyclohept[b]indol-5-yl)propanoic acid (0.150 g, 0.472 mmol) was dissolved in dichloromethane (3 mL) and cooled to 0° C. Oxalyl chloride (0.061 mL, 0.708 mmol) was added drop-wise to the reaction mixture. A catalytic amount (1 drop) of dimethyl formamide was added and reaction mixture was stirred for 1 h at room temperature. Excess oxalyl chloride was distilled off under reduced pressure. The residue was dissolved in dichloromethane (2 mL) and a solution of 1-acetyl piperazine (0.067 mL, 0.519 mmol) in 2 mL dichloromethane and 4-N,N-dimethylaminopyridine (0.069 g, 0.566 mmol) was added. The reaction mixture was stirred for 30 min at room temperature, quenched with water, and basified with 10% NaHCO$_3$. The product was extracted with ethyl acetate (10 mL×2) and the combined organic layer was dried over sodium sulfate, concentrated under reduced pressure to afford the product as a TFA salt (17 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). The NMR data for the compound is as follows: $^1$H NMR (DMSO)—10.05 (bs, 1H), 7.62 (d, 1H), 7.5-7.58 (m, 1H), 7.18 (d, 1H), 5.02-5.18 (m, 1H), 4.4-4.2 (m, 3H), 3.5-3.1 (m, 8H), 3.1-3.0 (m, 1H), 2.9 (s, 3H), 2.8 (m, 2H), 2.7 (m, 1H), 2.4-2.3 (m, 1H), 2.2-2.1 (m, 2H), 2.0 (s, 3H), 1.9-1.8 (m, 1H).

Example 9A

Preparation of Compound 9

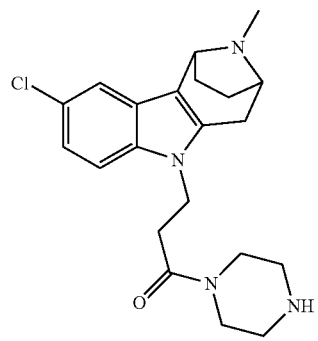 [SMILES: CN1C2CCC1c1c(n(CCC(=O)N3CCNCC3)c3ccc(Cl)cc13)C2]

Compound 9 was prepared according to a general method detailed herein.

In one method, the title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with piperazine (General Method 6). The compound is purified by normal phase or reverse phase chromatography and is characterized by HPLC, LCMS and $^1$H NMR.

Example 9b

Preparation of Compound 9

A mixture of 3-(2-Chloro-11-methyl-5,6,7,8,9,10-hexahydro-7,10-iminocyclohept[b]indol-5-yl)propanoic acid (0.1 g, 0.31 mmol), piperazine (0.026 g, 0.302 mmol), 1,3-dicyclohexylcarbodiimide (0.078 g, 0.37 mmol), and 4-N,N-dimethylaminopyridine (0.058 g, 0.47 mmol) in anhydrous dichloromethane (2.5 mL) was stirred at RT for 3 h. Water (10 mL) was added to the reaction mixture and extracted with dichloromethane (3×10 mL). The combined organic layers were dried over sodium sulfate and concentrated under reduced pressure to obtain the product as TFA salt (15 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). The NMR data for the compound is as follows: $^1$H NMR (DMSO)—10.14 (bs, 1H), 8.88 (bs, 2H), 7.63 (d, 1H), 7.52 (d, 1H), 7.16 (d, 1H), 5.0-5.11 (m, 1H), 4.4-4.22 (m, 3H), 3.8 (m, 1H), 3.7-3.6 (m, 4H), 3.6-3.43 (m, 4H), 3.2-3.1 (m, 1H), 3.0 (s, 3H), 2.8 (m, 2H), 2.4-2.3 (m, 1H), 2.2-2.1 (m, 2H), 1.9-1.8 (m, 1H).

Example 10A

Preparation of Compound 10

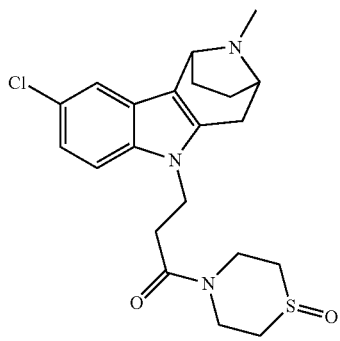 [SMILES: CN1C2CCC1c1c(n(CCC(=O)N3CCS(=O)CC3)c3ccc(Cl)cc13)C2]

Compound 10 was prepared according to a general method detailed herein.

In one method, the title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with thio-morpholine sulfoxide (General Method 6). The compound is purified by normal phase or reverse phase chromatography and is characterized by HPLC, LCMS and $^1$H NMR.

Example 10B

Preparation of Compound 10

A mixture of 3-(2-chloro-11-methyl-5,6,7,8,9,10-hexahydro-7,10-iminocyclohept[b]indol-5-yl)propanoic acid (0.1 g, 0.31 mmol), thiomorpholinesulphoxide (0.041 g, 0.31 mmol), 1,3-dicyclohexylcarbodiimide (0.078 g, 0.37 mmol), and 4-N,N-dimethylaminopyridine (0.058 g, 0.47 mmol) were mixed in anhydrous dichloromethane (2.5 mL) and stirred at RT for 3 h. The reaction mixture was diluted with water (10 mL) and extracted with dichloromethane (3×10 mL). The combined organic layers were dried over sodium sulfate and concentrated under reduced pressure to obtain the product as TFA salt (15 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). The NMR data for the compound is as follows: $^1$H NMR (DMSO)—10.05 (bs, 1H), 7.62 (d, 1H), 7.56 (d, 1H), 7.18 (d, 1H), 5.18-5.05 (m, 1H), 4.4-4.1 (m, 3H), 3.7-3.6 (m, 4H), 3.6-3.4 (m, 4H), 3.2-3.1 (m, 1H), 3.0-2.9 (m, 1H), 2.9 (s, 3H), 2.8 (bs, 2H), 2.5-2.4 (m, 1H), 2.4-2.3 (m, 2H), 1.9-1.8 (m, 1H).

Example 11A

Preparation of Compound 11

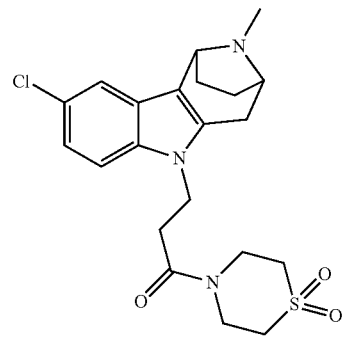 [SMILES: CN1C2CCC1c1c(n(CCC(=O)N3CCS(=O)(=O)CC3)c3ccc(Cl)cc13)C2]

Compound 11 was prepared according to a general method detailed herein.

In one method, the title compound is prepared according to General Methods 2, 3, 4 and 6, by reacting 4-chlorophenyl hydrazine with 3-chloroe or bromo ethyl propionate (General Method 2), followed by Fischer indole cyclization with tropinone (General Method 3), further followed by hydrolysis of the ester (General Method 4) and amide bond formation under standard conditions with thiomorpholinesulfone (General Method 5). The compound is purified by normal phase or reverse phase chromatography and is characterized by HPLC, LCMS and $^1$H NMR.

Example 11B

Preparation of Compound 11

A mixture of 3-(2-Chloro-11-methyl-5,6,7,8,9,10-hexahydro-7,10-iminocyclohept[b]indol-5-yl)propanoic acid (0.1 g, 0.31 mmol), thiomorpholinesulfone (0.046 g, 0.35 mmol), 1,3-dicyclohexylcarbodiimide (0.078 g, 0.37 mmol), and 4-N,N-dimethylaminopyridine (0.058 g, 0.47 mmol) were mixed in anhydrous dichloromethane (2.5 mL) and stirred at RT for 3 h. The reaction mixture was diluted with water (10 mL) and extracted with dichloromethane (3×10 mL), the combined organic layers were dried over sodium sulfate and concentrated under reduced pressure to obtain the product as TFA salt (20 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). The NMR data for the compound is as follows: $^1$H NMR (DMSO)—10.2 (bs, 1H), 7.62 (d, 1H), 7.46 (dd, 1H), 7.18 (d, 1H), 5.09 (m, 1H), 4.4-3.8 (m, 3H), 3.9-3.8 (m, 4H), 3.8-3.6 (m, 4H), 3.5-3.4 (m, 1H), 3.1-3.0 (m, 1H), 2.9 (s, 3H), 2.85 (bs, 2H), 2.5-2.4 (m, 1H), 2.4-2.3 (m, 2H), 1.9-1.8 (m, 1H).

Example 12A

Preparation of Compound 12

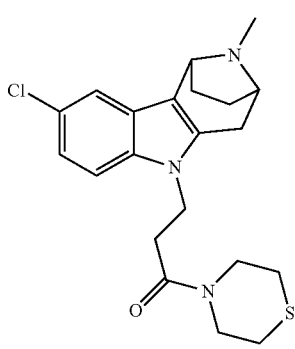 [SMILES: CN1C2CCC1c1c(n(CCC(=O)N3CCSCC3)c3ccc(Cl)cc13)C2]

Compound 12 was prepared according to a general method detailed herein.

In one method, the title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with thio-morpholine (General Method 6). The compound is purified by normal phase or reverse phase chromatography and is characterized by HPLC, LCMS and $^1$H NMR.

Example 12B

Preparation of Compound 12

A mixture of 3-(2-chloro, 11-methyl-5,6,7,8,9,10-hexahydro-7,10-iminocyclohept[b]indol-5-yl)propanoic acid (0.1 g, 0.31 mmol), thiomorpholine (0.032 g, 0.314 mmol), 1,3-dicyclohexylcarbodiimide (0.078 g, 0.37 mmol), and 4-N,N-dimethylaminopyridine (0.058 g, 0.47 mmol) were mixed in anhydrous dichloromethane (2.5 mL) and stirred at RT for 3 h. The reaction mixture was diluted with water (10 mL) and extracted with dichloromethane (3×10 mL). The combined organic layers were dried over sodium sulfate and concentrated under reduced pressure to obtain the product as TFA salt (30 mg) after purification by reverse-phase chromatography (C-18, 500 mm×50 mm, Mobile Phase A=0.05% TFA in water, B=0.05% TFA in acetonitrile, Gradient: 10% B to 80% B in 30 min. injection volume 5 mL). The NMR data for the compound is as follows: $^1$H NMR (DMSO)—10.2 (bs, 1H), 7.61 (d, 1H), 7.53 (d, 1H), 7.14 (d, 1H), 5.1-5.05 (m, 1H), 4.4-3.6 (m, 3H), 3.7-3.6 (m, 4H), 3.6-3.4 (m, 4H), 3.2-3.1 (m, 1H), 2.8-2.7 (m, 1H), 2.8 (s, 3H), 2.5 (bs, 2H), 2.4-2.2 (m, 3H), 1.9-1.8 (m, 1H).

Example 13A

Preparation of Compound 13

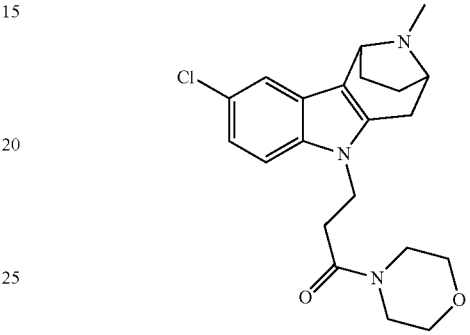

The title compound was prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with morpholine (General Method 6). The compound was purified by normal phase or reverse phase chromatography and is characterized by HPLC, LCMS and $^1$H NMR.

Example 13B

Preparation of Compound 13

To a solution of 3-(2-Chloro-11-methyl-5,6,7,8,9,10-hexahydro-7,10-iminocyclohept[b]indol-5-yl)propanoic acid (100 mg, 0.3 mmol) in dichloromethane (5 mL), morpholine (0.03 mL, 0.3 mmol), DMF (5 mL), 1-ethyl-3-(3-dimethylaminopropyl)carbodiimide monohydrochloride (0.12 mg, 0.6 mmol), 1-hydroxybenzotriazole (0.085 mg, 0.6 mmol), and triethylamine (0.1 mL, 0.7 mmol) was added and stirred at 25° C. for 16 h. After completion of the reaction (the progress of the reaction was monitored by LCMS), the reaction mixture was concentrated to dryness. The crude product was purified by reverse-phase chromatography (C-18, 500 mm×50 mm Mobile Phase A=0.05% TFA in water, B=0.05% TFA in acetonitrile, Gradient: 10% B to 80% B in 30 min, injection volume 5 mL) to yield the product as TFA salt (100 mg, Yield 83%). $^1$H NMR (TFA salt, CD$_3$OD) δ 7.55 (s, 1H), 7.48-7.42 (m, 1H), 7.20-7.16 (m, 1H), 5.2-5.0 (m, 1H), 4.6-4.3 (m, 3H), 3.5-3.2 (m, 8H), 3.4-3.1 (m, 1H), 3.0-2.9 (m, 1H), 2.9 (s, 3H), 2.8 (bs, 2H), 2.6-2.4 (m, 2H), 2.3-2.2 (m, 1H), 2.1-1.9 (m, 1H), MS m/z observed 388. HPLC (Method 3) RT 5.17 min.

Example 14

Preparation of Compound 14

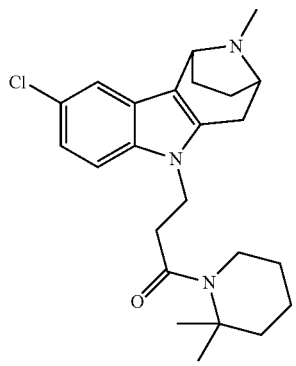 [SMILES: CN1C2CCC1c1c(n(CCC(=O)N3CCCCC3(C)C)c3ccc(Cl)cc13)C2]

The title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with 2,2-dimethylpiperidine (General Method 6). The compound is purified by normal phase or reverse phase chromatography and is characterized by HPLC, LCMS and $^1$H NMR.

Example 15

Preparation of Compound 15

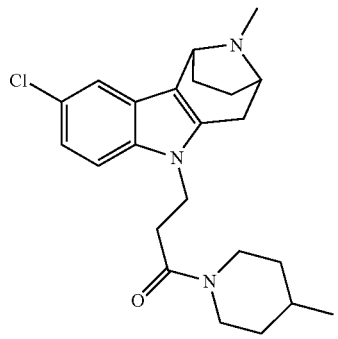 [SMILES: CC1CCN(C(=O)CCn2c3c(c4cc(Cl)ccc42)C2CCC(C3)N2C)CC1]

The title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with 4-methylpiperidine (General Method 5).

The compound is purified by normal phase or reverse phase chromatography and is characterized by HPLC, LCMS and $^1$H NMR.

Example 16

Preparation of Compound 16

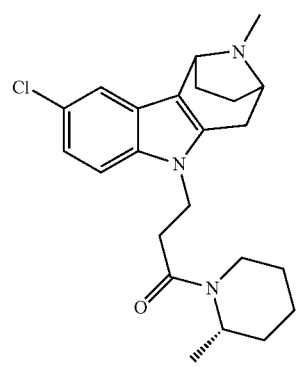 [SMILES: C[C@H]1CCCCN1C(=O)CCn1c2c(c3cc(Cl)ccc31)C1CCC(C2)N1C]

The title compound is prepared according to General Methods 2, 3, 4 and 6, by reacting 4-chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with (S)-2-methyl piperidine (General Method 6). The compound is purified by normal phase or reverse phase chromatography and is characterized by HPLC, LCMS and $^1$H NMR.

Example 17

Preparation of Compound 17

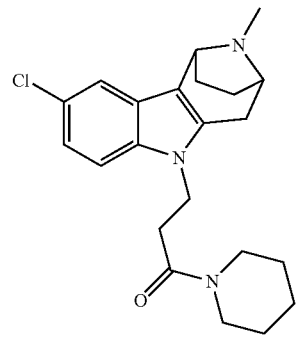 [SMILES: CN1C2CCC1c1c(n(CCC(=O)N3CCCCC3)c3ccc(Cl)cc13)C2]

The title compound is prepared according to General Methods 2, 3, 4 and 6, by reacting 4-chlorophenyl chlorophenyl hydrazine with 3-chloro or bromo ethyl propionate (General Method 2), followed by Fischer indole cyclization with tropinone (General Method 3), further followed by hydrolysis of the ester (General Method 4) and amide bond formation under standard conditions with piperidine (General Method Example 18

Preparation of Compound 18

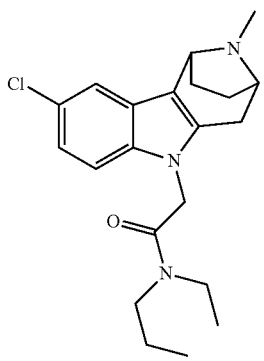 [SMILES: CCCN(CC)C(=O)Cn1c2c(c3cc(Cl)ccc31)C1CCC(C2)N1C]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), and further followed by hydrolysis of the ester (General Method 4) and amide bond formation under standard conditions with piperidine (General Method 6). The compound is purified by normal, phase or reverse phase chromatography and is characterized HPLC, LCMS and ¹H NMR.

Sodium hydride (100 mg, 4.0 mmol) was washed with hexane for removal of oil and dried under vacuum and added to THF (5 mL) at 0° C. 2-Chloro-11-methyl-5,6,7,8,9,10-hexahydro-7,10-iminocyclohept[b]indole (200 mg, 0.813 mmol) in THF (5 mL) was added dropwise to the reaction mixture at 0° C. and stirred for 0.5 h. 2-chloro-1-(piperidin-1-yl)ethanone (151 mg, 0.975 mmol) in THF (5 mL) was added drop wise at 0° C. and the reaction was stirred at RT for 3 h. The reaction mixture was quenched with ice water and the product extracted with ethyl acetate (50 mL×2). The organic layer was dried over Na₂SO₄ and concentrated under vacuum to obtain the crude product which was washed with hexane followed by diethyl ether to obtain the desired product (30 mg).

Example 19

Preparation of Compound 19

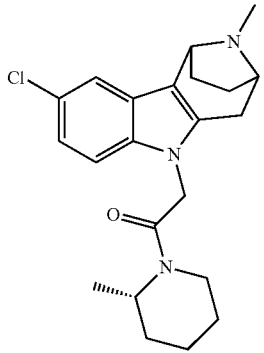 [SMILES: C[C@H]1CCCCN1C(=O)Cn1c2c(c3cc(Cl)ccc31)C1CCC(C2)N1C]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with (S)-2-methyl piperidine (General Method 6). The compound is purified by normal phase or reverse phase chromatography and is characterized by HPLC, LCMS and ¹H NMR.

Example 20

Preparation of Compound 20

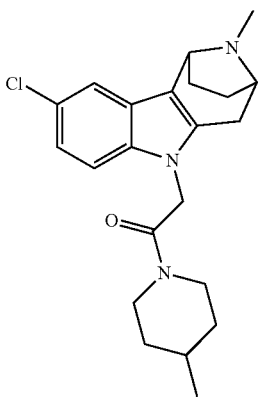 [SMILES: CC1CCN(C(=O)Cn2c3c(c4cc(Cl)ccc42)C2CCC(C3)N2C)CC1]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with 4-methyl piperidine (General Method 6). The compound is purified by normal phase or reverse phase chromatography and is characterized by HPLC, LCMS and ¹H NMR.

Example 21

Preparation of Compound 21

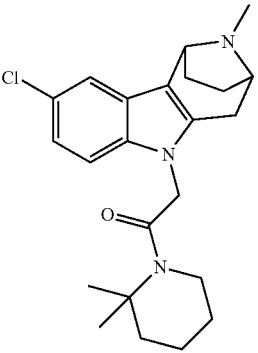 [SMILES: CN1C2CCC1c1c(n(CC(=O)N3CCCCC3(C)C)c3ccc(Cl)cc13)C2]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with 2,2-dimethyl piperidine (General Method 6). The compound is purified by normal phase or reverse phase chromatography and is characterized by HPLC, LCMS and $^1$H NMR.

Example 22

Preparation of Compound 22

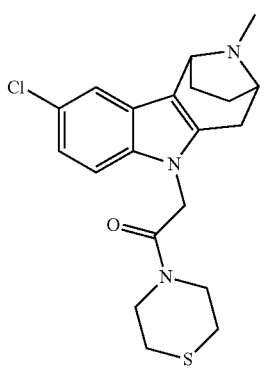 [SMILES: CN1C2CCC1c1c(n(CC(=O)N3CCSCC3)c3ccc(Cl)cc13)C2]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), and further followed by hydrolysis of the ester (General Method 4) and amide bond formation under standard conditions with thiomorpholine (General Method 6). The compound is purified by normal phase or reverse phase chromatography and is characterized by HPLC, LCMS and $^1$H NMR.

Example 23

Preparation of Compound 23

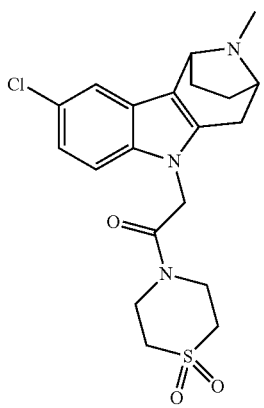 [SMILES: CN1C2CCC1c1c(n(CC(=O)N3CCS(=O)(=O)CC3)c3ccc(Cl)cc13)C2]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), and further followed by hydrolysis of the ester (General Method 4) and amide bond formation under standard conditions with thiomorpholinesulfone (General Method 6). The compound is purified by normal phase or reverse phase chromatography and is characterized by HPLC, LCMS and $^1$H NMR.

Example 24

Preparation of Compound 24

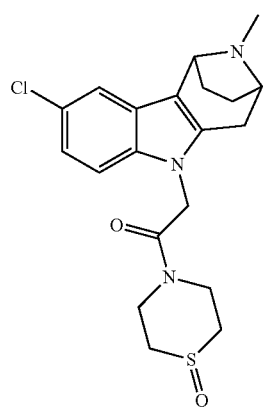 [SMILES: CN1C2CCC1c1c(n(CC(=O)N3CCS(=O)CC3)c3ccc(Cl)cc13)C2]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), and further followed by hydrolysis of the ester (General Method 4) and amide bond formation under standard conditions with thiomorpholinesulfone (General Method 6). The compound is purified by normal phase or reverse phase chromatography and is characterized by HPLC, LCMS and $^1$H NMR.

Example 25

Preparation of Compound 25

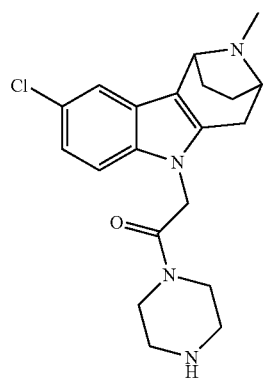 [SMILES: CN1C2CCC1c1c(n(CC(=O)N3CCNCC3)c3ccc(Cl)cc13)C2]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), and further followed by hydrolysis of the ester (General Method 4) and amide bond formation under standard conditions with piperazine (General Method 6). The compound is purified by normal phase or reverse phase chromatography and is characterized by HPLC, LCMS and $^1$H NMR.

$^1$H NMR (TFA salt, CD3OD) δ 1H NMR (CD$_3$OD): 8.25-8.20 (d, 1H), 8.10-7.90 (m, 1H), 7.70-7.60 (d, 1H), 7.60-7.50 (t, 1H), 7.40-7.30 (d, 1H), 7.20-7.00 (m, 2H), 5.20-5.10 (m, 1H), 4.60-4.40 (m, 4H), 3.60-3.50 (m, 1H), 2.95 (s, 3H), 2.62 (s, 3H), 2.50-2.40 (t, 2H), 2.30-2.20 (m, 2H), 1.90-1.80 m, 2H), MS m/z observed 349, HPLC (Method 3) RT 6.74 min.

Example 26

Preparation of Compound 26

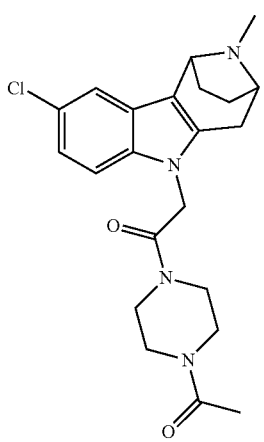 [SMILES: CC(=O)N1CCN(C(=O)Cn2c3c(c4cc(Cl)ccc42)C2CCC(C3)N2C)CC1]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with 1-acetylpiperazine (General Method 6). The compound is purified by normal phase or reverse phase chromatography and is characterized by HPLC, LCMS and $^1$H NMR.

Example 27

Preparation of Compound 27

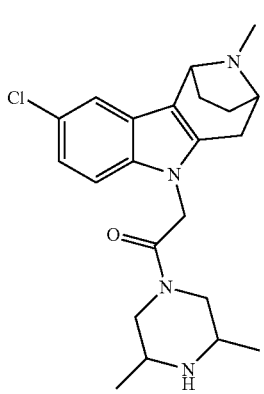 [SMILES: CC1CN(C(=O)Cn2c3c(c4cc(Cl)ccc42)C2CCC(C3)N2C)CC(C)N1]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with 2,6-dimethylpiperazine (General Method 6). The compound is purified by normal phase or reverse phase chromatography and is characterized by HPLC, LCMS and $^1$H NMR.

Example 28

Preparation of Compound 28

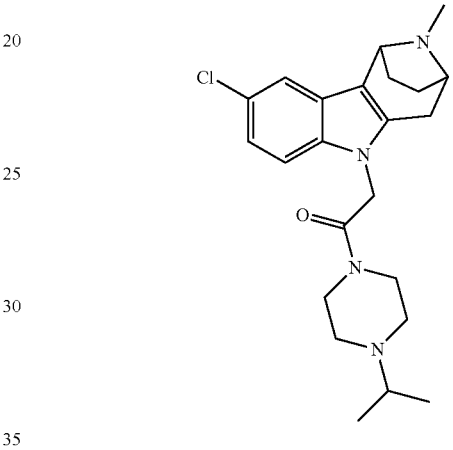

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with 1-isopropylpiperazine (General Method 6). The compound is purified by normal phase or reverse phase chromatography and is characterized by HPLC, LCMS and $^1$H NMR.

Example 29

Preparation of Compound 29

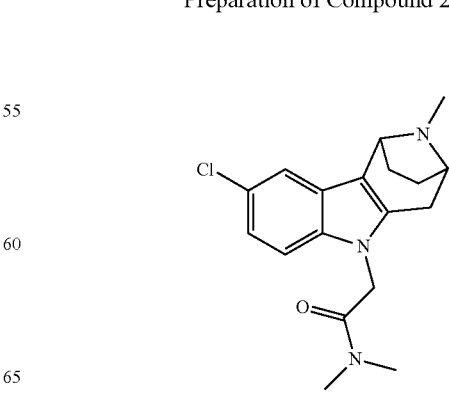

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with N,N-dimethylamine (General Method 6). The compound is purified by normal phase or reverse phase chromatography and is characterized by HPLC, LCMS and ¹H NMR.

Sodium hydride (50 mg, 2.08 mmol) washed with hexane, dried under vacuum was taken in THF (5 mL). 2-Chloro-11-methyl-5,6,7,8,9,10-hexahydro-7,10-iminocyclohept[b]indole (100 mg, 0.40 mmol) in THF (3 mL) was added dropwise to the reaction mixture at 0° C. and stirred at 0° C. for 30 minutes. N,N-dimethylchloroacetamide (100 mg, 0.80 mmol) in THF (3 mL) was added dropwise to the reaction mixture and stirred at RT for 3 h. After completion of the reaction, the reaction mixture was quenched with ice cold water and product extracted with ethyl acetate. The organic layer was washed with water, dried over sodium sulfate and concentrated under reduced pressure to obtain crude compound, which was washed with ether and hexane for removal of colored impurities to afford desired product (70 mg).

Example 30

Preparation of Compound 30

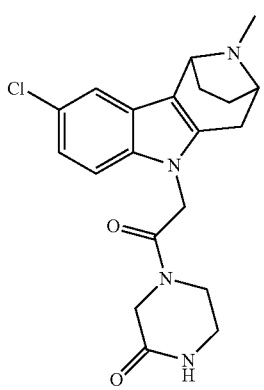 [SMILES: CN1C2CCC1c1c(n(CC(=O)N3CCNC(=O)C3)c3ccc(Cl)cc13)C2]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with 2-oxopiperazine (General Method 6). The compound is purified by normal phase or reverse phase chromatography and is characterized by HPLC, LCMS and ¹H NMR.

Example 31

Preparation of Compound 31

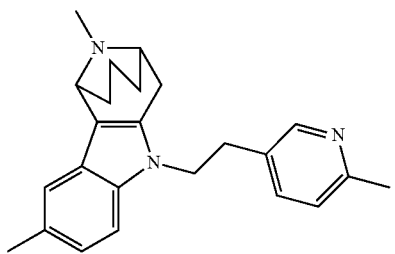

The title compound is prepared according to General Methods 2 and 3, by reacting of p-tolylhydrazine with 5-(2-bromoethyl)-2-methylpyridine (General Method 2), followed by Fischer indole cyclization with pseudopelletierine (General Method 3). The compound is purified by normal phase or reverse phase chromatography and is characterized by HPLC, LCMS and 1H NMR.

Example 32A

Preparation of Compound 32

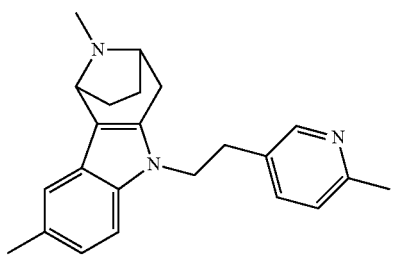

The title compound is prepared according to General Methods 3 and 8, by Fischer indole cyclization with of 4-methylphenyl hydrazine with tropinone (General Method 3) followed by reaction with 2-methyl-5-vinylpyridine (General Method 8). The compound is purified by normal phase or reverse phase chromatography and is characterized by HPLC, LCMS, and 1H NMR.

Example 32B

Preparation of Compound 32

To a solution of 2,11-Dimethyl-5,6,7,8,9,10-hexahydro-7,10-iminocyclohept[b]indole (150 mg, 0.6 mmol) in N-methyl-2-pyrrolidone (1.5 mL), powdered KOH (372 mg 5.0 mmol) was added and stirred for 10 min at 25° C. 2-methyl-5-vinylpyridine (157 mg, 1.32 mmol) was added slowly to the above solution and heated at 45° C. for 16 h. After completion of the reaction (the progress of the reaction was monitored by LCMS), the reaction mixture was concentrated to dryness and the resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to yield the product as TFA salt (12 mg, Yield 13%). The NMR data for the compound is as follows: $^1$H NMR (CD$_3$OD) 8.3 and 8.2 (s, 1H), 8.1 and 8.0 (d, 1H), 7.70 (d, 1H), 7.3 (m, 1H), 7.2-7.1 (d, 1H), 7.0 and 6.9 (d, 1H), 5.1 (m, 1H), 4.5-4.3 (m, 3H), 3.6-3.5 (m, 1H), 3.3-3.2 (m, 2H), 2.95 and 2.75 (s, 3H), 2.9 (m, 1H), 2.6 and 2.55 (s, 3H), 2.61 and 2.60 (s, 3H), 2.6-2.4 (m, 2H), 2.3-2.2 (m, 1H). 1.9-1.8 (m, 1H).

Example 33A

Preparation of Compound 33

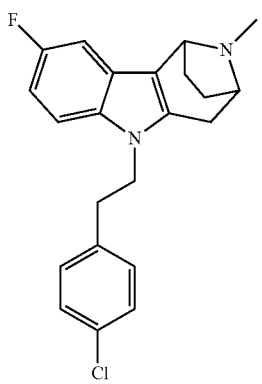 [SMILES: CN1C2CCC1c1c(n(CCc3ccc(Cl)cc3)c3ccc(F)cc13)C2]

The title compound was prepared according to General Methods 2 and 3, by reacting of 4-fluorophenyl hydrazine with 4-chlorophenethyl bromide (General Method 2), followed by Fischer indole cyclization with tropinone (General Method 3). The compound was purified by normal phase or reverse phase chromatography and is characterized by HPLC, LCMS and 1H NMR.

Example 33B

Preparation of Compound 33

1-(4-Chlorophenethyl)-1-(4-fluorophenyl)hydrazine (7.9 mmol) was dissolved in 7% H$_2$SO$_4$-dioxane and 8-methyl-8-azabicyclo[3.2.1]octan-3-one (7.9 mmol) was added to the solution. The reaction mixture was heated at 120° C. for 15 h. NaHCO$_3$ was added to the reaction mixture and the product was extracted with ethyl acetate. The ethyl acetate layer was dried over sodium sulfate and concentrated under vacuum to obtain crude product which was purified by column chromatography followed by preparative HPLC to obtain the product as TFA salt. $^1$H NMR (DMSO) δ 10.1-9.9 (bs, 1H), 7.65-7.40 (m, 1H), 7.40-7.15 (m, 3H), 7.10-6.80 (m, 3H), 5.30 and 5.0 (mm, 1H), 4.4-4.0 (m, 3H), 3.4-3.3 (m, 1H), 3.2 and 2.90 (s, 3H), 3.0-2.9 (m, 2H), 2.75-2.6 (m, 1H), 2.3-2.2 (m, 1H), 2.0-1.9 (m, 2H), 1.6-1.4 (m, 1H), MS m/z observed 369. HPLC (Method 3) RT 676 min.

Example 34A

Preparation of Compound 34

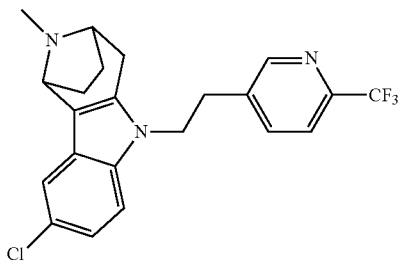 [SMILES: CN1C2CCC1c1c(n(CCc3ccc(C(F)(F)F)nc3)c3ccc(Cl)cc13)C2]

Compound 34 was prepared according to a general method detailed herein.
By one method, the title compound is prepared according to General Methods 3 and 8, by Fischer indole cyclization with of 4-chlorophenyl hydrazine with tropinone (General Method 3) followed by reaction with 2-(trifluoromethyl)-5-vinylpyridine (General Method 8). The compound is purified by normal phase or reverse phase chromatography and is characterized by HPLC, LCMS and 1H NMR.

Example 34B

Preparation of Compound 34

2-Chloro-11-methyl-5,6,7,8,9,10-hexahydro-7,10-iminocyclohept[b]indole (0.2 g, 0.81 mmol) and powdered KOH (0.460 g) were mixed in N-methyl-2-pyrrolidone (2.5 mL) and stirred for 10 min at 25° C. 2-(trifluoromethyl)-5-vinylpyridine (0.280 g, 1.61 mmol) was added slowly to the reaction mixture and stirred for 4 h at 25° C. The reaction was quenched with water, extracted with ethyl acetate, the combined organic layers were dried over sodium sulfate and evaporated to obtain the crude product which was purified by reverse-phase chromatography obtain product as a TFA salt (5 mg). The NMR data for the compound is as follows: $^1$H NMR (CD$_3$OD)-8.20-8.0 (m, 2H), 7.70-7.10 (m, 4H), 5.0-4.9 (m, 1H), 4.6-4.3 (m, 2H), 4.3-4.1 (m, 1H), 3.3-3.2 (m, 1H), 3.0-2.9 (m, 2H), 2.9 and 2.6 (s, 3H), 2.5-2.4 (m, 1H), 2.4-2.2 (m, 2H), 1.7-1.4 (m, 2H).

Example 35A

Preparation of Compound 35

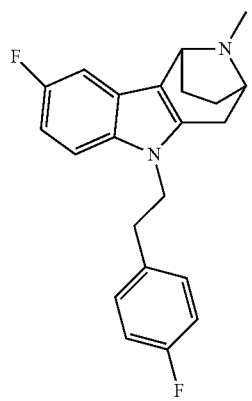 [SMILES: CN1C2CCC1c1c(n(CCc3ccc(F)cc3)c3ccc(F)cc13)C2]

The title compound was prepared according to following General Methods 2 and 3, by reacting of 4-fluorophenyl hydrazine with 4-fluorophenethyl bromide (General Method 2), followed by Fischer indole cyclization with tropinone (General Method 3). The compound was purified by normal phase or reverse phase chromatography and is characterized by HPLC, LCMS and 1H NMR. The NMR data for the compound is as follows: $^1$H NMR (DMSO)—7.60-7.50 (dd, 1H), 7.50-7.45 (dd, 1H), 7.40-7.30 (t 1H), 7.15-6.90 (m, 4H), 5.15-4.90 (t, 1H), 4.40-4.30 (m, 1H), 4.30-4.15 (t, 2H), 3.40-3.30 (d, 2H), 3.10-2.90 (t, 2H), 2.80 (s, 3H), 2.10-1.90 (m, 2H), 1.70-1.40 (m, 2H).

Example 35A

Preparation of Compound 35. Resolution of Compound 35 to Provide Compounds 94 and 95

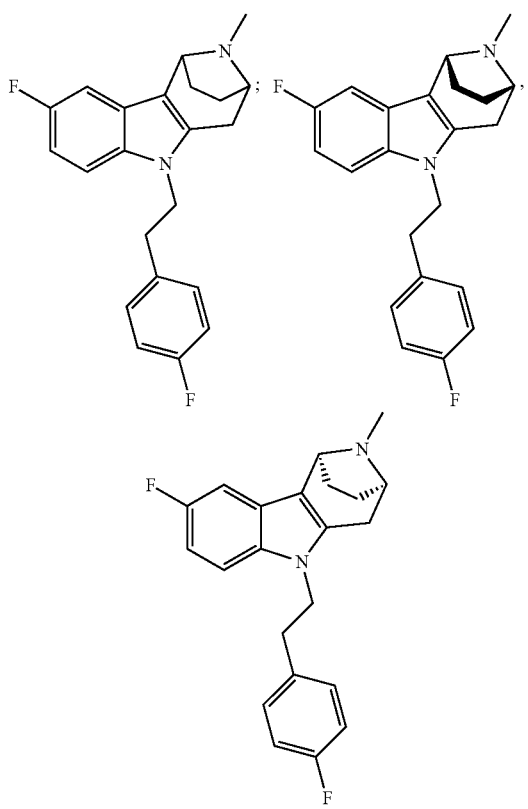

1-(4-fluorophenethyl)-1-(4-fluorophenyl)hydrazine (30.86 mmol) and 8-methyl-8-azabicyclo[3.2.1]octan-3-one (4.3 g, 30.86 mmol) were mixed in 7% H$_2$SO$_4$-dioxane (250 mL) and stirred for 15 min at RT followed by 14 h at 80° C. The reaction mixture was concentrated to dryness and basified with aq. saturated NaHCO$_3$, extracted with ethyl acetate; the organic layer was separated, dried over Na$_2$SO$_4$ and concentrated. The resulting crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the title compound as TFA salt (1.05 g, Yield 50%). The product was resolved by chiral separation on preparative HPLC (Chiralpak AD, 10% iso-propanol in heptane, 0.1% diethylamine, flow rate 1 mL/min, concentration 10 mg/mL) to obtain (+)-(7S,10R)-2-Fluoro-5-(4-fluorophenethyl)-11-methyl-5,6,7,8,9,10-hexahydro-7,10-iminocyclohept[b]indole and (−)-(7R,10S)-2-Fluoro-5-(4-fluorophenethyl)-11-methyl-5,6,7,8,9,10-hexahydro-7,10-iminocyclohept[b]indole. $^1$H NMR (DMSO) of oxalate salt of Compound 94—7.60-7.50 (dd, 1H), 7.50-7.45 (dd, 1H), 7.40-7.30 (t, 1H), 7.15-6.90 (m, 4H), 5.15-4.90 (t, 1H), 4.40-4.30 (m, 1H), 4.30-4.15 (t, 2H), 3.40-3.30 (d, 2H), 3.10-2.90 (t, 2H), 2.8 (s, 3H), 2.10-1.90 (m, 2H), 1.70-1.40 (m, 2H), (M+1) 353. $^1$H NMR (DMSO) of the oxalate salt of Compound 95—7.60-7.50 (dd, 1H), 7.50-7.45 (dd, 1H), 7.40-7.30 (t, 1H), 7.15-6.90 (m, 4H), 5.15-4.90 (t, 1H), 4.40-4.30 (m, 1H), 4.30-4.15 (t, 2H), 3.40-3.30 (d, 2H), 3.10-2.90 (t, 2H), 2.80 (s, 3H), 2.10-1.90 (m, 2H), 1.70-1.40 (m, 2H), (M+1) 353.

Example 36

Preparation of Compound 36

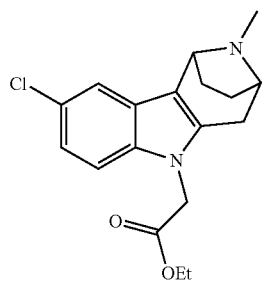 [SMILES: CCOC(=O)Cn1c2c(c3cc(Cl)ccc31)C1CCC(C2)N1C]

The title compound is prepared according to General Methods 2 and 3, by reacting 4-Chlorophenylhydrazine hydrochloride (10 g, 55 mmol) with ethyl bromoacetate (7.2 mL, 55 mmol) and triethylamine (23 mL, 165 mmol) (General Method 2), followed by Fischer indole cyclization with tropinone (7.8 g, 55.7 mmol) in ethanol (100 ml) to obtain the product after purification on neutral alumina chromatography eluting with dichloromethane-hexane gradient.

Example 37A

Preparation of Compound 37

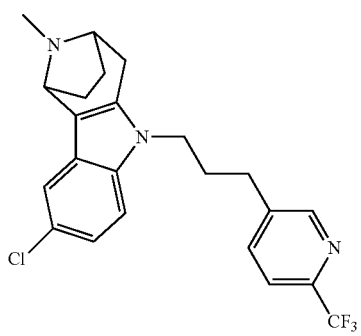 [SMILES: CN1C2CCC1c1c(n(CCCc3ccc(C(F)(F)F)nc3)c3ccc(Cl)cc13)C2]

The title compound is prepared according to General Methods 2 and 3, by reacting 4-chlorophenyl hydrazine with 5-(3-bromopropyl)-2-trifluoromethylpyridine (General Method 2), followed by Fischer indole cyclization with tropinone (General Method 3). The compound is purified by normal phase or reverse phase chromatography and is characterized by HPLC, LCMS and $^1$H NMR.

Example 37B

Preparation of Compound 37

Tetrabutylammonium chloride (56 mg, 0.2026 mmol) was dissolved in 50% NaOH (20 mL) followed by addition of 2-chloro-11-methyl-5,6,7,8,9,10-hexahydro-7,10-iminocyclohept[b]indole (100 mg, 0.4052 mmol). The reaction mixture was stirred for 5 min at RT, and 5-(2-bromoethyl)-2-(trifluoromethyl)pyridine (108 mg, 0.4052 mmol) was added and stirred at 100° C. for 12 h. The reaction was quenched with water and the product was extracted in dichloromethane. The combined organic layers were dried over sodium sulfate and concentrated under vacuum. The resulting crude product was purified by reverse phase chromatography. The NMR data for the compound is as follow: $^1$H NMR (CD$_3$OD)-8.50 (s, 1H), 7.90-7.80 (d, 1H), 7.70-7.60 (d, 1H), 7.50 (s, 1H), 7.40-7.30 (d, 1H), 7.20-7.10 (d, 1H), 4.20-4.10 (t, 2H), 2.90 (s, 3H), 2.80-2.90 (m, 4H), 2.60-2.50 (t, 2H), 2.40-2.10 (m, 6H).

Example 38A

Preparation of Compound 38

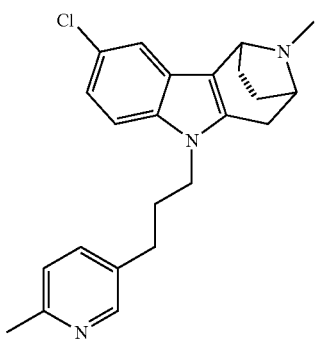

The title compound is prepared, according to General Methods 2 and 3, by reacting 4-chlorophenyl hydrazine with 5-(3-bromopropyl)-2-methylpyridine (General Method 2), followed by Fischer indole cyclization with tropinone (General Method 3). The compound is purified by normal phase or reverse phase chromatography and is characterized by HPLC, LCMS and $^1$H NMR.

Example 38B

Preparation of Compound 38

2-Chloro-11-methyl-5,6,7,8,9,10-hexahydro-7,10-iminocyclohept[b]indole (100 mg, 4 mmol), 5-(3-bromopropyl)-2-methylpyridine (95 mg, 0.4 mmol) was added to vigorously stirred mixture of tetra-n-butyl ammonium chloride (5 mg, 0.2 mmol) in 50% aq NaOH solution (2 mL) and the resultant mixture was heated to 60° C. for 6 h. Upon completion (the reaction was monitored by LCMS), water was added and extracted with dichloromethane; the combined organic layers were separated, dried over Na$_2$SO$_4$ and concentrated. The crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the product as TFA salt (15 mg, Yield 9.7%). The NMR data for the compound is as follows: $^1$H NMR (DMSO)—10.2 and 10.6 (s, 1H), 8.8 (s, 1H), 8.2 (m 1H), 7.4-7.8 (m, 1H), 7.2 (d, 1H), 5.1 (m, 1H), 4.4-4.0 (m, 3H), 3.6-3.3 (m, 1H), 3.2-3.0 (t, 2H), 2.9 (s, 3H), 2.7 (m, 1H), 2.6 (s, 3H), 2.4-2.3 (m, 1H), 2.2-2.0 (m, 4H), 1.9-1.8 (m, 1H).

Example 39A

Preparation of Compound 39

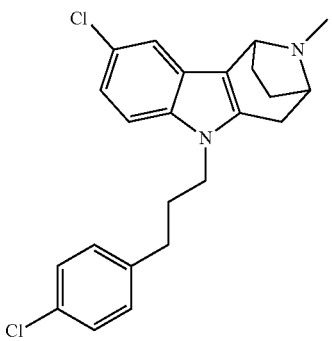 [SMILES: CN1C2CCC1c1c(n(CCCc3ccc(Cl)cc3)c3ccc(Cl)cc13)C2]

The title compound is prepared according to General Methods 2 and 3, by reacting 4-chlorophenyl hydrazine with 1-(3-bromopropyl)-4-chlorobenzene (General Method 2), followed by Fischer indole cyclization with tropinone (General Method 3). The compound is purified by normal phase or reverse phase chromatography and is characterized by HPLC, LCMS and $^1$H NMR.

Example 39B

Preparation of Compound 39

2-Chloro-11-methyl-5,6,7,8,9,10-hexahydro-7,10-iminocyclohept[b]indole (0.05 g, 0.2 mmol) was added to a solution of tetra n-butyl ammonium chloride (0.002 g, 0.01 mmole) in 50% aq NaOH (1 mL), stirred for 30 minutes. 1-(3-bromopropyl)-4-chlorobenzene (0.047 g, 0.2 mmol) was added and the reaction mixture was heated at 60° C. for 15 h. The progress of the reaction was monitored by LCMS, TLC. After complete reaction, the reaction mixture was quenched with water and extracted with ethyl acetate. The combined organic layers were dried over sodium sulfate and concentrated under reduced pressure. The crude product was first purified by column chromatography (SiO$_2$—100-200 mesh) followed by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to yield the product as a TFA salt (50 mg) after purification. The NMR data for the compound is as follows: $^1$H NMR (DMSO)—10.1 and 9.9 (bs, 1H), 7.6-7.5 (m, 2H), 7.4-7.3 (m, 3H), 7.2-7.1 (m, 2H), 5.1-5.0 (m, 1H)

4.5-4.2 (m, 3H), 3.4 (m, 1H), 3.1-3.0 (m, 1H), 2.9 (m, 2H), 2.7 (s, 3H), 2.4-2.3 (m, 2H), 2.2-1.8 (m, 4H).

Example 40

Preparation of Compound 40

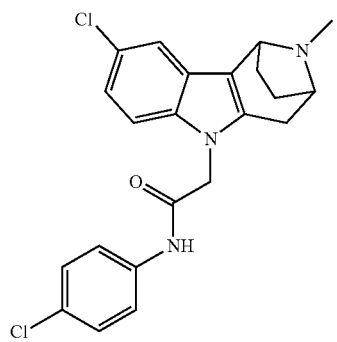 [SMILES: CN1C2CCC1c1c(n(CC(=O)Nc3ccc(Cl)cc3)c3ccc(Cl)cc13)C2]

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), further followed by hydrolysis of the ester (General Method 4) and amide bond formation under standard conditions with 4-chloroaniline (General Method 6). The compound is purified by normal phase or reverse phase chromatography and is characterized by HPLC, LCMS and $^1$H, NMR.

Example 41

Preparation of Compound 41

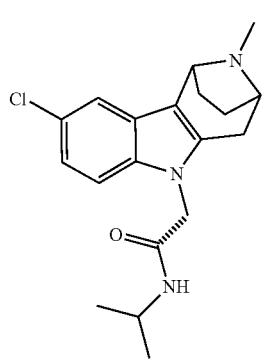

The title compound is prepared according to General Methods 2, 3, 4 and 6, by reacting 4-chlorophenyl hydrazine with ethyl bromo (or chloro) acetate (General Method 2), followed by Fischer indole cyclization with tropinone (General Method 3), and further followed by hydrolysis of the ester (General Method 4) and amide bond formation under standard conditions with isopropylamine (General Method 6). The compound is purified by normal phase or reverse phase chromatography and is characterized by HPLC, LCMS and $^1$H NMR.

Example 42

Preparation of Compound 42

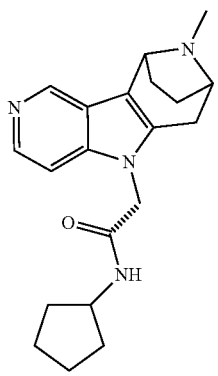

The title compound is prepared according to General Methods 2, 3, 4 and 6, by reacting 4-pyridyl hydrazine with ethyl bromo (of chloro) acetate (General Method 2), followed by Fischer indole cyclization with tropinone (General Method 3), and further followed by hydrolysis of the ester (General Method 4) and amide bond formation under standard conditions with pyrrolidine (General Method 6). The compound is purified by normal phase or reverse phase chromatography and is characterized by HPLC, LCMS and $^1$H NMR.

Example 43

Preparation of Compound 43

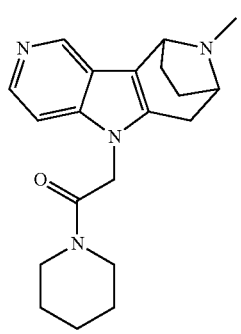 [SMILES: CN1C2CCC1c1c(n(CC(=O)N3CCCCC3)c3ccncc13)C2]

The title compound is prepared according to General Methods 2, 3, 4 and 6, by reacting 4-pyridyl hydrazine with ethyl bromo (or chloro) acetate (General Method 2), followed by Fischer indole cyclization with tropinone (General Method 3), and further followed by hydrolysis of the ester (General Method 4) and amide bond formation under standard condition with piperidine (General Method 6). The com-

Example 44

Preparation of Compound 44

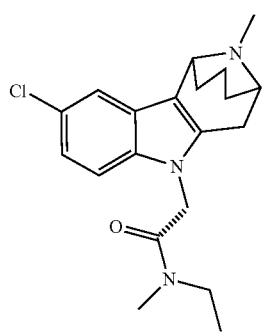

The title compound is prepared according to General Methods 2, 3, 4 and 6, by reacting 4-pyridyl hydrazine with ethyl bromo (or chloro) acetate (General Method 2), followed by Fischer indole cyclization with pseudopelletierine (General Method 3), further followed by hydrolysis of the ester (General Method 4) and amide bond formation under standard conditions with ethyl methyl amine (General Method 6). The compound is purified by normal phase or reverse phase chromatography and is characterized by HPLC, LCMS and $^1$H NMR.

Example 45

Preparation of Compound 45

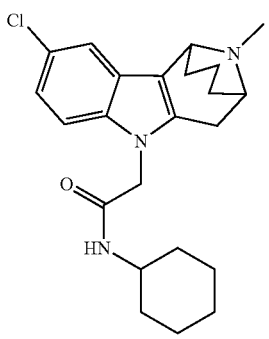 [SMILES: CN1C2CCCC1c1c(n(CC(=O)NC3CCCCC3)c3ccc(Cl)cc13)C2]

The title compound is prepared according to General Methods 2, 3, 4 and 6, by reacting 4-pyridyl hydrazine with ethyl bromo (or chloro) acetate (General Method 2) followed by Fischer indole cyclization with pseudopelletierine (General Method 3), and further followed by hydrolysis of the ester (General Method 4) and amide bond formation under standard conditions with cyclohexylamine (General Method 6). The compound is purified by normal phase or reverse phase chromatography and is characterized by HPLC, LCMS and $^1$H, NMR.

Example 46

Preparation of Compound 46

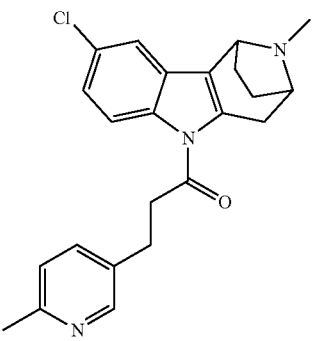

The title compound is prepared according to General Methods 3 and 9, by reacting 4-chlorophenyl hydrazine with tropinone under typical Fischer indole conditions (General Method 3) to provide an unsubstituted carboline. The carboline is reacted with the acid chloride of 3-(6-methylpyridin-3-yl) propanoic acid (General Method 9) to provide the crude product. The compound is purified by normal phase or reverse phase chromatography and is characterized by HPLC, LCMS and 1H NMR.

Example 47

Preparation of Compound 47

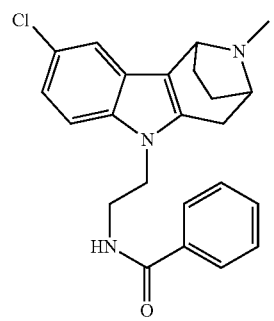 [SMILES: CN1C2CCC1c1c(n(CCNC(=O)c3ccccc3)c3ccc(Cl)cc13)C2]

The title compound is prepared according to General Methods 2, 3, 10 and 11, by reacting 4-chlorophenylhydrazine with bromo (iodo or chloro) acetonitrile (General Method 2), followed by Fischer indole cyclization with tropinone (General Method 3), and further followed by reduction of nitrile (General Method 10) and amide bond formation under standard conditions with benzoic acid (General

Example 48

Preparation of Compound 48

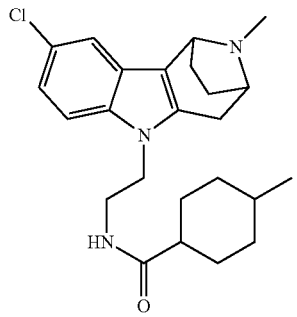 [SMILES: CC1CCC(C(=O)NCCn2c3c(c4cc(Cl)ccc42)C2CCC(C3)N2C)CC1]

The title compound is prepared according to General Methods 2, 3, 10 and 11, by reacting 4-chlorophenylhydrazine with bromo (iodo or chloro) acetonitrile (General Method 2), followed by Fischer indole cyclization with tropinone (General Method 3), and further followed by reduction of nitrile (General Method 10) and amide bond formation under standard conditions with 4-methylcyclohexanecarboxylic acid (General Method 11). The compound is purified by normal phase or reverse phase chromatography and is characterized by HPLC, LCMS and ¹H NMR.

Example 49

Preparation of Compound 49

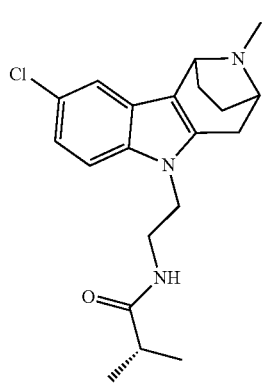

The title compound is prepared according to General Methods 2, 3, 10 and 11, by reacting 4-chlorophenylhydrazine with bromo (iodo or chloro) acetonitrile (General Method 2), followed by Fischer indole cyclization with tropinone (General Method 3), and further followed by reduction of nitrile (General Method 10) and amide bond formation under standard conditions with isobutyric acid (General Method 11). The compound is purified by normal phase or reverse phase chromatography and is characterized by HPLC, LCMS and ¹H NMR.

Example 50

Preparation of Compound 50

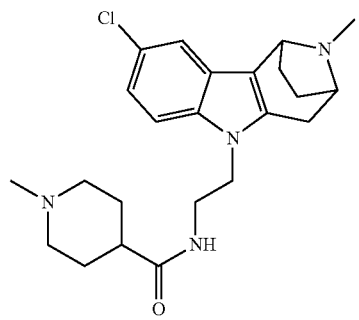

The title compound is prepared according to General Methods 2, 3, 10 and 11, by reacting 4-chlorophenylhydrazine with bromo (iodo or chloro) acetonitrile (General Method 2), followed by Fischer indole cyclization with tropinone (General Method 3), and further followed by reduction of nitrile (General Method 10) and amide bond formation under standard conditions with 1-methylpiperidine-4-carboxylic acid (General Method 11). The compound is purified by normal phase or reverse phase chromatography and is characterized by HPLC, LCMS and ¹H NMR.

Example 51

Preparation of Compound 51

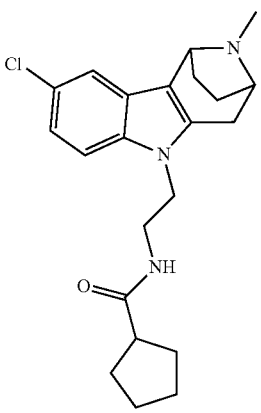 [SMILES: CN1C2CCC1c1c(n(CCNC(=O)C3CCCC3)c3ccc(Cl)cc13)C2]

The title compound is prepared according to General Methods 2, 3, 10 and 11, by reacting 4-chlorophenylhydrazine with bromo (iodo or chloro) acetonitrile (General Method 2), followed by Fischer indole cyclization with tropinone (General Method 3), and further followed by reduction of nitrile (General Method 10) and amide bond formation under standard conditions with cyclopentanecarboxylic acid (General Method 11). The compound is purified by normal

Example 52A

Preparation of Compound 52

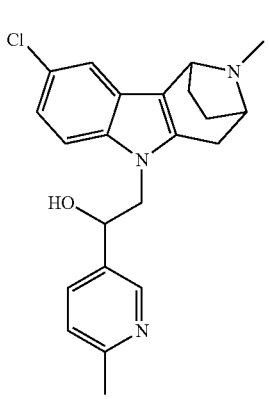 [SMILES: Cc1ccc(C(O)Cn2c3c(c4cc(Cl)ccc42)C2CCC(C3)N2C)cn1]

The title compound is prepared according to General Methods 3 and 7, by reacting 4-chlorophenyl hydrazine with tropinone under typical Fischer indole conditions (General Method 3) to provide an unsubstituted carboline. The carboline is reacted with 2-methyl-5-(oxiran-2-yl)pyridine (General Method 7) to provide the crude product. The compound is purified by normal phase or reverse phase chromatography and is characterized by HPLC, LCMS and 1H NMR.

Example 52

Preparation of Compound 52

2-Chloro-11-methyl-5,6,7,8,9,10-hexahydro-7,10-iminocyclohept[b]indole (246 mg, 1 mmol) was dissolved in DMF (2 mL) and added to a solution of sodium hydride (50%, 100 mg, 2.2 mmole) in portions at RT and stirred for 100 min. A solution of 2-methyl-5-(oxiran-2-yl)pyridine (270 mg, 2 mmol) in DMF (1 mL) was added dropwise for 10 min and stirred overnight at RT. The reaction was monitored by LCMS. The reaction mixture was quenched with methanol and concentrated to dryness. Water was added to the residue and extracted in ethyl acetate (3×50 mL), the combined organic layer were dried over anhydrous sodium sulfate and evaporated under reduced pressure. The crude product was purified by reverse phase chromatography to get pure product as TFA salt (122 mg, 24.64%). The NMR data for the compound is as follows: $^1$H NMR (DMSO)—9.95 (bm, 1H), 8.66-8.56 (m, 1H), 8.0-7.78 (m, 1H), 7.70-7.40 (m, 3H), 7.20-7.10 (m, 1H), 6.05.85 (m, 1H), 5.10-4.96 (m, 1H), 4.40-4.10 (m, 2H), 2.82 (s, 3H), 2.43 (s, 3H), 2.40-2.25 (m, 3H), 2.18-2.02 (m, 2H), 1.80-1.64 (m, 2H).

Example 53

Preparation of Compound 53

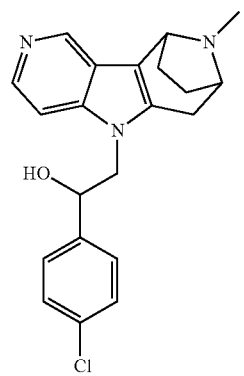 [SMILES: CN1C2CCC1c1c(n(CC(O)c3ccc(Cl)cc3)c3ccncc13)C2]

The title compound is prepared according to General Methods 3 and 7, by reacting 4-pyridylhydrazine with tropinone under typical Fischer indole conditions (General Method 3) to provide an unsubstituted carboline. The carboline is reacted with 4-chlorostyrene oxide (General Method 7) to provide the crude product. The compound is purified by normal phase or reverse phase chromatography and is characterized by HPLC, LCMS and 1H NMR.

Example 54A

Preparation of Compound 54

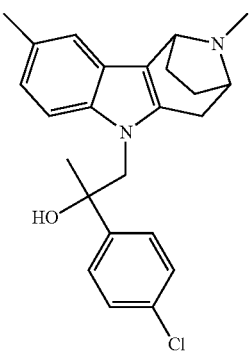

The title compound is prepared according to General Methods 3 and 7, by reacting p-tolylhydrazine with tropinone under typical Fischer indole conditions (General Method 3) to provide an unsubstituted carboline. The carboline is reacted with 2-(4-chlorophenyl)-2-methyloxirane (General Method 7) to provide the crude product. The compound is purified by normal phase or reverse phase chromatography and is characterized by HPLC, LCMS and 1H NMR. $^1$H NMR (CD$_3$OD) of the oxalate salt 7.40 (m, 2H), 7.30-7.20 (m, 3H), 7.10 (m, 1H), 6.90 (m, 1H), 4.30 (m, 1H) 4.15 (m, 2H), 3.05 (m, 1H), 2.90 (m, 2H), 2.70 (m, 3H), 2.40 (s, 3H), 2.20 (m, 2H), 1.80 (m, 2H) 1.50 (m, 3H). (M+1) 395.

Example 54B

Preparation of Compound 54

Sodium hydride (38 mg, 1.6 mmol, 1.45 equiv) was added to a solution of 3-chloro-11-methyl-6,7,8,9,10,11-Hexahydro-7,11-iminocyclooct[b]indole (290 mg, 1.11 mmol, 1.0 equiv.) in DMF (6 mL), and heated to 120° C. for 1 h with stirring. The reaction mixture was cooled to 0° C. and 2-methyl-5-(2-methyloxiran-2-yl)pyrimidine (400 mg, 2.66 mmol, 2.4 equiv) was added dropwise over 5 minutes. The temperature was raised to 120° C. and stirred for 2 hours. The reaction mixture was cooled to RT and partitioned between ethyl acetate (60 mL) and water (15 mL). The organic layer was separated and the aqueous layer was extracted with ethyl acetate (1×20 mL). The combined organic layers were washed with water followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. The pure compound was converted to its oxalate salt. The analytical sample was prepared by dissolving free base in THF (10 mL) and treatment with 1 equiv. of oxalic acid dihydrate.

Example 55

Preparation of Compound 55

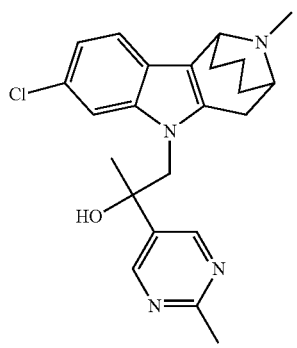 [SMILES: Cc1ncc(C(C)(O)Cn2c3c(c4ccc(Cl)cc42)C2CCCC(C3)N2C)cn1]

The title compound is prepared according to General Methods 3 and 7, by reacting p-tolylhydrazine with pseudopelletierine under typical Fischer indole conditions (General Method 3) to provide an unsubstituted carboline. The carboline is reacted with 2-methyl-5-(2-methyloxiran-2-yl)pyrimidine (General Method 7) to provide the crude product. The compound is purified by normal phase or reverse phase chromatography and is characterized by HPLC, LCMS and 1H NMR.

Sodium hydride (38 mg, 1.6 mmol, 1.45 equiv.) was added to a solution of 3-chloro-11-methyl-6,7,8,9,10,11-Hexahydro-7,11-iminocyclooct[b]indole (290 mg, 1.11 mmol, 1.0 equiv.) in DMF (6 mL) and the resulting mixture was stirred at 120° C. for 1 h. The reaction mixture was cooled to 0° C. and 2-methyl-5-(2-methyloxiran-2-yl)pyrimidine (400 mg, 2.66 mmol, 2.4 equiv) was added drop wise in 5 minutes. The temperature was increased to 120° C. and the reaction mixture was stirred for another 2 h. The reaction mixture was cooled to RT and partitioned between ethyl acetate (60 mL) and water (15 mL). The organic layer was separated and the aqueous layer was extracted with ethyl acetate (1×20 mL). The combined organic layer was washed with water followed by brine, dried over sodium sulfate and concentrated under vacuum to obtain the crude product, which was purified by flash column chromatography over silica gel (230-400 mesh, deactivated with 1% triethylamine/hexane) using a gradient of 5 to 15% methanol/ethyl acetate to yield the free base which was converted to its oxalate salt. The analytical sample was prepared by dissolving free base in THF (10mL) and treatment with oxalic acid dehydrate (1 equiv.).

Example 56A

Preparation of Compound 56

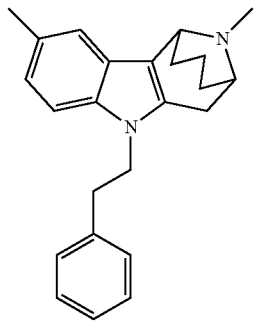

The title compound was prepared according to General Methods 2 and 3 by reacting p-tolylhydrazine hydrochloride (10 g, 63 mmol) with phenethyl bromide (11.6 g, 63 mmol) and triethylamine (19.4 g, 189 mmol) (General Method 2) followed by Fischer indole cyclization with pseudopelletierine (338 mg, 2.2 mmol) in ethanol (100 mL) (General Method 3) to obtain the product after purification on silica gel (230-400 mesh) chromatography eluting with methanol-dichloromethane gradient followed by reverse-phase chromatography (C-18, 500 mm×50 mm. Mobile Phase A=0.05% TFA in water, B=0.05% TFA in acetonitrile, Gradient: 10% B to 80% B in 30 min, injection vol. 5 mL).

Example 56B

Preparation of Compound 56

1-phenethyl-1-p-tolylhydrazine (500 mg, 2.21 mmol) and pseudopelletierine (238 mg, 2.21 mmol) in ethanolic HCl (10 mL) was stirred at 120° C. for 16 h (the progress of the reaction was monitored by LCMS). After completion of the reaction, the reaction mixture was concentrated to dryness and basified with aq. saturated $NaHCO_3$, extracted in ethyl acetate, the organic layer was dried over $Na_2SO_4$ and concentrated. The crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the product as TFA salt (5 mg). $^1$H NMR ($CDCl_3$) δ 12.0 (bs, 1H), 7.40-7.30 (d, 1H), 7.20 (s, 2H), 7.15-7.10 (d, 2H), 6.90-6.80 (t, 3H), 4.80 (m, 1H), 4.4-4.2 (m, 2H), 3.7-3.6 (m, 1H), 3.3-3.2 (m, 3H), 2.5 (m, 1H), 2.5 (s, 3H), 2.4-2.3 (m, 1H), 2.3-2.1 (m, 1H), 2.1 (s, 3H), 1.9-1.8 (m, 1H), 1.5-1.3 (m, 2H), 1.1 (m, 1H), MS m/z observed 345. HPLC (Method 3) RT 6.85 min.

Example 57A

Preparation of Compound 57

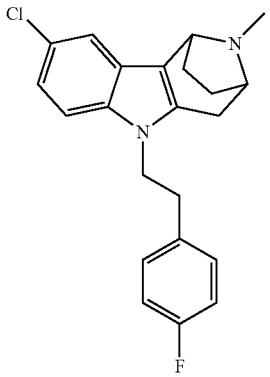 [SMILES: CN1C2CCC1c1c(n(CCc3ccc(F)cc3)c3ccc(Cl)cc13)C2]

The title compound was prepared according to General Methods 2 and 3 by reacting 4-chlorophenylhydrazine hydrochloride (500 mg, 3.1 mmol) with 4-fluorophenethyl bromide (639 mg, 3.1 mmol) and triethylamine (1.3 ml, 9.4 mmol) (General Method 2) followed by Fischer indole cyclization with tropinone (105 mg, 0.7 mmol) in ethanol (10 ml) (General Method 2) to obtain 10 mg of product after purification by revere-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) followed by purification on neutral alumina chromatography elating with methanol-dichloromethane gradient.

Example 57B

Preparation of Compound 57

1-(4-fluorophenethyl)-1-(4-chlorophenyl)hydrazine (200 mg, 0.75 mmol) and 8-methyl-8-aza-bicyclo[3.2.1]octan-3-one hydrochloride (105 mg, 0.75 mmol) were taken in ethanolic HCl (10 mL), and stirred at RT for 15 min, after which the solvent was removed in vacuo. The reaction mixture was taken in ethanol (10 mL) and heated at 120° C. for 2 h. After completion of the reaction (the progress of the reaction was monitored by LCMS), the reaction mixture was concentrated to dryness and basified with aq. saturated $NaHCO_3$, extracted in ethyl acetate, the organic layer was separated, dried over $Na_2SO_4$ and concentrated. The crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 0.5 mL) to obtain the product as TFA salt (10 mg, Yield 3.5%). $^1$H NMR (HCl salt, DMSO) δ 7.55-7.50 (d, 1H), 7.45-7.40 (d, 1H), 7.25-7.20 (d, 1H), 7.20-7.00 (m, 2H), 6.90-6.80 (m, 2H), 5.2-4.8 (mm, 1H), 4.40-4.0 (m, 3H), 3.3-3.25 (m, 1H), 3.0-2.9 (m, 2H), 2.8 (s, 3H), 2.7-2.6 (m, 1H), 2.3-2.2 (m, 2H), 2.0-1.9 (m, 1H), 1.5-1.3 (m, 1H). MS m/z observed 369. HPLC (Method 3) RT 6.77 min.

Example 58A

Preparation of Compound 58

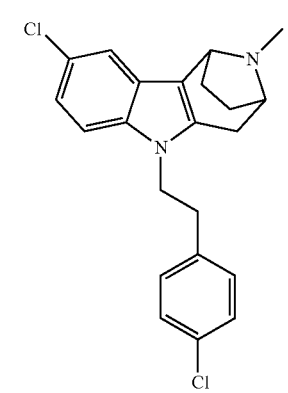 [SMILES: CN1C2CCC1c1c(n(CCc3ccc(Cl)cc3)c3ccc(Cl)cc13)C2]

The title compound was prepared according to General Methods 2 and 3 by reacting 4-chlorophenylhydrazine hydrochloride (500 mg, 3.1 mmol) with 4-chlorophenethyl bromide (691 mg, 3.1 mmol) and triethylamine (1.3 ml, 9.4 mmol) (General Method 2) followed by Fischer indole cyclization with tropinone (198 mg, 1.4 mmol) in ethanol (20 ml) (General Method 3) to obtain the product after purification by revere-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 58B

Preparation of Compound 58

1-(4-chlorophenethyl)-1-(4-chlorophenyl)hydrazine (400 mg, 1.42 mmol) and 8-methyl-8-aza-bicyclo[3.2.1]octan-3-one hydrochloride (198 mg, 1.42 mmol) in ethanolic HCl (20 mL) was stirred at RT for 15 minutes. The solvent was removed in vacuo and the reaction mixture was dissolved in ethanol (20 mL) and heated at 120° C. for 3 h (the progress of the reaction was monitored by LCMS). The reaction mixture was concentrated to dryness and basified with aq. saturated $NaHCO_3$, extracted in ethyl acetate, the organic layer was dried over $Na_2SO_4$ and concentrated. The crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the product as TFA salt (47 mg, yield=8.5%). $^1$H NMR ($CDCl_3$-$D_2O$) δ 7.45 (s, 1H), 7.26-7.25 (d, 2H), 7.05-7.00 (d, 2H), 6.80-6.60 (d, 2H), 4.8 (m, 1H), 4.30-4.20 (bs, 2H), 4.10 (bs, 1H), 3.1-3.0 (bs, 3H), 2.7-2.4 (m, 4H), 2.2-2.0 (m, 2H), 1.6 (m, 1H), 1.5-1.3 (m, 1H), MS m/z observed 385. HPLC (Method 3) RT 6.98 min.

Example 59A

Preparation of Compound 59

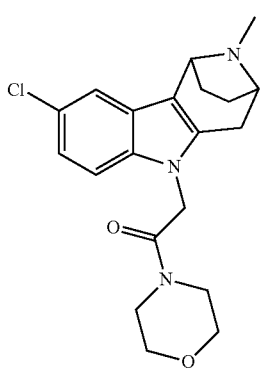 [SMILES: CN1C2CCC1c1c(n(CC(=O)N3CCOCC3)c3ccc(Cl)cc13)C2]

Compound 59 was prepared. A mixture of compound 36 (200 mg) obtained by following General Methods 2 and 3, and morpholine (2 ml) was heated at 120° C. for 15 h (by following General Method 12) to obtain 2-(2-chloro-11-methyl-5,6,7,8,9,10-Hexahydro-7,10-iminocyclohept[b]indol-5-yl)-1-morpholinoethanone after purification on neutral alumina chromatography eluting with methanol-dichloromethane gradient. The free base was converted into its HCl salt by treatment of ethanol-HCl.

Example 59B

Preparation of Compound 59

2-(2-Chloro-11-methyl-5,6,7,8,9,10-hexahydro-7,10-iminocyclohept[b]indol-5-yl)acetate (400 mg, 1.0 mmol) was added to morpholine (4.0 mL, 45.0 mmol) and heated the mixture at 120° C. for 15 h. After completion of the reaction (the completion of the reaction was monitored by LCMS), the reaction mixture was concentrated to dryness. The crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the product as TFA salt (9 mg, Yield 1.62%). $^1$H NMR (HCl salt, DMSO) δ 7.80-7.70 (d, 1H), 7.60-6.70 (dd, 1H), 7.20-7.15 (d, 1H), 5.20 (m, 1H), 5.24 (d, 1H), 5.0 (m, 1H), 4.2 (d, 1H), 3.7-3.5 (m, 8H), 3.2-3.1 (m, 1H), 3.0-2.9 (m, 1H), 2.9 (s, 3H), 2.4-2.3 (m, 1H), 2.2-2.0 (m, 2H), 1.9-1.8 (m, 1H), MS m/z observed 374, HPLC (Method 3) RT 10.18 min.

Example 60A

Preparation of Compound 60

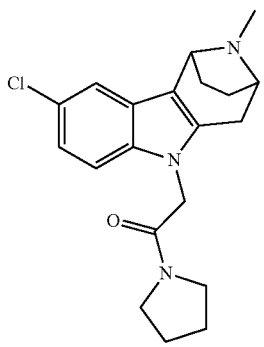 [SMILES: CN1C2CCC1c1c(n(CC(=O)N3CCCC3)c3ccc(Cl)cc13)C2]

Compound 60 was prepared. A mixture of compound 36 (100 mg) obtained by following General Methods 2 and 3, and pyrrolidine (1 ml) was heated at 120° C. for 12 h (by following General Method 12) to obtain the product as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, infection vol. 5 mL).

Example 60B

Preparation of Compound 60

2-(2-Chloro-11-methyl-5,6,7,8,9,10-hexahydro-7,10-iminocyclohept[b]indol-5-yl)acetate (100 mg, 0.3 mmol) was added to pyrrolidine (4.0 mL, 4.7 mmol) and the reaction mixture was heated at 120° C. for 12 h. After completion of the reaction (the progress of the reaction was monitored by LCMS), the reaction mixture was concentrated to dryness. The crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the product as TFA salt (10 mg, Yield 9.3%). $^1$H NMR (CDCl$_3$) δ 13.3 (bs, 1H), 7.42 (s, 1H), 7.20-7.18 (d, 1H), 7.16-7.14 (d, 1H), 4.9 (d, 1H), 4.8 (d, 1H), 4.6 (d, 1H), 4.3 (bs, 1H), 3.7-3.0 (t, 1H), 3.5-3.4 (t, 2H), 3.4-3.3 (m, 1H), 2.9 (s, 3H), 2.6-2.5 (m, 1H), 2.3-2.0 (m, 3H), 1.9-1.8 (m, 1H), 1.4-1.2 (m, 4H), MS m/z observed 358. HPLC (Method 3) RT 5.50 min.

Example 61A

Preparation of Compound 61

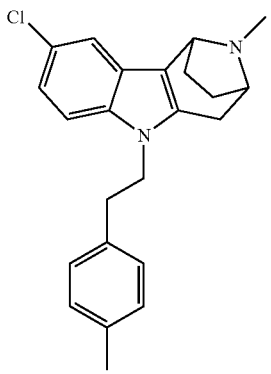 [SMILES: Cc1ccc(CCn2c3c(c4cc(Cl)ccc42)C2CCC(C3)N2C)cc1]

The title compound was prepared according to General Methods 2 and 3, by using 0.5 g 4-chlorophenylhydrazine hydrochloride, 0.42 mL 4-methylphenethyl bromide and 1.16 mL triethylamine (General Method 2) and tropinone (0.23 g) in 10 mL ethanol-HCl (General Method 3) at 120° C. for 18 h to obtain the product after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) followed by silica gel chromatography eluting with methanol-dichloromethane gradient. The free base was converted into its HCl salt by treatment of ethanol-HCl.

Example 61B

Preparation of Compound 61

1-(2-(6-methylpyridin-3-yl)ethyl)-1-p-chlorophenylhydrazine (450 mg, 1.7 mmol) and 8-methyl-8-aza-bicyclo[3.2.1]octan-3-one hydrochloride (230 mg, 1.7 mmol) were dissolved in ethanolic HCl (10 mL) and stirred at RT for 15 minutes. The solvent was removed in vacuo. The reaction mixture was dissolved in ethanol (10 mL) and heated at 120° C. for 16 h. After completion of the reaction (as monitored by LCMS), the reaction mixture was concentrated to dryness and basified with aq. saturated NaHCO$_3$, and extracted in ethyl acetate. The organic layer was dried over Na$_2$SO$_4$ and concentrated. The crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the product as TFA salt (7 mg (1.0%). $^1$H NMR (HCl salt, CD3OD) δ 7.55 (s, 1H), 7.50-7.40 (d, 1H), 7.35-7.15 (m, 1H), 7.15-6.90 (t, 2H), 6.90-6.60 (t, 2H), 4.9 (m, 1H), 4.5 (d, 1H), 4.3 (d, 1H), 4.2-4.0 (m, 1H), 3.3-3.2 (m, 1H), 3.10-3.0 (m, 2H), 2.9 (s, 3H), 2.8-2.7 (m, 1H), 2.5 (s, 3H), 2.2-2.1 (m, 2H), 1.64-1.3 (m, 2H). MS m/z observed 365. HPLC (Method 3) RT 6.89 min.

Example 62A

Preparation of Compound 62

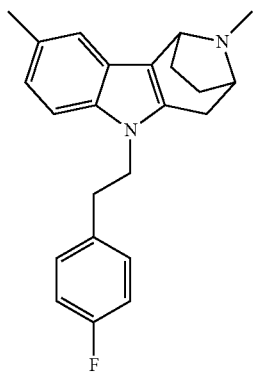

The title compound was prepared, according to General Methods 2 and 3, by using p-tolylhydrazine hydrochloride (0.5 g), 4-fluorophenethlbromide (0.7 g) and triethylamine (0.44 mL) (General Method 2) and tropinone (0.44 g, 55.7 mmol) in ethanol-HCl (10 ml) (General Method 3) to obtain the product as a TFA salt after purification on neutral alumina chromatography elating with dichloromethane-hexane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 62B

Preparation of Compound 62

1-(4-fluorophenethyl)-1-p-tolylhydrazine (4.0 gm, 16.3 mmol) and 8-methyl-8-azabicyclo[3.2.1]octan-3-one (2.2 gm, 16.3 mmol) were taken in ethanolic HCl (40 mL), and stirred at RT for 15 min, after which the solvent was removed in vacuo. The reaction mixture was taken in ethanol (40 mL) and heated at 90° C. for 3 hrs. After completion of the reaction (the progress of the reaction was monitored by LCMS), the reaction mixture was concentrated to dryness and basified with aq. saturated NaHCO$_3$, extracted in ethyl acetate, the organic layer was separated dried over Na$_2$SO$_4$ and concentrated. The crude product was purified by reverse phase to get pure compound (310 mg). 1-(4-fluorophenethyl)-1-p-tolylhydrazine (0.7 g) and 8-methyl-8-azabicyclo[3.2.1]octan-3-one (0.438 g) were mixed ethanol-HCl (10 mL) and heated at 90° C. for 4 h, the solvent was removed under reduced pressure and the residue was basified with saturated aq. NaHCO$_3$ and extracted with ethyl acetate. The combined organic layer was dried over sodium sulfate and evaporated to obtain the crude product which was purified on neutral alumina using hexanes ethyl acetate eluent followed by reverse phase chromatography to obtain the product as a TFA salt (50 mg). The NMR data for the compound is as follows: $^1$H NMR (DMSO)—7.60-7.45 (d, 1H), 7.45-7.40 (d, 1H), 7.20-6.80 (m, 5H), 4.40-4.00 (m, 3H), 3.10-2.90 (m, 3H), 2.80-2.70 (d, 2H), 2.40 (s, 3H), 2.20 (s, 3H), 2.10-1.90 (m, 2H), 1.60-1.30 (m, 2H).

Example 63

Preparation of Compound 63

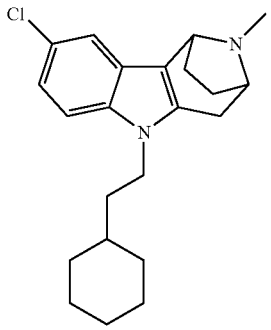 [SMILES: CN1C2CCC1c1c(n(CCC3CCCCC3)c3ccc(Cl)cc13)C2]

The title compound is prepared according to General Methods 2 and 3 by reacting 4-chlorophenylhydrazine with (2-bromoethyl)cyclohexane (General Method 2) followed by Fischer indole cyclization with tropinone (General Method 3). The compound is purified by normal phase or reverse phase chromatography and is characterized by HPLC, LCMS and $^1$H NMR.

Example 64

Preparation of Compound 64

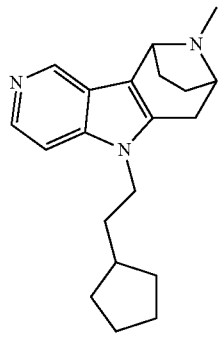 [SMILES: CN1C2CCC1c1c(n(CCC3CCCC3)c3ccncc13)C2]

207

The title compound is prepared according to General Methods 2 and 3 by reacting 4-pyridylhydrazine with 2-bromoethyl)cyclopentane (General Method 2) followed by Fischer indole cyclization with tropinone (General Method 3). The compound is purified by normal phase or reverse phase chromatography and is characterized by HPLC, LCMS and ¹H NMR.

Example 65

Preparation of Compound 65

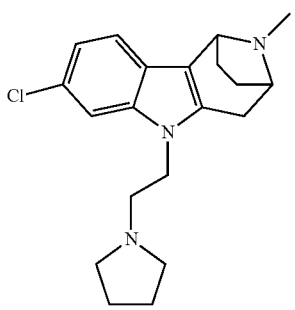 [SMILES: CN1C2CCC1c1c(n(CCN3CCCC3)c3cc(Cl)ccc13)C2]

The title compound is prepared according to General Methods 2 and 3 by reacting 3-chlorophenylhydrazine with 1-(2-bromoethyl)pyrrolidine (General Method 2) followed by Fischer indole cyclization with tropinone (General Method 3). The compound is purified by normal phase or reverse phase chromatography and is characterized by HPLC, LCMS and ¹H NMR.

Example 66

Preparation of Compound 66

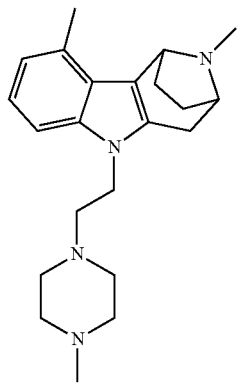 [SMILES: Cc1cccc2c1c1c(n2CCN2CCN(C)CC2)CC2CCC1N2C]

The title compound is prepared according to General Methods 2 and 3 by reacting m-tolylhydrazine with 1-(2-bromoethyl)-4-methylpiperazine (General Method 2) followed by Fischer indole cyclization with tropinone (General Method 3). The compound is purified by normal phase or reverse phase chromatography and is characterized by HPLC, LCMS and ¹H NMR.

208

Example 67

Preparation of Compound 67

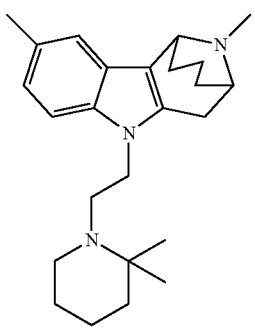

The title compound is prepared according to General Methods 2 and 3 by reacting p-tolylhydrazine with 1-(2-bromoethyl)-2,2-dimethylpiperidine (General Method 2) followed by Fischer indole cyclization with pseudopelletierine (General Method 3). The compound is purified by normal phase or reverse phase chromatography and is characterized by HPLC, LCMS and ¹H NMR.

Example 68

Preparation of Compound 68

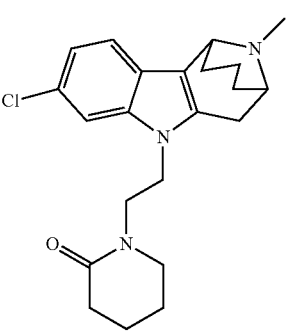 [SMILES: CN1C2CCCC1c1c(n(CCN3CCCCC3=O)c3cc(Cl)ccc13)C2]

The title compound is prepared according to General Methods 2 and 3 by reacting 3-chlorophenylhydrazine with 1-(2-bromoethyl)piperidin-2-one (General Method 2) followed by Fischer indole cyclization with pseudopelletierine (General Method 3). The compound is purified by normal phase or reverse phase chromatography and is characterized by HPLC, LCMS and ¹H NMR.

Example 69

Preparation of Compound 69

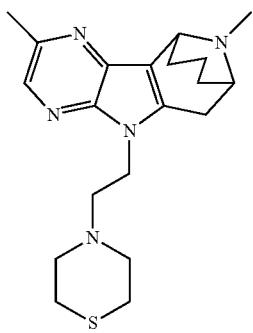

The title compound is prepared according to General Methods 2 and 3 by reacting 2-hydrazinyl-5-methylpyrimidine with 4-(2-bromoethyl)thiomorpholine (General Method 2) followed by Fischer indole cyclization with pseudopelletierine (General Method 3). The compound is purified by normal phase or reverse phase chromatography and is characterized by HPLC, LCMS and $^1$H NMR.

Example 70

Preparation of Compound 70

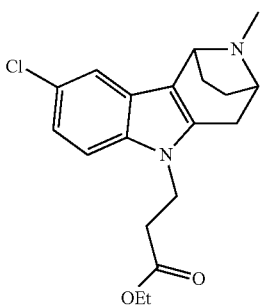 [SMILES: CCOC(=O)CCn1c2c(c3cc(Cl)ccc31)C1CCC(C2)N1C]

Compound 70 was prepared according to a general method detailed herein. 2-Chloro-11-methyl-5,6,7,8,9,10-hexahydro-7,10-iminocyclohept[b]indole (0.5 g, 2.03 mmol) was dissolved in DMSO (7 mL); CuI (0.038 g, 0.020 mmol), L-proline (0.046 g, 0.041 mmol) and $K_3PO_4$ (0.865 g, 4.06 mmol) were added to the reaction mixture and stirred for 10 min at RT. 3-bromo propionate (0.31 mL, 2.44 mmol) was added drop wise and the reaction mixture was heated to 90° C. for 12 h. Upon completion (the progress of the reaction was monitored by TLC and LCMS), 10 mL of brine was added to the reaction mixture, followed by extraction with diisopropyl ether (10 mL×3). The combined ether layers were dried over sodium sulfate and concentrated under reduced pressure to obtain crude viscous product which was further purified by column chromatography using 10:90 (methanol/dichloromethane) to obtain ethyl 3-(2-chloro-11-methyl-5,6,7,8,9,10-hexahydro-7,10-iminocyclohept[b]indol-5-yl)propanoate (0.4 g). The product (0.01 g 0.03 mmol) was further dissolved in THF (3 mL), oxalic acid (3.7 mg, 0.03 mmol) added and the resulting mixture was stirred for 10 min at RT and then concentrated under reduced pressure to provide the product as an oxalate salt (12 mg). The NMR data for the compound is as follows: $^1$H NMR (DMSO)—7.6 (s, 1H), 7.5 (d, 1H), 7.2 (d, 1H), 5.15-4.90 (m, 1H), 4.4-4.2 (m, 3H), 3.5-3.4 (d, 1H), 3.1-3.0 (d, 1H), 4.0 (q, 2H), 2.9 (bs, 3H), 2.7-2.6 (bs, 2H), 2.4 (bs, 2H), 2.2-2.1 (m, 1H), 1.9-1.8 (m, 1H), 1.1 (t, 3H).

Example 71

Preparation of Compound 71

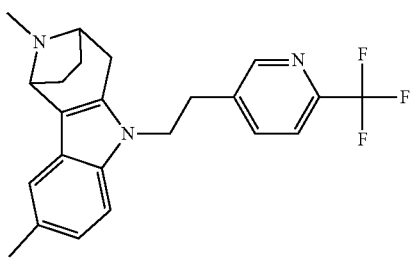 [SMILES: Cc1ccc2c(c1)c1c(n2CCc2ccc(C(F)(F)F)nc2)CC2CCC1N2C]

Compound 71 was prepared according to a general method detailed herein. 2,11-Dimethyl-5,6,7,8,9,10-hexahydro-7,10-iminocyclohept[b]indole (0.2 g, 0.81 mmol) and powdered KOH (0.45 g) were mixed in 2.5 mL N-methyl-2-pyrrolidone and stirred for 10 min at 25° C. 2-(trifluoromethyl)-5-vinylpyridine (0.278 g, 1.61 mmol) was added slowly to the reaction mixture and stirred for 4 h at 25° C. The reaction mixture was quenched with water, extracted with ethyl acetate; the combined organic layers were dried over sodium sulfate and evaporated to obtain the crude product. Purification by reverse-phase chromatography generated the product as a TFA salt (10 mg). The NMR data for the compound is as follows: $^1$H NMR ($CD_3OD$)-8.10-8.0 (m, 1H), 7.70-7.60 (m, 2H), 7.40-7.20 (m, 2H), 7.10-7.0 (d, 1H), 5.0-4.95 (m, 1H), 4.5-4.3 (m, 1H), 4.3 (m, 1H), 4.05-4.2 (m, 1H), 3.3 (m, 1H), 3.2-3.1 (m, 2H), 2.9 and 2.7 (s, 3H), 2.6 (m, 1H), 2.5 and 2.1 (s, 3H), 2.4-2.3 (m, 2H), 2.1-2.0 (m, 1H), 1.6-1.4 (m, 1H).

Example 72

Preparation of Compound 72

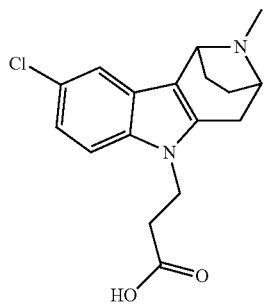 [SMILES: CN1C2CCC1c1c(n(CCC(=O)O)c3ccc(Cl)cc13)C2]

Compound 72 was prepared according to a general method detailed herein. 3-(2-Chloro-11-methyl-5,6,7,8,9,10-hexahydro-7,10-iminocyclohept[b]indol-5-yl)propanoic acid ethyl ester (0.255 g, 0.650 mmol) was dissolved in methanol (20 mL) and a solution of KOH (0.110 g, 1.95 mmol) in water (1 mL) was added to the reaction mixture and heated to reflux for 30 min. The reaction was monitored by TLC and LCMS, and after completion of the reaction, the reaction mixture was concentrated under reduced pressure. Water (10 mL) was added to the concentrate, the pH was adjusted to 2 and the reaction mixture was extracted with ethyl acetate (2×10 mL). The combined organic layers were dried over sodium sulfate and concentrated under reduced pressure to afford the product (16 mg). The NMR data for the compound is as follows: ¹H NMR (DMSO)—11.46 and 10.6 (bs, 1H), 7.55 (d, 1H), 7.45-7.48 (dd, 1H), 7.13 (d, 1H), 5.1-5.0 (m, 1H), 4.4-4.1 (m, 3H), 3.4-3.3 (dd, 1H), 3.1 (t, 2H), 2.6-2.4 (m, 1H), 2.8 (s, 3H), 2.3-2.2 (m, 2H), 2.1-2.0 (m, 1H), 1.9-1.7 (m, 1H).

Example 73

Preparation of Compound 73

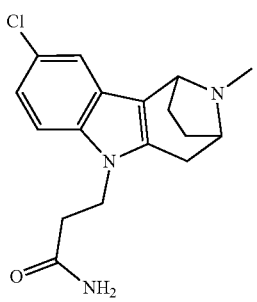 [SMILES: CN1C2CCC1c1c(n(CCC(N)=O)c3ccc(Cl)cc13)C2]

Compound 73 was prepared according to a general method detailed herein. 3-(2-Chloro-11-methyl-5,6,7,8,9,10-hexahydro-7,10-iminocyclohept[b]indol-5-yl)propanoic acid (0.150 g, 0.472 mmol) dissolved in dichloromethane (2 mL) and cooled to 0° C. Oxalyl chloride (0.061 mL, 0.708 mmol) was added drop-wise, followed by addition of a catalytic amount (1 drop) of N,N-dimethylformamide and the reaction mixture was stirred for 1 h at RT. Excess oxalyl chloride was distilled off under reduced pressure, the residue was dissolved in toluene and the resulting solution was purged with ammonia gas until pH was basic. The reaction mixture was stirred for 30 min at RT. After completion of reaction, reaction mixture was quenched with water and extracted with ethyl acetate (2×10 mL). The combined organic levels were dried over sodium sulfate and concentrated under reduced pressure to obtain the product as a TFA salt (8.1 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). The NMR data for the compound is as follows: ¹H NMR (DMSO)—10.1 and 10.0 (s, 1H), 7.8 (s, 1H), 7.70 (d, 1H), 7.6 (d, 1H, NH), 7.2 (d, 1H), 6.9 (d, 1H, NH), 5.15-5.1 (m, 1H), 4.4-4.2 (m, 3H), 3.5-3.3 (dd, 1H), 3.1-3.0 (t, 2H), 2.9 and 2.7 (s, 3H), 2.5 (m, 1H), 2.4-2.3 (m, 1H), 2.2-2.0 (m, 2H), 1.9-2.8 (m, 1H).

Example 74

Preparation of Certain Intermediate Compounds

The following compounds were prepared according to a general method (e.g. General Method 3) detailed herein:

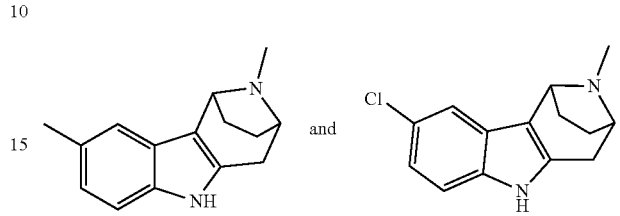

Example 75

Preparation of Compound 90

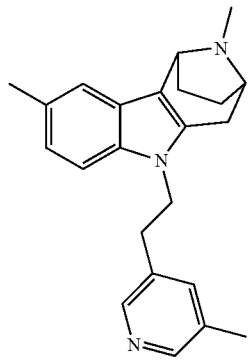

Tetra butyl ammonium chloride (0.012 g, 0.044 moles) was added to 50% aq. NaOH solution (5 mL) and stirred at RT for 15 minutes. 2,11-dimethyl-5,6,7,8,9,10-hexahydro-7,10-iminocyclohept[b]indole (0.2 g, 0.088 mmol) was added to it and the reaction mixture was stirred for 10 minutes at RT. This was followed by addition of 3-methyl-5-vinylpyridine (0.115 g, 0.097 mmol). The reaction mixture was heated at 100° C. for 8 h. The reaction mixture was cooled at RT extracted with ethyl acetate dried over anhydrous sodium sulfate and concentrated to obtain the crude product. The crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to get N-alkylated product (5 mg). The NMR data for the compound is as follows: The NMR data for the compound is as follows: ¹H NMR (DMSO) 1.65-1.8, 2H (m); 2.0-2.15, 2H (m); 2.25-2.4, 6H (s); 2.45-2.5, 2H (m); 2.6-2.65, 1H (m); 2.85-3.0, 3H (s); 3.05-3.2, 2H (m); 3.4-3.55, 1H (m); 4.2-4.4, 2H (m); 6.85-7.0, 1H (m), 7.25-7.45, 2H (m); 7.95, 1H (s); 8.4, 1H (m); 8.6, 1H (s); 10.4-10.85, 1H (m).

Example 76

Preparation of Compound 117

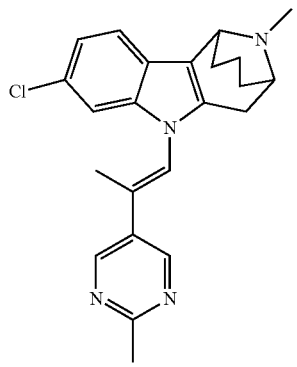 [SMILES: C/C(=C\n1c2c(c3ccc(Cl)cc31)C1CCCC(C2)N1C)c1cnc(C)nc1]

2-(2-methylpyrimidin-5-yl)-1-[(3-chloro-11-methyl-5,6,7,8,9,10,11-heptahydro-7,11-iminocyclooct[b]indole-5-yl)]propan-2-ol (1 g, 2.43 mmol) is refluxed with 25% sulfuric acid (7 mL) for 2 h. The reaction mixture is cooled to 5° C. with an ice-water bath. KOH (15% aq. solution) is added dropwise to the reaction mixture until pH of 9-10 is achieved. The reaction mixture is extracted with ethyl acetate (3×10 mL). The combined organic layers are washed with water (10 mL) followed by brine, dried over sodium sulfate and evaporated under vacuum. The crude product is purified by column chromatography over silica gel (100-200 mesh) using a gradient of methanol-ethyl acetate (0-10%) to obtain a mixture of isomers, which are separated by preparative HPLC.

Example 77

Preparation of Compound 121

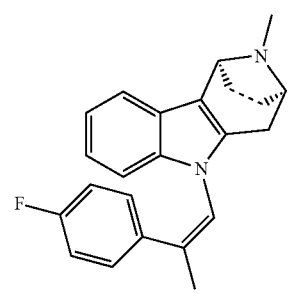

(−)-2-(4-fluorophenyl)-1-(11-methyl-5,6,7,8,9,10-hexahydro-7,10-iminocyclohept[b]indol-5-yl)propan-2-ol (60 mg, 0.16 mmol) was taken in 25% $H_2SO_4$ in water (10 mL), and stirred at 90° C. for 2 h. The reaction was monitored by TLC and LCMS. The reaction mixture was cooled and basified with aq. KOH solution and extracted with ethyl acetate. The combined organic layers were dried over anhydrous sodium sulfate and evaporated under reduced pressure. The crude product was purified using reverse phase chromatography to obtain the title compound as TFA salt (6 mg). The NMR data for the compound is as follows: $^1H$ NMR ($CD_3OD$)-7.75-7.60 (m, 1H). 7.60-7.50 (d, 1H). 7.30-7.10 (m, 5H), 7.05-6.95 (d, 1H), 5.25-5.20 (d, 1H), 5.15-5.00 (t, 1H), 4.40-430 (t, 1H), 3.60-3.50 (t, 1H), 3.00 (s, 3H), 2.95-2.90 (d, 1H), 2.70-2.60 (m, 2H), 2.40-2.30 (m, 1H), 2.25-2.15 (m, 1H), 1.95 (s, 3H).

Example 78

Preparation of Compound 119

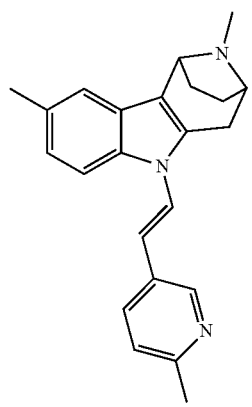 [SMILES: Cc1ccc2c(c1)c1c(n2/C=C/c2ccc(C)nc2)CC2CCC1N2C]

2-(4-methylpyridyl)-1-(2,11-dimethyl-6,7,8,9,10-pentahydro-7,10-iminocyclohept[b]indol-5-yl)ethanol (1 g, 2.77 mmol) is refluxed with 25% sulfuric acid (7 mL) for 2 h. The reaction mixture is cooled to 5° C. with an ice-water bath. KOH (15% aq. solution) is added dropwise to the reaction mixture till pH of 9-10 is achieved. The reaction mixture is extracted with ethyl acetate (3×10 mL). The combined organic layers are washed with water (10 mL), followed by brine, dried over sodium sulfate and evaporated under vacuum. The crude product is purified by column chromatography over silica gel (100-200 mesh) using a gradient of methanol-ethyl acetate (0-10%).

Example 79

Preparation of Compound 103

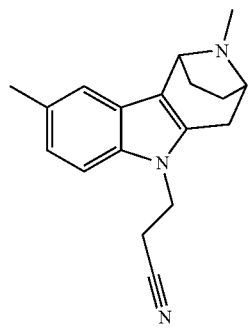 [SMILES: Cc1ccc2c(c1)c1c(n2CCC#N)CC2CCC1N2C]

2,11-Dimethyl-5,6,7,8,9,10-hexahydro-7,10-iminocyclohept[b]indole (0.450 g, 2.25 mmol) was stirred in benzene (4 mL) and toluene (8 mL). Acrylonitrile (0.150 mL, 2.25 mmol) was added to the reaction mixture and stirred at 0° C. for 10 minutes, followed by addition of Triton-B (40% in MeOH, 1 drop) and stirring at RT for 4 h. The reaction was monitored by TLC (mobile phase 10% methanol-dichloromethane). The reaction was quenched with water, extracted in ethyl acetate; the organic layer was washed with water, dried over sodium sulfate and concentrated. The residue was purified by column chromatography over silica gel (100-200) using 0-10% methanol/dichloromethane as eluent. $^1$H NMR (CDCl$_3$) of the oxalate salt—7.65 (s, 1H), 7.20 (d, 1H), 6.98 (m, 1H), 4.18 (m, 1H), 3.58 (m, 1H), 3.22 (m, 1H), 2.42 (s, 3H), 2.38 (s, 3H), 2.30-2.20 (m 6H), 1.90 (m, 1H), 1.60 (m, 2H), (M+1) 280.

Example 80

Preparation of Compound 91

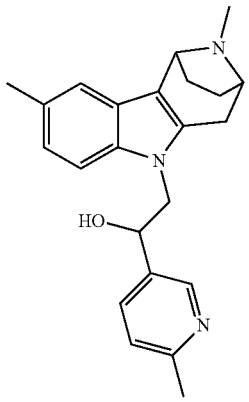 [SMILES: Cc1ccc2c(c1)c1c(n2CC(O)c2ccc(C)nc2)CC2CCC1N2C]

2,11-Dimethyl-5,6,7,8,9,10-hexahydro-7,10-iminocyclohept[b]indole (225 mg, 1 mmol) was taken in DMF (2 mL) and added to a solution of sodium hydride (50%) (100 mg, 2.2 mmol) in portions at RT and stirred at RT for 10 min. A solution of 2-methyl-5-(oxiran-2-yl)pyridine (270 mg, 2 mmol) in DMF (1 mL) was added drop wise for 10 min and stirred overnight at RT. The progress of the reaction was monitored by LCMS. Upon completion, the reaction mixture was quenched with methanol and concentrated to dryness. Water was added to the residue and the product was extracted in ethyl acetate (3×50 mL). The organic layer was dried over anhydrous sodium sulfate and evaporated under reduced pressure. The crude product was purified by reverse phase chromatography to obtain the product as TFA salt (85 mg, 17.89%). The NMR data for the compound is as follows; $^1$H NMR (DMSO)—10.12-9.90 (bm, 1H) 8.70-8.35 (m, 1H), 8.20-7.90 (m, 1H), 7.7-7.20 (m, 3H), 7.0-6.90 (m, 1H), 6.10-5.90 (m, 1H), 5.15-5-4.96 (m, 1H), 4.38-4.10 (m, 2H), 2.82 (s, 3H), 2.65-2.06 (m, 1H), 2.40 (s, 6H), 2.33-2.28 (m, 1H), 2.16-2.0 (m, 3H), 1.83-1.70 (m, 2H).

Example 81

Preparation of Compound 124

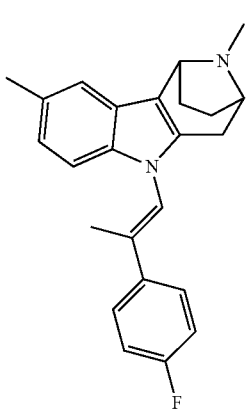

2,11-dimethyl-5,6,7,8,9,10-hexahydro-7,10-iminocyclohept[b]indole (50 mg, 0.22 mmol), beta-bromo-4-fluoro-alpha methylstyrene (57 mg, 0.26 mmol), L-proline (6 mg, 0.05 mmol), copper iodide (4.2 mg, 0.022 mmol), potassium phosphate tribasic (93 mg, 0.44 mmol) and DMF were mixed and stirred overnight under nitrogen atmosphere at 85° C. DMF was evaporated and the residue was stirred in water, filtered and dried under vacuum to obtain the crude product which was purified by reverse phase HPLC to obtain title compound as TFA salt. $^1$H NMR (CD$_3$OD) of the TFA salt—7.62 (m, 2H), 7.38 (s, 1H), 7.15 (m, 3H), 6.95 (m, 1H), 6.60 (d, 1H), 5.10 (m, 1H), 4.30 (m, 1H), 3.50 (m, 1H), 2.95 (s, 3H), 2.80 (m, 1H), 2.60 (m, 1H), 2.50 (m, 1H), 2.40 (s, 3H), 2.30 (m, 1H), 2.05 (m, 1H), 1.90 (s, 3H), (M+1) 361.

Example 82

Preparation of Compound 115

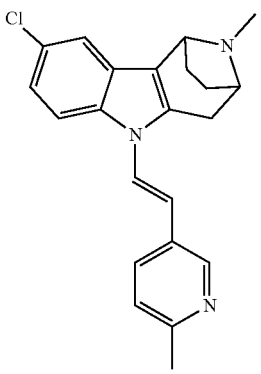 [SMILES: Cc1ccc(/C=C/n2c3c(c4cc(Cl)ccc42)C2CCC(C3)N2C)cn1]

2-[(2-chloro-11-methyl-5,6,7,8,9,10-hexahydro-7,10-iminocyclohept[b]indole-5-yl)]-1-(6-methylpyridin-3-yl) ethanol (1 g, 2.62 mmol) is refluxed with 25% sulfuric acid (7 mL) for 2 h. The reaction mixture is cooled to 5° C. with an ice-water bath. KOH (15% aq, solution) is added dropwise to the reaction mixture till pH of 9-10 is achieved. The reaction mixture is extracted with ethyl acetate (3×10 mL). The combined organic layers are washed with water (10 mL) followed by brine, dried over sodium sulfate and evaporated under vacuum. The crude product is purified by column chromatography over silica gel (100-200 mesh) using a gradient of methanol-ethyl acetate (0-10%).

Example 83

Preparation of Compound 116

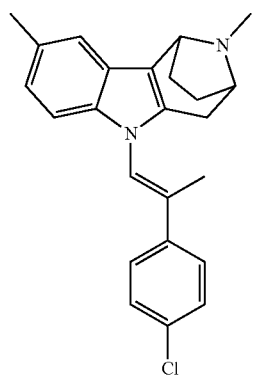

2-[(4-chlorophenyl)-1-(1,11-dimethyl-5,6,7,8,9,01-hexahydro-7,10-iminocyclohept[b]indol-5-yl)]propan-2-ol (1 g, 2.53 mmol) was refluxed with 25% sulfuric acid (7 mL) for 2 h. The reaction mixture was cooled to 5° C. with an ice-water bath. KOH (15% aq. solution) was added dropwise to the reaction mixture till pH of 9-10 was achieved. The reaction mixture was extracted with ethyl acetate (3×10 mL). The combined organic layers were washed with water (10 mL) followed by brine, dried over sodium sulfate and evaporated under vacuum. The crude product was purified by column chromatography over silica gel (100-200 mesh) using a gradient of methanol-ethyl acetate (0-10%). $^1$H NMR (CDCl3) the free base—7.57-7.40 (m, 5H), 7.22-7.1 (m, 2H), 6.9 (s, 1H), 4.23-4.15 (m, 2H), 2.84-2.7 (m, 2H), 2.5 (s, 3H), 1.97 (s, 3H), 1.78-1.5 (m, 4H), 1.4-1.2 (m, 4H), (M+1) 377.

Example 84

Preparation of Compound 107

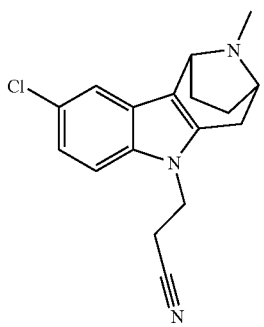 [SMILES: CN1C2CCC1c1c(n(CCC#N)c3ccc(Cl)cc13)C2]

2-Chloro-11-methyl-5,6,7,8,9,10-hexahydro-7,10-iminocyclohept[b]indole (1 g, 4.2 mmol) was stirred in benzene (15 mL) and toluene (20 mL). Acrylonitrile (0.8 mL, 4.2 m moles) was added to this solution and stirred at 0° C. for 10 minutes. Triton-B (0.6 mL) was added dropwise and the reaction mixture was stirred at RT for 4 h. The reaction was monitored by TLC (mobile phase 10% Methanol-dichloromethane. The reaction was quenched with water, extracted in ethyl acetate; the combined organic layers were washed with water, dried over sodium sulfate and concentrated. The residue was purified by column chromatography over silica gel (100-200) using 0-100% methanol/dichloromethane as eluent. $^1$H NMR (DMSO) of the oxalate salt—7.62 (s, 1H), 7.55 (m, 1H), 7.18 (d, 1H), 5.0 (m, 1H), 4.40 (m, 2H), 4.22 (m, 1H), 3.60 (m, 1H), 3.38 (m, 2H), 3.05 (m, 1H), 2.90 (m, 2H), 2.80 (m, 2H), 2.62 (m, 1H), 2.0 (m, 1H), 1.82 (m, 1H). (M+1) 300.

Example 85

Preparation of Compound 110

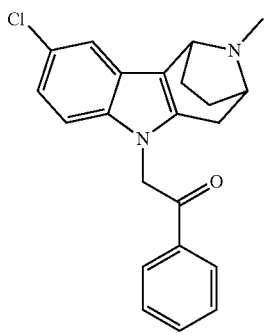 [SMILES: CN1C2CCC1c1c(n(CC(=O)c3ccccc3)c3ccc(Cl)cc13)C2]

2-Chloro-11-methyl-5,6,7,8,9,10-hexahydro-7,10-iminocyclohept[b]indole (246 mg, 10 mmol) was dissolved in N-methyl-2-pyrrolidone (2 mL). KOH (560 mg, 100 mmol) was added to the reaction mixture followed by addition of 2-bromoacetophenone (199 mg, 10 mmol). The reaction was stirred overnight at RT and monitored by TLC, LC/MS. The reaction was quenched with water and extracted with ethanol, the combined organic layers were dried over Na$_2$SO$_4$ and concentrated to yield dark brown crude oil (60 mg) which was purified by column chromatography using 100-200 mesh silica in 4% methanol/dichloromethane. $^1$H NMR (CDCl$_3$) of the TFA salt—8.0 (m, 2H), 7.70 (m, 1H), 7.67 (m, 2H), 7.60 (m, 1H), 7.20 (d, 1H), 7.10 (d, 1H), 5.50 (m, 1H), 5.30 (m, 1H), 5.0 (m, 1H), 4.40 (m, 1H), 3.20 (m, 1H), 2.82 (s, 3H), 2.70 (m, 2H), 2.50 (m, 1H), 2.30 (m, 1H), 1.80 (m, 1H), (M+1) 365.

Example 86

Preparation of Compound 111

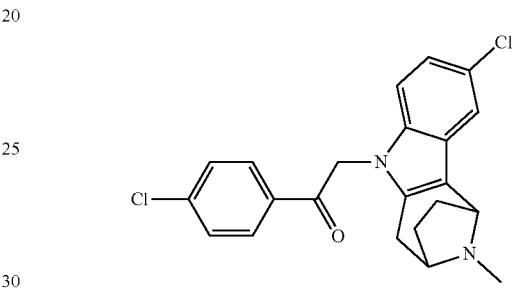

2-chloro-11-methyl-5,6,7,8,9,10-hexahydro-7,10-iminocyclohept[b]indole (246 mg, 1 mmol) was dissolved in N-methyl-2-pyrrolidone (2 mL) and KOH (560 mg, 10 mmol) followed by 2-Bromo-1-(4-chloro-phenyl)ethanone (233 mg, 1 mmol) were added, the reaction mixture was stirred overnight at RT. The reaction was quenched with water, extracted with ethyl acetate; the combined organic layers were dried and concentrated. The crude product was purified by column chromatography using (#100-200) using 0-45 methanol/dichloromethane as eluent. The compound was further purified by reverse phase chromatography. $^1$H NMR (CD$_3$OD) of the TFA salt—8.10 (m, 2H), 7.60 (m, 3H), 7.30 (m, 1H) 7.10 (m, 1H), 5.90 (m, 1H), 5.75 (m, 1H), 5.10 (dd, 1H), 4.30 (m, 1H), 3.40 (m, 1H), 3.20 (m, 1H), 2.90 (s, 3H), 2.60 (m, 1H), 2.50 (m, 1H), 2.30 (m 1H), 2.0 (m, 1H). (M+1) 399.

Example 87

Preparation of Compound 123

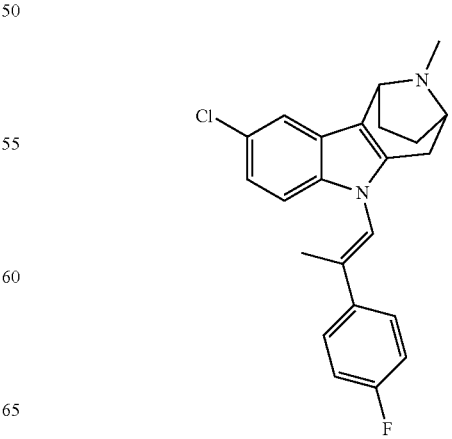

2-chloro-11-methyl-5,6,7,8,9,10-hexahydro-7,10-iminocyclohept[b]indole (246 mg, 1 mmol), beta-bromo-4-fluoro-alpha-methylstyrene (258 mg, 1.2 mmol), L-proline (23 mg, 0.2 mmol), copper iodide (19 mg, 0.1 mmol) and potassium phosphate (tribasic) (539 mg, 2 mmol) and DMF were mixed and stirred overnight under nitrogen atmosphere at 85° C. for, DMF was evaporated and the residue was stirred in water, filtered and dried under vacuum to obtain the crude product which was purified by silica gel chromatography (100-200 mesh) using 0-5% methanol/dichloromethane as eluent. $^1$H NMR (DMSO) of the oxalate salt—7.70 (m, 3H), 7.30 (m, 3H), 7.20 (d, 1H), 7.10 (d, 1H), 5.05 (m, 1H), 4.20 (m, 1H), 2.90 (m, 2H), 2.80 (m, 2H), 2.50 (s, 3H), 2.20 (m, 2H), 2.80 (s, 3H). (M+1) 381.

Example 88

Preparation of Compound 77

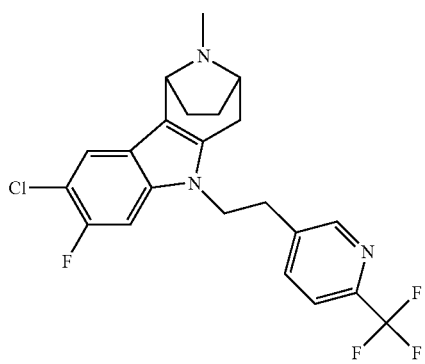 [SMILES: CN1C2CCC1c1c(n(CCc3ccc(C(F)(F)F)nc3)c3cc(F)c(Cl)cc13)C2]

2-Chloro-3-fluoro-11-methyl-5,6,7,8,9,10-hexahydro-7,10-iminocyclohept[b]indole (60 mg, 0.227 mmol, 1 equiv) and 2-trifluoromethyl-5-vinylpyridine (43 mg, 0.249 mmol, 1.1 equiv.) were heated to 115° C. with KOH (44.5 mg, 0.79 mmol. 3.5 equiv) in N-methyl-2-pyrrolidone (0.15 mL). After 15 h brine (5 mL) was added to the reaction mixture followed by extraction with ethyl acetate (2×10 mL), the combined organic layers were dried over sodium sulfate and evaporated under vacuum. The crude product was filtered in a column over neutral alumina using 10, 20, 50 and 100% methanol in ethyl acetate. Compound containing fractions (detected by LCMS) were pooled and purified by reverse phase chromatography to obtain the product as TFA salt (20 mg). The NMR data for the compound is as follows: $^1$H NMR (CD$_3$OD)-8.3 and 8.1 (s, 1H), 7.9-7.6 (m, 3H), 7.4 (d, 1H), 5.05-4.95 (m, 1H), 4.5-4.4 (m, 1H), 4.3 (m, 1H), 4.2-4.1 (m, 1H), 3.5-3.4 (m, 1H), 3.5-3.1 (m, 2H), 2.9 (m, 1H), 2.9 and 2.5 (s, 3H), 2.5 (m, 2H), 2.3-2.1 (m, 1H), 1.7-1.52 (m, 1H).

Example 89

Preparation of Compound 114

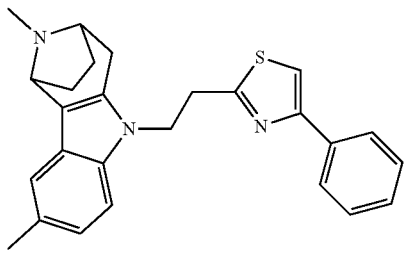 [SMILES: Cc1ccc2c(c1)c1c(n2CCc2nc(-c3ccccc3)cs2)CC2CCC1N2C]

3-(2,11-Dimethyl-5,6,7,8,9,10-hexahydro-7,10-iminocyclohept[b]indol-5-yl)propanethioamide (200 mg, 0.63 mmol) was added to 2-Bromoacetophenone (160 mg, 0.00081 moles) in ethanolic HCl (6 mL). The reaction mixture was heated at 80° C. in a sealed vessel for 20 min. The reaction mixture was basified with 1M NaOH solution and diluted with ethyl acetate. The organic layer was separated, washed with water, dried over sodium sulfate and concentrated. The crude product was purified by silica gel column chromatography (100-200) using 0-10% MeOH: dichloromethane as eluent. $^1$H NMR (CDCl$_3$) of the HCL salt—7.80 (m, 2H), 7.42 (m, 3H), 7.35 (m, 3H), 7.10 (m, 2H), 4.70 (m, 1H), 4.50 (m, 2H), 3.90 (m, 1H), 3.50 (m, 3H), 2.40 (m, 6H), 2.20 (m, 2H), 1.40-1.20 (m, 2H). (M+1) 414.

Example 90

Preparation of Compound 81

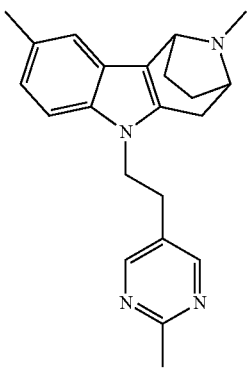

A solution of 2,11-dimethyl-5,6,7,8,9,10-hexahydro-7,10-iminocyclohept[b]indole (0.15 g, 0.66 mmol), 2-methyl-5-vinylpyrimidine (0.15 g, 1.32 mmol) and KOH (0.37 g, 6.63 mmol) were mixed in N-methyl-2-pyrrolidone (1 mL) and stirred overnight at 100° C. The progress of the reaction was monitored by LCMS. Upon completion, the reaction mixture was evaporated to dryness and the crude product was purified by reverse phase chromatography to provide the product as TFA salt (10 mg). The NMR data for the compound is as follows: $^1$H NMR (DMSO-D$_2$O)—8.30 and 8.1 (s, 2H), 7.4-7.2 (m, 2H), 6.95 and 6.85 (d, 1H), 5.0-4.8 (m, 1H), 4.4-4.0 (m, 3H), 3.5 (d, 1H), 3.1-3.0 (m, 2H), 2.5 (m, 1H), 2.8 (s, 3H), 2.5 (s, 3H), 2.3 (s, 3H), 2.2-2.0 (m, 3H), 1.7-1.5 (bs, 1H).

Example 91

Preparation of Compound 82

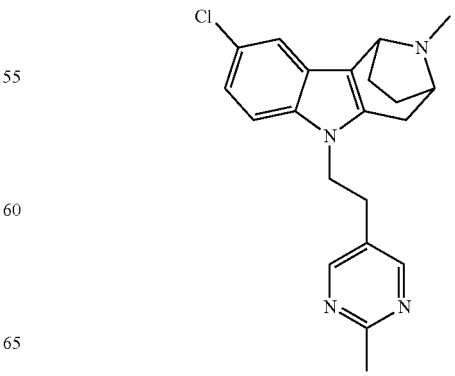

221

A solution of 2-Chloro-11-methyl-5,6,7,8,9,10-hexahydro-7,10-iminocyclohept[b]indole (0.15 g, 0.61 mmol), 2-methyl-5-vinylpyrimidine (0.146 g, 1.21 mmol) and KOH (0.342 g, 6.09 mmol) were mixed in N-methyl-2-pyrrolidone (1 mL) and stirred overnight at 100° C. The progress of the reaction was monitored by LCMS. Upon completion, the mixture was evaporated to dryness and the crude product was purified by reverse phase chromatography to provide the product as TFA salt (90 mg). The NMR data for the compound is as follows: $^1$H NMR (DMSO)—11.5 (d, 1H), 10.3 and 10.0 (d, 1H), 8.40 and 8.3 (s, 2H), 7.7-7.5 (m, 1H), 7.4 and 7.5 (d, 1H), 7.10 and 7.20 (d, 1H), 5.2-5.0 (m, 1H), 4.5-4.2 (m, 3H), 3.5-3.3 (m, 1H), 3, 1-2.9 (m, 1H), 2.9 and 2.7 (s, 3H), 2.6 (m, 1H), 2.5 (s, 3H), 2.3-2.2 (m, 1H), 2.1-1.8 (m, 2H), 1.6-1.5 (m, 1H).

Example 92

Preparation of Compound 93

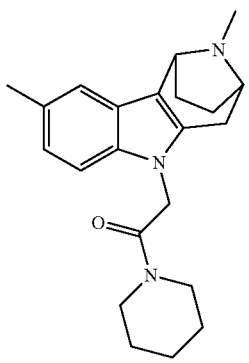 [SMILES: Cc1ccc2c(c1)c1c(n2CC(=O)N2CCCCC2)CC2CCC1N2C]

Sodium hydride (27 mg, 1.1 mmol) was washed with hexane for removal of oil, dried under vacuum and suspended in THF and 2,11-dimethyl-5,6,7,8,9,10-hexahydro-7,10-iminocyclohept[b]indole (0.1 g, 0.47 mmol) was added dropwise as a solution in THF at 0° C. The reaction mixture stirred for 0.5 h and a solution of 2-chloro-1-(piperidin-1-yl)ethanone (0.091 g, 0.56 mmol) in THF was added drop-wise. Then reaction mixture stirred at RT for additional 2 h. After completion of reaction (the progress of the reaction was monitored by TLC), the reaction mixture was quenched with water. THF was evaporated and the aqueous layer was extracted with ethyl acetate, the combined organic layers were dried over anhydrous sodium sulfate and evaporated under reduced pressure. The resulting crude product was purified by preparative TLC to obtain title compound (45 mg) that was converted into the corresponding HCl salt by treatment with ethanolic HCl. The NMR data for the compound is as follows: $^1$H NMR (DMSO)—11.3 (bs, 1H), 10.30 (bs, 1H), 7.20-7.40 (m, 2H). 6.96 (d, 1H), 5.22 (d, 1H), 4.90-5.10 (m, 3H), 4.18-4.30 (m, 2H), 3.30-3.50 (m, 2H), 3.20 (s, 3H), 2.80-2.95 (m, 2H), 2.40 (s, 3H), 2.00-2.20 (m, 2H), 1.80-1.92 (m, 2H), 1.40-1.74 (m, 6H).

Example 93

Preparation of Compound 101

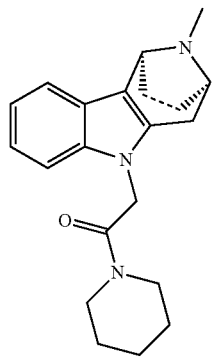

Sodium hydride (50%) (23 mg, 0.98 mmol) was taken in THF (5 mL) and stirred for 10 min, followed by addition of (−)-11-methyl-5,6,7,8,9,10-hexahydro-7,10-iminocyclohept[b]indole (70 mg, 0.32 mmol) and stirred for 10 min. 2-chloro-1-(piperidin-1-yl)ethanone (63 mg, 0.39 mmol) was added and stirred at RT for 14 h. The progress of the reaction was monitored by TLC and LCMS. Upon completion, the reaction mixture was quenched with water and extracted with ethyl acetate. The combined organic layers were dried over anhydrous sodium sulfate and evaporated under reduced pressure. The crude product was purified by reverse phase chromatography to yield the title compound as TFA salt (6 mg). The NMR data for the compound is as follows: $^1$H NMR (CD$_3$OD)-7.60-7.50 (d, 1H), 37.30-7.20 (m, 1H), 7.15-7.00 (m, 2H), 4.40-4.20 (m, 2H), 3.75-3.60 (t, 2H), 3.60-3.50 (t, 2H), 3.40-3.30 (m, 2H), 3.20-3.15 (m, 1H), 2.95 (s, 3H), 2.60-2.50 (m, 2H), 2.35-2.20 (d, 2H), 1.90-1.85 (m, 4H), 1.75-1.70 (m, 1H), 1.60-1.50 (m, 2H).

Example 94

Preparation of Compound 84

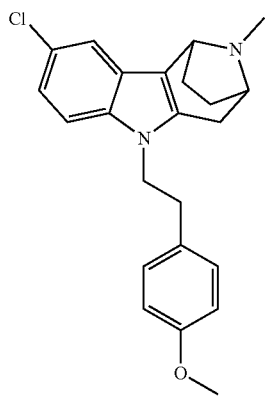 [SMILES: COc1ccc(CCn2c3c(c4cc(Cl)ccc42)C2CCC(C3)N2C)cc1]

Tetrabutylammonium chloride (0.2 g, 0.77 mmol) is taken in 50% NaOH which is stirred at RT for 10 min, followed by addition of 2-chloro-11-methyl-5,6,7,8,9,10-hexahydro-7,10-iminocyclohept[b]indole (4.0 mmol) and stirred at RT for 15 min. 4-methoxyphenylethylbromide (0.68 g, 4.0 mmol) was added and the reaction mixture was stirred at RT for 15 minute and at 70° C. for 15 h. The reaction mixture was poured in water (2 mL) and extracted with dichloromethane, dried over sodium sulfate and concentrated under vacuum. The crude so obtained is purified by column chromatography (silica-100-200) and reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to obtain the product as TFA salt (50 mg). The NMR data for the compound is as follows: $^1$H NMR (CD$_3$OD)-7.60-7.50 (d, 1H), 7.40-7.20 (d, 1H), 7.10-7.0 (t, 1H), 7.0-6.90 (d, 2H), 6.90-6.80 (d, 2H), 5.0-4.90 (t, 2H), 4.60-4.50 (t, 1H), 4.50-4.40 (t, 2H), 3.70-3.60 (s, 3H), 3.20-3.10 (d, 2H), 3.10-3.0 (m, 1H) 2.40 (s, 3H), 1.90-1.80 (m, 2H), 1.20-1.10 (m, 2H).

Example 95

Preparation of Compound 89

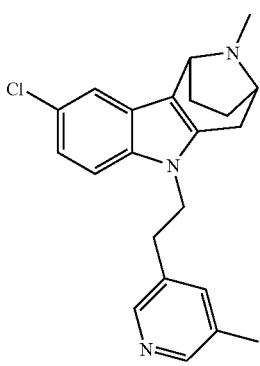 [SMILES: Cc1cncc(CCn2c3c(c4cc(Cl)ccc42)C2CCC(C3)N2C)c1]

Tetra butyl ammonium chloride (0.012 g, 0.044 mmol) was taken in 50% aq. NaOH solution (5 mL) and stirred for 15 minutes at RT. 2-Chloro-11-methyl-5,6,7,8,9,10-hexahydro-7,10-iminocyclohept[b]indole (0.044 mmol) was added and stirred for 10 min. at RT. 3-methyl-5-vinylpyridine (0.088 mmol) was added and reaction mixture was heated at 100° C. for 8 h. The reaction mixture was cooled to RT, extracted with ethyl acetate, dried over anhydrous sodium sulfate and concentrated to obtain the crude product. The crude was purified by reverse-phase chromatography (C-18, 500 mm×50 mm, Mobile Phase A=0.05% TFA in water, B=0.05% TFA in acetonitrile. Gradient: 10% B to 80% B in 30 min, injection volume 5 mL) to obtain the product as TFA salt (5 mg). The NMR data for the compound is as follows: $^1$H NMR (DMSO) 1.6-1.8, 2H (m); 1.95-2.15, 2H (m); 2.25-2.35, 6H (s); 2.8-2.95, 3H (m); 3.05-3.2, 2H (m): 4.1-4.2, 2H (m); 7.05-7.2, 1H (m); 7.45-7.5, 1H (d; 7.6-7.75, 1H (m), 7.85-7.9, 1H (m); 8.3-8.4, 1H (m), 8.5-8.55, 1H (m), 10.3-10.8, 1H (m).

Example 96

Preparation of Compound 97

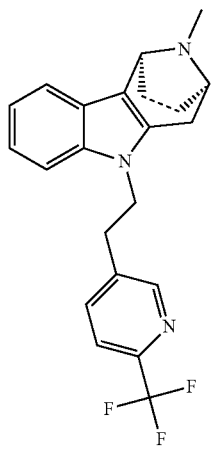

Tetrabutylammonium bromide (7 mg, 0.02 mmol) was added to a solution of (−)-11-methyl-5,6,7,8,9,10-hexahydro-7,10-iminocyclohept[b]indole (100 mg, 0.469 mmol) in 50% sodium hydroxide solution, followed by the addition of 2-trifluoromethyl-5-vinylpyridine (88 mg, 0.5 mmol) and stirred at RT for 14 h. The progress of the reaction was monitored by LCMS. The reaction mixture was quenched with water and extracted with ethyl acetate. The combined organic layer were washed with brine, dried over anhydrous sodium sulfate and evaporated under reduced pressure. The crude product was purified by reverse phase chromatography to yield the title compound (100 mg). The NMR data for the compound is as follows: $^1$H NMR (DMSO)—8.40 (s, 1H), 7.80-7.70 (t, 2H), 7.60-7.40 (m, 2H), 7.20-7.00 (m, 2H), 5.10-5.00 (t, 1H), 4.50-4.40 (m. 2H), 3.50-3.40 (m, 1H), 3.20-3.00 (m, 4H), 2.80 (s, 3H), 2.40 (s, 3H), 1.40-1.20 (m, 2H), 1.00-0.80 (m, 2H).

Example 97

Preparation of Compound 102

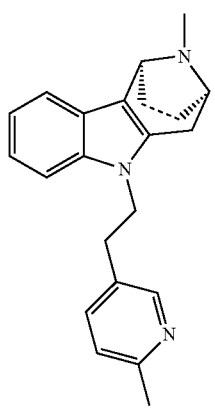

TBAB (8 mg, 0.0234 mmol) was added to a solution of (−)-11-methyl-5,6,7,8,9,10-hexahydro-7,10-iminocyclohept[b]indole (0.1 g, 0.499 mmol) in 50% sodium hydroxide solution (10 mL), followed by the addition of 2-methyl 5-vinyl pyridine (61 mg, 0.516 mmol) and stirred at 80° C. for 14 h. After completion of the reaction (the progress of the reaction was monitored by TLC and LCMS), ethyl acetate (100 mL) was added, washed with water and extracted with ethyl acetate. The combined organic layers were dried over anhydrous sodium sulfate and evaporated under reduced pressure. The crude product was purified by reverse phase chromatography to yield TFA salt (10 mg). The NMR data for the compound is as follows: $^1$H NMR (CD$_3$OD)-8.25-8.20 (d, 1H), 8.10-7.90 (m, 1H), 7.70-7.60 (d, 1H), 7.60-7.50 (t, 1H), 7.40-7.30 (d, 1H), 7.20-7.00 (m, 2H), 5.20-5.20 (m, 1H), 4.60-4.40 (m, 4H), 3.60-3.50 (m, 1H), 2.95 (s, 3H), 2.62 (s, 3H), 2.50-2.40 (t, 2H), 2.30-2.20 (m, 2H), 1.90-1.80 (m, 2H).

Example 98

Preparation of Compound 92

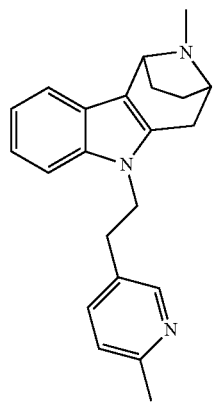 [SMILES: Cc1ccc(CCn2c3c(c4ccccc42)C2CCC(C3)N2C)cn1]

TBAB (8 mg, 0.0234 mmol) was added to a solution of 11-methyl-5,6,7,8,9,10-hexahydro-7,10-iminocyclohept[b]indole (0.1 g, 0.469 mmol) in 50% sodium hydroxide solution (10 mL) followed by the addition of 2-methyl-5-vinyl pyridine (61 mg, 0.516 mmol) and stirred at 80° C. for 14 h. After completion of the reaction (the progress of the reaction was monitored by TLC and LCMS), ethyl acetate (100 mL) was added, washed with water and extracted with ethyl acetate. The combined organic layers were dried over anhydrous sodium sulfate and evaporated under reduced pressure. The crude product was purified by reverse phase chromatography to yield TFA salt (6 mg). The NMR data for the compound is as follows: $^1$H NMR (CD$_3$OD)-8.25-8.20 (d, 1H), 8.10-7.90 (m, 1H), 7.70-7.60 (d, 1H), 7.60-7.50 (t, 1H), 7.40-7.30 (d, 1H), 7.20-7.00 (m, 2H), 5.20-5.10 (m, 1H), 4.60-4.40 (m, 4H), 3.60-3.50 (m, 1H), 2.95 (s, 3H), 2.62 (s, 3H), 2.50-2.40 (t, 2H), 2.30-2.20 (m, 2H), 1.90-1.80 (m, 2H).

Example 99

Preparation of Compound 86

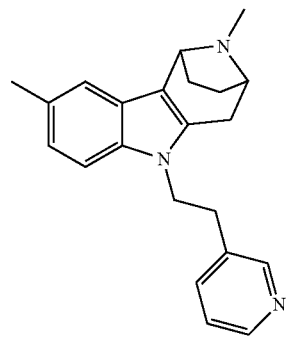 [SMILES: Cc1ccc2c(c1)c1c(n2CCc2cccnc2)CC2CCC1N2C]

Powdered potassium hydroxide (0.376 g, 0.0049 mol) was added to a solution of 2,11-dimethyl-5,6,7,8,9,10-hexahydro-7,10-iminocyclohept[b]indole (0.19 g. 0.00084 mol) in N-methyl 2-pyrolidone (1.3 mL) and allowed to stir for 10 min at RT. 3-vinyl pyridine (0.264 g, 0.00252 mol) was added and stirred for further 4 h at 80° C. The reaction was monitored by TLC. Upon completion, the reaction mixture was diluted with water (20 mL) and extracted with ethyl acetate (3×10 mL). The combined organic layers were dried over anhydrous sodium sulfate and concentrated under reduced pressure using rotary evaporator. The crude was semi-purified through column chromatography (7% Methanol/dichloromethane in silica 100-200 mesh. Diameter of column—2.5 cm, Height of silica—approx. 5 inch), and further purified by preparation HPLC to yield the desired compound (free base) as yellow oil (0.080 g, 29% yield). The free base (0.040 g, 00012 mol) was dissolved in THF (1.0 mL). A solution of oxalic acid dihydrate (0.015 g, 0.00012 mol) in THF (1.0 mL) was added and stirred for 30 min at RT. The precipitate obtained was filtered, washed with ether and dried to obtain the product as oxalate salt (0.018 g, 36% yield). The NMR data for the compound is as follows: $^1$H NMR (CD$_3$OD)-8.4 (s, 1H), 7.9 (d, 1H), 7.5 (d, 1H), 7.3 (m, 3H), 7.1 and 7.05 (d, 1H), 5.0 (m, 1H), 4.5 (m, 2H), 4.3 (m, 1H), 3.7 (m, 1H), 3.4 (m, 2H), 3.2-3.1 (m, 1H), 2.9 and 2.6 (s, 3H), 2.5 and 2.4 (s, 3H), 2.3 (m, 2H), 2.2 (m, 1H), 1.6 (m, 1H).

Example 100

Preparation of Compound 80

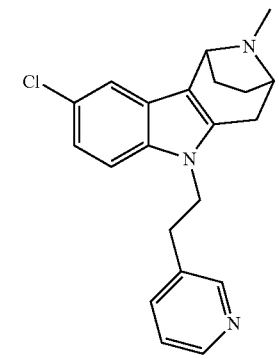 [SMILES: CN1C2CCC1c1c(n(CCc3cccnc3)c3ccc(Cl)cc13)C2]

Powdered potassium hydroxide (0.4 g, 0.00715 mol) was added to a solution of 2-Chloro-11-methyl-5,6,7,8,9,10-hexahydro-7,10-iminocyclohept[b]indole (0.22 g, 0.000894 mol) in N-methyl 2-pyrolidone (1.0 mL) and stirred for 10 min at RT. 3-vinylpyridine (0.281 g, 0.00 268 mol) was added and stirred for further 12 h at 80° C. The progress of the reaction was monitored by TLC. After completion, the reaction mixture was diluted with water (20 mL) and extracted with ethyl acetate (3×100 mL). The combined organic layers were dried over anhydrous sodium sulfate and concentrated under reduced pressure using rotary evaporator. The crude product was purified through column chromatography (8% Methanol/dichloromethane in silica 100-200 mesh. Diameter of column—2.5 cm, Height of silica—approx. 5 inch), and further purified by preparative HPLC to yield the desired compound (free base) as yellow oil (0.120 g, 38.3% yield). The free base (0.060 g, 0.00017 mol) was dissolved in THF (1.0 mL). A solution of oxalic acid dihydrate (0.021 g, 0.00017 mol) in THF (1.0 mL) was added and stirred for 30 min at RT. The precipitate was filtered, washed with ether and dried to provide the oxalate salt of product as light yellow solid (0.035 g, 46.5% yield). The NMR data for the compound is as follows: $^1$H NMR (CD$_3$OD)-8.38 (s, 1H), 7.98-7.93 (d, 1H), 7.56-7.53 (m, 2H), 7.51-7.33 (m, 2H), 7.14-7.11 (dd, 1H), 5.01-4.98 (m, 1H), 4.65-4.13 (m, 3H), 3.45-3.35 (m, 1H), 3.2-3.1 (m, 2H), 2.91 and 2.65 (s, 3H), 2.6-2.5 (m, 1H), 2.5-2.49 (m, 1H), 2.4-2.3 (m, 1H), 2.25-2.1 (m, 1H), 1.65-1.5 (m, 1H).

Example 101

Preparation of Compound 83

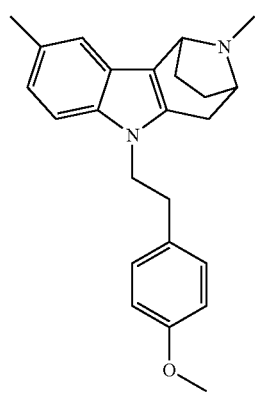

Triethylamine (5.2 mL 37.8 mmol) and (1-(2-Bromoethyl)-4-methoxybenzene (1.9 mL, 12.60 mmol) were added to a solution of p-tolylhydrazine hydrochloride (2 gm, 12.60 mmol) in ethanol (30 mL) and the resulting solution was stirred at RT for an 1 h after which it was heated at 90° C. for 2-3 h. The reaction mixture was concentrated to dryness and basified with aq. saturated NaHCO$_3$, and extracted in ethyl acetate. The combined organic layers was dried over Na$_2$SO$_4$ and concentrated to obtain (1-(4-methoxyphenyl)-1-p-tolyhydrazine (2.8 g). (1-(4-methoxyphenyl)-1-p-tolyhydrazine (2.8 g, 10.9 mmol) and 8-methyl-8-azabicyclo[3.2.1]octan-3-one (1.5 gm, 10.9 mmol) were taken in ethanolic HCl (30 mL), and stirred at RT for 15 min and the solvent was removed in vacuo. The residue was taken in ethanol (30 mL) and heated at 90° C. for 3. After completion of the reaction (the progress of the reaction was monitored by LCMS), the reaction mixture was concentrated to dryness and basified with aq. saturated NaHCO$_3$. The product was extracted in ethyl acetate and the organic layers were separated, dried over Na$_2$SO$_4$ and concentrated. The resulting crude product was purified over neutral alumina (10% Me—OH in dichloromethane) to obtain the product as free base (500 mg). The NMR data for the compound is as follows: $^1$H NMR (DMSO)—7.40-7.35 (d, 1H), 7.25 (s, 1H), 6.00-6.85 (d, 1H), 6.85-6.80 (d, 2H), 6.80-6.75 (d, 2H), 4.25-4.10 (t, 2H), 3.85-3.75 (m, 1H), 3.65 (s, 3H), 3.00-2.80 (t, 2H), 2.65-2.55 (d, 2H) 2.30 (s, 3H), 2.20-2.00 (m, 1H), 1.95 (s, 3H), 1.45-1.40 (m, 2H), 1.40-1.35 (m, 2H).

Example 102

Preparation of Compound 99

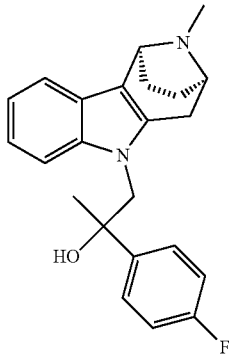

(−)-11-Methyl-5,6,7,8,9,10-hexahydro-7,10-iminocyclohept[b]indole (100 mg, 0.469 mmol) was added to a solution of sodium hydride (32 mg, 1.33 mmol) in DMF (6 mL). A solution of 2-(4-fluorophenyl)-2-methyloxirane (106 mg, 0.697 mmol) in DMF (4 mL) was added drop wise and stirred for 14 h at RT. The reaction was monitored by LCMS. Upon completion, the reaction mixture was quenched with water and extracted with ethyl acetate. The organic layer was washed with brine, dried over anhydrous sodium sulfate and evaporated under reduced pressure. The crude product was purified by silica column to obtain pure product as free base (80 mg). The free base (20 mg. 0.0549 mmol) was dissolved in THF (0.25 mL) and oxalic acid (7 mg, 0.0549 mmol) in THF (0.25 mL) was added drop wise. The mixture was stirred and the precipitated oxalate salt was filtered to yield off white solid (17.5 mg). The NMR data for the compound is as follows: $^1$H NMR (DMSO)—7.50-7.20 (m, 4H), 7.10-6.90 (m, 4H), 4.90-4.80 (m, 1H), 4.20-4.00 (m, 2H), 2.80-2.70 (d, 2H), 2.55 (s, 3H), 2.40-2.20 (m, 4H), 1.90 (s, 1H), 1.60-1.50 (t, 3H).

Example 103

Preparation of Compound 85

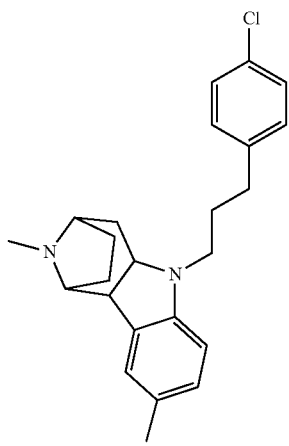 [SMILES: Cc1ccc2c(c1)C1C(CC3CCC1N3C)N2CCCc1ccc(Cl)cc1]

2,11-Dimethyl-5,6,7,8,9,10-hexahydro-7,10-iminocyclohept[b]indole (0.2 g, 0.88 mmol) was added to a solution of tetra n-butyl ammonium chloride (0.012 g, 0.044 mmol) in 50% aq NaOH (2 mL), stirred for 30 minutes. 1-(3-bromopropyl)-4-chlorobenzene (0.206 g, 0.88 mmol) was added and the reaction mixture was heated at 60° C. for 5 h. After completion reaction, mixture was quenched with water and extracted with ethyl acetate. The combined organic layers were dried over sodium sulfate and concentrated under reduced pressure. The crude product was first purified by column chromatography (SiO$_2$—100-200 mesh) followed by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL) to yield the product as a TFA salt (70 mg) after purification. The NMR data for the compound is as follows: $^1$H NMR (DMSO)—10.1 and 9.9 (bs, 1H), 7.4-7.2 (m, 6H), 7.0 (d, 1H), 5.1-5.0 (m, 1H), 4.3-4.2 (m, 1H), 4.1-3.9 (m, 2H), 3.4-3.3 (m, 1H), 3.1-2.9 (m, 1H), 2.9-2.8 (m, 2H), 2.7 (s, 3H), 2.4 (s, 3H), 2.4-2.3 (m, 2H), 2.1-1.8 (m, 4H).

Example 104

Preparation of Compound 88

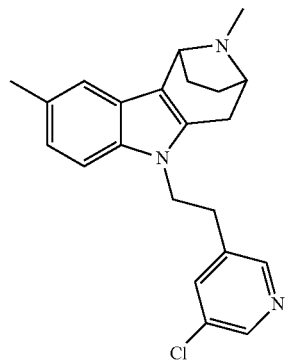 [SMILES: Cc1ccc2c(c1)c1c(n2CCc2cncc(Cl)c2)CC2CCC1N2C]

2,11-Dimethyl-5,6,7,8,9,10-hexahydro-7,10-iminocyclohept[b]indole (0.226 g, 1.0 mmol) was added to a solution of tetra n-butyl ammonium chloride (0.013 g, 0.05 mmol) in 50% aq NaOH (3 mL), stirred for 5 minutes and followed by addition of 3-chloro-5-vinylpyridine (0.167 g, 1.1 mmol) and heated at 100° C. for 6 h. The progress of the reaction was monitored by LCMS, TLC. After completion, the reaction mixture was quenched with water and extracted with ethyl acetate. The combined organic layers were dried over sodium sulfate and concentrated under reduced pressure to obtain crude product which was further purified by using column chromatography (SiO$_2$—100-200 mesh) followed by reverse-phase chromatography (C-18, 500 mm×50 mm, Mobile Phase A=0.05% TFA in water, B=0.05% TFA in acetonitrile, Gradient: 10% B to 80% B in 30 min. injection volume 5 mL) to yield the product as a TFA salt (110 mg). The NMR data for the compound is as follows: $^1$H NMR (DMSO)—10.1 and 9.9 (bs, 1H), 8.5 (bs, 1H), 8.3 and 8.1 (s, 1H), 7.7 and 7.6 (s, 1H), 7.5 and 7.4 (d, 1H), 7.3 (d, 1H), 7.1-6.9 (m, 1H), 5.1-5.0 (m, 1H), 4.4-4.1 (m, 3H), 3.4 (m, 1H), 3.1-2.9 (s, 2H), 2.9 (s, 3H), 2.7-2.5 (m, 1H), 2.4 (s, 3H), 2.3-2.2 (m, 2H), 2.1-1.9 (m, 1H), 1.7-1.5 (m, 1H).

Example 105

Preparation of Compound 87

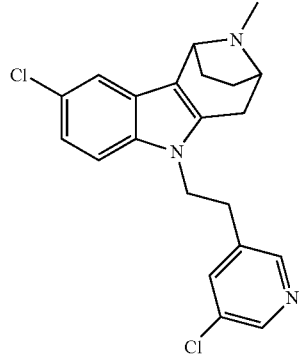 [SMILES: CN1C2CCC1c1c(n(CCc3cncc(Cl)c3)c3ccc(Cl)cc13)C2]

2-Chloro-11-methyl-5,6,7,8,9,10-hexahydro-7,10-iminocyclohept[b]indole (0.246 g, 1.0 mmol) was added to a solution of tetra n-butyl ammonium chloride (0.013 g, 0.05 mmol) in 50% aq NaOH (3 mL), stirred for 5 minutes followed by addition of 3-chloro-5-vinylpyridine (0.107 g, 1.1 mmol) and heated at 100° C. for 6 h. The progress of the reaction was monitored by LCMS, TLC. After completion, the reaction mixture was quenched with water and extracted with ethyl acetate. The combined organic layers were dried over sodium sulfate and concentrated under reduced pressure to obtain crude product which was purified by column chromatography (SiO$_2$—100-200 mesh) to obtain compound as a free base (0.180 mg). The free base (0.080 g 0.2 mmol), was dissolved in THF (5 mL) and oxalic acid (0.026 g, 0.2 mmol) in THF (3 mL) was added to it. The resulting mixture was further stirred for 30 min at RT, the precipitate was filtered, and dried under vacuum to yield the product as oxalate salt (50 mg). The NMR data for the compound is as follows: $^1$H NMR (CD$_3$OD)-8.4 (s, 1H), 8.0 (d, 1H), 7.5 (s, 1H), 7.4 (s, 1H), 7.3 (d, 1H), 7.3-7.1 (m, 1H), 5.4-4.0 (m, 4H), 3.8-3.0 (m, 4H), 2.9 and 2.6 (s. 3H), 2.6-2.3 (m, 2H), 2.2-2.1 (m, 1H), 1.8-1.6 (m, 1H).

Example 106

Preparation of Compound 79

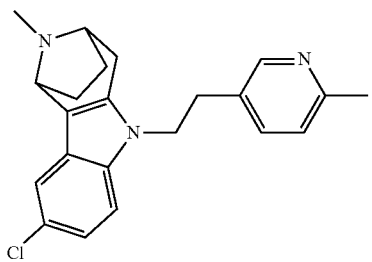 [SMILES: Cc1ccc(CCn2c3c(c4cc(Cl)ccc42)C2CCC(C3)N2C)cn1]

2-Chloro-11-methyl-5,6,7,8,9,10-hexahydro-7,10-iminocyclohept[b]indole (0.5 g, 2.0 mmol) was added to a solution of tetra n-butyl ammonium chloride (0.028 g, 0.1 mmol) in 50% aq NaOH (5 mL), stirred for 10 min followed by addition of 2-methyl-5-vinylpyridine (0.28 g, 2.4 mmol) and heated at 100° C. for 16 h. The progress of the reaction was monitored by LCMS and TLC. After completion of the reaction, the reaction mixture was quenched with water and extracted with ethyl acetate. The combined organic layers were dried over anhydrous sodium sulfate and concentrated under reduced pressure. The resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min. injection volume 5 mL) to yield the product as a TFA salt (55 mg). The NMR data for the compound is as follows: $^1$H NMR (DMSO-D$_2$O)—8.38 (s, 1H), 7.7 (d, 1H), 7.6 (d, 1H), 7.5 (d, 1H), 7.4 (d, 1H), 7.02-7.16 (m, 2H), 4.3-4.4 (m, 2H), 3.38-3.42 (m, 1H), 3.19-3.22 (m, 2H), 2.8 (s, 3H), 2.79-2.84 (m, 2H), 2.58 (s, 3H), 2.22-2.38 (m, 1H), 1.99-2.1 (m, 2H), 1.6-1.7 (m, 1H).

Example 107

Preparation of Compound 138

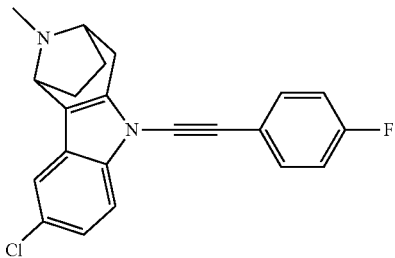 [SMILES: CN1C2CCC1c1c(n(C#Cc3ccc(F)cc3)c3ccc(Cl)cc13)C2]

Potassium carbonate (0.168 gm, 1.21 mmol) and 1.10 phenanthroline (0.021 gm, 0.121 mmol) were added to a stirred solution of 2-chloro-11-methyl-5,6,7,8,9,10-hexahydro-7,10-iminocyclohept[b]indole (0.15 gm, 0.609 mmol) and copper sulfate (0.015 gm, 0.0600 mmol) in toluene (5 mL) and stirred for 5 minutes at RT. A solution of 1-Bromoethynyl-4-fluoro-benzene (0.134 gm, 0.67 mmol) in toluene (2 mL) was added to the reaction mixture and was stirred for 2 h at 80° C. After completion of the reaction (the reaction was monitored by TLC), the solvent was removed under reduced pressure, crude compound was purified by column chromatography (2% methanol/dichloromethane in silica 100-200 mesh. Diameter of column—5.0 cm, Height of silica—approx. 5 inch) to provide the desired compound as yellow colored oil (0.03 gm, 14% yield). The purified compound (0.03 gm, 0.0824 mmol) was dissolved in THF (1.0 mL). A solution of oxalic acid dihydrate (0.01 g, 0.0793 mmol) in THF (2 mL) was added and stirred for 30 min at RT, the precipitate obtained was filtered and dried to give oxalate salt as off white solid (0.025 g, 67% yield). $^1$H NMR (CD$_3$OD) of the oxalate salt—7.67 (m, 1H), 7.60 (m, 3H), 7.36 (d, 1H), 7.16 (m, 2H), 5.1 (m, 1H), 4.40 (m, 1H), 3.60 (m, 2H), 3.20 (m, 1H), 3.10 (m, 1H), 2.80 (m, 3H), 2.60 (m, 2H). (M+1) 365.

Example 108

Preparation of Compound 154

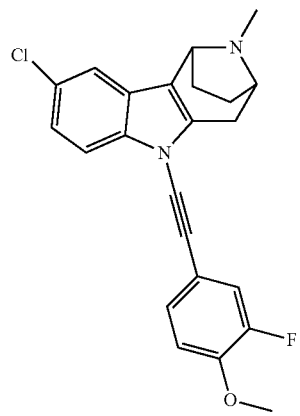 [SMILES: COc1ccc(C#Cn2c3c(c4cc(Cl)ccc42)C2CCC(C3)N2C)cc1F]

2-Chloro-11-methyl-5,6,7,8,9,10-hexahydro-7,10-iminocyclohept[b]indole (100 mg, 0.40 mmol), CuSO$_4$.5H$_2$O (20 mg, 0.08 mmol), 1,10-Phenanthroline (29 mg, 0.16 mmol), K$_3$PO$_4$ (172 mg, 0.81 mmol) and 4-(bromoethynyl)-2-fluoro-1-methoxybenzene (102 mg 0.44 mmol) were mixed in toluene (5 mL) and flushed with nitrogen. The reaction mixture was heated overnight at 80° C. Upon completion (the progress of the reaction was monitored by LCMS), the reaction mixture was filtered through Celite, washed with DCM. The combined organic phase was concentrated and, purified by column chromatography (Silica gel—60-80% ethyl acetate in hexane) followed by re-purification by prep TLC to get product as blown solid (34 mg). $^1$H NMR (CDCl3) of the free base—7.45 (m, 2H), 7.25 (m, 2H), 7.20 (d, 1H), 6.95 (t, 1H), 4.10 (m, 1H), 3.90 (s, 3H), 3.61 (m, 1H), 3.22 (dd, 1H), 2.45 (m, 1H), 2.40 (s, 3H), 2.30 (m, 2H), 1.90 (m, 2H), (M+1) 395.

Example 109

Preparation of Compound 139

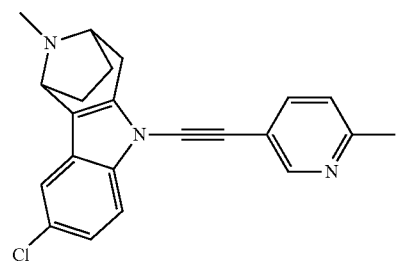 [SMILES: Cc1ccc(C#Cn2c3c(c4cc(Cl)ccc42)C2CCC(C3)N2C)cn1]

Potassium carbonate (0.168 gm, 1.21 mmol) and 1,10 phenanthroline (0.021 gm, 0.121 mmol) were added to a stirred solution of 2-chloro-11-methyl-5,6,7,8,9,10-hexahydro-7,10-iminocyclohept[b]indole (0.15 gm, 0.609 mmol) and copper sulfate (0.015 gm, 0.0609 mmol) in toluene (5 mL) and stirred for 5 minutes at RT. A solution of 5-(bromoethynyl)-2-methylpyridine (0.13 gm, 0.67 mmol) in toluene (2 mL) was added to the reaction mixture and stirred for 6 h at 80° C. After completion (the progress of the reaction was monitored by TLC), the solvent was removed under pressure, and the crude compound was purified by column chromatography (6% methanol/dichloromethane in silica 100-200 mesh, Diameter of column—5.0 cm, Height of silica—approx. 5 inch) to provide the desired compound as yellow colored oil (0.03 gm, 14% yield). The purified compound (0.03 gm, 0.083 mmol) was dissolved in THF (1.0 mL). A solution of oxalic acid dihydrate (0.01 g, 0.0793 mmol) in THF (2 mL) was added and stirred for 30 min at RT, the precipitate obtained was filtered and dried to give oxalate salt as off white solid (0.015 g, 40% yield). $^1$H NMR (CD$_3$OD) of the oxalate salt—8.62 (m, 1H), 7.90 (m, 1H0, 7.66 (m, 1H), 7.62 (m, 1H), 7.35 (d, 2H), 5.10 (m, 1H), 4.40 (m, 1H), 3.60 (m, 2H), 3.20 (m, 1H), 3.0 (m, 3H), 2.65 (m, 1H), 2.60 (s, 3H), 2.30 (m, 1H), 2.20 (m, 1H). (M+1) 362.

Example 110

Preparation of Compound 108

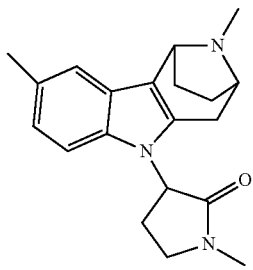

Sodium hydride (106 mg, 4.41 mmol) is washed with hexane and dried under vacuum and THF (5 mL) is added to the dry sodium hydride. 2,11-Dimethyl-5,6,7,8,9,10-hexahydro-7,10-iminocyclohept[b]indole (200 mg, 0.88 mmol) in THF (3 mL) is added dropwise to the reaction mixture at 0° C. The resulting reaction mixture is stirred for 30 minutes at 0° C. 3-bromo-1-methylpyrrolidin-2-one (314 mg, 1.76 mmol) in THF (3 mL) is added dropwise and the reaction mixture is stirred at RT for 3 h. After completion of the reaction, the reaction mixture is quenched with ice cold water and the product extracted with ethyl acetate. The organic layer is washed with water, dried over sodium sulfate and evaporated to obtain the crude compound, which is washed with ether and hexane for removal of colored impurities to yield the desired product.

Example 111

Preparation of Compound 112

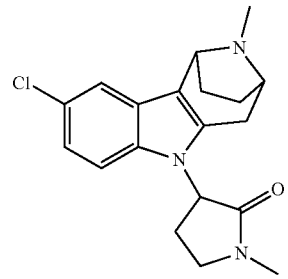 [SMILES: CN1CCC(n2c3c(c4cc(Cl)ccc42)C2CCC(C3)N2C)C1=O]

Sodium hydride (97.2 mg, 4.05 mmol) is washed with hexane and dried under vacuum and THF (5 mL) is added to dry sodium hydride. 2-Chloro-11-methyl-5,6,7,8,9,10-hexahydro-7,10-iminocyclohept[b]indole (200 mg, 0.810 mmol) in THF (3 mL) is added dropwise to the reaction mixture at 0° C. The reaction mixture is stirred for 30 minutes at 0° C. 3-bromo-1-methylpyrrolidin-2-one (288 mg, 1.62 mmol) in THF (3 mL) is added dropwise and the solution is stirred at RT for 3 h. After completion of the reaction, the reaction mixture is quenched with ice cold water and the product extracted with ethyl acetate. The organic layer is washed with water, dried over sodium sulfate and evaporated to obtain the crude compound, which is washed with ether and hexane for removal of colored impurities to obtain the desired product.

Example 112

Preparation of Compound 113

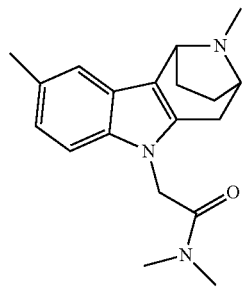

Sodium hydride (73 mg, 3.06 mmol) washed with hexane, dried under vacuum was taken in THF (5 mL). 2,11-dimethyl-5,6,7,8,9,10-hexahydro-7,10-iminocyclohept[b]indole (200 mg, 0.61 mmol) in THF (3 mL) was added dropwise to the reaction mixture at 0° C. The reaction mixture was stirred at 0° C. for 30 minutes. N,N-dimethylchloroacetamide (111 mg, 0.92 mmol) in THF (3 mL) was added dropwise to the reaction mixture and stirred at RT for 3 h. After completion of the reaction, the reaction mixture was quenched with ice cold water and the product was extracted with ethyl acetate. The organic layer was washed with water, dried over sodium sulfate and concentrated under reduced pressure to obtain the crude compound, which was washed with ether and hexane for removal of colored impurities to obtain desired product (63 mg). The NMR data for the compound is as follows: 1H NMR (CDCl$_3$) of the freebase—7.25 (s, 1H), 7.05 (d, 1H), 6.95 (d, 1H), 4.75 (m, 2H), 4.20 (m, 1H), 3.60 (m, 1H), 3.15 (m, 1H), 3.0 (s, 3H), 2.95 (s, 3H), 2.40 (s, 3H), 2.38 (s, 3H), 2.20 (m, 3H), 1.90 (m, 1H), 1.60 (m, 1H). MS m/z observed 312 (M+1).

Example 113

Preparation of Compound 125

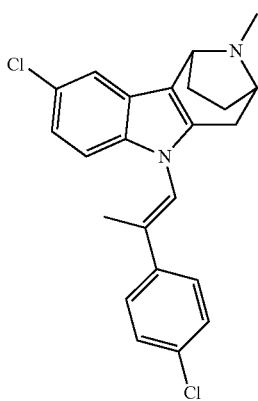 [SMILES: C/C(=C\n1c2c(c3cc(Cl)ccc31)C1CCC(C2)N1C)c1ccc(Cl)cc1]

2-Chloro-11-methyl-5,6,7,8,9,10-hexahydro-7,10-iminocyclohept[b]indole (89 mg, 0.36 mmol), CuI (6 mg. 0.036 mmol), L-proline (8 mg, 0.072 mmol), K$_3$PO$_4$ (154 mg, 0.72 mmol) were mixed in DMF (6 mL) and the reaction mixture was stirred for 10 min. at room temperature. 1-(1-bromoprop-1-en-2-yl)-4-chlorobenzene (100 mg, 0.434 mmol) was added drop wise to the reaction mixture and heated overnight at 80° C. After completion of reaction, DMF was evaporated under reduced pressure and extracted with ethyl acetate and brine. The organic layer was dried over Na$_2$SO$_4$ and concentrated under reduced pressure. The crude compound was purified by column chromatography to afford the desired compound (90 mg). 1H NMR (CDCl$_3$) of the HCL salt—7.48-7.44 (m, 2H), 7.43-7.40 (m, 2H), 7.26-7.03 (m, 3H), 6.87-6.80 (m, 1H), 4.30-4.18 (m, 1H), 3.53-3.64 (m, 1H), 3.20-3.08 (m, 1H), 2.48-2.43 (m, 2H), 2.42-2.30 (m, 1H), 2.27 (s, 3H), 2.10-2.03 (m, 2H), 1.98 (s, 3H), (M+1) 397.

Example 114

Preparation of Compound 126

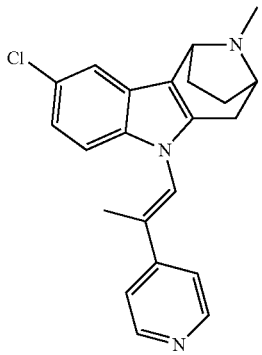 [SMILES: C/C(=C\n1c2c(c3cc(Cl)ccc31)C1CCC(C2)N1C)c1ccncc1]

2-Chloro-11-methyl-5,6,7,8,9,10-hexahydro-7,10-iminocyclohept[b]indole (0.1 g, 0.4 mmol). CuI (7 mg, 0.04 mmol), L-proline (9 mg, 0.08 mmol). K$_3$PO$_4$ (0.72 g, 0.8 mmol), CuSO4 (1 mg, 0.004 mmol), 1,10-Phenanthroline (1 mg, 0.004 mmol) and 4-(1-bromoprop-1-en-2-yl)pyridine (0.08 g, 0.4 mmol) were mixed in DMF (3 mL). The reaction mixture was stirred at 90° C. for 12 h. The reaction was monitored by LC/MS and TLC. After completion of the reaction, water was added to the reaction mixture and extracted with ethyl acetate. The organic layer was dried over Na$_2$SO$_4$ and concentrated under vacuum to obtain the crude product which was purified by column chromatography followed by prep TLC to get pure desired compound (23 mg). 1H NMR (CD$_3$OD) of the TFA salt 8.78 (d, 2H), 8.10 (d, 2H), 7.70 (s, 1H), 7.60 (d, 1H), 7.25 (m, 2H), 5.10 (m, 1H), 4.36 (m, 1H), 3.50 (m, 1H), 3.10 (m, 1H), 3.0 (s, 3H), 2.65 (m, 2H), 2.38 (m, 2H), 2.05 (s, 3H). (M+1) 364.

Example 115

Preparation of Compound 128

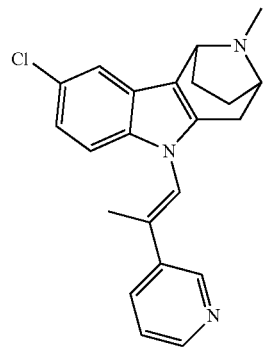 [SMILES: C/C(=C\n1c2c(c3cc(Cl)ccc31)C1CCC(C2)N1C)c1cccnc1]

2-Chloro-11-methyl-5,6,7,8,9,10-hexahydro-7,10-iminocyclohept[b]indole (100 mg, 0.0406 mmol), CuI (8 mg, 0.0406 mmol), L-proline (9 mg, 0.081 mmol), K$_3$PO$_4$ (172 mg, 0.8 mmol) were mixed in DMF (4 mL) and stirred for 10 min at room temperature. 3-(1-bromoprop-1-en-2-yl)pyridine (96 mg, 0.48 mmol) was added dropwise to the reaction mixture and heated at 90° C. for 18 h. After completion of the reaction, DMF was evaporated under reduced pressure and extracted with ethyl acetate. The combined organic layer was dried over Na$_2$SO$_4$ and concentrated under reduced pressure to obtain the crude compound, which was purified by column chromatography to afford 80 mg of the desired compound. $^1$H NMR (CD3OD) of the TFA salt—8.92 (m, 1H), 8.65 (m, 1H), 8.38 (d, 1H), 7.72 (m, 1H), 7.62 (s, 1H), 7.36-7.20 (m, 3H), 5.10 (dd, 1H), 4.36 (m, 1H), 3.56 (m, 1H), 3.0 (s, 3H), 2.90 (s, 1H), 2.63 (m, 1H), 2.50 (m, 1H), 2.36 (m, 1H), 2.10 (m, 1H), 2.0 (s, 3H). (M+1) 364.

Example 116

Preparation of Compound 129

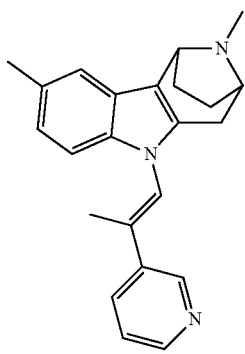

2,11-Dimethyl-5,6,7,8,9,10-hexahydro-7,10-iminocyclohept[b]indole (200 mg, 0.884 mmol), CuI (16 mg, 0.0884 mmol), L-proline (20 mg, 0.17 mmol), $K_3PO_4$ (376 mg, 1.7 mmol) were mixed in DMF (6 mL) and the reaction mixture was stirred for 10 min at room temperature. 3-(1-bromoprop-1-en-2-yl)pyridine (210 mg, 1.06 mmol) was added dropwise to the reaction mixture and heated at 90° C. for 18 h. After completion of the reaction, DMF was evaporated under reduced pressure and extracted with ethyl acetate. The combined organic layer was dried over $Na_2SO_4$ and concentrated under reduced pressure to obtain the crude compound which was purified by column chromatography to afford the desired compound (70 mg). $^1$H NMR ($CD_3OD$) of the TFA salt—9.10 (m 1H), 8.88 (m, 1H), 8.62 (d, 1H), 7.92 (m, 1H), 7.40 (s, 1H), 7.32 (d, 1H), 7.18 (t, 1H), 7.10 (m, 1H), 5.15 (dd, 1H), 4.30 (m, 1H), 3.50 (m, 1H), 3.0 (s, 3H), 2.90 (s, 1H), 2.62 (m, 2H), 2.42 (s, 3H), 2.36 (m, 1H), 2.10 (m, 4H), (M+1) 344.

Example 117

Preparation of Compound 130

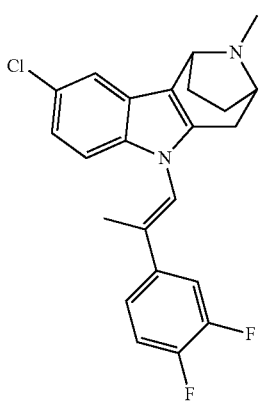 [SMILES: C/C(=C\n1c2c(c3cc(Cl)ccc31)C1CCC(C2)N1C)c1ccc(F)c(F)c1]

2-Chloro-11-methyl-5,6,7,8,9,10-hexahydro-7,10-iminocyclohept[b]indole (88 mg, 0.36 mmol), CuI (8 mg, 0.036 mmol), L-proline (9 mg, 0.086 mmol), $K_3PO_4$ (183 mg, 0.86 mmol) were mixed in DMF (6 mL) and the reaction mixture was stirred for 10 min at room temperature, 4-(1-bromoprop-1-en-2-yl)-1,2-difluorobenzene (100 mg, 0.43 mmol) was added dropwise to the reaction mixture was and heated overnight at 80° C. After completion of the reaction, the reaction mixture was extracted with ethyl acetate and brine solution. The organic layer was dried over $Na_2SO_4$ and concentrated under reduced pressure. The crude compound was purified by column chromatography to afford the desired compound (110 mg). $^1$H NMR ($CD_3OD$) of the oxalate salt—7.60 (m, 2H), 7.50 (m, 1H), 7.38 (m, 1H), 7.20 (m, 2H), 7.05 (d, 1H), 5.10 (m, 1H), 4.30 (m, 1H), 3.50 (m, 1H), 2.90 (s, 3H), 2.82 (m, 1H), 2.65 (m, 1H), 2.50 (m, 1H), 2.30 (m, 1H), 2.10 (m, 1H), 1.90 (s, 3H). (M+1) 399.

Example 118

Preparation of Compound 131

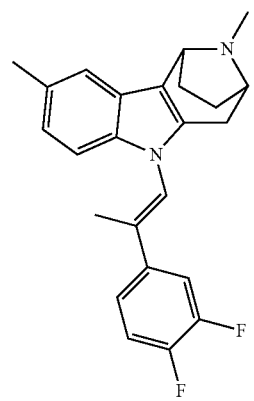

2,11-Dimethyl-5,6,7,8,9,10-hexahydro-7,10-iminocyclohept[b]indole (81 mg, 0.36 mmol), CuI (8 mg, 0.036 mmol), L-proline (9 mg, 0.085 mmol), and $K_3PO_4$ (183 mg, 0.86 mmol) were mixed in DMF (6 mL) and the reaction mixture was stirred for 10 min at room temperature. 4-(1-bromoprop-1-en-2-yl)-1,2-difluorobenzene (100 mg, 0.43 mmol) was added dropwise to the reaction mixture was and heated overnight at 80° C. overnight. After completion of the reaction, the reaction mixture was extracted with ethyl acetate and brine solution. The combined organic layer was dried over $Na_2SO_4$ and concentrated under reduced pressure to obtain the crude compound which was purified by column chromatography to afford the desired compound (63 mg). $^1$H NMR ($CD_3OD$) of the TFA salt 7.58 (m, 1H), 7.42 (m, 1H), 7.38 (s, 1H), 7.30 (m, 1H), 7.10 (m, 2H), 7.0 (s, 1H), 5.10 (m, 1H), 4.30 (m, 1H), 3.50 (m, 1H), 3.30 (m, 1H), 2.95 (s, 3H), 2.60 (m, 1H), 2.50 (m, 1H), 2.40 (s, 3H), 2.30 (m, 1H), 2.02 (m, 1H), 1.95 (s, 3H). (M+1) 379.

Example 119

Preparation of Compound 132

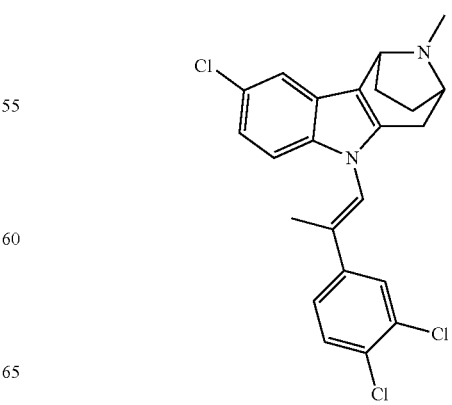

239

2-Chloro-11-methyl-5,6,7,8,9,10-hexahydro-7,10-iminocyclohept[b]indole (77 mg, 0.31 mmol), CuI (6 mg, 0.032 mmol), L-proline (7 mg, 0.063 mmol) and K$_3$PO$_4$ (134 mg, 0.63 mmol) were mixed in DMF (5 mL) and the mixture was stirred for 10 min at room temperature. 4-(1-bromoprop-1-en-2-yl)-1,2-dichlorobenzene (100 mg, 0.378 mmol) was added drop wise so the reaction mixture was heated overnight at 80° C. After completion of the reaction, product was extracted with ethyl acetate and brine solution. The combined organic layer was dried over Na$_2$SO$_4$ and concentrated under reduced pressure to obtain the crude compound which was purified by column chromatography to afford the desired compound (80 mg). $^1$H NMR (CD$_3$OD) of the TFA salt 7.82 (d, 1H), 7.63 (d, 1H), 7.58 (d, 2H), 7.22 (d, 2H), 7.08 (d, 1H), 5.10 (m, 1H), 4.30 (m, 1H), 3.45 (m, 1H), 2.98 (s, 3H), 2.85 (s, 1H), 2.62 (m, 1H), 2.50 (m, 1H), 2.30 (m, 1H), 2.10 (m, 1H), 1.95 (s, 3H). (M+1) 431.

Example 120

Preparation of Compound 133

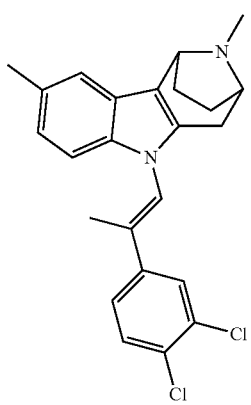

2,11-Dimethyl-5,6,7,8,9,10-hexahydro-7,10-iminocyclohept[b]indole (71 mg, 0.31 mmol), CuI (6 mg, 0.032 mmol), L-proline (7 mg, 0.063 mmol) and K$_3$PO$_4$ (134 mg, 0.63 mmol) were mixed in DMF (5 mL) and the reaction mixture was stirred for 10 min at room temperature. 4-(1-bromoprop-1-en-2-yl)-1,2-dichlorobenzene (100 mg, 0.378 mmol) was added drop wise to the reaction mixture and heated overnight at 80° C. After completion of the reaction, the reaction mixture was extracted with ethyl acetate and brine solution. The combined organic layer was dried over Na$_2$SO$_4$ and concentrated under reduced pressure to obtain the crude compound which was purified by column chromatography to afford the desired compound (80 mg). $^1$H NMR (DMSO) of the oxalate salt—7.95 (s, 1H), 7.70 (d, 1H), 7.62 (d, 1H), 7.38 (s, 1H), 7.22 (s, 1H), 7.18 (d, 1H), 7.0 (d, 1H), 5.0 (m, 1H), 4.20 (m, 2H), 3.30 (m, 2H), 2.90 (m, 1H), 2.80 (m, 3H), 2.40 (s, 3H), 2.10 (m, 1H), 1.90 (s, 3H), 1.80 (m, 1H). (M+1) 411.

240

Example 121

Preparation of Compound 134

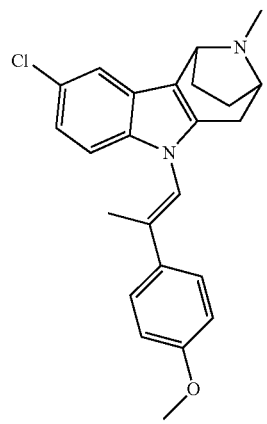 [SMILES: COc1ccc(/C(C)=C/n2c3c(c4cc(Cl)ccc42)C2CCC(C3)N2C)cc1]

2-Chloro-11-methyl-5,6,7,8,9,10-hexahydro-7,10-iminocyclohept[b]indole (200 mg, 0.81 mmol), CuI (15 mg, 0.081 mmol), L-proline (18 mg, 0.16 mmol) and K$_3$PO$_4$ (346 mg, 1.6 mmol) were mixed in DMF (6 mL) and the reaction mixture was stirred for 10 min at room temperature. 1-(1-bromoprop-1-en-2-yl)-4-methoxybenzene (221 mg, 0.97 mmol) was added drop wise to the reaction mixture and heated at 90° C. for 18 h. After completion of the reaction, DMF was evaporated under reduced pressure and the compound extracted with ethyl acetate. The combined organic layer was dried over Na$_2$SO$_4$ and concentrated under reduced pressure. The crude compound was purified by column chromatography to afford the desired compound (45 mg). $^1$H NMR (DMSO) FREE BASE: 7.80-7.60 (m, 2H), 7.50-7.30 (m, 1H), 7.30-6.90 (m, 5H), 4.30-4.20 (t, 1H), 3.90-3.70 (m, 4H), 2.40-2.30 (m, 3H), 2.20-2.00 (m, 2H), 1.90 (s, 2H), 1.80 (s, 2H), 1.60-1.40 (m, 3H). MS m/z observed 393 (M+1).

Example 122

Preparation of Compound 135

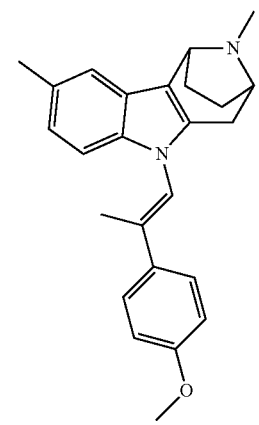

2,11-Dimethyl-5,6,7,8,9,10-hexahydro-7,10-iminocyclohept[b]indole (82 mg, 0.36 mmol), CuI (7 mg, 0.036 mmol). L-proline (8 mg, 0.073 mmol) and K$_3$PO$_4$ (156 mg, 0.734 mmol) were mixed in DMF (6 mL) and the reaction mixture was stirred for 10 min at room temperature. 1-(1-bromoprop-1-en-2-yl)-4-methoxybenzene (100 mg, 0.44 mmol) was added dropwise to the reaction mixture and heated overnight at 80° C. After completion of the reaction, the reaction mixture was extracted with ethyl acetate and brine solution. The combined organic layer was dried over Na$_2$SO$_4$ and concentrated under reduced pressure to obtain the crude compound which was purified by column chromatography to afford the desired compound (90 mg). $^1$H NMR (DMSO) of the oxalate salt—7.60 (d, 2H), 7.36 (s, 1H), 7.10 (d, 1H), 7.0 (m, 4H), 5.05 (m, 1H), 4.20 (m, 2H), 3.80 (s, 3H) 3.40 (m, 4H), 2.90-2.70 (m, 3H), 2.40 (s, 3H), 2.10 (s, 1H), 1.82 (s, 3H). (M+1) 373.

Example 123

Preparation of Compound 136

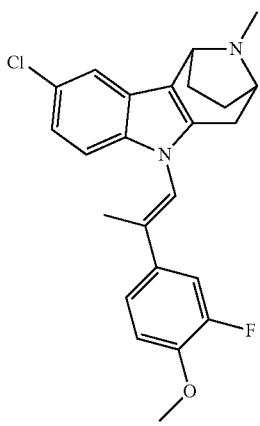 [SMILES: COc1ccc(/C(C)=C/n2c3c(c4cc(Cl)ccc42)C2CCC(C3)N2C)cc1F]

2-(2-Chloro-11-methyl-5,6,7,8,9,10-hexahydro-7,10-iminocyclohept[b]indol-5-yl)-1-(3-fluoro-4-methoxyphenyl) ethanol (500 mg, 1.1 mmol) was stirred with thionyl chloride for 2 h at room temperature. The solvents were removed under reduced pressure and the residue was dissolved in NMP (2 mL) followed by addition of powdered KOH (443 mg, 7.8 mmol) and the reaction mixture was stirred at 100° C. for 12 h. The progress of the reaction was monitored by LCMS. Water (10 ml) was added to the reaction mixture and extracted with ethyl acetate (3×15 mL). The combined organic layer was dried over anhydrous sodium sulfate and concentrated; the resulting crude product was purified by reverse phase chromatography. $^1$H NMR (CDCl3) of the TFA salt—7.60 (s, 1H), 7.30 (m, 3H), 7.18 (m, 2H), 7.05 (m, 1H), 6.80 (s, 1H), 5.0 (m, 1H), 4.40 (m, 1H), 3.90 (s, 3H), 3.20 (m, 1H), 2.95 (m, 1H), 2.80 (s, 3H), 2.20 (m, 1H), 1.95 (s, 3H), 1.80 (m, 2H). (M+1) 411.

Example 124

Preparation of Compound 137

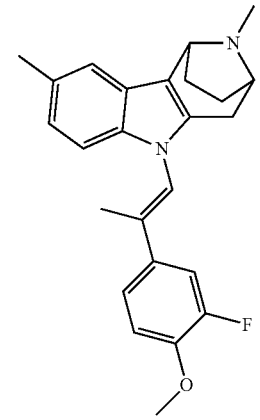

2,11-Dimethyl-5,6,7,8,9,10-hexahydro-7,10-iminocyclohept[b]indole (77 mg, 0.34 mmol), CuI (6 mg, 0.034 mmol), L-proline (8 mg, 0.068 mmol) and K$_3$PO$_4$ (145 mg, 0.68 mmol) were mixed in DMF (6 mL) and the reaction mixture was stirred for 10 min at room temperature. 4-(1-bromoprop-1-en-2-yl)-2-fluoro-1-methoxybenzene (100 mg, 0.34 mmol) was added dropwise to the reaction mixture was heated overnight at 80° C. After completion of the reaction, the reaction mixture was extracted with ethyl acetate and brine solution. The combined organic layer was dried over Na$_2$SO$_4$ and concentrated under reduced pressure to obtain the crude compound which was purified by column chromatography to afford desired compound (45 mg). $^1$H NMR (CD$_3$OD) of the oxalate salt 7.42 (m, 2H), 7.36 (s, 1H), 7.18 (d, 1H), 7.10 (m, 2H), 6.95 (s, 1H), 4.30 (m, 1H), 3.90 (s, 3H), 3.70 (m, 1H), 3.50 (m, 1H), 2.90 (s, 3H), 2.80 (m, 1H), 2.60 (m, 2H), 2.42 (s, 3H), 2.30 (m, 1H), 2.05 (m, 1H), 1.90 (s, 3H). (M+1) 391.

Example 125

Preparation of Compound 141

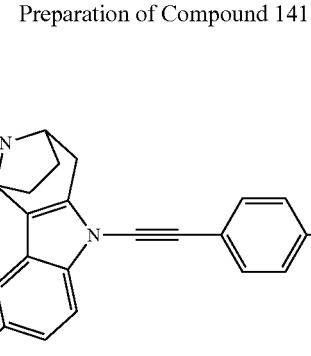

2,11-Dimethyl-5,6,7,8,9,10-hexahydro-7,10-iminocyclohept[b]indole (226 mg, 1 mmol), CuSO$_4$.5H$_2$O (24.9 mg, 0.1 mmol), 1,10-phenanthroline (36 mg, 0.2 mmol), K$_3$PO$_4$ (276 mg, 2 mmol) and 1-(bromoethynyl)-4-fluorobenzene (220 mg, 1.1 mmol) were dissolved in toluene (8-10 ml). The reaction mixture was purged with nitrogen gas and heated at 80° C. for 16 h. The reaction mixture was filtered through Celite, and the Celite bed was rinsed with dichloromethane. The combined organic layer was concentrated and the residue was purified by silica gel column chromatography using methanol-dichloromethane gradient. $^1$H NMR (CDCl$_3$) of the free base—7.50 (m 3H), 7.22 (s, 1H), 7.16 (m, 1H), 7.10 (m, 2H), 4.60 (m, 1H), 4.05 (m, 1H), 3.40 (m, 1H), 2.80 (m, 1H), 2.70 (s, 3H), 2.50 (s, 3H), 2.10 (m, 2H), 1.80 (m, 2H), (M+1) 345.

Example 126

Preparation of Compound 142

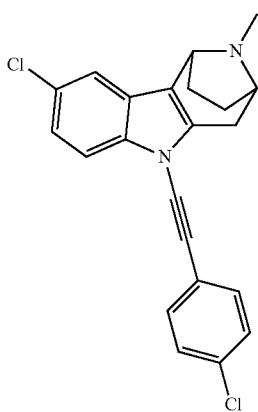 [SMILES: CN1C2CCC1c1c(n(C#Cc3ccc(Cl)cc3)c3ccc(Cl)cc13)C2]

2-Chloro-11-methyl-5,6,7,8,9,10-hexahydro-7,10-iminocyclohept[b]indole (245 mg, 1 mmol), CuSO$_4$.5H$_2$O (50 mg, 0.2 mmol), 1,10-Phenanthroline (72 mg, 0.4 mmol), K$_3$PO$_4$ (425 mg, 2 mmol) and 1-(bromoethynyl)-4-chlorobenzene (237 mg, 1.1 mmol) were mixed in toluene (8-10 mL) and the resulting mixture was flushed with nitrogen and heated overnight at 80° C. The reaction was monitored by LCMS, and upon completion, the reaction mixture was filtered through Celite, washed with DCM. The combined organic layer was concentrated, purified by silica gel column chromatography using 60-80% ethyl acetate in hexane as eluent to obtain the pure compound as brown semi solid (130 mg). 1H NMR (CDCl$_3$) of the TFA salt 7.50 (s, 1H) 7.49-7.40 (m, 3H), 7.38-7.32 (m, 2H), 7.25-7.20 (d, 1H), 4.22-4.20 (d, 1H), 3.73-3.70 (m, 1H), 3.31-3.22 (m, 1H), 2.57 (m, 1H), 2.60 (s, 3H), 2.40-2.36 (m, 1H), 1.98-1.90 (m, 1H), 1.65-1.60 (m, 2H), (M+1) 381.

Example 127

Preparation of Compound 143

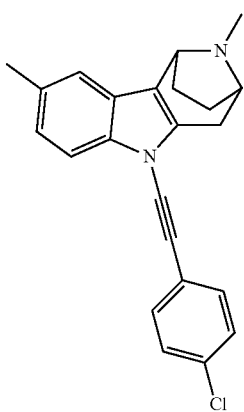

2,11-Dimethyl-5,6,7,8,9,10-hexahydro-7,10-iminocyclohept[b]indole (225 mg, 1 mmol), CuSO$_4$.5H$_2$O (50 mg. 0.2 mmol), 1,10-Phenanthroline (72 mg, 0.4 mmol), K$_3$PO$_4$ (425 mg, 2 mmol) and 1-(bromoethynyl)-4-chlorobenzene (237 mg, 1.1 mmol) were mixed in toluene (8-10 mL) and flushed with nitrogen and the reaction mixture was heated overnight at 80° C. The reaction was monitored by LCMS; upon completion the reaction mixture was filtered through Celite and washed with DCM. The combined organic layer was concentrated, purified by silica gel column chromatography using 60-80% ethyl acetate in hexane to obtain the desired product as brown semi solid (107 mg). 1H NMR (CDCl$_3$) of the free base—7.50 (s, 1H) 7.47-7.40 (m, 3H), 7.38-7.32 (m, 2H), 7.25-7.20 (d, 1H), 4.31-4.26 (d, 1H) 3.80-3.76 (d, 1H), 3.31-3.26 (m, 1H), 2.52 (s, 6H), 2.42-2.40 (m, 1H), 2.10-1.96 (m, 2H), 1.70-1.60 (m, 2H). MS m/z observed 361 (M+1).

Example 128

Preparation of Compound 155

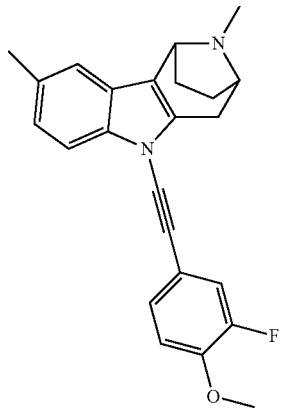 [SMILES: COc1ccc(C#Cn2c3c(c4cc(C)ccc42)C2CCC(C3)N2C)cc1F]

2,11-dimethyl-5,6,7,8,9,10-hexahydro-7,10-iminocyclohept[b]indole (100 mg, 0.44 mmol), CuSO$_4$.5H$_2$O (23 mg, 0.088 mmol), 1,10-Phenanthroline (32 mg, 0.17 mmol), K$_3$PO$_4$ (188 mg, 0.88 mmol) and 4-(bromoethynyl)-2-fluoro-1-methoxybenzene (11.1 mg, 0.48 mmol) were mixed in toluene (5 mL) and flushed with nitrogen, and the reaction mixture was heated overnight at 80° C. The reaction was monitored by LCMS: upon completion the reaction mixture was filtered through Celite and washed with DCM. The combined organic layer was concentrated and the crude obtained was purified by silica gel column chromatography using 60-80% ethyl acetate in hexane. The compound was re-purified by prep TLC to obtain desired product as brown solid (20 mg). $^1$H NMR (CDCl$_3$) of the free base—7.42 (d, 1H), 7.25 (m, 3H), 7.10 (d, 1H), 6.90 (t, 1H), 4.18 (m, 1H), 3.90 (s, 3H), 3.62 (m, 1H), 3.20 (dd, 1H), 2.45 (s, 3H), 2.42 (m, 1H), 2.40 (s, 3H), 2.30 (m, 3H), 1.90 (m, 1H). (M+1) 375.

Example 129

Preparation of Compound 160

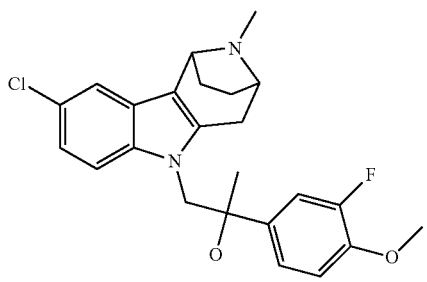 [SMILES: COc1ccc(C(C)(O)Cn2c3c(c4cc(Cl)ccc42)C2CCC(C3)N2C)cc1F]

Sodium hydride 60% (461 mg, 1.15 mmol) was charged in DMF and the solution stirred at RT for 10 minutes. 2-Methyl-8-chloro-5,6,7,8,9,10-hexahydro-7,10-iminocyclohept[b]indole (0.930 g, 3.8 mmol) was added to the reaction mixture and stirred at RT for 1 h. 2-(3-fluoro-4-methoxyphenyl)-2-methyloxirane (1 g, 5.4 mmol) was added to the reaction mixture and stirred overnight at RT. The reaction mixture was quenched with ice water extracted with ethyl acetate. The combined organic layer was washed with water and concentrated to afford crude compound, which was purified on silica (100-200 mesh) using 0-5% MeOH/DCM as eluent. $^1$H NMR (DMSO) of the oxalate salt—7.58 (d, 1H), 7.42 (m, 1H), 7.20 (m, 1H), 7.02 (m, 3H), 5.0 (m, 1H), 4.22 (m, 4H), 4.0 (m, 2H), 3.80 (s, 3H), 2.78 (m, 3H), 2.0 (m, 2H), 1.70 (m, 2H), 1.10 (d, 3H). (M+1) 429.

Example 130

Preparation of Compound 161

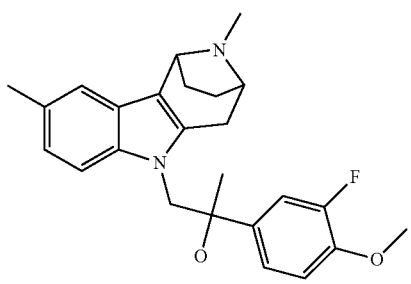

Sodium hydride 60% (461 mg, 1.15 mmol) was charged in DMF and the solution stirred at RT for 10 minutes. 2,11-dimethyl-8-5,6,7,8,9,10-hexahydro-7,10-iminocyclohept[b]indole (0.869 g, 3.84 mmol) was added to the reaction mixture and stirred at RT for 1 h. 2-(4-fluoro-4-methoxyphenyl)-2-methyloxirane (1 g, 5.4 mmol) was added to the reaction mixture and stirred overnight at RT. The reaction mixture was quenched with ice water and extracted with ethyl acetate. The combined organic layer was washed with water and concentrated to afford crude compound, which was purified on silica (100-200 mesh) using 0-5% MeOH/DCM as eluent. $^1$H NMR (CD$_3$OD) of the oxalate salt—7.25 (d, 2H), 7.10 (m, 1H), 7.0 (m, 2H), 6.90 (m, 1H), 5.0 (m, 2H), 4.30-4.15 (m, 4H), 3.80 (s, 3H), 2.80 (s, 3H), 2.40 (s, 3H), 2.20 (m, 2H), 1.90 (m, 1H), 1.70 (m, 1H), 1.60 (d, 3H) (M+1) 409.

Example 131

Preparation of Compound 162

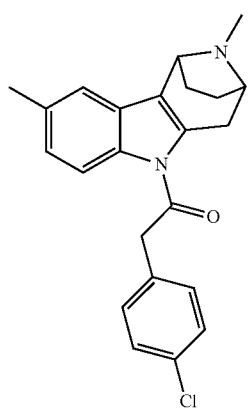 [SMILES: Cc1ccc2c(c1)c1c(n2C(=O)Cc2ccc(Cl)cc2)CC2CCC1N2C]

2,11-dimethyl-8-5,6,7,8,9,10-hexahydro-7,10-iminocyclohept[b]indole (225 mg, 1 mmol), CuSO$_4$.5H$_2$O (50 mg, 0.2 mmol), 1,10-Phenanthroline (72 mg, 0.4 mmol), K$_3$PO$_4$ (425 mg, 2 mmol) and 1-(bromoethynyl)-4-chlorobenzene (237 mg, 1.1 mmol) were mixed in toluene (8-10 mL) and flushed with nitrogen, the reaction mixture was heated overnight at 80° C. The reaction was monitored by LCMS; upon completion, the reaction mixture was filtered through Celite and washed with DCM. The combined organic layer was concentrated, purified by silica gel column chromatography using 60-80% ethyl acetate in hexane to yield product as brown semi solid (107 mg). The product was stirred with trifluoroacetic acid in acetonitrile/water mixture at 50° C. to obtain the title compound as TFA salt. $^1$H NMR (CD$_3$OD) of the TFA salt 8.0 (m, 1H), 7.35 (m, 4H), 7.25 (m, 2H), 7.20 (m, 1H), 5.10 (m, 2H), 4.30 (m, 1H), 3.70 (m, 2H), 3.40 (m, 1H), 3.0 (s, 3H), 2.60 (m, 2H), 2.42 (s, 3H), 2.30 (m, 1H). (M+1) 379.

Example 132

Preparation of Compound 163

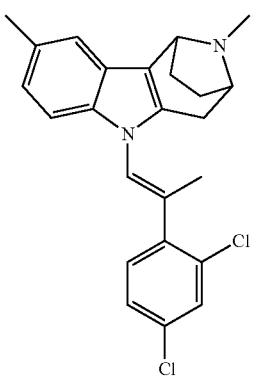

2,11-dimethyl-8-5,6,7,8,9,10-hexahydro-7,10-iminocyclohept[b]indole (200 mg, 1 mmol), 1-(1-bromoprop-1-en-2-yl)-2,4-dichlorobenzene (319 mg, 1.2 mmol), L-proline (23 mg, 0.2 mmol), CuI (19 mg, 0.1 mmol) and $K_3PO_4$ (tribasic, 424 mg, 2 mmol) were added to DMF (5 mL). The reaction mixture was purged with nitrogen and stirred overnight at 85° C. The progress of the reaction was monitored by TLC. On completion of the reaction, DMF was evaporated and water was added to the residue. The precipitate obtained was filtered and dried under vacuum. The compound was purified on silica gel (100-200 mesh) using 0-1% MeOH/DCM as eluent, the isomers were separated through reverse phase chromatography. $^1$H NMR (CDCl$_3$) of the TFA salt—7.38 (d, 1H), 7.22 (m, 2H), 7.05 (m, 2H), 6.95 (d, 1H), 6.80 (m, 2H), 4.80 (m, 1H), 4.20 (m, 1H), 2.80 (m, 1H), 2.60 (m, 1H), 2.50 (m, 3H), 2.38 (s, 3H), 2.30 (s, 3H). (M+1) 411.

Example 133

Preparation of Compound 164

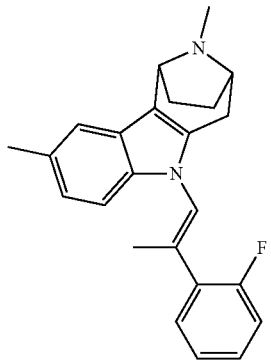 [SMILES: C/C(=C\n1c2c(c3cc(C)ccc31)C1CCC(C2)N1C)c1ccccc1F]

2,11-dimethyl-8-5,6,7,8,9,10-hexahydro-7,10-iminocyclohept[b]indole (226 mg, 1 mmol), 1-(1-bromoprop-1-en-2-yl)-2-fluorobenzene (260 mg, 1.2 mmol), L-proline (0.2 mmol), CuI (19 mg, 0.1 mmol) and $K_3PO_4$ (424 mg, 2 mmol) tribasic were added in DMF. The reaction mixture was purged with nitrogen heated overnight at 85° C. The progress of reaction was monitored by TLC, DMF was evaporated and water added to the residue. The precipitate obtained was filtered and purified on silica gel (100-200 mesh) using 0-5% MeOH/DCM as eluent. The isomers were separated by reversed phase column chromatography. $^1$H NMR (CD$_3$OD) of the TFA salt 7.20 (m, 2H), 7.10 (d, 1H), 6.95 (m, 4H), 6.82 (s, 1H), 4.20 (m, 2H), 3.0 (m, 1H), 2.90 (s, 3H), 2.06 (m, 2H), 2.50 (m, 1H), 2.38 (s, 3H), 2.30 (s, 3H), 2.10 (m, 2H). (M+1) 361.

Example 134

Preparation of Compounds 74, 75, 76, 78, 96, 98, 100, 104, 105, 106, 109, 118, 120, 122, 127, 140, 144, 145, 146, 147, 148, 149, 150, 151, 152, 153, 158, 159 and 165

Compounds 98 is made according to the procedure outlined in General Method 7. Compounds 78 and 96 are made according to the procedure outlined in General Method 8. Compound 120 is made according to the procedure outlined in General Method 14. Compounds 122 and 127 are made according to the procedure outlined in General Method 13. Compounds 140, 144, 145, 146, 147, 148, 149, 150, 151, 152, 153 and 165 are made according to the procedure outlined in General Method 15A. Compounds 74, 75, 76, 100, 104, 105, 106, 109, 118, 158 and 159 are made according to the procedure outlined in General Method 15B.

Example B1

Determination of the Ability of Compounds of the Invention to Bind a Histamine Receptor Histamine H1

To evaluate in radioligand binding assays the activity of compounds of the invention, human recombinant histamine H1 receptor expressed Chinese hamster ovary (CHO) cells (De Backer, M. D. et al., Biochem. Biophys. Rev. Comm. 197(3):1601, 1993) in a modified Tris-HCl buffer (50 mM Tris-HCl, pH 7.4, 2 mM MgCl$_2$, 100 mM NaCl, 250 mM Sucrose) was used. Compounds of the invention were incubated with 1.2 nM [$^3$H]Pyrilamine for 180 minutes at 25° C. Non-specific binding was estimated in the presence of 1 µM pyrilamine. Receptor proteins were filtered and washed, the filters were then counted to determine [$^3$H]Pyrilamine specifically bound. Compounds were screened at 1 µM or lower, using 1% DMSO as vehicle. Biochemical assay results are presented as the percent inhibition of specific binding in Table 2.

Histamine H2

To evaluate in radioligand binding assays the activity of compounds of the invention, human recombinant histamine H2 receptor expressed in Chinese hamster ovary (CHO) K1 cells (Ruat, M., Proc. Natl. Acad. Sci. USA. 87(5):1658, 1990) in a 50 mM Phosphate buffer, pH 7.4 was used. Compounds of the invention were incubated with 0.1 nM [$^{125}$I] Aminopotentidine for 120 minutes at 25° C. Non-specific binding was estimated in the presence of 3 µM Tiotidine. Receptor proteins were filtered and washed, the filters were then counted to determine [$^{125}$I] Aminopotentidine specifically bound. Compounds were screened at 1 µM or lower, using 1% DMSO as vehicle. Biochemical assay results are presented as the percent inhibition of specific binding in Table 2.

Histamine H3

To evaluate in radioligand binding assays the activity of compounds of the invention, human recombinant histamine H$_3$ receptor expressed in Chinese hamster ovary (CHO-K1) cells (Yanai K et al., Jpn J Pharmacol. 65(2): 107, 1994; Zhu Y et al. Mol Pharmacol. 59(3): 434, 2001) in a modified Tris-HCl buffer (50 mM Tris-HCl, pH 7.4, 5 mM MgCl$_2$, 0.04% BSA) is used. Compounds of invention are incubated with 3 nM [$^3$H]R(-)-α-Methylhistamine for 90 minutes at 25° C. Non-specific binding is estimated in the presence of 1 µM R(-)-α-Methylhistamine. Receptor proteins are filtered and washed, the filters are counted to determine [$^3$H]R(-)-α-Methylhistamine specifically bound. Compounds are screened at 1 µM or lower, using 1% DMSO as vehicle. Compounds of the invention are tested in this biochemical assay and percent inhibition of specific binding is determined.

Example B2

Determination of the Ability of Compounds of the Invention to bind a Imidazoline I$_2$ Receptor Central Imidazoline I$_2$ To evaluate in radioligand binding assays the activity of compounds of the invention, rat central imidazoline I$_2$ receptor obtained from Wistar Rat cerebral cortex (Brown, C. M. et al., br. J. Pharmacol. 99:803, 1990) in a modified Tris-HCl buffer (50 mM tris-HCl buffer, pH 7.4, 0.5 mM EDTA) was used. Compounds of the invention were incubated with 2 NM [$^3$H]Idazoxan for 30 minutes at 25° C. Non-specific binding was estimated in the presence of 1 µM Idazoxan. Receptor proteins were filtered and washed, the filters were then counted to determine [$^3$H]Idazoxan specifically bound. Compounds were screened at 1 µM or lower, using 1% DMSO as vehicle. Compounds of the invention were tested in this biochemical assay and percent inhibition of specific binding was determined. Certain compounds showed inhibition of specific binding by at least about 80%.

TABLE 2

| Example No. | Compound No. | Imidazoline I$_2$ Central (1 µM) | Histamine Binding (1 µM) H1 | H2 |
|---|---|---|---|---|
| 2 | 2 | 70 | 99; 85.0 (0.1 µM); 42.0 (10.0 nM) | 43 |
| 3 | 3 | | 12 | 2 |
| 5 | 5 | 25 | 32 | −9 |
| 8 | 8 | | 16 | 9 |
| 9 | 9 | | 6 | 3 |
| 10 | 10 | | 7 | 1 |
| 11 | 11 | | 2 | 9 |
| 12 | 12 | | 29 | −2 |
| 13 | 13 | −7 | 28 | −2 |
| 32 | 32 | | 94 | 13 |
| 33 | 33 | 6 | 86 | 18 |
| 34 | 34 | | 52.0/55.0 | 12.0/24.0 |
| 35 | 35 | 33 | 93 | 27 |
| 37 | 37 | | 78 | 7 |
| 38 | 38 | | 96 | 9 |
| 39 | 39 | | 91 | 86 |
| 52 | 52 | | 91 | 2 |
| 54 | 54 | | 63 | 50 |
| 56 | 56 | 27 | 86 | 16 |
| 57 | 57 | 8 | 96 | 37 |
| 58 | 58 | 8 | 98 | 52 |
| 59 | 59 | −8 | 7 | 15 |
| 60 | 60 | 1 | 21 | 3 |
| 61 | 61 | 22 | 98 | 52 |
| 62 | 62 | 52 | 98 | 52 |
| 70 | 70 | | 65 | 7 |
| 71 | 71 | | 33.0/46.0 | 0.0/20.0 |
| 72 | 72 | | 14 | 7 |
| 73 | 73 | | 10 | −1 |
| 88 | 77 | | 32 | 7 |
| 106 | 79 | | 93 | 1 |
| 100 | 80 | | 94 | −3 |
| 90 | 81 | | 51 | −9 |
| 91 | 82 | | 44 | −8 |
| 101 | 83 | | 98 | 15 |
| 94 | 84 | | 83 | 63 |
| 103 | 85 | | 99 | 81 |
| 99 | 86 | | 99 | 26 |
| 105 | 87 | | 96 | 7 |
| 104 | 88 | | 95 | 5 |
| 95 | 89 | | 92 | −1 |
| 75 | 90 | | 93 | −1 |
| 80 | 91 | | 51 | 9 |
| 98 | 92 | | 54 | 11 |
| 92 | 93 | | 4 | −5 |
| 35 | 94 | | 92 | 4 |
| 35 | 95 | | 55 | 8 |
| 96 | 97 | | 26 | 11 |
| 102 | 99 | | 21 | 6 |
| 93 | 101 | | 48 | 19 |
| 97 | 102 | | 52 | 3 |
| 79 | 103 | | 85 | 1 |
| 79 | 103 | | 85 | 1 |
| 84 | 107 | | 72 | −4 |

TABLE 2-continued

| Example No. | Compound No. | Imidazoline I$_2$ Central (1 µM) | Histamine Binding (1 µM) H1 | H2 |
|---|---|---|---|---|
| 85 | 110 | | 36 | 27 |
| 86 | 111 | | 66 | 33 |
| 89 | 114 | | 93 | 10 |
| 83 | 116 | | 23 | 81 |
| 77 | 121 | | 17 | 21 |
| 87 | 123 | | 62 | 93 |
| 81 | 124 | | 31 | 79 |
| 113 | 125 | | 82 | 96 |
| 115 | 128 | | 15 | 21 |
| 116 | 129 | | 5 | 26 |
| 119 | 132 | | 87 | 99 |
| 123 | 136 | | 69 | 100 |
| 107 | 138 | | 57 | 70 |
| 109 | 139 | | 57 | 34 |
| 125 | 141 | | 2 | 25 |
| 126 | 142 | | 34 | 71 |
| 108 | 154 | | 30 | 87 |
| 128 | 155 | | 10 | 84 |
| 129 | 160 | | 86 | 22 |
| 130 | 161 | | 84 | 20 |
| 131 | 162 | | 0 | 47 |
| 132 | 163 | | 72 | 66 |
| 133 | 164 | | 65 | 41 |

Example B3

Determination of the Ability of Compounds of the Invention to Bind an Adrenergic Receptor Adrenergic $\alpha_{1A}$ To evaluate in radioligand binding assays the activity of compounds of the invention, rat adrenergic $\alpha_{1A}$ receptor obtained from Wistar Rat submaxillary glands (Michel, A. D. et al., Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 minutes at 25° C. Non-specific binding was estimated in the presence of 10 µM phentolamine. Receptor proteins were filtered and washed, the filters were then counted to determine [$^3$H]Prozosin specifically bound. Compounds of the invention were screened at 1 µM or lower, using 1% DMSO as vehicle. Compounds of the invention were tested in this biochemical assay and percent inhibition of specific binding was determined. Certain compounds showed inhibition of specific binding by at least about 80%.

Adrenergic $\alpha_{1B}$

To evaluate in radioligand binding assays the activity of compounds of the invention, rat adrenergic $\alpha_1$B receptor obtained from Wistar Rat liver (Garcia-S'ainz, J. A. et al., Biochem. Biophys. Res. Commun. 186:760, 1992; Michel A. D. et al., Br. J. Pharmacol, 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 minutes at 25° C. Non-specific binding was estimated in the presence of 10 µM phentolamine. Receptor proteins were filtered and washed, the filters were then counted to determine [$^3$H]Prozosin specifically bound. Compounds were screened at 1 µM or lower, using 1% DMSO as vehicle. Compounds of the invention were tested in this biochemical assay and percent inhibition of specific binding was determined. Certain compounds showed inhibition of specific binding by at least about 80%.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. A. et al. Br. J. Pharmacol. 115(6):981, 1995) in a 50 mM Tris-HCl buffer. pH 7.4, was used. Compounds of invention were incubated with 0.6 nM [$^3$H]Prozosin for 60 minutes at 25° C. Non-specific binding was estimated in the presence of 10 μM phentolamine. Receptor proteins were filtered and washed, the filters were then counted to determine [$^3$H]Prozosin specifically bound. Compounds were screened at 1 μM or lower, using 1% DMSO as vehicle. Biochemical assay results are presented as the percent inhibition of specific binding in Table 3.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 minutes at 25° C. MK912 is (2S-trans)-1,3,4,5',6,6',7,12b-octahydro-1',3'-dimethyl-spiro[2H-benzofuro[2,3-a]quinolizine-2,4'(1'H)-pyrimidin]-2'(3'H)-one hydrochloride Non-specific binding was estimated in the presence of 10 μM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 μM or lower, using 1% DMSO as vehicle. Biochemical assay results are presented as the percent inhibition of specific binding in Table 3.

Adrenergic $\alpha_{2B}$

To evaluate in radioligand binding assays the activity of compounds of the invention, human recombinant adrenergic $\alpha_{2B}$ receptor expressed in Chinese hamster ovary (CHO-K1) cells (Uhlen S et al. Eur J Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [$^3$H]Rauwolscine for 60 minutes at 25° C. Non-specific binding was estimated in the presence of 10 μM Prozosin. Receptor proteins were filtered and washed, the filters were then counted to determine [$^3$H]Rauwolscine specifically bound. Compounds were screened at 1 μM or lower, using 1% DMSO as vehicle. Biochemical assay results are presented as the percent inhibition of specific binding in Table 3.

Adrenergic $\alpha_{2C}$

To evaluate in radioligand binding assays the activity of compounds of the invention, human recombinant adrenergic $\alpha_{2C}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of the invention were incubated with 1 nM [$^3$H]MK-912 for 60 minutes at 35° C. Non-specific binding was estimated in the presence of 10 μM WB-4101. Receptor proteins were filtered and washed, the filters were then counted to determine [$^3$H]MK-912 specifically bound. Compounds were screened at 1 μM or lower, using 1% DMSO as vehicle. Compounds of the invention were tested in this biochemical assay and percent inhibition of specific binding was determined. Certain compounds showed inhibition of specific binding by at least about 80%.

Example B4

Determination of the Ability of Compounds of the Invention to Bind a Dopamine Receptor Dopamine $D_{2L}$ To evaluate in radioligand binding assays the activity of compounds of the invention, human recombinant dopamine $D_{2L}$ receptor expressed in Chinese hamster ovary (CHO) cells (Grandy, D. K. et al. Proc. Natl. Acad. Sci. USA, 86:9762, 1989; Hayes, G. et al., Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H]Spiperone for 120 minutes at 25° C. Non-specific binding was estimated in the presence of 10 μM Haloperidol. Receptor proteins were filtered and washed, the filters were then counted to determine [$^3$H]Spiperone specifically bound. Compounds were screened at 1 μM or lower, using 1% DMSO as vehicle. Biochemical assay results are presented as the percent inhibition of specific binding in Table 3.

TABLE 3

Inhibition of ligand binding to aminergic G protein-coupled receptors by compounds of the invention:

| Example No. | Compound No. | Adrenergic (1 μM Ligand Concentration) | | | | | | Dopamine (1 μM) |
|---|---|---|---|---|---|---|---|---|
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 2 | 2 | 98; 97.0 (0.3 μM); 66.0 (0.03 μM) | 99; 89.0 (0.3 μM); 63.0 (0.03 μM) | 94; 85.0 (0.3 μM); 44.0 (0.03 μM) | 100; 47.0 (10.0 nM); 88.0 (0.1 μM) | 98; 85.0 (10.0 nM); 108.0 (0.1 μM) | 97; 69.0 (0.3 μM); 14.0 (0.03 μM) | |
| 3 | 3 | | | 6 | 8 | −17 | | −3 |
| 5 | 5 | | | 21 | 4 | 30 | | 10 |
| 8 | 8 | | | 8 | −2 | −9 | | 1 |
| 9 | 9 | | | 9 | 9 | −15 | | 7 |
| 10 | 10 | | | 7 | −7 | 7 | | −2 |
| 11 | 11 | | | −11 | −10 | 1 | | 2 |
| 12 | 12 | | | 3 | 0 | 10 | | −4 |
| 13 | 13 | | | 8 | 2 | 7 | | 13 |
| 32 | 32 | | | 53 | 17 | 82 | | 10 |
| 34 | 34 | | | 61.0/56.0 | 42.0/39.0 | 103.0/100.0 | | −0.875 |
| 33 | 33 | | | 36 | 69 | 100 | | 17 |
| 35 | 35 | | | 78 | 93 | 110 | | 67 |
| 37 | 37 | | | 12 | 10 | 51 | | 2 |
| 38 | 38 | | | 50 | 33 | 76 | | −5 |
| 39 | 39 | | | 11 | 68 | 54 | | 2 |
| 52 | 52 | | | 33 | 46 | 85 | | 10 |
| 54 | 54 | | | 25 | 75 | 94 | | 14 |
| 56 | 56 | 94 | 80 | 65 | 92 | 100 | 55 | |

TABLE 3-continued

Inhibition of ligand binding to aminergic G protein-coupled receptors by compounds of the invention:

| Example No. | Compound No. | Adrenergic (1 μM Ligand Concentration) | | | | | | Dopamine (1 μM) |
|---|---|---|---|---|---|---|---|---|
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 57 | 57 | 90 | 87 | 69 | 96 | 98 | 83 | |
| 58 | 58 | 89 | 83 | 74 | 98 | 99 | 89 | |
| 59 | 59 | | | 2 | 17 | 20 | | 6 |
| 60 | 60 | | | 1 | 2 | 5 | | 0 |
| 61 | 61 | | | 80 | 97 | 96 | | 44 |
| 62 | 62 | | | 83 | 96 | 104 | | 41 |
| 70 | 70 | | | 26 | 3 | 51 | | −3 |
| 71 | 71 | | | 62.0/63.0 | 28.0/48.0 | 99.0/98.0 | | −2 |
| 72 | 72 | | | −9 | 6 | − | | 3 |
| 73 | 73 | | | 19 | 6 | 73 | | −4 |
| 88 | 77 | | | 37 | 30 | 75 | | 4 |
| 106 | 79 | | | 72 | 14 | 87 | | 9 |
| 100 | 80 | | | 54 | 21 | 95 | | −3 |
| 90 | 81 | | | 42 | −5 | 40 | | 9 |
| 91 | 82 | | | 40 | 5 | 47 | | 2 |
| 101 | 83 | | | 80 | 77 | 94 | | 12 |
| 94 | 84 | | | 19 | 76 | 98 | | −6 |
| 103 | 85 | | | 43 | 73 | 92 | | −2 |
| 99 | 86 | | | 87 | 63 | 106 | | 4 |
| 105 | 87 | | | 70 | 21 | 98 | | −6 |
| 104 | 88 | | | 73 | 32 | 104 | | 4 |
| 95 | 89 | | | 44 | 5 | 76 | | 9 |
| 75 | 90 | | | 40 | 26 | 75 | | −4 |
| 80 | 91 | | | 24 | 29 | 67 | | −5 |
| 98 | 92 | | | 8 | 15 | 34 | | 0 |
| 92 | 93 | | | −18 | 4 | −6 | | −19 |
| 35 | 94 | | | 77 | 56 | 102 | | 14 |
| 35 | 95 | | | 82 | 65 | 36 | | 50 |
| 96 | 97 | | | 19 | 26 | 103 | | −10 |
| 102 | 99 | | | 20 | 25 | 92 | | −6 |
| 93 | '101 | | | 74 | 18 | 76 | | 10 |
| 97 | 102 | | | 1 | 4 | 42 | | −1 |
| 79 | 103 | | | 86 | 57 | 94 | | 4 |
| 84 | 107 | | | 47 | 42 | 57 | | −5 |
| 85 | 110 | | | 40 | 48 | 92 | | 14 |
| 86 | 111 | | | 40 | 89 | 96 | | 6 |
| 89 | 114 | | | 68 | 46 | 107 | | 11 |
| 83 | 116 | | | 40 | 83 | 95 | | −2 |
| 77 | 121 | | | 80 | 55 | 100 | | 19 |
| 87 | 123 | | | 79 | 95 | 103 | | 80 |
| 81 | 124 | | | 67 | 91 | 101 | | 33 |
| 113 | 125 | | | 54 | 92 | 103 | | 5 |
| 115 | 128 | | | | | | | 21 |
| 116 | 129 | | | | | | | 8 |
| 119 | 132 | | | | | | | |
| 123 | 136 | | | 61 | 91 | 87 | | 11 |
| 107 | 138 | | | 60 | 95 | 109 | | 42 |
| 109 | 139 | | | 65 | 93 | 115 | | −4 |
| 125 | 141 | | | 20 | 61 | 95 | | −4 |
| 126 | 142 | | | 27 | 82 | 95 | | 0 |
| 108 | 154 | | | | | | | 13 |
| 128 | 155 | | | | | | | 10 |
| 129 | 160 | | | 0 | 63 | 80 | | 7 |
| 130 | 161 | | | 30 | 55 | 95 | | 12 |
| 131 | 162 | | | 34 | 59 | 83 | | 2 |
| 132 | 163 | | | 53 | 95 | 104 | | −16 |
| 133 | 164 | | | | | | | 12 |

Example B5

Determination of the Ability of Compounds of the Invention to Bind a Serotonin Receptor Serotonin (5-Hydroxytryptamine) 5-HT$_{1A}$ To evaluate in radioligand binding assays the activity of compounds of the invention, human recombinant serotonin (5-Hydroxytryptamine) 5-HT$_{1A}$ receptor expressed in Chinese hamster ovary (CHO-K1) cells (Martin G R and Humphrey P P A, Neuropharmacol. 33:261, 1994; May J A, et al. J Pharmacol Exp Ther. 306(1):301, 2003) in a modified Tris-HCl buffer (50 mM Tris-HCl, pH 7.4, 0.1% Ascorbic Acid, 0.5 mM EDTA, 10 mM MgSO$_4$) is used. Compounds of invention are incubated with 1.5 nM [$^3$H]8-OH-DPAT for 60 minutes at 25° C. Non-specific binding is estimated in the presence of 10 μM Metergoline. Receptor proteins are filtered and washed, the filters are then counted to determine [$^3$H] 8-OH-DPAT specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{1B}$

To evaluate in radioligand binding assays the activity of compounds of the invention, serotonin (5-Hydroxytryptamine) 5-HT$_{1B}$ receptor from Wistar Rat cerebral cortex (Hoyer et al. Eur J Pharmaco. 118: 1, 1985; Pazos et al. Eur J Pharmacol. 106: 531, 1985) in a modified Tris-HCl buffer (50 mM Tris-HCl, pH 7.4, 154 mM NaCl, 10 μM Pargyline, 30 μM Isoprenaline) is used. Compounds of invention are incubated with 10 μM [$^{125}$I]Cyanopindolol for 90 minutes at 37° C. Non-specific binding is estimated in the presence of 10 μM Serotonin (5-HT). Receptor proteins are filtered and washed, the filters are then counted to determine [$^{125}$I]Cyanopindolol specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5HT$_{2A}$

To evaluate in radioligand binding assays the activity of compounds of the invention, human recombinant serotonin (5-Hydroxytryptamine) 5-HT$_{2A}$ receptor expressed in Chinese hamster ovary (CHO-K1) cells (Bonhous, D. W. et al. Br. J. Pharmacol. 115:622, 1993; Saucier, C. and Albert, P. R., J. Neurochem. 68:1998, 1997) in a 50 mM Tris-HCl buffer, pH 7.4, was used. Compounds of the invention were incubated with 0.5 nM [$^{3}$H]Ketanserin for 60 minutes at 25° C. Non-specific binding was estimated in the presence of 1 μM Mianserin. Receptor proteins were filtered and washed, the filters were then counted to determine [$^{3}$H]Ketanserin specifically bound. Compounds were screened at 1 μM or lower, using 1% DMSO as vehicle. Biochemical assay results are presented as the percent inhibition of specific binding in Table 4.

Serotonin (5-Hydroxytryptamine) 5-HT$_{2B}$

To evaluate in radioligand binding assays the activity of compounds of the invention, human recombinant serotonin (5-Hydroxytryptamine) 5-HT$_{2B}$ receptor expressed in Chinese hamster ovary (CHO-K1) cells (Bonhaus, D. W. et al., Br., J. Pharmacol. 115:622, 1995) in a modified Tris-HCl buffer (50 mM Tris-HCl, pH 7.4, 4 mM CaCl$_2$, 0.1% Ascorbic Acid) was used. Compounds of invention were incubated with 1.2 nM [$^{3}$H]Lysergic acid diethylamide (LSD) for 60 minutes at 37° C. Non-specific binding was estimated in the presence of 10 μM Serotonin (5-HT). Receptor proteins were filtered and washed, the filters were then counted to determine [$^{3}$H]LSD specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 4.

Serotonin (5-Hydroxytryptamine) 5-HT$_{2C}$

To evaluate its radioligand binding assays the activity of compounds of the invention, human recombinant serotonin (5-Hydroxytryptamine) 5-HT$_{2C}$ receptor expressed in Chinese hamster ovary (CHO-K1) cells (Wolf, W. A, and Schulz, J. S., J. Neurochem. 69:1449, 1997) in a modified Tris-HCl buffer (50 mM Tris-HCl, pH 7.4, 0.1% Ascorbic Acid, 10 μM Pargyline) was used. Compounds of the invention were incubated with 1 nM [$^{3}$H]Mesulergine for 60 minutes at 25° C. Non-specific binding was estimated in the presence of 1 μM Mianserin. Receptor proteins were filtered and washed, the filters were then counted to determine [$^{3}$H]Mesulergine specifically bound. Compounds were screened at 1 μM or lower, using 1% DMSO as vehicle. Biochemical assay results are presented as the percent inhibition of specific binding in Table 4.

Serotonin (5-Hydroxytryptamine) 5-HT$_3$

To evaluate in radioligand binding assays the activity of compounds of the invention, human recombinant serotonin (5-Hydroxytryptamine) 5-HT$_3$ receptor expressed in human embryonic kidney (HEK-293) cells (Miller K et al. Synapase, 11:58, 1992; Boess F G et al. Neuropharmacology. 36:637, 1997) in a modified Tris-HCl buffer (50 mM Tris-HCl, pH 7.4, 1 mM EDTA, 5 mM MgCl$_2$) is used. Compounds of invention are incubated with 0.69 nM [$^{3}$H]GR-65630 for 60 minutes at 25° C. Non-specific binding is estimated in the presence of 10 μM MDL-72222. Receptor proteins are filtered and washed, the filters are then counted to determine [$^{3}$H]GR-65630 specifically bound. Compounds are screened at 1 μM or lower, using 1% DMSO as vehicle, Compounds of the invention are tested in this biochemical assay and percent inhibition of specific binding is determined.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman C J et al. Br J Pharmacol. 109:618, 1993) in a 50 mM Tris-HCl, pH 7.4, is used. Compounds of invention are incubated with 0.7 nM [$^{3}$H]GR-113808 for 30 minutes at 25° C. Non-specific binding is estimated in the presence of 30 μM Serotonin (5-HT). Receptor proteins are filtered and washed, the filters are then counted to determine [$^{3}$H]GR-113808 specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT$_{5A}$ receptor expressed in Chinese hamster ovary (CHO-K1) cells (Rees, S. et al., FEBS Lett. 355:242, 1994) in a modified Tris-HCl buffer (50 mM Tris-HCl, pH 7.4, 10 mM MgCl$_2$, 0.5 mM EDTA) was used. Compounds of the invention were incubated with 1.7 nM [$^{3}$H]Lysergic acid diethylamide (LSD) for 60 minutes at 37° C. Non-specific binding was estimated in the presence of 100 μM Serotonin (5-HT). Receptor proteins were filtered and washed, the filters were then counted to determine [$^{3}$H]LSD specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 4.

Serotonin (5-Hydroxytryptamine) 5-HT$_6$

To evaluate in radioligand binding assays the activity of compounds of the invention, human recombinant serotonin (5-Hydroxytryptamine) 5-HT6 receptor expressed in human HeLa cells (Monsma, F. H. Jr. et al., Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 minutes at 37° C. Non-specific binding was estimated in the presence of 5 μM Serotonin (5-HT). Receptor proteins were filtered and washed, the filters were then counted to determine [3H]LSD specifically bound. Compounds were screened at 1 μM or lower, using 1% DMSO as vehicle. Biochemical assay results are presented as the percent inhibition of specific binding in Table 4.

Serotonin (5-Hydroxytryptamine) 5-$HT_7$

To evaluate in radioligand binding assays the activity of compounds of the invention, human recombinant serotonin (5-Hydroxytryptamine) 5-$HT_7$ receptor expressed in Chinese hamster ovary (CHO) cells (Roth, B. L. et al., J. Pharmacol. Exp. Ther. 268: 1403, 1994; Shen, Y. et al., J. Biol. Chem. 268:18200, 1993) in a modified Tris-HCl buffer (50 mM Tris-HCl, pH 7.4, 10 mM $MgCl_2$, 0.5 mM EDTA) was used. Compounds of invention were incubated with 5.5 nM [$^3$H] Lysergic acid diethylamide (LSD) for 2 hours at 25° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Biochemical assay results are presented as the percent inhibition of specific binding in Table 4.

TABLE 4

Inhibition of ligand binding to aminergic G protein-coupled receptors by compounds of the invention:

| Example No. | Compound No. | Serotonin (1 μM Ligand Concentration) | | | | | |
|---|---|---|---|---|---|---|---|
| | | 5-$HT_{2A}$ | 5-$HT_{2B}$ | 5-$HT_{2C}$ | 5-$HT_{5A}$ | 5-$HT_6$ | 5-$HT_7$ |
| 2 | 2 | 96 | 71; 88.0 (0.3 μM); 37.0 (0.03 μM) | 79 | 86 | 82 38.0 (3.0 nM); | 98; 81.0 (0.03 μM) |
| 3 | 3 | 3 | | 2 | | 3 | |
| 5 | 5 | | | −9 | | 7 | |
| 8 | 8 | 1 | | −6 | | −1 | |
| 9 | 9 | 15 | | 5 | | 2 | |
| 10 | 10 | −5 | | 4 | | −13 | |
| 11 | 11 | −8 | | 13 | | −16 | |
| 12 | 12 | 10 | | 26 | | −1 | |
| 13 | 13 | | | 8 | | 10 | |
| 32 | 32 | 15 | | −3 | | 13 | |
| 33 | 33 | | | 64 | | 14 | |
| 34 | 34 | 36.0/65.0 | | 27.0/28.0 | | 20.0/28.0 | |
| 35 | 35 | | | 86 | | 70 | |
| 37 | 37 | 23 | | 26 | | 22 | |
| 38 | 38 | 13 | | 23 | | 17 | |
| 39 | 39 | 87 | | 94 | | 24 | |
| 52 | 52 | 21 | | 11 | | 16 | |
| 54 | 54 | 100 | | 93 | | 26 | |
| 56 | 56 | 31 | −11 | 36 | 40 | 30 | 92 |
| 57 | 57 | 79 | 48 | 88 | 48 | 46 | 94 |
| 58 | 58 | 79 | 32 | 84 | 69 | 25 | 93 |
| 59 | 59 | | | 8 | | 0 | |
| 60 | 60 | | | 15 | | 9 | |
| 61 | 61 | | | 86 | | 41 | |
| 62 | 62 | | | 87 | | 71 | |
| 70 | 70 | 16 | | 4 | | 3 | |
| 71 | 71 | 22.0/34.0 | | −0.259 | | 8.0/2.0 | |
| 72 | 72 | −6 | | −4 | | −1 | |
| 73 | 73 | −9 | | 5 | | −4 | |
| 88 | 77 | 26 | | −8 | | 21 | |
| 106 | 79 | 28 | | 13 | | 10 | |
| 100 | 80 | 33 | | 16 | | 6 | |
| 90 | 81 | −12 | | 25 | | 12 | |
| 91 | 82 | −16 | | 60 | | 13 | |
| 101 | 83 | 71 | | 82 | | 23 | |
| 94 | 84 | 77 | | 93 | | 13 | |
| 103 | 85 | 95 | | 89 | | 52 | |
| 99 | 86 | 64 | | 72 | | 60 | |
| 105 | 87 | 51 | | 30 | | 23 | |
| 104 | 88 | 55 | | 31 | | 25 | |
| 95 | 89 | 27 | | 26 | | 10 | |
| 75 | 90 | 30 | | 27 | | 6 | |
| 80 | 91 | 2 | | −4 | | −5 | |
| 98 | 92 | 16 | | 9 | | 3 | |
| 92 | 93 | −12 | | 7 | | −4 | |
| 35 | 94 | 81 | | 75 | | 21 | |
| 35 | 95 | 57 | | 55 | | 41 | |
| 96 | 97 | 25 | | 97 | | 8 | |
| 102 | 99 | 73 | | 75 | | −2 | |
| 93 | 101 | 93 | | 94 | | 15 | |
| 97 | 102 | 11 | | −6 | | −5 | |
| 79 | 103 | 13 | | 33 | | 7 | |
| 84 | 107 | 5 | | 25 | | −3 | |
| 85 | 110 | 83 | | 62 | | 48 | |
| 86 | 111 | 94 | | 81 | | 38 | 78 |
| 89 | 114 | 88 | | 59 | | 29 | |
| 83 | 116 | 90 | | 97 | | 10 | 92 |
| 77 | 121 | 98 | | 88 | | 65 | |
| 87 | 123 | 97 | | 95 | | 98 | 97 |

TABLE 4-continued

Inhibition of ligand binding to aminergic G protein-coupled receptors by compounds of the invention:

| Example No. | Compound No. | Serotonin (1 µM Ligand Concentration) | | | | | |
|---|---|---|---|---|---|---|---|
| | | 5-HT$_{2A}$ | 5-HT$_{2B}$ | 5-HT$_{2C}$ | 5-HT$_{5A}$ | 5-HT$_6$ | 5-HT$_7$ |
| 81 | 124 | 97 | | 86 | | 85 | 91 |
| 113 | 125 | 101 | | 99 | | 33 | 95 |
| 115 | 128 | 91 | | 77 | | 62 | 66 |
| 116 | 129 | 88 | | 72 | | 19 | 80 |
| 119 | 132 | 100 | | 95 | | 31 | 81 |
| 123 | 136 | 99 | | 100 | | 31 | 79 |
| 107 | 138 | 98 | | 97 | | 45 | 91 |
| 109 | 139 | 88 | | 93 | | 26 | 97 |
| 125 | 141 | 93 | | 89 | | 21 | 48 |
| 126 | 142 | 98 | | 100 | | 36 | 57 |
| 108 | 154 | 96 | | 97 | | 31 | 21 |
| 128 | 155 | 100 | | 99 | | 49 | 24 |
| 129 | 160 | 95 | | 93 | | 29 | 75 |
| 130 | 161 | 96 | | 92 | | 25 | 69 |
| 131 | 162 | 92 | | 93 | | 23 | 43 |
| 132 | 163 | 94 | | 94 | | 36 | 87 |
| 133 | 164 | 94 | | 93 | | 57 | 96 |

Example B6

Determination of Serotonin (5-Hydroxytryptamine) 5-HT$_{2A}$ Agonist/Antagonist Activity of Compounds of the Invention To determine for agonist or antagonist activity of compounds of the invention in functional assays, human recombinant serotonin 5-HT$_{2A}$ receptor expressed in human embryonic kidney (HEK-293) cells (Jerman J C, Brough S J, Gager T, Wood M, Coldwell M C, Smart D and Middlemiss D N. Eur J Pharmacol, 414: 23-30, 2001) is used. Cells are suspended in DMEM buffer, and distributed in microplates. A cytoplasmic calcium fluorescent indicator which varies proportionally to the free cytosolic Ca$^{2+}$ ion concentration is mixed with probenicid in HBSS buffer complemented with 20 mM Hepes (pH 7.4), added into each well and equilibrated with the cells for 30 min at 37° C. followed by 30 min at 22° C.

To measure agonist effects, compounds of the invention, reference agonist or HBSS buffer (basal control) is added to the cells and changes in fluorescence intensity are measured using a microplate leader. For stimulated control measurements, 5-HT at 100 nM is added in separate assay wells.

The results are expressed as a percent of the control response to 100 nM 5-HT. The standard reference agonist is 5-HT, which is tested in each experiment at several concentrations to generate a concentration-response curve from which its EC$_{50}$ value is calculated.

To measure antagonist effects, the addition of the compounds of the invention, reference antagonist or HBSS buffer is followed by the addition of 3 nM 5-HT or HBSS buffer (basal control) prior the fluorescence measurements. The results are expressed as a percent inhibition of the control response to 3 nM 5-HT. The standard reference antagonist is ketanserin, which is tested in each experiment at several concentrations to generate a concentration-response curve from which its IC$_{50}$ value is calculated. Compounds are screened at 3 µM of lower, using DMSO as vehicle.

Example B7

Determination of Serotonin (5-Hydroxytryptamine) 5-HT$_6$ Agonist/Antagonist Activity of Compounds of the Invention To determine for agonist or antagonist activity of compounds of the invention in functional assays, human recombinant 5-HT$_6$ receptor is transfected in CHO cells (Kohen, R., Metcalf, M. A., Khan, N., Druck, T., Huebner, K., Lachowicz, J. E., Meltzer, H. Y., Sibley, D. R., Roth, B. L. And Hamblin, M, W. Cloning, characterisation and chromosomal localization of a human 5-HT6 serotonin receptor, J. Neurochem., 66: 47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 µM IBMX, and then distributed in microplates and incubated for 45 min at 37° C. in the absence (control) or presence of compounds of the invention or the reference agonist or antagonist.

For agonist determinations, stimulated control measurement, separate assay wells contain 10 µM 5-HT. Following incubation, the cells are lysed and the fluorescence acceptor (D2-labeled cAMP) and fluorescence donor (anti-cAMP antibody labeled with europium cryptate) are added. After 60 min at room temperature, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 µM 5-HT. The standard reference agonist is 5-HT, which is tested in each experiment at several concentrations to generate a concentration-response curve from which its EC$_{50}$ value calculated.

For antagonist determinations, the reference agonist 5-HT is added at a final concentration of 100 nM. For basal control measurements, separate assay wells do not contain 5-HT. Following 45 min incubation at 37° C., the cells are lysed and the fluorescence acceptor (D2-labeled cAMP) and fluorescence donor (anti-cAMP antibody labeled with europium cryptate) are added.

After 60 min at room temperature, the fluorescence transfer is measured as mentioned above. The results are expressed as a percent inhibition of the control response to 100 nM 5-HT. The standard reference antagonist is methiothepin

Example B8

Determination of Dopamine $D_{2L}$ Antagonist Activity of Compounds

To determine for agonist or antagonist activity of compounds of the invention in functional assays, human recombinant dopamine $D_{2L}$ receptor stably expressed in Chinese hamster ovary (CHO) cells (Senogles S E et al. et al. J Biol Chem. 265(8): 4507, 1990) is used. Compounds of invention are pre-incubated with the membranes (0.1 mg/ml) and 10 mM GDP in modified HEPES buffer (20 mM HEPES, pH 7.4, 100 mM NaCl, 10 mM $MgCl_2$, 1 mM DTT, 1 mM EDTA) for 20 minutes and Scintillation Proximity Assay (SPA) beads are added for another 60 minutes at 30° C. The reaction is initiated by 0.3 nM [$^{35}$S]GTPγS for an additional 15 minute incubation period. Increase of [$^{35}$S]GTPγS binding by 50 percent or more (≥50%) relative to the 1 mM dopamine response by compounds of the invention indicates possible dopamine $D_{2L}$ receptor agonists activity. Inhibition of a 10 μM dopamine-induced increase of [$^{35}$S]GTPγS binding response by 50 percent or more (≥50%) by compounds of the invention indicates receptor antagonist activity. Compounds are screened at 3 μM or lower, using 0.4% DMSO as vehicle. Assay results are presented as the percent response of specific binding.

Example B9

Determination of Dopamine $D_{2S}$ Antagonist Activity of Compounds of the Invention To determine for agonist or antagonist activity of compounds of the invention in functional assays, human recombinant dopamine $D_{2S}$ receptor stably expressed in Chinese hamster ovary (CHO) cells (Gilliland S L and Alper R H. Naunyn-Schmiedeberg's Archives of Pharmacology, 361:498, 2000) is used. Compounds of invention are pre-incubated with the membranes (0.05 mg/ml) and 3 μM GDP in modified HEPES buffer (20 mM HEPES, pH 7.4, 100 mM NaCl, 10 mM $MgCl_2$, 1 mM DTT, 1 mM EDTA) for 20 minutes and Scintillation Proximity Assay (SPA) beads are then added for another 60 minutes at 30° C. The reaction is initiated by 0.3 nM [$^{35}$S]GTPγS for an additional 30 minute incubation period. Increase of [$^{35}$S]GTPγS binding by 50 percent or more (≥50%) relative to the 100 μM dopamine response by compounds of the invention indicates possible dopamine $D_{2S}$ receptor agonists activity. Inhibition of a 3 μM dopamine-induced increase of [$^{35}$S]GTPγS binding response by 50 percent or more (≥50%) by compounds of the invention indicates receptor antagonist activity. Compounds are screened at 3 μM or lower, using 0.4% DMSO as vehicle. Assay results are presented as the percent response of specific binding.

Example B10

Determination for Agonist or Antagonist Activity of Compounds of the Invention in a Histamine H1 Functional Assay To determine for agonist or antagonist activity of compounds of the invention in functional assays, human recombinant Histamine $H_1$ receptor expressed in human embryonic kidney (HEK-293) cells (Miller, T. R., Witte, D. G., Ireland, L. M. Kang, C. H., Roch, J. M., Masters, J. N., Esbenshade, T. A And Hancock, A. A. J. Biomol. Screen., 4:249-258, 1999) is used. Cells are suspended in DMEM buffer, and then distributed in microplates. A cytoplasmic calcium fluorescent indicator—which varies proportionally to the free cytosolic $Ca^{2+}$ ion concentration—is mixed with probenicid in HBSS buffer complemented with 20 mM Hepes (pH 7.4) and is then added into each well and equilibrated with the cells for 30 min at 37° C. and then for another 30 min at 22° C. To measure agonist effects, compounds of the invention, reference agonist or HBSS buffer (basal control) are added to the cells and changes in fluorescence intensity are measured using a microplate reader. For stimulated control measurements, histamine at 10 μM is added to separate assay wells.

The results are expressed as a percent of the control, response to 10 μM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 μM or lower, using DMSO as vehicle.

Example B11

Increase of Neurite Outgrowth

Neurite Outgrowth in Cortical Neurons

Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation was prepared in Leibovitz's medium (L15; Gibco). The cortex is dissected out, and the meninges were removed. Trypsin (Gibco) is used to dissociate cortical C with DNAse I. The cells are triturated for 30 minutes with a pipette in Dulbecco's Modified Eagle Media ("DMEM"; Gibco) with 10% Fetal Bovine Serum ("FBS") (Gibco) and centrifuged at 350×g for 10 minutes at room temperature. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or compounds of the invention are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth. Several pictures (~80) of cells with neurites are taken per condition with a camera. The length measurements are made by analysis of the pictures using software from Image-Pro Plus (France). The results are expressed as mean (s.e.m). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue was cut to small pieces. The cells are separated by 15-min incubation with DNase and papain. The cells are collected by centrifugation (1500 rpm, 5 min). The tissue is triturated with a pipette and the cells are plated using the micro-islet protocol (20 000 cells in 25 μl medium) on poly-L-lysine coated 48 wells, in MEM supplemented with 2 mM glutamine, 0.1 µg/ml gentamicin, 10% heat-inactivated fetal bovine serum (FBS-HI) and 10% heat-inactivated horse serum (HS-HI). After the cells attach to the well, 250 µl medium is added to the wells. Four hours after plating the medium is changed to fresh medium (MEM with supplements and 5% HS-HI) containing test compound at 0.5, 5 and 50 nM concentrations. As positive controls BDNF (50, 100 and/or 150 ng/ml), and/or NGF (50 ng/ml and/or 100 ng/ml) are used. After 2 days in vitro, the cell's conditioned media are collected from plates before fixing the cells. The media samples are centrifuged 13 000 rpm 3 min to get rid of cell debris. The samples are stored at −20° C. for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min and washed once with PBS. The fixed cells are first permeabilized and non-specific binding is blocked by a 30-min incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells are visualized by a fluorescence microscope equipped with appropriate filter set, and documented by a high resolution image capturing. The number of cells per field (4 field per well) are counted, and the neurite outgrowth is quantified using Image Pro Plus software.

The number of wells per compound concentration used is 6 (n=6). All data are presented as means± standard deviation (SD) or standard error of means (SEM), and differences are considered to be statistically significant at the p<0.05 level. Statistical analysis is performed using StatsDirect statistical software. Differences between group means are analyzed by using 1-way-ANOVA followed by Dunnet's test (comparison to the vehicle treated group).

Example B12

Use of an In Vivo Model to Evaluate the Ability of Compounds to Enhance Cognition Learning and Memory in Scopolamine Treated Rats The two-trial object recognition paradigm developed by Ennaceur and Delacour in the rat is used as a model of episodic/short-term memory. Ennaceur, A., and Delacour, J. (1988), *Behav. Brain Res.* 31:47-69. The paradigm is based on spontaneous exploratory activity of rodents and does not involve rule learning or reinforcement. The novel object recognition paradigm is sensitive to the effects of ageing and cholinergic dysfunction. See, e.g., Scali, C., et al., (1994), *Neurosci. Letts.* 170:117-120; and Bartolini, L., et al., (1996), *Biochem, Behav.* 53:277-283.

Male Sprague-Dawley rats between six and seven weeks old, weighing between 220-300 grams are obtained, e.g., from Centre d'Elevage (Rue Janvier, B. P. 55, Le Genest-Saint-Isle 53940, France). The animals are housed in groups of 2 to 4 in polypropylene cages (with a floor area of 1032 cm$^2$) under standard conditions: at room temperature (22±2° C.), under a 12 hour light/12 hour dark cycle, with food and water provided ad libitum. Animals are permitted to acclimate to environmental conditions for at least 5 days before the experiment begins, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for three minutes in the presence of two objects (habituation). Animals to be tested are placed in the experimental room at least 30 minutes before testing.

Novel object recognition test is comprised of two trials separated by an interval of 120 minutes or 24 hours. When agents that disrupt memory such as the cholinergic antagonist scopolamine are used an inter-trial interval of 120 minutes is preferred. Alternatively a 24 hours inter-trial interval is used when studying effect of natural forgetting on novel object recognition task. During the first, or acquisition, trial ($T_1$), rats are placed in the arena, where two identical objects have been previously placed. The time required for each animal to complete 15 seconds of object exploration is determined, with a cut-off time of four minutes. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object is left in place. Rats are placed back in the arena for three minutes, and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured as part of the novel object recognition task: (1) time required to achieve 15 seconds of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\Delta T_{Novel}-T_{Familiar}$) is evaluated. The % of animals in each group with $T_{Novel}-T_{Familiar}$ greater than or equal to 5 seconds is also derived; described as % of good learners.

Animals not meeting a minimal level of object exploration are excluded from the study as having naturally low levels of spontaneous exploration. Thus, only rats exploring the objects for at least five seconds ($T_{Novel}+T_{Familiar}>5$ second) are included in the study.

Animals are randomly assigned to groups of 14. Compounds of the invention and controls are administered to animals the groups as follows: Solutions of compounds are prepared freshly each day at a concentration of 0.25 mg/ml using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Queutin Fallavier, France) is dissolved in saline to a concentration of 0.06 mg/mL.

Donepezil or its vehicle and scopolamine are administered intraperitoneally forty minutes before the acquisition trial ($T_1$). Compounds or their vehicle are administered by gavage twenty-five minutes before the acquisition trial ($T_1$), i.e., five minutes after administration of scopolamine. The volume of administration is 5 ml/kg body weight for compounds administered intraperitoneally, and 10 ml/kg for compounds administered orally. Recognition, scorns and % of good learners for compounds are determined.

Example B13

Use of an In Vivo Model to Determine the Ability of Compounds to Treat, Prevent and/or Delay the Onset and/or the Development of Schizophrenia in PCP Treated Animals In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidine (PCP), which is administered to the animal (e.g., non-primate (rat) or primate (monkey)), resulting in dysfunctions similar to those seen in schizophrenic humans. See Jentsch et al., 1997, Science 277:953-955 and Piercey et al., 1988, Life Sci, 43(4):375-385). Standard experimental protocols may be employed in this or in other animal models. One protocol involves PCP-induced hyperactivity.

Male mice (various strains, e.g., C57B1/6J) from appropriate vendor (for example, Jackson Laboratories (Bar Harbor, Me.) are used. Mice are received at 6-weeks of age. Upon receipt, mice are assigned unique identification numbers (tail marked) and are group housed with 4 mice/cage in OPTI mouse ventilated cages. All animals remain housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12/12 light/dark cycle. The room temperature is maintained between 20 and 23° C. with a relative humidity maintained between 30% and 70%. Food and water are provided ad libinam for the duration of the study. In each test, animals are randomly assigned across treatment groups.

The open filed (OF) test assesses locomotor behavior, i.e. to measure mouse locomotor activity at baseline and in response to pharmacological agents. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis is configured to divide the open field into a center and periphery zone such that the infrared photobeams allow measurement of activity in the center and periphery of the field. Distance traveled is measured from horizontal beam breaks as the mouse moved whereas rearing activity is measured from vertical beam breaks.

Mice (10 to 12 animals per treatment group) are brought to the activity experimental room for at least 1 hr acclimation to the experimental room conditions prior to testing. Eight animals are tested in each run. Mice are administered vehicle (e.g. 10% DMSO or 5% PEG200 and 1% Tween 80), compound of the invention, clozapine (positive control, 1 mg/kg ip) and placed in the OF chambers for 30 min following which they are injected with either water or PCP and placed back in the OF chambers for a 60-minute session. At the end of each OF test session the OF chambers are thoroughly cleaned.

PCP Hyperactivity Mouse Model of Schizophrenia

The test compound at the desired dose is dissolved in appropriate vehicle, e.g., 5% PEG200, 1% Tween80 and administered orally 30 mm prior to PCP injection. Clozapine (1 mg/kg) is dissolved in 10% DMSO and administered i.p. 30 min prior to PCP injection. PCP (5 mg/kg) is dissolved in sterile injectable saline solution and administered i.p.

Data are analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fell above or below 2 standard deviations from the mean are removed from the final analyses. An effect is considered significant if $p<0.05$. Total distances traveled and total rearing following PCP administration are compared between group treated with compounds and groups treated with vehicle and positive control clozapine.

PCP Hyperactivity Mouse Model of Schizophrenia

Protocol is as described above with the exception of the treatment groups which are as follows: All injections are at a dose volume of 10 ml/kg. The test compound at the desired dose is dissolved in Phosphate Buffered Saline (PBS) and administered orally 30 min prior to PCP injection. Clozapine (0.5 and 1.0 mg/kg) is dissolved in 10% DMSO and administered i.p. 30 min prior to Phencyclidine (PCP) injection. PCP (5.0 mg/kg) is dissolved in sterile injectable saline and administered i.p. Total distances traveled for is determined.

Example B14

Use of an In Vivo Model to Determine the Ability of Compounds to Treat, Prevent and or Delay the Onset and/or the Development of Schizophrenia in Amphetamine Treated Animals Male mice (various strains e.g., C57B1/6J) from appropriate supplier (for example Jackson Laboratories, Bar Harbor, Me.) are used. Mice typically are received at 6-week of age. Mice are acclimated to the colony room for at least two weeks prior to testing. During the period of acclimation, mice are examined on a regular basis, handled, and weighed to assure adequate health and suitability and maintained on a 12/12 light/dark cycle. The room temperature is maintained between 20 and 23° C. with a relative humidity maintained between 20% an d70%. Food and water are provided ad libitum for the duration of the study. In each test, animals are randomly assigned between treatment groups.

The open field test (OF) is used to assess motor activity. The open field chambers are plexiglass square chambers (e.g., 27.3×27.3×20.3 cm: Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1 hr acclimation prior to start of treatment. Animals are administered with vehicle, haloperidol (positive control, 0.1 mg/kg ip) or test compound and placed in the OF. The time of administration of client compound to each animal is recorded. Baseline activity is recorded for 30 min following which mice receive amphetamine (4 mg/kg) or water and are placed back in the OF chambers for a 60-minute session. At the end of each open field test session the OF chambers are thoroughly cleaned. Typically ten to twelve mice are tested in each group. Test compound doses typically range from 0.01 mg/kg to 60 mg/kg.

Data are analyzed by analysis of variance (ANOVA) followed by post-hoc comparisons with Fisher Tests when appropriate. Baseline activity is measured during the first 30 min of the test prior to amphetamine injection. Amphetamine-induced activity is measured during the 60 min following amphetamine injection. Statistical outliers that fall above or below 2 standard deviations from the mean are removed from the final analyses. An effect is considered significant if $p<0.05$. Total distance traveled and total rearing following amphetamine administration are compared between groups treated with compound and groups treated with vehicle and positive control haloperidol.

Example B15

Use of the In Vivo Conditioned Avoidance Response (CAR) Model to Determine the Ability of Compounds to Treat, Prevent and/or Delay the Onset and/or the Development of Schizophrenia All currently approved antipsychotic agents (typical and atypical) are known to have the ability to selectively suppress conditioned avoidance response (CAR) behavior in the rat. This evidence makes CAR one of the primary tests to assess antipsychotic activity of novel compounds.

Rats (various strains, 2 months of age) are trained and tested in a computer-assisted, two-way active avoidance apparatus (shuttle box). This box consists of two compartments of equal size divided by a stainless steel partition containing an opening of 7×7 cm. Each compartment is equipped with an electrified grid floor made of stainless steel rods spaced 1 cm apart. Rats trained to avoid the foot shock are placed each day in the shuttle box for a 4 minute habituation period followed by 30 trials spaced by inter-trial interval varying at random between 20 and 30 seconds. Each trial consists of a 10-second stimulus light (conditioned stimulus, CS) followed by a 10-second foot shock (unconditioned stimulus, US) in presence of the light presented in the compartment where the rat is located. If the animal leaves the compartment prior to the delivery of the foot shock, the response is considered an avoidance response. If the rat does not change compartment during the 10-second light period and during the 10-second shock+ light period, an escape failure is recorded. This test requires animals to be trained 5 days/week. On each training day, rats are submitted to one training session of 30-trials. Treatment with test compound is initiated only when rats reach an avoidance performance of at least 80% on at least two consecutive training sessions. The test compound is administered orally at various doses and various pre-treatment times (depending upon specific pharmacokinetic properties).

Compounds with antipsychotic profile inhibit conditioned avoidance responses with or without increases in escape failures. Statistical analysis is performed using a Friedman two-way ANOVA by ranks followed by the Wilcoxon matched-pairs signed-ranks test to test each dose of the test compound administered versus vehicle control treated rats.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

All references throughout, such as publications, patents, patent applications and published patent applications, are incorporated herein by reference in their entireties.

What is claimed is:

1. A method of treating a disorder in an individual in need thereof, wherein the disorder is schizophrenia, comprising administering to the individual an effective amount of a compound of the formula (A-2):

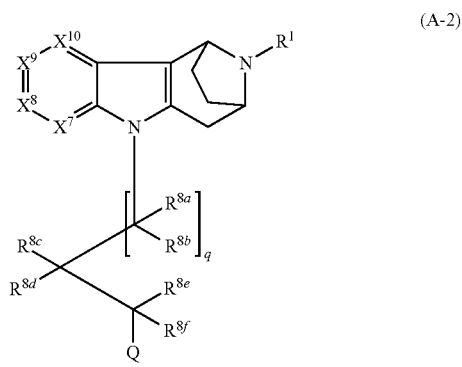

wherein:

$R^1$ is unsubstituted $C_1$-$C_8$ alkyl;

each $X^7$, $X^8$, $X^9$ and $X^{10}$ is independently N or $CR^4$;

q is 0;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$ and $R^{8f}$ is independently H, hydroxyl, $C_1$-$C_8$ alkyl, $C_1$-$C_8$ perhaloalkyl, carboxy or carbonylalkoxy;

$R^{8e}$ is independently hydroxyl, $C_1$-$C_8$ alkyl, $C_1$-$C_8$ perhaloalkyl, carboxy or carbonylalkoxy; and Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, unsubstituted amino, substituted amino, alkoxy, aminoacyl, acyloxy, carbonylalkoxy, aminocarbonylalkoxy or acylamino;

or a pharmaceutically acceptable salt thereof.

2. The method of claim 1, wherein in the compound, or a pharmaceutically acceptable salt thereof, $R^{8c}$, $R^{8d}$, $R^{8e}$ and $R^{8f}$ are taken together with the carbon atoms to which they are attached form a moiety selected from the group consisting of:

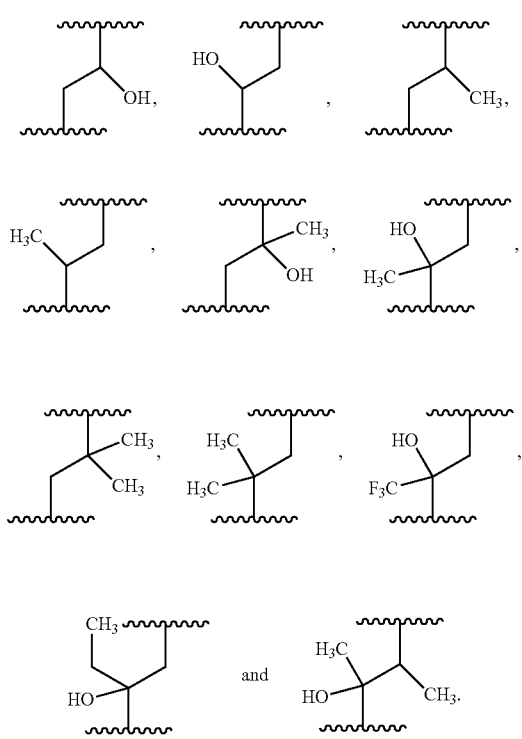
3. The method of claim 1, wherein the compound is selected from the group consisting of compounds 52, 53, 54 and 55:
| Compound # | Structure |
|---|---|
| 52 | 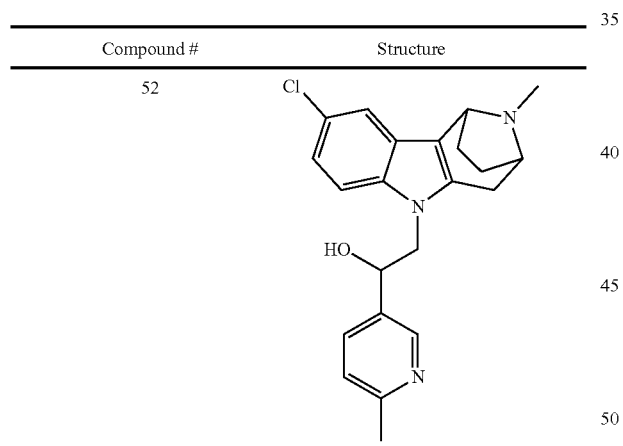 |
| 53 | 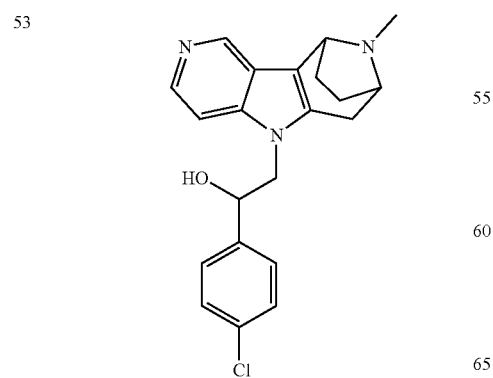 |
| 54 | 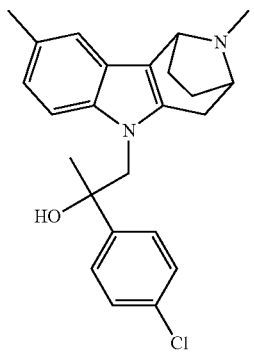 |
| 55 | 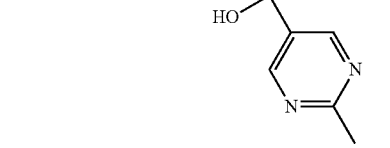 |
or a pharmaceutically acceptable salt thereof.
4. The method of claim 1, wherein the compound is selected from the group consisting of compounds 91, 98 and 99:
| Compound # | Structure |
|---|---|
| 91 | 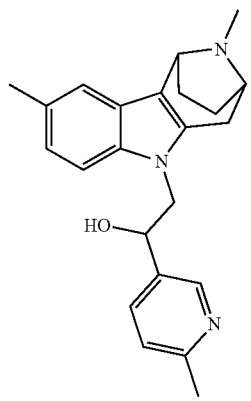 [SMILES: Cc1ccc2c(c1)c1c(n2CC(O)c2ccc(C)nc2)CC2CCC1N2C] |

271
-continued

| Compound # | Structure |
|---|---|
| 98 | |
| 99 | | or a pharmaceutically acceptable salt thereof.

5. The method of claim 1, wherein the compound is selected from the group consisting of compounds 160 and 161:

| Compound # | Structure |
|---|---|
| 160 | |
| 161 | | or a pharmaceutically acceptable salt thereof.

6. A method of treating a disorder in an individual in need thereof, wherein the disorder is schizophrenia, comprising administering to the individual an effective amount of a compound of the formula (A-2):

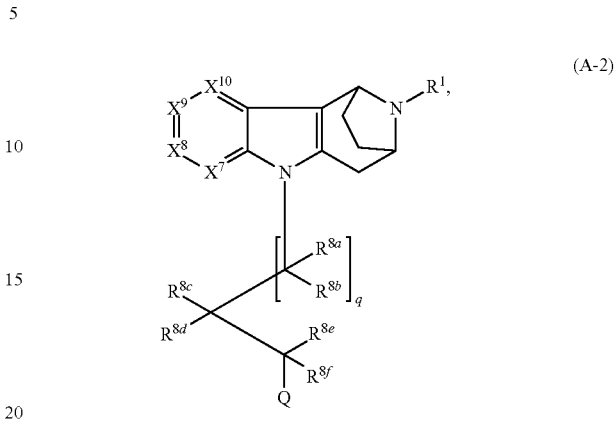

(A-2)

or a pharmaceutically acceptable salt thereof,
wherein each $X^8$ and $X^9$ is independently $CR^4$ where $R^4$ is H, halo or methyl; each $X^7$ and $X^{10}$ is CH; $R^1$ is methyl; q is 0 or 1; each $R^{8a}$ and $R^{8b}$ is H when present; each $R^{8c}$ and $R^{8d}$ is H; each $R^{8e}$ and $R^{8f}$ is independently H, hydroxy or methyl and Q is selected from the group consisting of:

7. The method of claim 6, wherein the compound is selected from the group consisting of compounds 32, 34, 35, 37, 38, 57, 61, 62 and 71:

| Compound # | Structure |
|---|---|
| 32 | 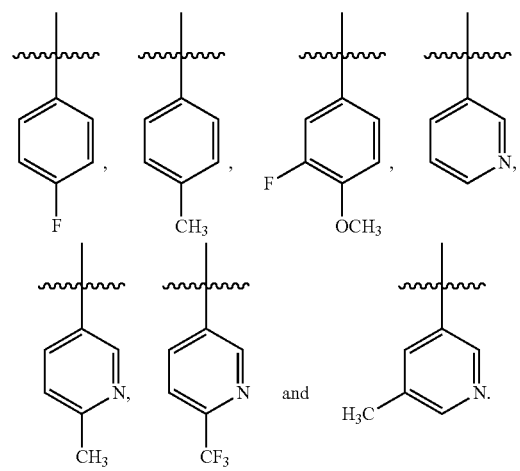 |

| Compound # | Structure |
|---|---|
| 34 | |
| 35 | |
| 37 | |
| 38 | |
| 57 | |
| 61 | |
| 62 | |
| 71 | | or a pharmaceutically acceptable salt thereof.

8. The method of claim 6, wherein the compound is selected from the group consisting of compounds 77, 79, 80, 86, 89, 90, 92, 94, 95, 96, 97 and 102:

| Compound # | Structure |
|---|---|
| 77 | 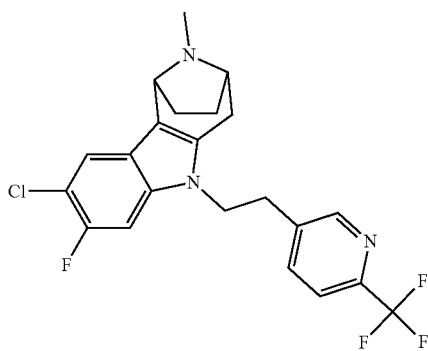 [SMILES: CN1C2CCC1c1c(n(CCc3ccc(C(F)(F)F)nc3)c3cc(F)c(Cl)cc13)C2] |
| 79 | 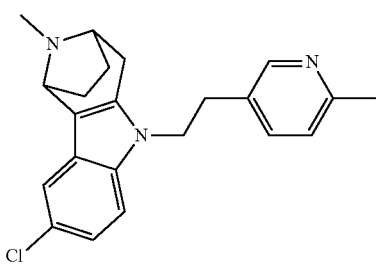 |
| 80 | 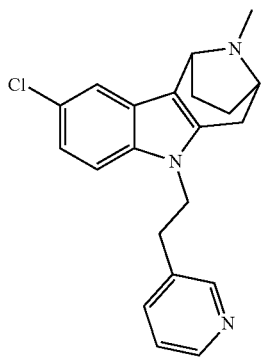 [SMILES: CN1C2CCC1c1c(n(CCc3cccnc3)c3ccc(Cl)cc13)C2] |
| 86 | 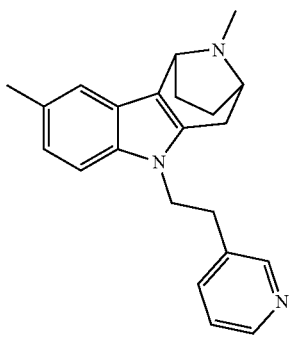 [SMILES: Cc1ccc2c(c1)c1c(n2CCc2cccnc2)CC2CCC1N2C] |
-continued
| Compound # | Structure |
|---|---|
| 89 | 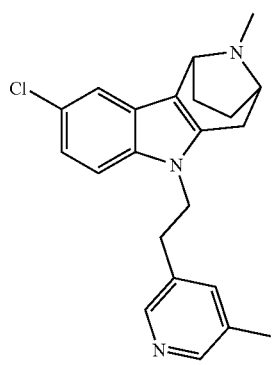 [SMILES: Cc1cncc(CCn2c3c(c4cc(Cl)ccc42)C2CCC(C3)N2C)c1] |
| 90 | 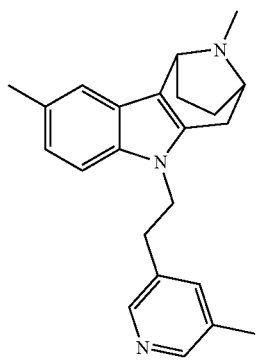 |
| 92 | 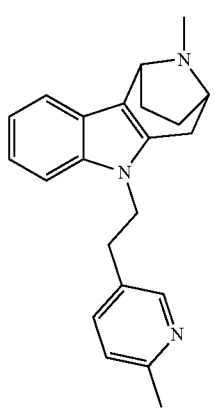 [SMILES: Cc1ccc(CCn2c3c(c4ccccc42)C2CCC(C3)N2C)cn1] |
| 94 | 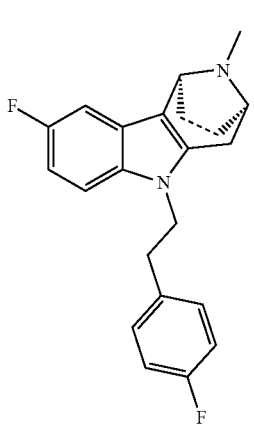 |

| Compound # | Structure |
|---|---|
| 95 | 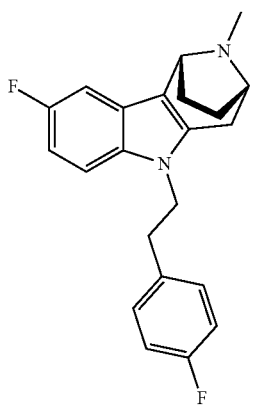 |
| 96 | 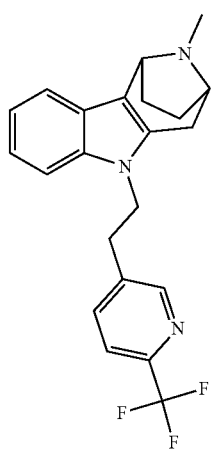 [SMILES: CN1C2CCC1c1c(n(CCc3ccc(C(F)(F)F)nc3)c3ccccc13)C2] |
| 97 | 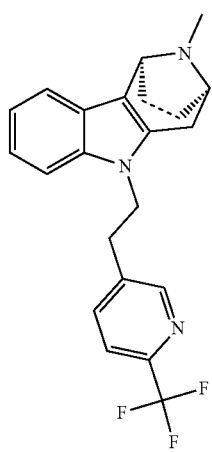 |

| Compound # | Structure |
|---|---|
| 102 | 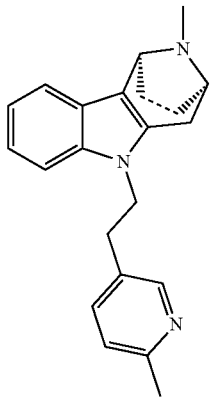 | or a pharmaceutically acceptable salt thereof.

9. A method of treating a disorder in an individual in need thereof, wherein the disorder is schizophrenia, comprising administering to the individual an effective amount of a compound of the formula (F-1):

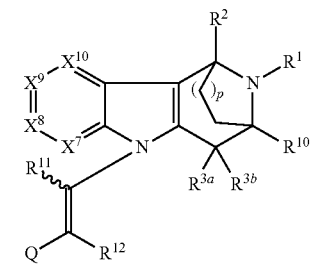

(F-1)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;
each $R^2$ and $R^{10}$ is independently H, hydroxyl, alkoxyl or substituted or unsubstituted $C_1$-$C_8$ alkyl;
each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy; or $R^{3a}$ and $R^{3b}$ are taken together to form a cycloalkyl or a carbonyl moiety;
p is 1 or 2;
each $X^7$, $X^8$, $X^9$ and $X^{10}$ is independently N or $CR^4$;
each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

$R^{11}$ and $R^{12}$ are independently H, $C_1$-$C_8$ alkyl, $C_1$-$C_8$ perhaloalkyl, carboxy, carbonylalkoxy, or taken together with the carbon atoms to which they are attached to form substituted or unsubstituted $C_3$-$C_8$ cycloalkenyl or substituted or unsubstituted heterocyclyl moiety or are taken together to form a bond, thereby providing an acetylenyl moiety; ∿∿ indicates the presence of either an E or Z double bond configuration; and Q is a substituted or unsubstituted aryl, substituted or unsubstituted heteroaryl, substituted or unsubstituted cycloalkyl, substituted or unsubstituted cycloalkenyl, substituted or an unsubstituted heterocyclyl, unsubstituted amino, substituted amino, alkoxy, aminoacyl, acyloxy, carbonylalkoxy, aminocarbonylalkoxy, acylamino, carboxy, alkynyl or cyano;

or a pharmaceutically acceptable salt thereof.

10. The method of claim 9, wherein in the compound, or a pharmaceutically acceptable salt thereof, $R^1$ is methyl; each $R^2$, $R^{3a}$, $R^{3b}$ and $R^{10}$ is H; p is 1; $X^9$ is $CR^4$ where $R^4$ is halo or methyl; each $X^7$, $X^8$ and $X^{10}$ is CH; $R^{11}$ is H; $R^{12}$ is methyl and Q is substituted phenyl.

11. The method of claim 9, wherein the compound is of the formula (F-2):

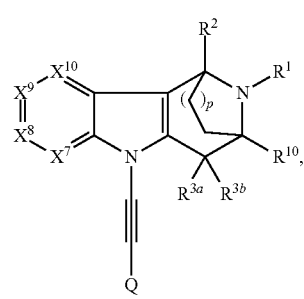

(F-2)

or a pharmaceutically acceptable salt thereof.

12. The method of claim 11, wherein in the compound, or a pharmaceutically acceptable salt thereof, $R^1$ is methyl; each $R^2$, $R^{3a}$, $R^{3b}$ and $R^{10}$ is H; p is 1; $X^9$ is $CR^4$ where $R^4$ is halo or methyl; each $X^7$, $X^8$ and $X^{10}$ is CH and Q is substituted pyridyl.

13. The method of claim 9, wherein in the compound, or a pharmaceutically acceptable salt thereof, $R^{11}$ is H and Q is substituted or unsubstituted aryl or substituted or unsubstituted heteroaryl.

14. The method of claim 13, wherein in the compound, or a pharmaceutically acceptable salt thereof, $R^{12}$ is H or methyl.

15. The method of claim 14, wherein in the compound, or a pharmaceutically acceptable salt thereof, R1 is methyl, p is 1, and X9 is CR4 where R4 is halo or methyl.

16. The method of claim 9, wherein the compound is selected from the group consisting of compounds 115, 116, 117, 119, 120, 121, 122, 123, 124, 125, 126, 127, 128, 129, 130, 131, 132, 133, 134, 135, 136 and 137:

| Compound # | Structure |
|---|---|
| 115 | 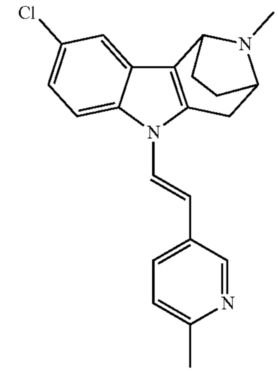 [SMILES: Cc1ccc(/C=C/n2c3c(c4cc(Cl)ccc42)C2CCC(C3)N2C)cn1] |
| 116 | 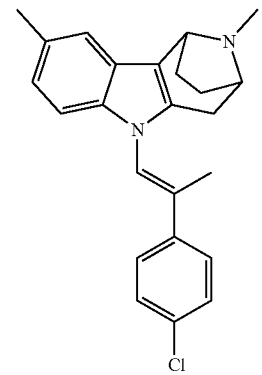 |
| 117 | 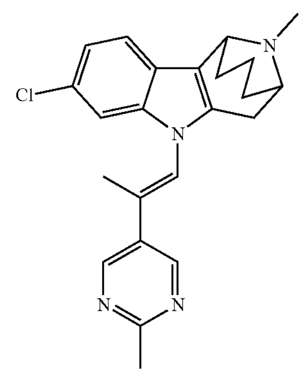 [SMILES: C/C(=C\n1c2c(c3ccc(Cl)cc31)C1CCCC(C2)N1C)c1cnc(C)nc1] |
| 119 | 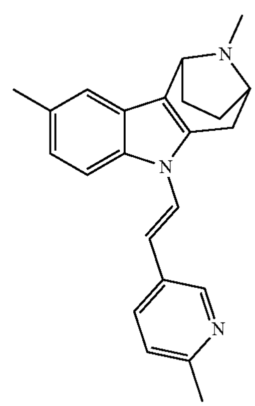 [SMILES: Cc1ccc2c(c1)c1c(n2/C=C/c2ccc(C)nc2)CC2CCC1N2C] |

| Compound # | Structure |
|---|---|
| 120 | 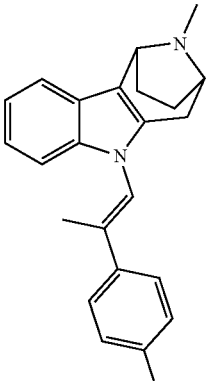 |
| 121 | 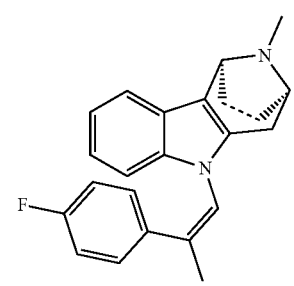 |
| 122 | 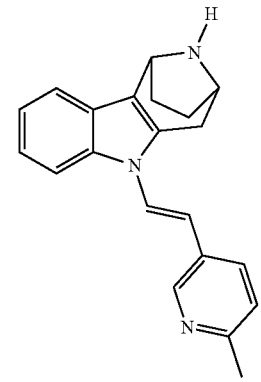 [SMILES: Cc1ccc(/C=C/n2c3c(c4ccccc42)C2CCC(C3)N2)cn1] |
| 123 | 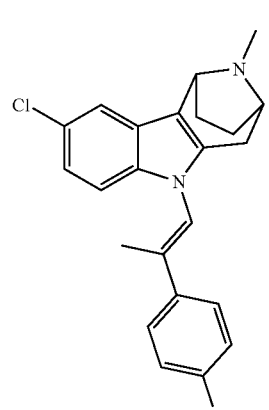 |
| Compound # | Structure |
|---|---|
| 124 | 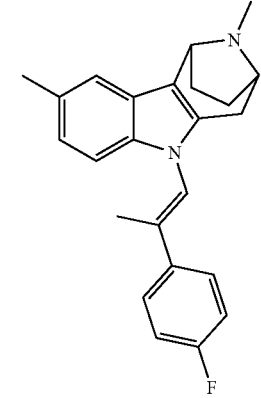 [SMILES: C/C(=C\n1c2c(c3cc(C)ccc31)C1CCC(C2)N1C)c1ccc(F)cc1] |
| 125 | 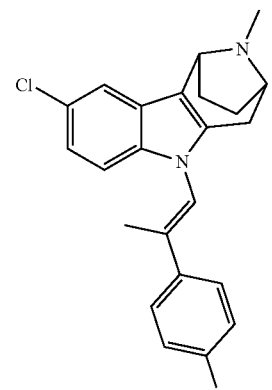 |
| 126 | 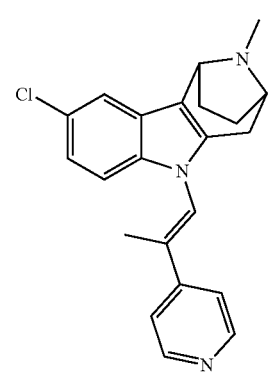 [SMILES: C/C(=C\n1c2c(c3cc(Cl)ccc31)C1CCC(C2)N1C)c1ccncc1] |
| 127 | 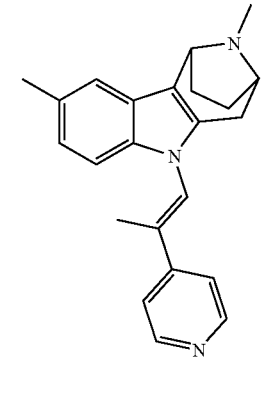 [SMILES: C/C(=C\n1c2c(c3cc(C)ccc31)C1CCC(C2)N1C)c1ccncc1] |

| Compound # | Structure |
|---|---|
| 128 | 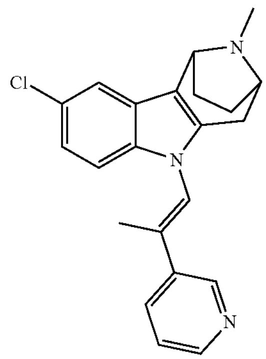 [SMILES: C/C(=C\n1c2c(c3cc(Cl)ccc31)C1CCC(C2)N1C)c1cccnc1] |
| 129 | 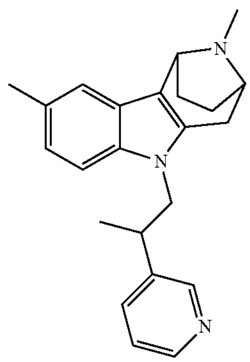 [SMILES: Cc1ccc2c(c1)c1c(n2CC(C)c2cccnc2)CC2CCC1N2C] |
| 130 | 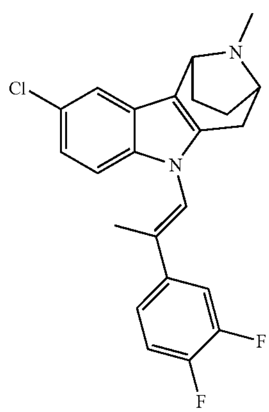 [SMILES: C/C(=C\n1c2c(c3cc(Cl)ccc31)C1CCC(C2)N1C)c1ccc(F)c(F)c1] |
| 131 | 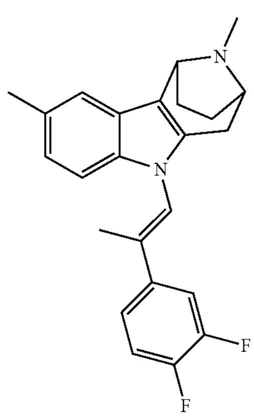 [SMILES: C/C(=C\n1c2c(c3cc(C)ccc31)C1CCC(C2)N1C)c1ccc(F)c(F)c1] |
| 132 | |
| 133 | |
| 134 | |

| Compound # | Structure |
|---|---|
| 135 | |
| 136 | |
| 137 | | or a pharmaceutically acceptable salt thereof.

17. The method of claim 9, wherein the compound is selected from the group consisting of compounds 163 and 164:

| Compound # | Structure |
|---|---|
| 163 | |
| 164 | | or a pharmaceutically acceptable salt thereof.

18. The method of claim 11, wherein the compound is selected from the group consisting of compounds 138, 139, 140, 141, 142, 143, 144, 145, 146, 147, 148, 149, 150, 151, 152, 153, 154 and 155:

| Compound # | Structure |
|---|---|
| 138 | 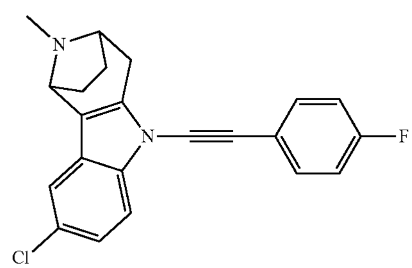 [SMILES: CN1C2CCC1c1c(n(C#Cc3ccc(F)cc3)c3ccc(Cl)cc13)C2] |
| 139 | 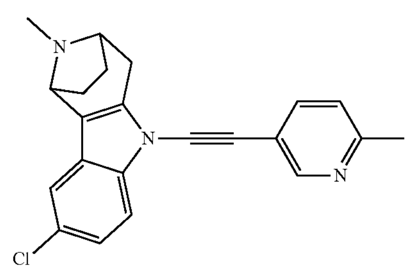 |

| Compound # | Structure |
|---|---|
| 140 | 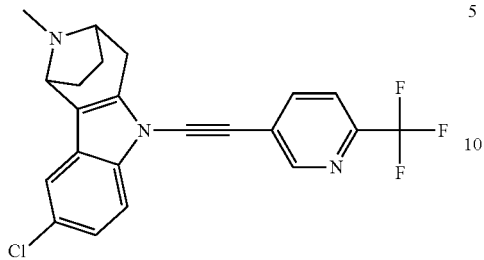 |
| 141 | 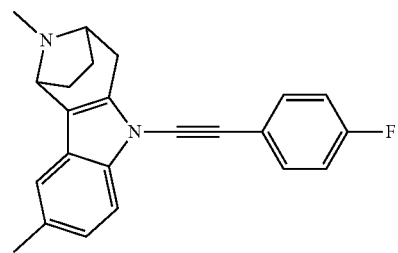 [SMILES: Cc1ccc2c(c1)c1c(n2C#Cc2ccc(F)cc2)CC2CCC1N2C] |
| 142 | 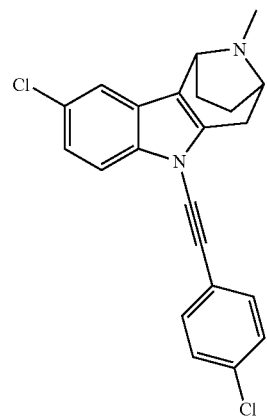 [SMILES: CN1C2CCC1c1c(n(C#Cc3ccc(Cl)cc3)c3ccc(Cl)cc13)C2] |
| 143 | 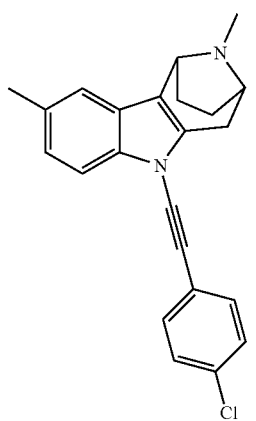 [SMILES: Cc1ccc2c(c1)c1c(n2C#Cc2ccc(Cl)cc2)CC2CCC1N2C] |
| Compound # | Structure |
|---|---|
| 144 | 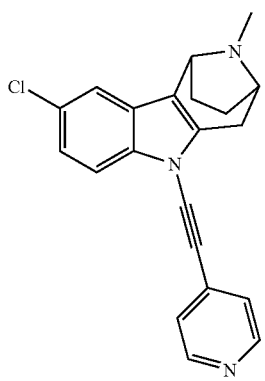 [SMILES: CN1C2CCC1c1c(n(C#Cc3ccncc3)c3ccc(Cl)cc13)C2] |
| 145 | 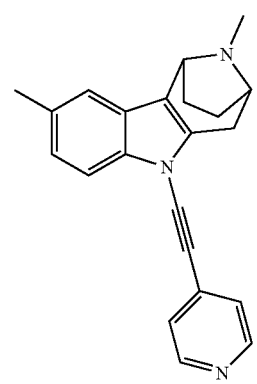 [SMILES: Cc1ccc2c(c1)c1c(n2C#Cc2ccncc2)CC2CCC1N2C] |
| 146 | 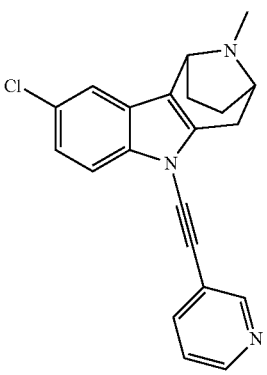 [SMILES: CN1C2CCC1c1c(n(C#Cc3cccnc3)c3ccc(Cl)cc13)C2] |
| 147 | 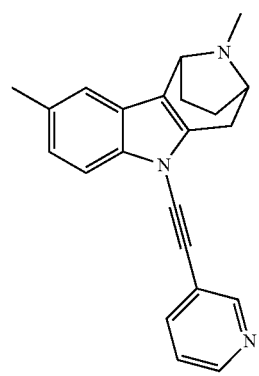 [SMILES: Cc1ccc2c(c1)c1c(n2C#Cc2cccnc2)CC2CCC1N2C] |

289
-continued
| Compound # | Structure |
|---|---|
| 148 | 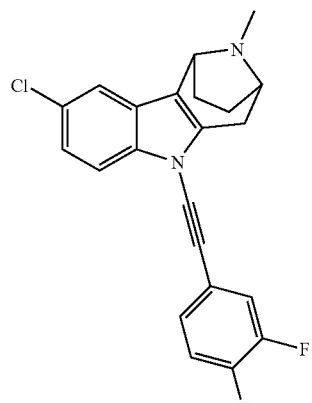 |
| 149 | 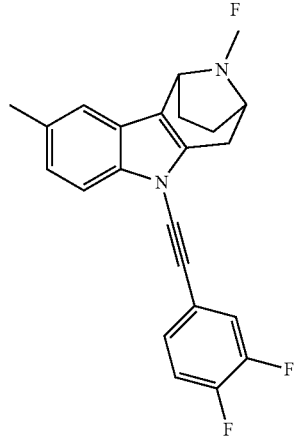 |
| 150 | 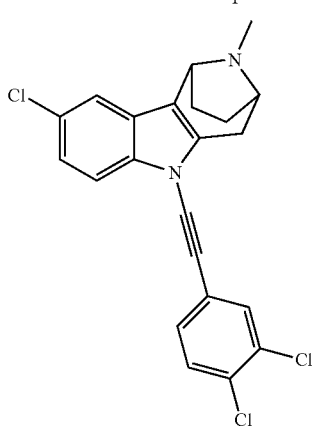 |
| 151 | 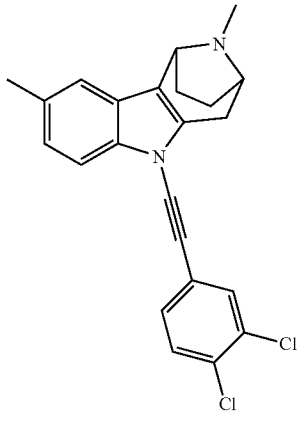 [SMILES: Cc1ccc2c(c1)c1c(n2C#Cc2ccc(Cl)c(Cl)c2)CC2CCC1N2C] |
290
-continued
| Compound # | Structure |
|---|---|
| 152 | 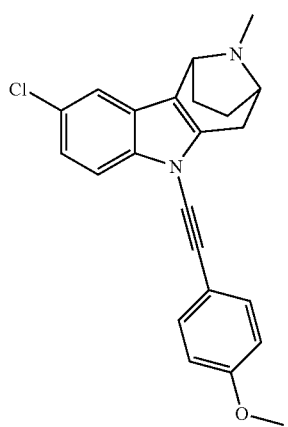 [SMILES: COc1ccc(C#Cn2c3c(c4cc(Cl)ccc42)C2CCC(C3)N2C)cc1] |
| 153 | 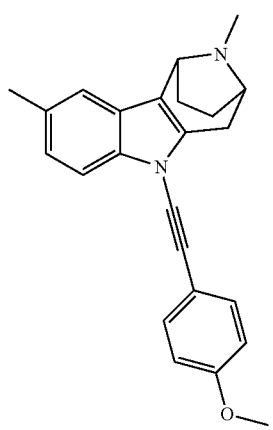 |
| 154 | 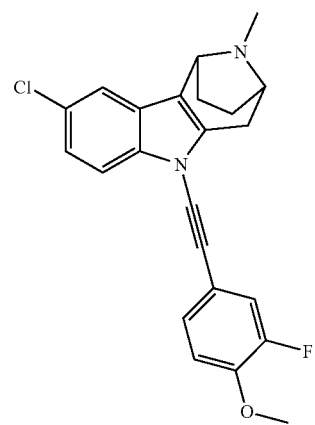 [SMILES: COc1ccc(C#Cn2c3c(c4cc(Cl)ccc42)C2CCC(C3)N2C)cc1F] |

-continued
| Compound # | Structure |
|---|---|
| 155 | 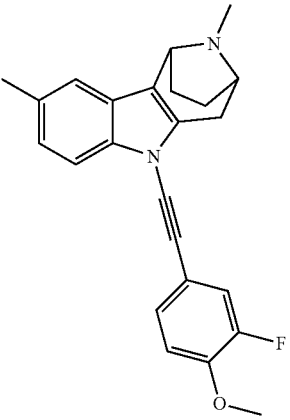 [SMILES: COc1ccc(C#Cn2c3c(c4cc(C)ccc42)C2CCC(C3)N2C)cc1F] |
or a pharmaceutically acceptable salt thereof.
19. The method of claim 11, wherein the compound is compound 165:
| Compound # | Structure |
|---|---|
| 165 | 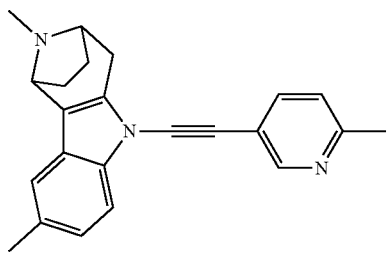 |
or a pharmaceutically acceptable salt thereof.
* * * * *